United States Patent
Larkin

(10) Patent No.: US 12,043,672 B2
(45) Date of Patent: Jul. 23, 2024

(54) COMPOSITIONS COMPRISING BISPECIFIC ANTIBODIES TO HUMAN ADAMTS5 AND NERVE GROWTH FACTOR

(71) Applicant: SYNOA THERAPEUTICS, LLC, Philadelphia, PA (US)

(72) Inventor: Jonathan Larkin, Philadelphia, PA (US)

(73) Assignee: SYNOA THERAPEUTICS, LLC, Philadelphia, PA (US)

( * ) Notice: Subject to any disclaimer, the term of this patent is extended or adjusted under 35 U.S.C. 154(b) by 0 days.

(21) Appl. No.: 18/463,037

(22) Filed: Sep. 7, 2023

(65) Prior Publication Data

US 2024/0092939 A1    Mar. 21, 2024

Related U.S. Application Data

(60) Provisional application No. 63/404,273, filed on Sep. 7, 2022.

(51) Int. Cl.
*C07K 16/40* (2006.01)
*C07K 16/22* (2006.01)

(52) U.S. Cl.
CPC .............. *C07K 16/40* (2013.01); *C07K 16/22* (2013.01); *C07K 2317/21* (2013.01); *C07K 2317/24* (2013.01); *C07K 2317/31* (2013.01); *C07K 2317/76* (2013.01); *C07K 2317/92* (2013.01)

(58) Field of Classification Search
CPC .... C07K 16/40; C07K 16/22; C07K 2317/21; C07K 2317/24; C07K 2317/31; C07K 2317/76; C07K 2317/92
See application file for complete search history.

(56) References Cited

U.S. PATENT DOCUMENTS

| | | |
|---|---|---|
| 2008/0311113 A1 | 12/2008 | Morris et al. |
| 2012/0095193 A1 | 4/2012 | Burden et al. |
| 2021/0008160 A1 | 1/2021 | Steffensen et al. |
| 2021/0246451 A1 | 8/2021 | Aoki |

OTHER PUBLICATIONS

La Porte, Sherry L. et al., "Generation of a high-fidelity antibody against nerve growth factor using library scanning mutagenesis and validation with structures of the initial and optimized Fab-antigen complexes", mAbs 6:4, 1059-1068; Jul./Aug. 2014; 2014 Landes Bioscience.

Covaceuszach, Sonia et al., "Single Cycle Structure-Based Humanization of an Anti-Nerve Growth Factor Therapeutic Antibody", PLoS ONE 7(3): e32212. doi:10.1371/journal.pone.0032212.

Abdiche, Yasmina Noubia et al., "Probing the binding mechanism and affinity of tanezumab, a recombinant humanized anti-NGF monoclonal antibody, using a repertoire of biosensors", Protein Science (2008), 17:1326-1335. Published by Cold Spring Harbor Laboratory Press.

Wehrman, Tom et al., "Structural and Mechanistic Insights into Nerve Growth Factor Interactions with the TrkA and p75 Receptors", Neuron 53, 25-38, Jan. 4, 2007.

Larkin et al., "Translational development of an ADAMTS-5 antibody for osteoarthritis disease modification", Osteoarthritis and Cartilage, vol. 23, Iss. 8, Aug. 2015 [retrieved on Nov. 30, 2023]. Retrieved from the Internet: <URL: https://www.sciencedirect.com/science/article/pii/S 1063458415008547>. pp. 1254-1266.

International Seaerch Report and Written Opinion Issued Jan. 18, 2024 In Corresponding PCT Application No. PCT/US2023/073657.

*Primary Examiner* — Robert S Landsman
(74) *Attorney, Agent, or Firm* — DUANE MORRIS LLP

(57) ABSTRACT

Provided herein are novel bispecific antibodies for the treatment of chronic pain. The bispecific antibodies comprise two or more antigen binding components, wherein at least one antigen binding component is capable of binding to human ADAMTS5, and wherein at least one antigen binding component is capable of binding to nerve growth factor (NGF).

16 Claims, 12 Drawing Sheets

Specification includes a Sequence Listing.

SynOA Bispecific and Control Antibodies

SynOA CrossMab    SynOA DVD1    SynOA DVD2    SynOA Bi-Feat

ADAMTS5 Control mAb    NGF Control mAbs Tanezumab / NGF Control mAb    Isotype Control mAb

- Knob-In-Hole Mutations
- Effector Function Disabled (AA) Mutations

FIG. 3A

Quantitative Binding of Antibodies and Targets (Octet Kinetics Studies)

Binding Replicate Mean Values

| Antibody (Relative Conc) | Ab Load (nm ± SD) | rhADAMTS5 Binding (nm ± SD) | rhNGF Binding (nm ± SD) |
|---|---|---|---|
| Tanezumab Control (1x) | 3.45 ± 0.240 | 0.0001 ± 0.00 | 0.78225 ± 0.038 |
| NGF mAb Control (1x) | 3.66 ± 0.240 | 0.0001 ± 0.00 | 0.8698 ± 0.005 |
| SynOA DVD1 (1x) | 2.33 ± 0.297 | 0.29315 ± 0.122 | 0.0119 ± 0.002 |
| SynOA DVD2 (1x) | 2.435 ± 0.304 | 0.0001 ± 0.00 | 0.38875 ± 0.097 |
| SynOA CrossMab (1x) | 2.825 ± 0.169 | 0.2459 ± 0.009 | 0.3244 ± 0.091 |
| SynOA CrossMab (0.33x) | 1.1159 ± 0.00 | 0.1957 ± 0.004 | 0.118 ± 0.047 |
| SynOA CrossMab (0.165x) | 0.5304 ± 0.039 | 0.18545 ± 0.004 | 0.0569 ± 0.033 |
| SynOA CrossMab (0.0825x) | 0.28675 ± 0.016 | 0.1889 ± 0.001 | 0.0264 ± 0.011 |
| SynOA Bi-Feat (1x) | 2.765 ± 0.021 | 1.19 ± 0.198 | 0.3375 ± 0.013 |
| ADAMTS5 mAb Control (1x) | 3.61 ± 0.212 | 1.355 ± 0.148 | 0.0001 ± 0.00 |
| Isotype Control mAb (1x) | 2.725 ± 0.134 | 0.0001 ± 0.00 | 0.0018 ± 0.002 |

Quantitative loading of bispecific and monoclonal antibodies to Octet human IgG Fc biosensors performed in duplicate and subsequent antibody-mediated binding of recombinant human target proteins (ADAMTS5 and NGF) was measured (shown as antibody-protein binding in nm wavelength shift +/- Std Dev). In order to maximize interpretation of bispecific binding potential and therapeutic relevance for affinity rank-ordering, ADAMTS5 and NGF binding was assessed during the 2nd association/dissociation step from sequential binding experiments (eg. affinity with both targets bound).

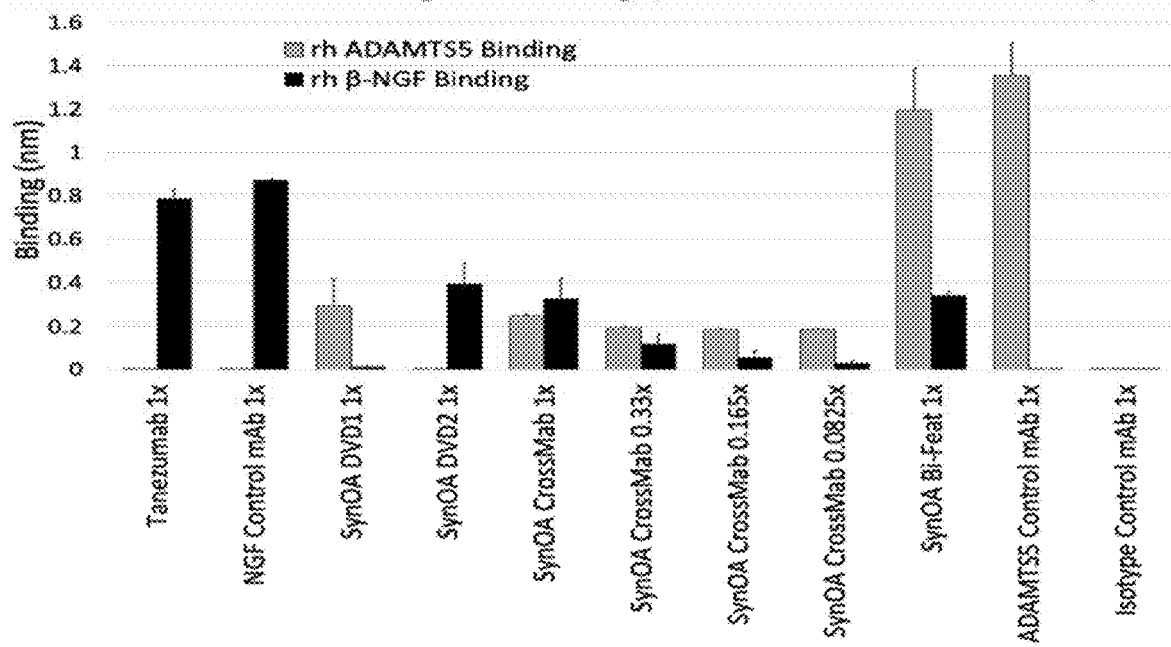
Bispecific and monoclonal binding (shown as antibody-protein binding in nm wavelength shift +/- Std Dev) from affinity rank-ordering experiments. ADAMTS5 and NGF binding was assessed during the 2nd association/dissociation step from sequential binding experiments (eg. affinity with both targets bound).

FIG. 4
SynOA Antibody Binding Affinity Kinetics (Octet)

rhADAMTS5 Binding

| Antibody (Loading Conc) | Kon (1/Ms) | Kdis (1/s) | KD (M) |
|---|---|---|---|
| Tanezumab (1x) | NB | NB | NB |
| NGF Control mAb (1x) | NB | NB | NB |
| SynOA DVD1 (1x) | 1.595 E+05 | 6.203 E-06 | 0.389 |
| SynOA DVD2 (1x) | NB | NB | NB |
| SynOA CrossMab (1x) | 7.291 E+05 | 6.943 E-04 | 0.952 |
| SynOA CrossMab (0.33x) | 1.471 E+06 | 1.924 E-03 | 1.308 |
| SynOA CrossMab (0.165x) | 6.391 E+03 | <1.0 E-07 | <0.01 |
| SynOA CrossMab (0.0825x) | 1.036 E+04 | <1.0 E-07 | <0.01 |
| SynOA Bi-Feat (1x) | 5.705 E+04 | <1.0 E-07 | <0.01 |
| ADAMTS5 Control mAb (1x) | 5.499 E+04 | <1.0 E-07 | <0.01 | rh β-NGF Binding

| Antibody (Loading Conc) | Kon (1/Ms) | Kdis (1/s) | KD (M) |
|---|---|---|---|
| Tanezumab (1x) | 2.144 E+05 | <1.0 E-07 | <0.01 |
| NGF Control mAb (1x) | 1.911 E+05 | 3.126 E-05 | 0.1636 |
| SynOA DVD1 (1x) | NB | NB | NB |
| SynOA DVD2 (1x) | 4.698 E+05 | <1.0 E-07 | <0.01 |
| SynOA CrossMab (1x) | 5.287 E+05 | 3.246 E-04 | 0.6139 |
| SynOA CrossMab (0.33x) | 1.183 E+06 | 2.567 E-04 | 0.2171 |
| SynOA CrossMab (0.165x) | 1.576 E+06 | 3.241 E-04 | 0.2057 |
| SynOA CrossMab (0.0825x) | 5.973 E+05 | <1.0 E-07 | <0.01 |
| SynOA Bi-Feat (1x) | 3.523 E+05 | 2.974 E-04 | 0.8443 |
| ADAMTS5 Control mAb (1x) | NB | NB | NB |

Affinities for bispecific and monoclonal antibodies shown as assessed during the 2nd association/dissociation step from sequential binding experiments (eg. affinity with both targets bound) with isotype control antibody subtraction. Kon (association constant – speed of target binding), Kdis (dissociation constant – speed of target dissociation) and KD (total affinity constant) are shown. NB = No binding vs isotype control.

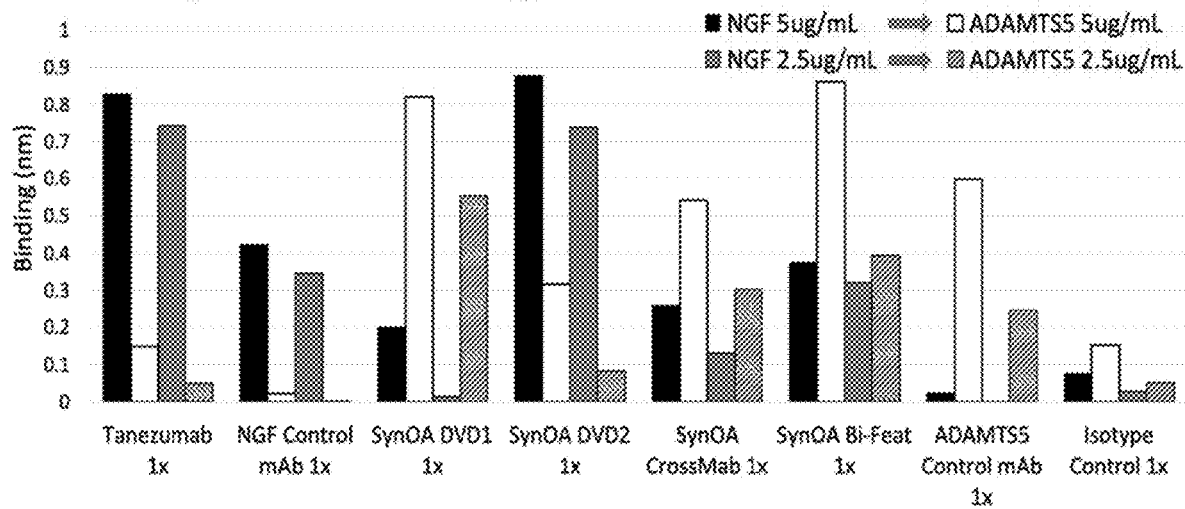

FIG. 5A

Quantitative Sequential Target Binding
(Octet Rank-Ordering Normalized to Antibody Load)

Comparative quantitation of different bispecific antibody capacity to bind both targets in relation to monoclonal and isotype control antibodies. Sequential binding of recombinant human targets at two concentrations (NGF first and ADAMTS5 second) assessed from bispecific and monoclonal antibody loaded Protein G Octet biosensors (data normalized to antibody load to the biosensors – shown as 1x relative antibody load).

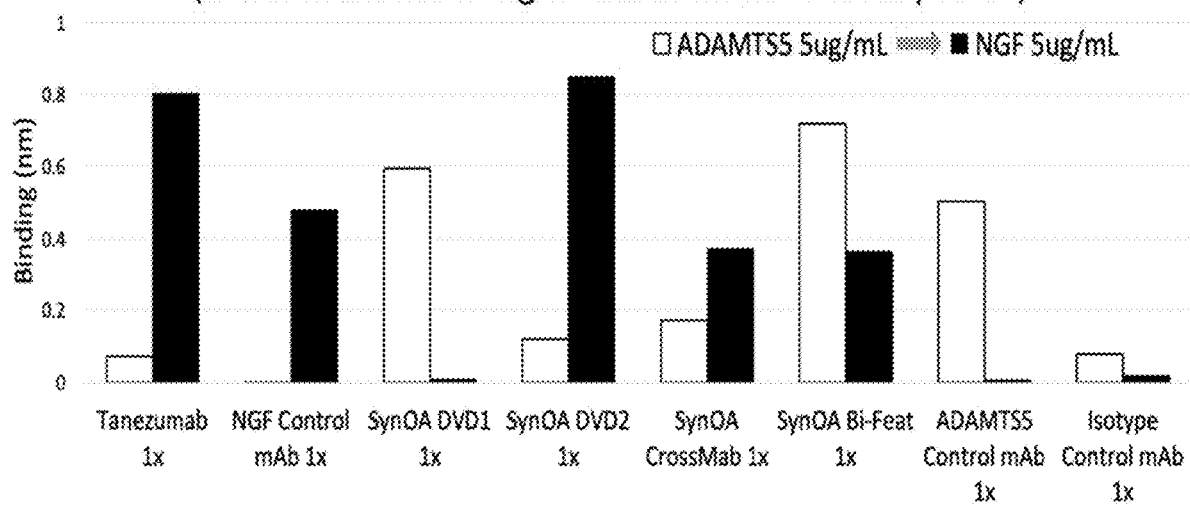

FIG. 5B

Comparative quantitation of different bispecific antibody capacity to bind both targets in relation to monoclonal and isotype control antibodies. Sequential binding of recombinant human targets at one concentration (ADAMTS5 first and NGF second) assessed from bispecific and monoclonal antibody loaded Protein G Octet biosensors (data normalized to antibody load to the biosensor – shown as 1x relative antibody load).

FIG. 6

| Construct Name | Heavy Chain 1 Amino Acid SEQ ID NO: | Heavy Chain 1 DNA SEQ ID NO: | Light Chain 1 Amino Acid SEQ ID NO: | Light Chain 1 DNA SEQ ID NO: | Heavy Chain 2 Amino Acid SEQ ID NO: | Heavy Chain 2 DNA SEQ ID NO: | Light Chain 2 Amino Acid SEQ ID NO: | Light Chain 2 DNA SEQ ID NO: | Construct Description |
|---|---|---|---|---|---|---|---|---|---|
| ADAMTS5 mAb (7B4) | 1 | | 2 | | | | | | ADAMTS5 7B4 mAb - Human IgG1 w/ Effector Disabled (AA) Mutation |
| ADAMTS5 mAb (12F4) | 3 | | 4 | | | | | | ADAMTS5 12F4 mAb - Human IgG1 w/ AA Mutation |
| Tanezumab | 5 | | 6 | | | | | | NGF Tanezumab mAb - Human IgG2 |
| Fulranumab | 7 | | 8 | | | | | | NGF Fulranumab mAb - Human IgG2 |
| Fasinumab | 9 | | 10 | | | | | | NGF Fasinumab mAb - Human IgG4 |
| M6495 | 11 | | | | | | | | ADAMTS5 M6495 Nanobody - Human HC Antibody CDRs |
| CRB0017 | 12 | | 13 | | | | | | ADAMTS5 CRB0017 mAb - Human IgG1 CDRs |
| p75NTR Fc | 14 | | | | | | | | Human p75NTR (NGFR/TNFRSF16) Receptor Fc Fusion |
| TrkA Fc | 15 | | | | | | | | Human TrkA (NTRK1) Receptor Fc Fusion |
| SynOA CM1 | 16 | 17 | 18 | 19 | 20 | 21 | 22 | 23 | ADAMTS5 (7B4) + NGF (Tanezumab) CrossMab w/ AA and Knob-In-Hole (KIH) Mutations |
| SynOA CM2 | 38 | | 39 | | 20 | 21 | 22 | 23 | ADAMTS5 (12F4) + NGF (Tanezumab) CrossMab w/ AA and KIH Mutations |
| SynOA CM3 | 16 | 17 | 18 | 19 | 103 | | 104 | | ADAMTS5 (7B4) + NGF (Fulranumab) CrossMab w/ AA and KIH Mutations |
| SynOA CM4 | 38 | | 39 | | 103 | | 104 | | ADAMTS5 (12F4) + NGF (Fulranumab) CrossMab w/ AA and KIH Mutations |
| SynOA CM5 | 16 | 17 | 18 | 19 | 56 | | 57 | | ADAMTS5 (7B4) + NGF (Fasinumab) CrossMab w/ AA and KIH Mutations |
| SynOA CM6 | 38 | | 39 | | 56 | | 57 | | ADAMTS5 (12F4) + NGF (Fasinumab) CrossMab w/ AA and KIH Mutations |
| SynOA CM7 | 16 | 17 | 18 | 19 | 58 | | | | ADAMTS5 (7B4) + NGF (p75NTR Fc) CrossMab w/ AA and KIH Mutations |
| SynOA CM8 | 38 | | 39 | | 58 | | | | ADAMTS5 (12F4) + NGF (p75NTR Fc) CrossMab w/ AA and KIH Mutations |
| SynOA CM9 | 16 | 17 | 18 | 19 | 50 | | 51 | | ADAMTS5 (7B4) + NGF (TrkA Fc) CrossMab w/ AA and KIH Mutations |
| SynOA CM10 | 38 | | 39 | | 51 | | | | ADAMTS5 (12F4) + NGF (TrkA Fc) CrossMab w/ AA and KIH Mutations |
| SynOA CM11 | 126 | | | | 20 | 21 | 22 | 23 | ADAMTS5 (M6495) + NGF (Tanezumab) CrossMab w/ AA and KIH Mutations |

FIG. 6 CONTINUED

| Construct Name | Construct Component Sequence Numbers ||||||| Construct Description |
|---|---|---|---|---|---|---|---|---|
| | Heavy Chain 1 || Light Chain 1 || Heavy Chain 2 || Light Chain 2 || |
| | Amino Acid SEQ ID NO: | DNA SEQ ID NO: | Amino Acid SEQ ID NO: | DNA SEQ ID NO: | Amino Acid SEQ ID NO: | DNA SEQ ID NO: | Amino Acid SEQ ID NO: | DNA SEQ ID NO: | |
| SynOA CM12 | 126 | | | | 103 | | 104 | | ADAMTS5 (M6495) + NGF (Fulranumab) CrossMab w/ AA and KIH Mutations |
| SynOA CM13 | 126 | | | | 56 | | 57 | | ADAMTS5 (M6495) + NGF (Tanezumab) CrossMab w/ AA and KIH Mutations |
| SynOA CM14 | 126 | | | | 90 | | 23 | | ADAMTS5 (M6495) + NGF (p75NTR Fc) CrossMab w/ AA and KIH Mutations |
| SynOA CM15 | 126 | | | | 51 | | | | ADAMTS5 (M6495) + NGF (TrkA Fc) CrossMab w/ AA and KIH Mutations |
| SynOA CM16 | 49 | | 128 | | 29 | 21 | 22 | | ADAMTS5 (CRB0017) + NGF (Tanezumab) CrossMab w/ AA and KIH Mutations |
| SynOA CM17 | 49 | | 128 | | 56 | | 57 | | ADAMTS5 (CRB0017) + NGF (Fasinumab) CrossMab w/ AA and KIH Mutations |
| SynOA CM18 | 49 | | 128 | | 103 | | 104 | | ADAMTS5 (CRB0017) + NGF (Fulranumab) CrossMab w/ AA and KIH Mutations |
| SynOA CM19 | 49 | | 128 | | 90 | | | | ADAMTS5 (CRB0017) + NGF (p75NTR Fc) CrossMab w/ AA and KIH Mutations |
| SynOA CM20 | 49 | | 128 | | 51 | | | | ADAMTS5 (CRB0017) + NGF (TrkA Fc) CrossMab w/ AA and KIH Mutations |
| SynOA DVD1 | 32 | 25 | 26 | 27 | | | | | ADAMTS5 (7B4) + NGF (Tanezumab) Dual Variable Domain Antibody w/ AA and SS Linkers |
| SynOA DVD2 | 28 | 29 | 30 | 31 | | | | | NGF (Tanezumab) + ADAMTS5 (7B4) Dual Variable Domain Antibody w/ AA and SS Linkers |
| SynOA DVD3 | 34 | | 35 | | | | | | ADAMTS5 (12F4) + NGF (Tanezumab) Dual Variable Domain Antibody w/ AA and SS Linkers |
| SynOA DVD4 | 36 | | 37 | | | | | | NGF (Tanezumab) + ADAMTS5 (12F4) Dual Variable Domain Antibody w/ AA and SS Linkers |
| SynOA DVD5 | 105 | | 106 | | | | | | ADAMTS5 (7B4) + NGF (Fulranumab) Dual Variable Domain Antibody w/ AA and SS Linkers |
| SynOA DVD6 | 109 | | 110 | | | | | | NGF (Fulranumab) + ADAMTS5 (7B4) Dual Variable Domain Antibody w/ AA and SS Linkers |
| SynOA DVD7 | 107 | | 108 | | | | | | ADAMTS5 (12F4) + NGF (Fulranumab) Dual Variable Domain Antibody w/ AA and SS Linkers |
| SynOA DVD8 | 111 | | 112 | | | | | | NGF (Fulranumab) + ADAMTS5 (12F4) Dual Variable Domain Antibody w/ AA and SS Linkers |
| SynOA DVD9 | 41 | | 42 | | | | | | ADAMTS5 (7B4) + NGF (Tanezumab) Dual Variable Domain Antibody w/ AA and LL Linkers |
| SynOA DVD10 | 43 | | 44 | | | | | | NGF (Tanezumab) + ADAMTS5 (7B4) Dual Variable Domain Antibody w/ AA and LL Linkers |
| SynOA DVD11 | 45 | | 46 | | | | | | ADAMTS5 (12F4) + NGF (Tanezumab) Dual Variable Domain Antibody w/ AA and LL Linkers |
| SynOA DVD12 | 47 | | 48 | | | | | | NGF (Tanezumab) + ADAMTS5 (12F4) Dual Variable Domain Antibody w/ AA and LL Linkers |
| SynOA DVD13 | 113 | | 114 | | | | | | ADAMTS5 (7B4) + NGF (Fulranumab) Dual Variable Domain Antibody w/ AA and LL Linkers |
| SynOA DVD14 | 117 | | 118 | | | | | | NGF (Fulranumab) + ADAMTS5 (7B4) Dual Variable Domain Antibody w/ AA and LL Linkers |

FIG. 6 CONTINUED

| Construct Name | Construct Component Sequence Numbers ||||||||| Construct Description |
|---|---|---|---|---|---|---|---|---|---|
| | Heavy Chain 1 || Light Chain 1 || Heavy Chain 2 || Light Chain 2 || |
| | Amino Acid SEQ ID NO: | DNA SEQ ID NO: | Amino Acid SEQ ID NO: | DNA SEQ ID NO: | Amino Acid SEQ ID NO: | DNA SEQ ID NO: | Amino Acid SEQ ID NO: | DNA SEQ ID NO: | |
| SynOA DVD15 | 115 | | 116 | | | | | | ADAMTS5 (12F4) + NGF (Fulranumab) Dual Variable Domain Antibody w/ AA and LL Linkers |
| SynOA DVD16 | 119 | | 120 | | | | | | NGF (Fulranumab) + ADAMTS5 (12F4) Dual Variable Domain Antibody w/ AA and LL Linkers |
| SynOA DVD17 | 58 | | 59 | | | | | | ADAMTS5 (7B4) + NGF (Fasinumab) Dual Variable Domain Antibody w/ AA and SS Linkers |
| SynOA DVD18 | 60 | | 61 | | | | | | ADAMTS5 (12F4) + NGF (Fasinumab) Dual Variable Domain Antibody w/ AA and SS Linkers |
| SynOA DVD19 | 62 | | 63 | | | | | | NGF (Fasinumab) + ADAMTS5 (7B4) Dual Variable Domain Antibody w/ AA and SS Linkers |
| SynOA DVD20 | 64 | | 65 | | | | | | NGF (Fasinumab) + ADAMTS5 (12F4) Dual Variable Domain Antibody w/ AA and SS Linkers |
| SynOA DVD21 | 66 | | 67 | | | | | | ADAMTS5 (7B4) + NGF (Fasinumab) Dual Variable Domain Antibody w/ AA and LL Linkers |
| SynOA DVD22 | 68 | | 69 | | | | | | ADAMTS5 (12F4) + NGF (Fasinumab) Dual Variable Domain Antibody w/ AA and LL Linkers |
| SynOA DVD23 | 70 | | 71 | | | | | | NGF (Fasinumab) + ADAMTS5 (7B4) Dual Variable Domain Antibody w/ AA and LL Linkers |
| SynOA DVD24 | 72 | | 73 | | | | | | NGF (Fasinumab) + ADAMTS5 (12F4) Dual Variable Domain Antibody w/ AA and LL Linkers |
| SynOA DVD25 | 74 | | 75 | | | | | | ADAMTS5 (CRB0017) + NGF (Tanezumab) Dual Variable Domain Antibody w/ AA and SS Linkers |
| SynOA DVD26 | 76 | | 77 | | | | | | ADAMTS5 (CRB0017) + NGF (Fasinumab) Dual Variable Domain Antibody w/ AA and SS Linkers |
| SynOA DVD27 | 78 | | 79 | | | | | | NGF (Tanezumab) + ADAMTS5 (CRB0017) Dual Variable Domain Antibody w/ AA and SS Linkers |
| SynOA DVD28 | 80 | | 81 | | | | | | NGF (Fasinumab) + ADAMTS5 (CRB0017) Dual Variable Domain Antibody w/ AA and SS Linkers |
| SynOA DVD29 | 82 | | 83 | | | | | | ADAMTS5 (CRB0017) + NGF (Tanezumab) Dual Variable Domain Antibody w/ AA and LL Linkers |
| SynOA DVD30 | 84 | | 85 | | | | | | ADAMTS5 (CRB0017) + NGF (Fasinumab) Dual Variable Domain Antibody w/ AA and LL Linkers |
| SynOA DVD31 | 86 | | 87 | | | | | | NGF (Tanezumab) + ADAMTS5 (CRB0017) Dual Variable Domain Antibody w/ AA and LL Linkers |
| SynOA DVD32 | 88 | | 89 | | | | | | ADAMTS5 (CRB0017) + NGF (Fulranumab) Dual Variable Domain Antibody w/ AA and LL Linkers |
| SynOA DVD33 | 90 | | 91 | | | | | | ADAMTS5 (CRB0017) + NGF (Fulranumab) Dual Variable Domain Antibody w/ AA and LL Linkers |
| SynOA DVD34 | 92 | | 93 | | | | | | NGF (Fasinumab) + ADAMTS5 (CRB0017) Dual Variable Domain Antibody w/ AA and LL Linkers |
| SynOA DVD35 | 94 | | 95 | | | | | | NGF (Fulranumab) + ADAMTS5 (CRB0017) Dual Variable Domain Antibody w/ AA and LL Linkers |
| SynOA DVD36 | 96 | | 97 | | | | | | NGF (Fulranumab) + ADAMTS5 (CRB0017) Dual Variable Domain Antibody w/ AA and LL Linkers |
| SynOA DM1 | 52 | | 18 | | 53 | | 54 | | ADAMTS5 (7B4 w/ F405L) + NGF (Tanezumab w/ K409R) DuoBody w/ AA Mutation |

FIG. 6 CONTINUED

| Construct Name | Heavy Chain 1 Amino Acid SEQ ID NO. | Heavy Chain 1 DNA SEQ ID NO. | Light Chain 1 Amino Acid SEQ ID NO. | Light Chain 1 DNA SEQ ID NO. | Heavy Chain 2 Amino Acid SEQ ID NO. | Heavy Chain 2 DNA SEQ ID NO. | Light Chain 2 Amino Acid SEQ ID NO. | Light Chain 2 DNA SEQ ID NO. | Construct Description |
|---|---|---|---|---|---|---|---|---|---|
| SynOA_DM2 | 160 | | 18 | | 134 | | 54 | | ADAMTS5 (7B4 w/ K409R) + NGF (Tanezumab w/ F405L) DuoBody w/ AA Mutation |
| SynOA_DM3 | 55 | | 39 | | 53 | | 54 | | ADAMTS5 (12F4 w/ F405L) + NGF (Tanezumab w/ K409R) DuoBody w/ AA Mutation |
| SynOA_DM4 | 162 | | 39 | | 135 | | 54 | | ADAMTS5 (12F4 w/ F405L) + NGF (Tanezumab w/ K409R) DuoBody w/ AA Mutation |
| SynOA_DM5 | 52 | | 18 | | 123 | | 122 | | ADAMTS5 (7B4 w/ F405L) + NGF (Fulranumab w/ K409R) DuoBody w/ AA Mutation |
| SynOA_DM6 | 160 | | 18 | | 123 | | 122 | | ADAMTS5 (7B4 w/ K409R) + NGF (Fulranumab w/ F405L) DuoBody w/ AA Mutation |
| SynOA_DM7 | 55 | | 39 | | 123 | | 122 | | ADAMTS5 (12F4 w/ F405L) + NGF (Fulranumab w/ K409R) DuoBody w/ AA Mutation |
| SynOA_DM8 | 162 | | 39 | | 123 | | 122 | | ADAMTS5 (12F4 w/ K409R) + NGF (Fulranumab w/ F405L) DuoBody w/ AA Mutation |
| SynOA_DM9 | 52 | | 18 | | 98 | | 99 | | ADAMTS5 (7B4 w/ F405L) + NGF (Fasinumab w/ K409R) DuoBody w/ AA Mutation |
| SynOA_DM10 | 160 | | 18 | | 98 | | 99 | | ADAMTS5 (7B4 w/ K409R) + NGF (Fasinumab w/ F405L) DuoBody w/ AA Mutation |
| SynOA_DM11 | 55 | | 39 | | 98 | | 99 | | ADAMTS5 (12F4 w/ F405L) + NGF (Fasinumab w/ K409R) DuoBody w/ AA Mutation |
| SynOA_DM12 | 162 | | 39 | | 98 | | 99 | | ADAMTS5 (12F4 w/ K409R) + NGF (Fasinumab w/ F405L) DuoBody w/ AA Mutation |
| SynOA_DM13 | 53 | | 128 | | 134 | | 54 | | ADAMTS5 (CR8017 w/ F405L) + NGF (Tanezumab w/ K409R) DuoBody w/ AA Mutation |
| SynOA_DM14 | 129 | | 128 | | 134 | | 54 | | ADAMTS5 (CR8017 w/ K409R) + NGF (Tanezumab w/ F405L) DuoBody w/ AA Mutation |
| SynOA_DM15 | 127 | | 128 | | 123 | | 122 | | ADAMTS5 (CR8017 w/ F405L) + NGF (Fulranumab w/ K409R) DuoBody w/ AA Mutation |
| SynOA_DM16 | 129 | | 128 | | 123 | | 122 | | ADAMTS5 (CR8017 w/ K409R) + NGF (Fulranumab w/ F405L) DuoBody w/ AA Mutation |
| SynOA_DM17 | 127 | | 128 | | 98 | | 99 | | ADAMTS5 (CR8017 w/ F405L) + NGF (Fasinumab w/ K409R) DuoBody w/ AA Mutation |
| SynOA_DM18 | 129 | | 128 | | 101 | | 99 | | ADAMTS5 (CR8017 w/ K409R) + NGF (Fasinumab w/ F405L) DuoBody w/ AA Mutation |
| SynOA_BF1 | 52 | | 18 | | | | | | ADAMTS5 (7B4) mAb with AA Mutation and C-Terminal NGF (Tanezumab) scFv |
| SynOA_BF2 | 130 | | 18 | | | | | | ADAMTS5 (7B4) mAb with AA Mutation and C-Terminal NGF (Fulranumab) scFv |
| SynOA_BF3 | 131 | | 18 | | | | | | ADAMTS5 (7B4) mAb with AA Mutation and C-Terminal NGF (Fasinumab) scFv |
| SynOA_BF4 | 40 | | 39 | | | | | | ADAMTS5 (12F4) mAb with AA Mutation and C-Terminal NGF (Tanezumab) scFv |
| SynOA_BF5 | 132 | | 39 | | | | | | ADAMTS5 (12F4) mAb with AA Mutation and C-Terminal NGF (Fulranumab) scFv |
| SynOA_BF6 | 133 | | 39 | | | | | | ADAMTS5 (12F4) mAb with AA Mutation and C-Terminal NGF (Fasinumab) scFv |

FIG. 6 CONTINUED

| | Construct Component Sequence Numbers | | | | | | | | |
|---|---|---|---|---|---|---|---|---|---|
| | Heavy Chain 1 | | Light Chain 1 | | Heavy Chain 2 | | Light Chain 2 | | |
| Construct Name | Amino Acid SEQ ID NO: | DNA SEQ ID NO: | Amino Acid SEQ ID NO: | DNA SEQ ID NO: | Amino Acid SEQ ID NO: | DNA SEQ ID NO: | Amino Acid SEQ ID NO: | DNA SEQ ID NO: | Construct Description |
| SynOA BF7 | 134 | | | | | | | | ADAMTS5 (M6495) HC Nanobody with AA Mutation and C-Terminal NGF (Tanezumab) scFv |
| SynOA BF8 | 135 | | | | | | | | ADAMTS5 (M6495) HC Nanobody with AA Mutation and C-Terminal NGF (Fulranumab) scFv |
| SynOA BF9 | 136 | | | | | | | | ADAMTS5 (M6495) HC Nanobody with AA Mutation and C-Terminal NGF (Fasinumab) scFv |
| SynOA BF10 | 137 | | 128 | | | | | | ADAMTS5 (CRB0017) mAb with AA Mutation and C-Terminal NGF (Tanezumab) scFv |
| SynOA BF11 | 138 | | 128 | | | | | | ADAMTS5 (CRB0017) mAb with AA Mutation and C-Terminal NGF (Fulranumab) scFv |
| SynOA BF12 | 139 | | 128 | | | | | | ADAMTS5 (CRB0017) mAb with AA Mutation and C-Terminal NGF (Fasinumab) scFv |

COMPOSITIONS COMPRISING BISPECIFIC ANTIBODIES TO HUMAN ADAMTS5 AND NERVE GROWTH FACTOR

PRIORITY CLAIM AND CROSS-REFERENCE

This application claims priority to U.S. Patent Application No. 63/404,273 filed on Sep. 7, 2022. The foregoing application, and all documents cited therein, together with any manufacturer's instructions, descriptions, mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

TECHNICAL FIELD

Embodiments of this disclosure relate generally to novel non-opioid therapeutics for the treatment of chronic pain, such as osteoarthritis, comprising the use of antibodies that address both pain and structural cartilage degeneration. Provided herein are novel bispecific antibodies, pharmaceutical compositions comprising the same, and methods for making and using the same.

SEQUENCE LISTING

The instant application contains a Sequence Listing which has been submitted electronically and is hereby incorporated by reference in its entirety. Said XML copy, was created Sep. 7, 2023, is named H6487-0003.xml and is 215,545 bytes in size.

BACKGROUND OF THE INVENTION

Chronic pain is a major public health problem. It is estimated to affect more than 100 million people in the United States and about 20-30% of the population worldwide. The prevalence of persistent pain is expected to rise in the near future as the incidence of associated diseases (including diabetes, obesity, cardiovascular disorders, arthritis, and cancer) increases in the aging U.S. population.

According to the Merck Manual, chronic pain may be the result of a variety of causes. In some instances, chronic pain can happen because of a long-term disease or an injury that fails to heal. Oftentimes, chronic pain can be caused by an ongoing problem such as a long-lasting disorder such as arthritis, diabetes, cancer, or fibromyalgia. Sometimes the nervous system becomes more sensitive than usual to pain signals resulting in chronic pain and often causing long-term nerve signaling disruption. Chronic pain can also lead to other symptoms such as feeling tired, problems sleeping, not feeling hungry, or not being interested in sex. Chronic pain can make it hard to work and do normal daily activities. Also associated with chronic pain are emotional symptoms, such as depression, anxiety, or withdrawing from social activities.

One of the most common causes of chronic pain is arthritis. Arthritis is not a single disease; the term refers to joint pain or joint disease, and there are more than 100 types of arthritis and related conditions. People of all ages, races and sexes live with arthritis, and it is the leading cause of disability in the U.S. It is most common among women, and although it is not a disease of aging, some types of arthritis occur in older people more than younger people. Common arthritis symptoms include swelling, pain, stiffness and diminished range of motion in joints. Symptoms vary from mild to severe and may come and go. Some may stay about the same for years, but symptoms can also progress and get worse over time. Severe arthritis can result in chronic pain, difficulty performing daily activities and make walking and climbing stairs painful and grueling.

Arthritis can also cause permanent joint changes. These may be visible, such as knobby finger joints, but often the damage can be seen only on X-rays. Some types of arthritis affect the heart, eyes, lungs, kidneys and skin as well as the joints.

Osteoarthritis (OA) is by far the most common type of arthritis. It can damage almost any joint but mainly occurs in the hands, spine, hips and knees. OA was once considered a wear-and-tear disease in which cartilage, the protective layer on the ends of bones, wore down after years of use. But with further research, the thinking about OA has changed. Doctors now know that OA is a disease of the whole joint, not just cartilage (although cartilage remains a primary focus). Bones in affected joints become weaker, the connective tissue that holds the joint together deteriorates and inflammation damages the joint lining. Contrary to decades of belief, inflammation plays a key role in OA, just as it does in most other types of arthritis.

Doctors generally threat chronic pain with medicines, physical therapy, occupational therapy as well as relaxation techniques, hypnosis, biofeedback, and other behavioral and psychological therapies including treatments for emotional symptoms.

Depending upon the severity of disease, pain may be managed with NSAIDs (non-steroidal anti-inflammatory drugs) such as over-the-counter pain medicines, for example, aspirin, ibuprofen or acetaminophen. Also used are antidepressants, corticosteroids, muscle relaxers, topical products, sedatives or medical marijuana.

In certain severe cases, opioids may be prescribed to help manage pain. Opioids are powerful analgesics which are commonly used and found to be effective for many types of pain. However, opioids can produce significant side effects, including constipation, nausea, mental clouding, and respiratory depression, which can sometimes lead to death. Additionally, opioids often don't work for the long term. Although opioids can be successfully used to treat moderate to severe pain ranging from cancer to broken bones, there is a growing epidemic of opioid addiction and abuse. Long-term opioid use can result in physical dependence, making it difficult to discontinue use even when the original cause of pain is no longer present. Furthermore, there is mounting evidence that long-term opioid use for pain can actually produce a chronic pain state, whereby patients find themselves in a vicious cycle, where opioids are used to treat pain caused by previous opioid use. Data from the Centers for Disease Control and Prevention indicate that the prescribing of opioids by clinicians has increased threefold in the last 20 years, contributing to the problem of prescription opioid abuse. Today, the number of people who die from prescription opioids exceeds the number of those who die from heroin and cocaine, combined.

Negative side-effects and complications related to therapeutic intervention are not restricted to opioids. Indeed, every medication has a potential for side effects, some happen to be more serious than others. Complications from medical treatments for chronic pain can include: acute liver failure from acetaminophen treatment, addiction and/or overdose, mood changes, confusion and respiratory issues from nerve pain medications, spinal cord damage or infection from spinal cord stimulators.

A further issue with currently available drugs and medicines, is that they are focused on treating one aspect of chronic pain, namely the pain component only. There are no medications currently available that are effective for treating pain, and for treating the underlying causes of pain, such as for example, cartilage degeneration. With issues and complications such as addiction, toxicity and modest long term efficacy, currently available pain treatments are inadequate to meet the needs of a majority of patients suffering from pain, chronic pain, osteoarthritis, and arthritis.

What is needed are non-opioid compositions and methods for treating chronic pain, including osteoarthritis. Such compositions and methods should be effective in treating pain and also address the underlying case of pain. What is also needed are single molecule therapeutics having dual function wherein such therapeutics are effective, non-toxic and non-addictive.

SUMMARY OF THE INVENTION

In an embodiment, the present disclosure relates to novel compositions and methods for treating chronic pain, wherein such novel methods and compositions simultaneously inhibit both pain and structural tissue degeneration. In certain embodiments, the compositions comprise a single therapeutic molecule, and in certain embodiments such therapeutic molecule may provide extended relief.

BRIEF DESCRIPTION OF FIGURES

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

FIG. 3A provides a tabular and FIG. 3B provides a graphical visualization of experimental results demonstrating quantitative target binding and affinity kinetics of bispecific and control antibodies. Experimental data was analyzed for quantitative antibody loading and target binding (measured as nm shift) and affinity kinetics (association [Kon], dissociation [Kdis] and equilibrium dissociation [KD] constants) using OCTET® Data Analysis Software.

FIG. 4 provides a table summarizing affinities for bispecific and monoclonal antibodies as assessed during the second association/dissociation step from sequential binding experiments.

FIGS. 5A-5B. FIG. 5A and FIG. 5B show graphs demonstrating comparative quantitation of different bispecific antibody capacities to bind both targets in relation to monoclonal and isotype control antibodies: FIG. 5A (NGF first and ADAMTS5 second), FIG. 5B (ADAMTS5 first and NGF second).

FIG. 6 provides a patent sequence table listing each of the constructs discussed herein together with the identification of amino acid and DNA sequences that comprise the heavy chains and light chains of the constructs.

DETAILED DESCRIPTION

Figure 1:
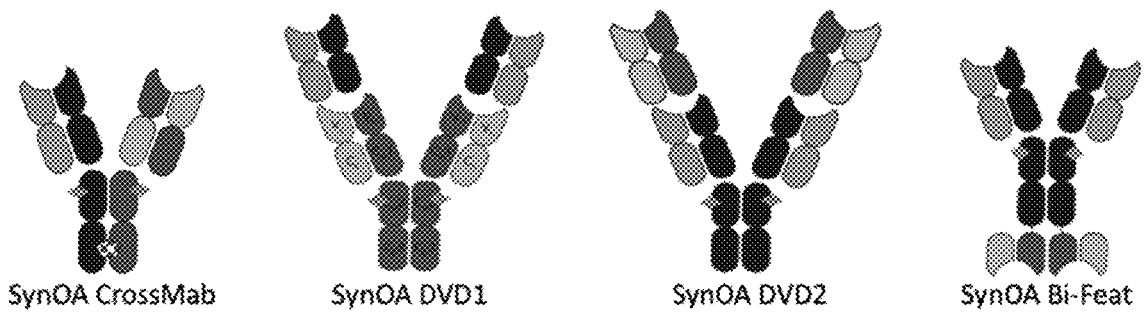
FIG. 1 provides schematic representations of certain bispecific and monoclonal control antibody constructs.
Figure 1:
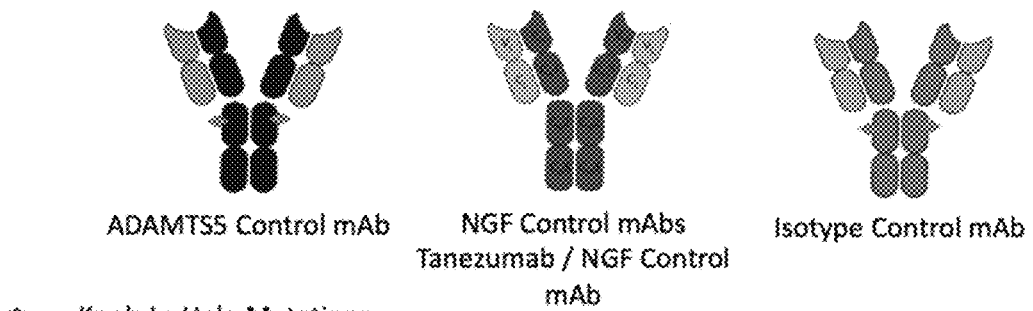

The following detailed description is exemplary and explanatory and is intended to provide further explanation of the present disclosure described herein. Other advantages, and novel features will be readily apparent to those skilled in the art from the following detailed description of the present disclosure. Texts and references mentioned herein are incorporated in their entirety, including U.S. Patent Application No. 63/404,273 and United States Patent Application Publication No. US2012-0095193 A1 and WO2012116260A1.

As used herein, the term "subject" should be construed to include subjects, for example medical or surgical subjects, such as humans and other animals requiring therapeutic intervention.

This description of the exemplary embodiments is intended to be read in connection with the accompanying figures, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the figure under discussion. These relative terms are for convenience of description and are not considered to be restrictive or limiting.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. Thus, for example, a reference to "an antibody" or "an antibody fragment" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to +10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

As used herein, term "amino acid" broadly refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid.

As used herein, an "antibody fragment" includes a portion of an intact antibody, such as, for example, the antigen-binding or variable region of an antibody. Examples of antibody fragments include Fab, Fab', F(ab')2, and Fv fragments. For example, antibody fragments include isolated fragments, "Fv" fragments (consisting of the variable regions of the heavy and light chains), recombinant single chain polypeptide molecules in which light and heavy chain variable regions are connected by a peptide linker ("scFv proteins"), recombinant single domain antibodies consisting of a variable region of an antibody heavy chain (e.g., VHH), and minimal recognition units consisting of the amino acid residues that mimic a hypervariable region (e.g., a hypervariable region of a heavy chain variable region (VH), a hypervariable region of a light chain variable region (VL), one or more CDR domains within the VH, and/or one or more CDR domains within the VL). In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, heavy chain variable region, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively, or additionally, antigen binding fragment of an antibody may be wholly or partially synthetically produced. An antigen binding fragment of an antibody may optionally comprise a single chain antibody fragment.

As used herein, the term "binding" typically refers to a non-covalent association between or among two or more entities, unless expressed indicated otherwise, for example, referring to covalent bonding. "Direct" binding involves physical contact between entities or moieties; indirect binding involves physical interaction by way of physical contact with one or more intermediate entities. Binding between two or more entities can typically be assessed in any of a variety of contexts-including where interacting entities or moieties are studied in isolation or in the context of more complex systems (e.g., while covalently or otherwise associated with a carrier entity and/or in a biological system or cell).

The term "domain" is used herein to refer to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively, or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecular (e.g., a small molecule, carbohydrate, a lipid, a nucleic acid, or a polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

As used herein, the term "bispecific antibody" generally refers to an antibody having two distinct binding domains that can bind to two antigens or two epitopes (an antigen part) of one or more antigens simultaneously. Typically, a bispecific antibody containing at least two (or more) such segments is considered to be a bispecific antibody if the two segments are moieties that (1) are not included in nature in the same antibody, and/or (2) have not previously been linked to one another in a single antibody, and/or (3) have been linked to one another through action of the hand of man. Bispecific antibodies with defined specificities, as contemplated herein, are artificial molecules, per se not found in nature. They are generated by biochemical, molecular or genetic means. The generation of bispecific IgG molecules is difficult due to the fact that the antigen-binding sites are built by the variable domains of the light and heavy chain (VL, VH). A bispecific antibody requires two different heavy chains, and two different light chains, and exhibits asymmetry due to the presence of, at least, two different Fv regions. Unrestrained pairing of heavy and light chains of two antibodies expressed in one cell can theoretically result in 16 different combinations (10 different molecules), with only one being bispecific and the remaining pairings resulting in non-functional or monospecific molecules. To direct and to force correct assembly of correct binding sites, i.e., heavy and light chains, is one of the challenges of generating bispecific antibodies, and the inventors herein have overcome these challenges in the context of engineering novel bispecific antibodies for the treatment and management of chronic pain. (Brinkmann et al. The making of bispecific antibodies. MAbs. 2017 February/March; 9(2):182-212. doi: 10.1080/19420862.2016.1268307. PMID: 28071970; PMCID: PMC5297537)

As used herein, "linker" refers to polypeptides typically added into antibody constructs most commonly to provide flexibility, fusion and/or increased distance between domains. For example, a glycine-serine (GS) repeat sequence is the most common linker sequence in the design of scFv-containing constructs due to their flexible nature. Inclusion of added linker sequence of various lengths between the VH/CH1 and VL/CL domains of Dual Variable Domain (DVD) bispecific antibodies provide increased distance and flexibility between the two antigen binding domains and also act to fuse the binding domains together in a single amino acid chain. The linkers employed in DVDs are derived from native antibody sequence, which is believed to reduce the immunogenic potential of these constructs following administration.

As used herein, "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues.

As used herein, the term "protein", refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

The abbreviations or acronyms used in the present disclosure have corresponding meanings as those skilled in the art understand. For example, the term "scFv" refers to a single chain antibody fragment. The terms "anti-IFN-γ scFv" and "IFN-γ scFv" may be used interchangeably, and the term "anti-" refers to an entity or portion targeting or to be bound with another entity or portion. The term "anti-IFN-γ scFv" refer to a single chain antibody fragment targeting or to be bound with IFN-γ.

Chronic pain is one of the most prevalent and costly health problems in the world. According to recent studies, chronic pain (pain that persists past normal healing time, typically for more that 3 to 6 months) affects an estimated 20% of people worldwide, and accounts for 15-20% of physician visits. In addition to an individual's suffering, the economic consequences of dealing with chronic pain have widespread implications including for example, increased medical expenses, lost income, lost productivity, compensation payments, as well as legal ramifications.

A major category of chronic pain consists of arthritis, within which osteoarthritis (OA) is one of the most common forms. OA is a serious disease characterized by significant pain and impaired quality of life for over 500 million patients affected worldwide and drives an ever-growing burden on global health and economics. Current pharmacologic options to treat the condition focus on pain relief, but are limited by modest efficacy, safety concerns in the setting of chronic administration, and growing evidence that they may accelerate disease progression. Joint replacements are limited to large joints with end-stage structural disease and, although broadly used and effective for many patients, have many access restrictions to the procedure, can result in unfavorable long-term outcomes and are not an option for those with moderate, but highly symptomatic OA. Together, these observations highlight the urgent need to develop safer and more effective therapeutics to treat OA patients.

Pain and structural degeneration in OA are primarily driven by distinct and uncoupled pathways. This observation underscores the complex nature of the disease and helps explain the heterogeneity of patients impacted by the condition, as independent mechanisms may contribute to pain and disease onset/progression. The present disclosure provides a highly successful and novel therapeutic that both decreases pain and prevents (or reverses) structural degeneration. In certain embodiments, the invention disclosed herein is also able to remain in the joint thereby prolonging its efficacy and minimizing off-target effects. In certain embodiments, the bispecific antibodies described herein are able to alleviate pain and contribute to cartilage repair over an extended period of time. Though not wishing to be bound by the following theory, through simultaneously inhibiting two molecular targets in a single bispecific drug; nerve growth factor (NGF), a molecule which potently transmits pain, and a protease (which causes cartilage breakdown and serves as a tissue anchor to keep the drug at the site of disease), the inventors herein have developed a transformational medicine for the treatment of chronic pain and OA.

In certain embodiments, the molecular target of the bispecific drug comprises proteinases such as ADAMTS5, that cleave substrates located in the extracellular matrix of tissues comprising aggrecan, versican, biglycan, brevican, decorin, fibromodulin, lumican and the like which is associated with degenerative disease processes. Though not wishing to be bound by the following theory, it is possible to target the substrate (for example aggrecan) at the ADAMTS5 proteolysis site with one binding component of the antibody, which would have the same inhibitory and anchoring effect as targeting ADAMTS5 directly.

In certain embodiments, the compositions of the invention comprise the utilization of bispecific antibody platform technology expertise to generate and select novel, long-acting NGF/ADAMTS5, targeting therapeutic candidates for clinical development. The novel compositions described herein enable therapeutic intervention for addressing chronic pain, including OA, comprising the use of non-opioid therapeutics. In certain embodiments, the novel compositions herein may be used for treating OA pain following intra-articular administration. In certain embodiments, the compositions may be utilized to treat all OA joints via systemic administration. In additional embodiments, the compositions may qualify for a disease modification label for other chronic pain indications, including but not limited to lower back pain and cancer-related pain. The compositions are useful for both humans and non-human animals, including for example for use in the field of veterinary medicine to treat OA in dogs, cats, horses and other animals.

Provided herein are novel methods and compositions for treating chronic pain, wherein such novel methods and compositions simultaneously inhibit both pain and structural tissue degeneration. The compositions described herein are unique in that they comprise a single therapeutic molecule, and in certain embodiments, the compositions are capable of providing sustained relief. The compositions may be used to treat chronic pain, including, but not limited to arthritis, osteoarthritis, osteochondritis, as well as other diseases and disorders associated with cartilage and bone issues. In certain embodiments, the compositions herein comprise a binding protein with two or more antigen binding components, wherein at least one antigen binding component is capable of binding to one more proteinases such as ADAMTS5 (which act on substrates, typically in the extracellular tissue matrix such as aggrecan, versican, biglycan, brevican, decorin, fibromodulin, lumican and the like), and wherein at least one antigen binding component is capable of binding to nerve growth factor (NGF). The antigen binding component may comprise an antibody, a monoclonal antibody, and/or (active) fragments thereof; the monoclonal antibody or fragment thereof may be mouse, chimeric, humanized, or fully human. In certain embodiments, the antigen binding component capable of binding to NGF may comprises a monoclonal antibody or Fc Fusion protein selected from the group including, but not limited to, tanezumab, fasinumab, fulranumab, TrkA Fc and/or p75NTR Fc.

In an embodiment, the novel compositions of the invention comprise a binding protein with two or more antigen binding components, wherein at least one antigen binding component is capable of binding to human ADAMTS5, and wherein at least one antigen binding component is capable of binding to nerve growth factor (NGF). The antigen binding component may comprise an antibody or fragment thereof; the antibody may comprise a monoclonal antibody or fragment thereof, wherein the monoclonal antibody or fragment thereof is mouse, chimeric, humanized, or fully human. In certain embodiments, the antigen binding components may comprise at least one complementarity determining region. The antigen binding components may selectively bind with high affinity to ADAMTS5 The antigen binding component capable of binding to NGF may comprise a monoclonal antibody selected from the group including, but not limited to, tanezumab, fasinumab, fulranumab, TrkA Fc and/or p75NTR Fc.

In certain embodiments, the novel composition comprises one antigen binding component that selectively binds with high affinity to one or more ADAMTS5 molecules and one antigen binding protein selectively binds with high affinity to one or more NGF molecules. Such a composition may comprise a bispecific antibody, represented by the constructs provided in FIG. 6.

In certain embodiments, the novel compositions and/or formulations of the invention may further comprise bone targeting agents, including but not limited to denosumab, and/or agents targeting RANK-L, romosozumab, and/or agents targeting sclerostin.

In certain embodiments, the novel compositions and/or formulations of the invention may further comprise vascular targeting agents, including but not limited, to bevacizumab, ramucirumab and/or agents targeting VEGF.

In certain embodiments, the novel compositions and/or formulations of the invention may further comprise TNF-alpha targeting agents, including but not limited, to adalimumab, infliximab and/or agents targeting TNF-alpha.

In certain embodiments, the novel compositions and/or formulations of the invention may further comprise interleukin targeting agents, including but not limited, to canakinumab, tocilizumab and/or agents targeting interleukins.

In certain embodiments, the novel compositions and/or formulations of the invention may further comprise an antigen binding protein capable of binding to an anti-tumor modulator, including, but not limited to PD-1.

In certain embodiments, the novel compositions of the invention may further comprise pharmaceutically acceptable excipients.

In an embodiment, provided herein are methods for treating the conditions of chronic pain, arthritis, or osteoarthritis in a subject, by administering to the subject a composition comprising a binding protein with two or more antigen binding components, wherein at least one antigen binding component is capable of binding to human ADAMTS5, and wherein at least one antigen binding component is capable of binding to nerve growth factor (NGF). In an embodiment, the composition may be administered intraarticularly, intravenously, intramuscularly, subcutaneously, orally, intranasally, and/or via respiratory inhaler. In an embodiment, the subject to be treated may be suffering from a disease of the cartilage.

In an embodiment, the novel compositions of the invention as disclosed herein, may be used to treat a subject suffering from one or more diseases selected from the group of: osteoarthritis, cancer, pain, chronic pain, neuropathic pain, postoperative pain, sports injuries, erosive arthritis, rheumatoid arthritis, psoriatic arthritis, Lyme arthritis, juvenile arthritis, ankylosing spondylosis, neuralgia, neuropathies, algesia, nerve injury, ischemia, neurodegeneration, inflammatory diseases, cartilage degeneration, diseases affecting the larynx, trachea, auditory canal, intervertebral discs, ligaments, tendons, joint capsules or bone development, intervertebral disc degeneration, osteopenia, or periodontal diseases, acute joint injury, and/or a disease related to joint destruction.

In certain embodiments, following administration of at least one dose of the novel compositions herein, the subject experiences a reduction in cartilage degradation.

In certain embodiments, following administration of at least one dose of the novel compositions herein, the subject experiences the inhibition or reduction in aggrecan proteolysis.

In an embodiment, provided herein are methods for treating osteoarthritis in a subject comprising the administration of a composition comprising: a protein with two or more antigen binding components, wherein at least one antigen binding component is capable of binding to human ADAMTS5, and wherein at least one antigen binding component is capable of binding to nerve growth factor (NGF). In an embodiment, the protein with two antigen binding components consists of a bispecific antibody, and one component thereof selectively binds with high affinity to ADAMTS5 and the other component thereof selectively binds with high affinity to NGF. The component that binds to ADAMTS5 is selected from the group including, but not limited to, constructs ADAMTS5 mAb (7B4), ADAMTS5 mAb (12F4), M6495, and CRB0017 (sec FIG. 6) the component capable of binding to NGF comprises a monoclonal antibody selected from the group including, but not limited to, tanezumab, fasinumab, fulranumab, TrkA Fc and/or p75NTR Fc. The bispecific antibody is represented by constructs identified in FIG. 6. In certain embodiments, the composition may be administered intraarticularly, intravenously, intramuscularly, subcutaneously, orally, intranasally, and/or via respiratory inhaler. In certain embodiments, administration of the bispecific antibody composition enables the alleviation of pain and also the reduction of cartilage degradation. In certain embodiments, administration of the bispecific antibody composition results in extended relief. In certain embodiments, the subject is a vertebrate, including but not limited to human, non-human mammal, cat, dog, horse, cattle, rabbit, or cow.

In certain embodiments, the antigen binding component capable of binding to ADAMTS5 is characterized in that it inhibits ADAMTS5-mediated aggrecanase activity. In certain embodiments, the antigen binding component capable of binding to ADAMTS5 is characterized in that it inhibits the production of aggrecanase activity biomarkers, including but not limited to ARGS neoepitope. Administration of at least one dose of said composition may reduce cartilage degradation in said subject.

In certain embodiments, the administration of the novel bispecific antibody compositions of the invention improves the conditions of a subject suffering from at least one disease selected from the group consisting of: osteoarthritis, cancer, pain, chronic pain, neuropathic pain, postoperative pain, sports injuries, erosive arthritis, rheumatoid arthritis, psoriatic arthritis, Lyme arthritis, juvenile arthritis, ankylosing spondylosis, neuralgia, neuropathies, algesia, nerve injury, ischaemia, neurodegeneration, inflammatory diseases, cartilage degeneration, diseases affecting the larynx, trachea, auditory canal, intervertebral discs, ligaments, tendons, joint capsules or bone development, intervertebral disc degeneration, osteopenia, or periodontal diseases, acute joint injury, and/or a disease related to joint destruction.

In certain embodiments, the therapeutic bispecific antibody formulation of the invention comprises an injectable formulation, oral formulation, or intravenous formulation. The therapeutic bispecific antibody may be in a concentration ranging between 0.01 to 10 µg/mL, 0.5 to 10 µg/mL, 0.5 to 5 µg/mL, 0.5 to 4 µg/mL, 0.1 to 500 µg/mL, 1 to 400 µg/mL, 1 to 50 µg/mL, 10 to 20 µg/mL, 100 to 300 µg/mL, 125 and 175 µg/mL, 1 to 100 mg/mL, 20 to 80 mg/mL, 30 to 70 mg/mL, 40 to 70 mg/mL, 40 to 60 mg/mL. In certain embodiments, pharmaceutically acceptable excipients are present in a concentration range between 1 to 100 mg/mL, between 20 to 80 mg/mL, between 30 to 70 mg/mL, between 30 to 70 mg/mL and between 40 to 60 mg/mL.

In certain embodiments, methods for treating pain, arthritis or OA are provided wherein the novel compositions of the invention are administered to an organism at the site of pain, for example at a joint, such as in the neck, shoulder, elbow, wrist, fingers, hips, knees, spine or ankles. As such, methods for treating pain comprise administering a dose between 0.01 µg to 100 mg of a bispecific antibody composition to an organism having pain at the site of pain, the composition comprising: bispecific antibodies and pharmaceutically acceptable excipients. The compositions or formulations may be administered as single or multiple doses and the doses may be administered as needed, for example, they may be administered twice daily, daily, every other day, every third day, three times per week, twice per week, weekly, biweekly, monthly, bimonthly, quarterly, semi-annually, or annually. In certain embodiments, the compositions are engineered to have sustained release and prolonged effect The dose amount may be determined based on factors known to those skilled in the art (such as clinical factors, weight, pharmacokinetic profiles and conditions to be treated and may vary from about 1 µg to about 10 µg, about 10 µg to about 50 µg, about 50 µg to about 150 µg, about 150 µg to about 250 µg, about 250 µg to about 500 µg, about 500 µg to about 750 µg, about 750 µg to about 1 mg, about 1 mg to about 50 mg, about 1 mg to about 100 mg, about 50 mg to about 100 mg. In certain embodiments, the bispecific antibody may be present in a concentration of between 0.01 to 15 µg/mL, 0.01 to 10 µg/mL, 0.5 to 10 µg/mL, 0.5 to 5 µg/mL, or 0.5 to 4 µg/mL.

The compositions and formulations described herein may be administered by standard routes. In general, the compositions and formulations may be administered by the topical, intraarticular, transdermal, intraperitoneal, intracranial, intracerebroventricular, intracerebral, intravaginal, intrauterine, oral, rectal or parenteral (e.g., intravenous, intraspinal, subcutaneous or intramuscular, epidural) ophthalmic (including intravitreal or intracameral), nasal, topical (including buccal and sublingual), administration. route. In certain embodiments, osmotic minipumps may also be used to provide controlled delivery of therapeutic agents through cannulae to the site of interest. The biodegradable polymers and their use are described, for example, in detail in Brem et al., J. Neurosurg. 74:441-446 (1991), which is hereby incorporated by reference in its entirety.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Suitable dosages of the compositions and formulations disclosed herein will depend on the level of pain, condition or disease state being treated and other clinical factors such as weight and condition of the human or animal and the route of administration of the compound. It is to be understood that the invention has application for both human and veterinary use. The methods of the invention contemplate single as well as multiple administrations, given either simultaneously or over an extended period of time.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

The following examples are given to illustrate exemplary embodiments of the present disclosure. It should be understood, however, that the present disclosure is not to be limited to the specific conditions or details described in these examples. Examples are provided below to facilitate a more complete understanding of the invention. The following examples illustrate the exemplary modes of making and practicing the invention.

EXAMPLES

Example 1

Bispecific Antibody Design

Sequences for the design of bispecific antibody constructs were derived from published monoclonal antibodies with single target specificity (SEQ ID NOS: 1-13) and/or human target receptor Fc fusion proteins (SEQ ID NOS: 14-15) and combined using multiple established bispecific antibody technology platforms. In some embodiments, the complementary determining regions (CDRs), and/or variable domains from the heavy and light chains of the published monoclonal antibodies were transferred from a human IgG2 framework into a human IgG1 framework. Where necessary and appropriate, mutations to the framework sequences were introduced to reduce immune effector function (AA mutant reducing ADCC, CDC activities) and/or enable efficient heterogeneous heavy and light chain pairing (for example, knob-in-hole, CH1-CL domain swapping and/or complementary heavy chain specific F405L and K409R). In some cases, linker sequences of various lengths were added between VH/CH1 and VL/CL domains (Dual Variable Domain bispecifics) and/or between the interface of CH3/VH and VH/VL domains (scFv containing constructs) to provide distance between target binding domains to increase binding potential or enable IgG/scFv fusion and VH/VL association within the scFv. Sequence ID numbers for the components of each bispecific antibody construct are summarized in Table 1 (SynOA Patent Sequence Table) and individual component sequences (SEQ ID NOS: 16-139) are appended (SynOA Bispecific Ab Patent Sequences). Schematic representations of example bispecific and monoclonal control antibody constructs are shown in FIG. 1 below.

Example 2

Bispecific Antibody Construct Generation

Sequences of selected constructs were codon optimized at the DNA level for downstream mammalian cellular expression system compatibility using standard methods. Construct sequences were synthesized using as GBLOCK™ fragments, (DNA fragments manufactured by Integrated DNA Technologies, Inc) and cloned into mammalian expression vectors. The final constructs were then verified by forward and reverse DNA sequencing to confirm accuracy.

Example 3

Bispecific Antibody Expression and Purification

Expression vectors containing appropriate combinations to produce the desired bispecific antibodies were co-transfected into a mammalian expression cell line (CHO), and stable pools expressing and secreting the bispecific antibodies were established under selection with appropriate antibiotics. After expansion of the stable pools to appropriate volumes, the cell culture supernatants were collected for antibody purification using protein G agarose beads (manufactured by MILLIPORE®, #16-266). Purified antibodies were dialyzed against PBS and the concentrations were measured using the BCA protein assay kit (ThermoFisher, #23250). Small fractions of the purified antibodies were assessed for purity and appropriate migration profiles on SDS-PAGE gels under reducing and non-reducing conditions, and the remaining antibodies were aliquoted and stored at −80° C.

Example 4

Bispecific Antibody Target Binding and Affinity Measurements

Figure 2:
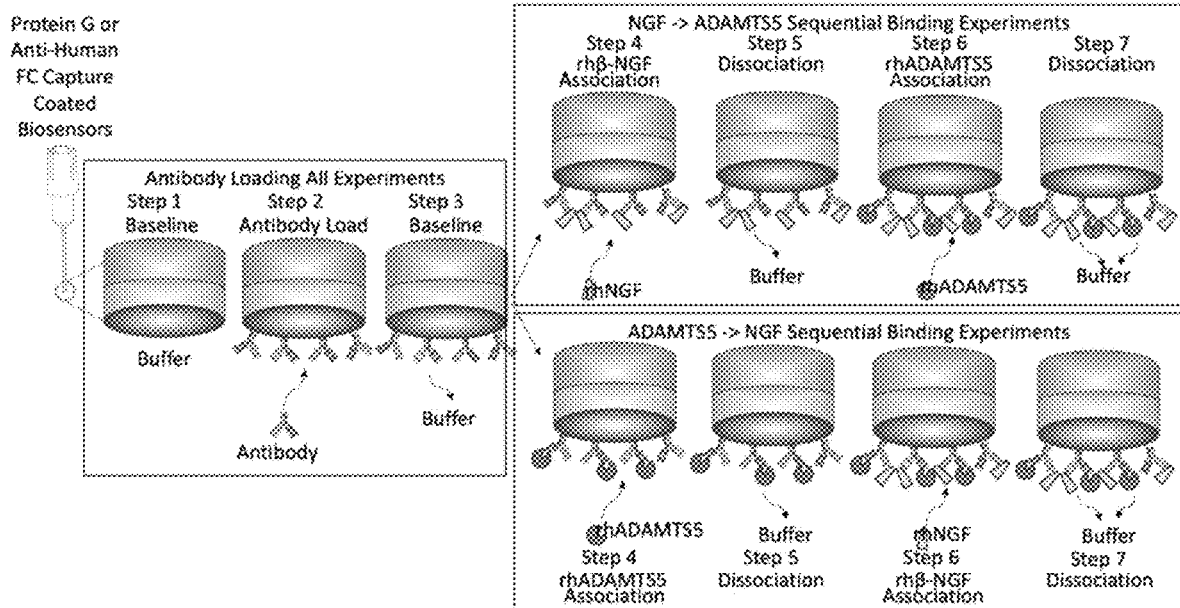
FIG. 2 provides a schematic showing the design of binding and affinity kinetics experiments performed using a Bio-Layer Intreferometry (BLI) technology platform (OCTET® RH16, Sartorius). Bispecific and monoclonal control antibodies were measured for binding to the target human proteins (ADAMTS5 and NGF) in sequential order and results were used to quantify binding and affinity to enable characterization and rank ordering (FIG. 2).

Binding and affinity kinetics of bispecific and monoclonal control antibodies to the target human proteins were measured using a Bio-Layer Interferometry (BLI) technology platform (OCTET® RH16, Sartorius) to enable characterization and rank ordering. For all experiments, Protein G and/or Anti-Human Fc-Capture coated OCTET® biosensors were first calibrated for loading of each bispecific and control antibody to identify comparable loading capacity. Subsequent target-specific real-time binding and affinity experiments using comparable antibody loading concentrations from calibrations were performed in multiple experiments for each target in sequential order using recombinant human ADAMTS5 (R&D Systems Cat #2198-AD) and recombinant human beta-NGF (R&D Systems Cat #256-GF-100/CF) each separated by a 10-minute PBS/Kinetics buffer wash/dissociation step (shown schematically in FIG. 2). To measure the ability of the bispecific antibodies to bind to both targets simultaneously and assess the potential of each target once bound to influence the binding stability of the other target, the sequential order of target addition was alternated in independent experiments. Monoclonal antibodies specific for each target (ADAMTS5 or beta-NGF), isotype-matched antibodies with specificities to targets not included in the experiments and buffer-only loading conditions were run as positive and negative controls, respectively. Experiments were designed and run using OCTET® Data Acquisition Software and all experiments were performed at 30° C. with continuous shaking of the reagent plate at 1000 RPM. In some experiments a dose range of antibody loading and/or target protein concentration was used to enable interpretation of results. Once acquired, the experimental data was analysed for quantitative antibody loading and target binding (measured as nm shift) and affinity kinetics (association [Kon], dissociation [Kdis] and equilibrium dissociation [KD] constants) using OCTET® Data Analysis Software (FIG. 2). Values reported for binding and affinity rank order characterization were calculated following the second sequential binding/association step for each target (e.g. with both targets bound) to maximize stringency and interpretation of therapeutic relevance (FIG. 3A and FIG. 3B). For affinity kinetics studies, the isotype control antibody loaded biosensors were used as a reference in the calculations to control for non-specific target binding (FIG. 4). Additional studies were conducted in order to assess comparative quantitation of different bispecific antibody capacity to bind both targets in relation to monoclonal and isotype control antibodies (FIG. 5A and FIG. 5B).

Example 5

Bispecific Antibody Functional Inhibition of ADAMTS5 Activity

Inhibition of ADAMTS5-mediated proteolysis of its native substrates (including, but not limited to, Aggrecan, Brevican, Versican) by antibodies, and other inhibitors, can be measured using multiple experimental assays to calculate and rank order the potency of inhibitors by IC50s (half maximal inhibitory concentrations). Functional ADAMTS5 assays typically involve incubating a fixed concentration of purified recombinant ADAMTS5 (human or other species) with a fixed concentration of a purified, recombinant or peptide version of a native substrate (most commonly aggrecan) in an assay buffer (containing ZnCl) at a physiological pH and temperature to allow for proteolysis of the substrate to progress. ADAMTS5 inhibitors are tested by conducting these assays in separate assay wells or tubes in the presence or absence of each inhibitor in a concentration dose-range to derive a functional potency IC50 calculation. Following a given time, the reaction is stopped by addition of an EDTA-containing solution and proteolysis of the substrate is detected.

ADAMTS5 mediated proteolysis in these experiments can be detected in numerous ways depending on the substrate used:

1) Purified and recombinant substrates—visual mobility of cleaved and uncleaved substrate in each assay sample following polyacrylamide gel electrophoresis and staining of the gel with a total protein dye.
2) Peptide substrate—Typically fluorescence resonance energy transfer (FRET) based assays that employ dual donor and acceptor fluorescence-tagged peptides containing the proteolytic cleavage site which emit a fluorescent signal when the peptide is cleaved. One example of an ADAMTS5 substrate peptide is WAAG-3R (Anaspec, Cat #60431-1).
3) All substrate forms—Using a neoepitope monoclonal antibody (such as OA-1 or BC-3 for the aggrecan ARGS neoepitope) that recognize an epitope that is generated following ADAMTS5-mediated proteolysis. This can be performed by western blotting or in various immunoassay-based methods for quantitation.

Each inhibitor and test condition is visualized by plotting the measured value or percent inhibition of each assay condition on the y-axis and the inhibitor concentration (log scale) on the x-axis and the IC50 can be calculated manually or by using software (such as GraphPad Prism, RStudio or MS Excel).

Example 6

Bispecific Antibody Functional Inhibition of Beta-NGF Activity

Inhibition of beta-NGF activity to derive an IC50 potency for rank ordering can be measured using an NGF receptor (TrkA [NTRK1] and/or p75NTR [NGFR/TNFRSF16]) expressing reporter cell line (such as the commercial TRKA Human RTK Kinase Cell-Based Antagonist Functional Assay from DiscoverX). To perform these assays a fixed concentration of recombinant human beta-NGF is pre-incubated for up to 1 hour at a physiological temperature in the presence or absence of a concentration dose range of the inhibitor and the NGF receptor reporter cell line is then treated with the sample in an assay plate. Following a subsequent incubation period, the reporter signal (typically by luminescence) is detected and the resulting data can be visualized by plotting the measured value or percent inhibition of each assay condition on the y-axis and the inhibitor concentration (log scale) on the x-axis and the IC50 for each inhibitor is calculated manually or by using software (such as GraphPad Prism, RStudio or MS Excel).

```
Source mAb Sequences for SynOA
bispecific antibodies
SEQ ID NO: 1:
Amino Acid 7B4 Heavy Chain:
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPSVFPLAPSSKSTSG

GTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPE

AAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALP

APIEKTISKAKGQPREPQVYTLPPSRDELTKNQVSLTCLVKGFYPSDI

AVEWESNGQPENNYKTTPPVLDSDGSFFLYSKLTVDKSRWQQGNVFSC

SVMHEALHNHYTQKSLSLSPGK

SEQ ID NO: 2:
Amino Acid 7B4 Light Chain:
DIQMTQSPSSLSASVGDRVTITCRTSENIYSYLAWYQQKPGKAPKLLI

YNAKTLAEGVPSRFSGSGSGTDFTLTISSLQPEDFATYYCQHHYGTPW

TFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SEQ ID NO: 3:
Amino Acid 12F4 Heavy Chain:
EVQLLESGGGLVQPGGSLRLSCAASGFTFSDAWMDWVRQAPGKGLEWV

AEIRHKANDHAIFYDESVKGRFTISRDSKNTVYLQMNSLRAEDTAVYY

CTSPFAYWGQGTLVTVSSASTKGPSVFPLAPSSKSTSGGTAALGCLVK

DYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLF

PPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKA

KGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNH

YTQKSLSLSPGK

SEQ ID NO: 4:
Amino Acid 12F4 Light Chain:
DIQMTQSPSSLSASVGDRVTITCKASQSVGTTIVWTQQLPGKAPKLLI

YSASNRHTGVPSRFSGSGSGTDFTLTISSLQPEDFATYYCQQYTSYPF

TFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SEQ ID NO: 5:
Amino Acid Tanezumab Heavy Chain:
QVQLQESGPGLVKPSETLSLTCTVSGFSLIGYDLNWIRQPPGKGLEWI

GIIWGDGTTDYNSAVKSRVTISKDTSKNQFSLKLSSVTAADTAVYYCA

RGGYWYATSYYFDYWGQGTLVTVSSASTKGPSVFPLAPCSRSTSESTA

ALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSV

FLFPPKPKDTLMISRTPEVTCVVVDVSHEDPEVQFNWYVDGVEVHNAK

TKPREEQFNSTFRVVSVLTVVHQDWLNGKEYKCKVSNKGLPSSIEKTI

SKTKGQPEPQVYTLPPSREEMTKNQVSLTCLVKGFYPSDIAVEWESNG

QPENNYKTTPPMLDSDGSFFLYSKLTVDKSRWQQGNVFSCSVMHEALH

NHYTQKSLSLSPGK

SEQ ID NO: 6:
Amino Acid Tanezumab Light Chain:
DIQMTQSPSSLSASVGDRVTITCRASQSISNNLNWYQQKPGKAPKLLI

YYTSRFHSGVPSRFSGSGSGTDFTFTISSLQPEDIATYYCQQEHTLPY

TFGQGTKLEIKRTVAAPSVFIFPP

SDEQLKSGTASVVCLLNNFYPREAKVQWKVDNALQSGNSQESVTEQDS

KDSTYSLSSTLTLSKADYEKHKVYACEVTHQGLSSPVTKSFNRGEC
```

SEQ ID NO: 7:
Amino Acid Fulranumab Heavy chain
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASTKGPSVFPLAPCSRSTSES

TAALGCLVKDYFPEPVTVSWNSGALTSGVHTFPAVLQSSGLYSLSSVV

TVPSSNFGTQTYTCNVDHKPSNTKVDKTVERKCCVECPPCPAPPVAGP

SVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEK

TISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHE

ALHNHYTQKSLSLSPGK

SEQ ID NO: 8:
Amino Acid Fulranumab Light chain
AIQLTQSPSSLSASVGDRVTITCRASQGISSALAWYQQKPGKAPKLLI

YDASSLESGVPSRFSGSGSGTDFTLTISSLQPEDFATYYCQQFNSYPL

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SEQ ID NO: 9:
Amino Acid Fasinumab Heavy chain
QVQLVQSGAEVKKPGASVKVSCKVSGFTLTELSIHWVRQAPGKGLEWM

GGFDPEDGETIYAQKFQGRVTMTEDTSTDTAYMELTSLRSEDTAVYYC

STIGVVTNFDNWGQGTLVTVSSASTKGPSVFPLAPCSRSTSESTAALG

CLVKDYFPEPVTVSWNSGALTSGVHTFPAVLQSSGLYSLSSVVTVPSS

SLGTKTYTCNVDHKPSNTKVDKRVESKYGPPCPPCPAPEFLGGPSVFL

FPPKPKDTLMISRTPEVTCVVVDVSQEDPEVQFNWYVDGVEVHNAKTK

PREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHN

HYTQKSLSLSLGK

SEQ ID NO: 10:
Amino Acid Fasinumab Light chain
DIQMTQSPSSLSASAGDRVTITCRASQAIRNDLGWYQQKPGKAPKRLI

YAAFNLQSGVPSRFSGSGSGTEFTLTISSLQPEDLASYYCQQYNRYPW

TFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SEQ ID NO: 11:
Amino Acid M6495 Heavy Chain CDRs
CDRH1 GRTVSSYAMG;

CDRH2 GISRSAERTY;

CDRH3 DLDPNRIFSREEYAY

SEQ ID NO: 12:
Amino Acide CRB0017 Heavy Chain CDRs
CDRH1-SYWMH;

CDRH2-YINPSTGYTEYNQKFK;

CDRH3-GGYDDLGY

SEQ ID NO: 13:
Amino Acid CRB0017 Light Chain CDRs
CDRL1-RSSKSLLYKDGKTYLY;

CDRL2-LMSTRAS;

CDRL3-QQLVUYPYT

SEQ ID NO: 14:
P75NTR IgG1 Fc Sequence w AA mutation
KEACPTGLYTHSGECCKACNLGEGVAQPCGANQTVCEPCLDSVTFSDV

VSATEPCKPCTECVGLQSMSAPCVEADDAVCRCAYGYYQDETTGRCEA

CRVCEAGSGLVFSCQDKQNTVCEECPDGTYSDEANHVDPCLPCTVCED

TERQLRECTRWADAECEEIPGRWITRSTPPEGSDSTAPSTQEPEAPPE

QDLIASTVAGVVTTVMGSSQPVVTRGTTDNDIEGRMDPKSCDKTHTCP

PCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQ

GNVFSCSVMHEALHNHYTQKSLSLSPGK

SEQ ID NO: 15:
TrkA IgG1 Fc Sequence w AA mutation
AAPCPDACCPHGSSGLRCTRDGALDSLHHLPGAENLTELYIENQQHLQ

HLELRDLRGLGELRNLTIVKSGLRFVAPDAFHFTPRLSRLNLSFNALE

SLSWKTVQGLSLQELVLSGNPLHCSCALRWLQRWEEEGLGGVPEQKLQ

CHGQGPLAHMPNASCGVPTLKVQVPNASVDVGDDVLLRCQVEGRGLEQ

AGWILTELEQSATVMKSGGLPSLGLTLANVTSDLNRKNVTCWAENDVG

RAEVSVQVNVSFPASVQLHTAVEMHHWCIPFSVDGQPAPSLRWLFNGS

VLNETSFIFTEFLEPAANETVRHGCLRLNQPTHVNNGNYTLLAANPFG

QASASIMAAFMDNPFEFNPEDPIPVSFSPVDTNSTGDPVEIEGRIDP

KSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKN

QVSLTCLVKGFYPSDIAVEWESNGQPENNYKTTPPVLDSDGSFFLYSK

LTVDKSRWQQGNVFSCSVMHEALHNHYTQKSLSLSPGK

SynOA Prototype Sequences
(Incl. AA and DNA Sequences)
SEQ ID NO: 16
SynOA CM1-7B4 Amino Acid Heavy Chain
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPSVFPLAPSSKSTSG

GTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPE

-continued
AAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALP

APIEKTISKAKGQPREPQVCTLPPSRDELTKNQVSLSCAVKGFYPSDI

AVEWESNGQPENNYKTTPPVLDSDGSFFLVSKLTVDKSRWQQGNVFSC

SVMHEALHNHYTQKSLSLSPGK

SEQ ID NO: 17
SynOA CM1-7B4 DNA Heavy Chain
GAAGTCCAACTTGTGGAAAGTGGTGGGGGACTTGTGCAACCTGGCGGA

TCACTCCGTCTCAGTTGTGCCGCTAGTGGTTTTACCTTTTCCGATGCT

TGGATGGATTGGGTTAGACAAGCTCCTGGGAAAGGATTGGAGTGGGTT

GCAGAAATCCGCAACAAGGCAAATAACCACGCCAGACACTACGCTGAG

AGTGTCAAGGTCGCTTTACTATAAGTAGAGATAACGCCAAAAATAGT

CTTTACTTGCAAATGAACTCCCTCCGGGCCGAGGACACTGCTGTTTAC

TACTGCGCAAGGACATACTATTACGGTAGCTCATACGGATATTGTGAT

GTTTGGGGACAAGGTACACTCGTTACCGTCAGTAGCGCTAGCACTAAG

GGGCCATCAGTATTCCCCCTGGCTCCCAGCTCCAAATCTACCTCAGGA

GGAACAGCAGCTCTGGGTTGCCTTGTAAAAGACTACTTTCCTGAACCT

GTTACTGTTAGCTGGAATAGTGGAGCTCTTACAAGCGGCGTACATACT

TTCCCTGCCGTGTTGCAGTCTAGTGGTCTTTACTCTCTTTCTTCTGTA

GTAACTGTACCTAGTAGCTCCTTGGGTACACAAACCTACATATGTAAC

GTCAATCATAAGCCTAGCAATACCAAAGTAGATAAAAAAGTTGAGCCT

AAAAGTTGTGACAAAACCCACACTTGCCCTCCCTGCCCTGCACCCGAG

GCCGCAGGGGGACCCTCAGTCTTCCTGTTTCCTCCAAAACCTAAAGAC

ACTTTGATGATATCCAGGACCCCCGAGGTAACCTGTGTGGTTGTAGAT

GTTAGCCATGAAGATCCCGAGGTAAAGTTCAACTGGTATGTTGATGGG

GTAGAGGTGCATAACGCTAAAACTAAACCTCGGGAGGAACAGTACAAT

TCAACTTACAGGGTTGTAAGCGTACTCACAGTCCTGCACCAAGACTGG

CTGAATGGCAAGGAGTATAAATGTAAAGTATCTAACAAGGCACTGCCC

GCTCCTATTGAAAAGACAATATCAAAAGCTAAGGGGCAGCCACGAGAA

CCCCAGGTGTGCACCCTCCCCCCATCCAGAGATGAACTTACCAAAAAT

CAAGTGAGCTTGTCCTGCGCTGTCAAAGGATTCTATCCTTCAGATATA

GCCGTGGAGTGGGAAAGTAACGGCCAGCCTGAAAACAATTATAAGACA

ACACCACCCGTGCTGGACAGCGATGGTAGTTTTTTTCTGGTCAGCAAG

TTGACTGTAGATAAGTCTCGATGGCAGCAGGGCAATGTTTTCAGTTGT

TCTGTAATGCACGAAGCTCTTCATAATCACTATACTCAGAAGTCTCTT

TCACTTAGCCCCGGCAAA

SEQ ID NO: 18
SynOA CM1-7B4 Amino Acid Light Chain
DIQMTQSPSSLSASVGDRVTITCRTSENIYSYLAWYQQKPGKAPKLLI

YNAKTLAEGVPSRFSGSGSGTDFTLTISSLQPEDFATYYCQHHYGTPW

TFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SEQ ID NO: 19
SynOA CM1-7B4 DNA Light Chain
GACATACAAATGACTCAATCTCCATCTTCCTTGTCTGCTTCAGTAGGA

GACCGAGTTACAATTACTTGCCGCACTTCCGAGAACATTTACTCATAT

CTGGCTTGGTATCAGCAAAAGCCAGGTAAGGCCCCAAAACTCCTTATC

TATAATGCTAAGACTCTTGCTGAGGGAGTACCCAGTAGGTTTTCCGGT

TCCGGTTCAGGCACAGATTTCACACTCACTATTTCTTCACTCCAGCCT

GAGGACTTCGCTACTTATTATTGCCAACATCACTACGGGACACCCTGG

ACTTTCGGCAAGGGACTAAACTGGAAATAAAACGTACCGTGGCTGCC

CCAAGTGTCTTCATATTTCCCCCATCTGATGAGCAACTCAAATCAGGT

ACTGCTTCTGTTGTTTGCCTTCTCAACAATTTTTATCCACGTGAGGCA

AAAGTCCAGTGGAAGGTGGACAACGCCCTGCAATCAGGTAACAGTCAG

GAGTCAGTGACAGAACAAGATAGCAAAGACAGTACTTATTCCCTTTCC

AGCACCCTGACCCTCTCTAAAGCTGACTATGAGAAACATAAGGTCTAC

GCCTGTGAAGTAACACATCAAGGTCTTTCATCTCCAGTCACCAAGTCT

TTCAACAGGGGGGAGTGT

SEQ ID NO: 20:
NGF mAb1 (Tanezumab) Amino Acid Heavy Chain:
QVQLQESGPGLVKPSETLSLTCTVSGFSLIGYDLNWIRQPPGKGLEWI

GIIWGDGTTDYNSAVKSRVTISKDTSKNQFSLKLSSVTAADTAVYYCA

RGGYWYATSYYFDYWGQGTLVTVSSASVAAPSVFIFPPSDEQLKSGTA

SVVCLLNNFYPREAKVQWKVDNALQSGNSQESVTEQDSKDSTYSLSST

LTLSKADYEKHKVYACEVTHQGLSSPVTKSFNRGECDKTHTCPPCPAP

EAAGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKAL

PAPIEKTISKAKGQPREPQVYTLPPCRDELTKNQVSLWCLVKGFYPSD

IAVEWESNGQPENNYKTTPPVLDSDGSFFLYSKLTVDKSRWQQGNVFS

CSVMHEALHNHYTQKSLSLSPGK

SEQ ID NO: 21:
Tanezumab DNA Heavy Chain
CAGGTGCAGCTCCAAGAATCAGGCCCAGGCTTGGTGAAACCCTCAGAA

ACTCTCAGCCTCACATGCACTGTGTCTGGCTTTAGCCTGATTGGTTAT

GACCTCAACTGGATTCGTCAACCCCCCGGCAAGGGTCTGGAATGGATC

GGAATCATCTGGGGAGATGGAACTACAGACTACAATAGTGCCGTAAAG

TCCCGAGTGACAATAAGTAAAGACACATCCAAGAACCAGTTTTCACTC

AAACTTTCCTCAGTCACCGCTGCTGACACAGCAGTCTATTATTGCGCA

AGAGGTGGATACTGGTATGCTACAAGCTACTACTTCGATTACTGGGA

CAGGGTACCCTTGTGACCGTATCCTCCGCATCCGTGGCAGCCCCTAGT

GTATTCATCTTCCCTCCTTCAGATGAGCAACTCAAGTCAGGAACTGCC

TCAGTCGTGTGTTTGTTGAATAACTTCTACCCACGTGAAGCAAAGTC

AATGGAAGGTCGATAATGCCTTGCAATCCGGGAACAGCCAAGAGTCA

GTGACCGAGCAGGACAGTAAAGACAGTACTTACTCTTTGTCATCTACC

CTTACCCTTTCCAAGGCTGACTACGAGAAACATAAGGTGTACGCTTGC

```
-continued
GAAGTAACTCACCAGGGACTCAGTAGCCCAGTTACCAAATCATTCAAC

AGAGGAGAATGTGATAAGACTCATACCTGCCCCCCTTGTCCTGCTCCC

GAGGCTGCTGGGGGCCCATCTGTCTTTCTGTTTCCCCCAAAGCCTAAG

GATACTCTGATGATTTCTCGAACTCCCGAGGTCACTTGCGTAGTAGTA

GACGTCAGTCACGAAGACCCAGAAGTCAAGTTCAATTGGTATGTAGAT

GGGGTAGAAGTGCATAATGCTAAGACTAAACCTCGAGAGGAGCAGTAC

AACTCAACTTACAGGGTCGTTAGCGTATTGACCGTCCTCCATCAAGAT

TGGCTCAACGGAAAAGAATACAAATGTAAAGTGTCTAATAAGGCCCTG

CCCGCACCTATCGAAAAACAATCTCTAAGGCTAAAGGGCAGCCACGT

GAACCACAAGTATATACTCTGCCACCTTGCCGCGATGAGTTGACTAAA

AACCAGGTGAGTTTGTGGTGTTTGGTAAAAGGCTTTTACCCTTCTGAC

ATAGCCGTGGAATGGGAGTCCAACGGGCAACCAGAGAACAATTACAAA

ACAACTCCTCCTGTCCTGGACAGTGACGGTTCTTTTTTTCTCTATTCA

AAGCTGACCGTGGACAAGTCAAGATGGCAACAGGGCAACGTCTTCTCT

TGTAGTGTGATGCACGAAGCCTTGCATAATCATTATACCCAGAAATCC

CTTTCACTCTCTCCTGGTAAG
SEQ ID NO: 22
SynOA CM1-Tanezumab Amino Acid Light Chain:
DIQMTQSPSSLSASVGDRVTITCRASQSISNNLNWYQQKPGKAPKLLI

YYTSRFHSGVPSRFSGSGSGTDFTFTISSLQPEDIATYYCQQEHTLPY

TFGQGTKVTVLSSASTKGPSVFPLAPSSKSTSGGTAALGCLVKDYFPE

PVTVSWNSGALTSGVHTFPAVLQSSGLYSLSSVVTVPSSSLGTQTYIC

NVNHKPSNTKVDKKVEPKSC
SEQ ID NO: 23:
SynOA CM1-Tanezumab DNA Light Chain
GACATACAGATGACACAGAGCCCCTCTTCCTTGTCTGCTTCTGTGGGT

GATCGCGTCACAATTACCTGCCGCGCTAGTCAATCCATATCAAACAAC

CTGAACTGGTATCAACAGAAGCCCGGAAAGGCCCCCAAGCTCCTCATT

TACTACACATCCAGATTCCACTCCGGTGTTCCATCTAGGTTCAGCGGC

TCAGGGTCTGGCACAGACTTCACATTCACAATCAGCTCACTTCAGCCC

GAGGACATAGCTACATACTATTGTCAGCAGGAACACACACTCCCTTAC

ACATTTGGCCAAGGAACCAAAGTAACTGTACTTTCATCCGCAAGCACT

AAGGGTCCATCAGTCTTTCCACTTGCACCTTCATCTAAATCACCTCA

GGTGGTACTGCAGCACTCGGTTGTTTGGTAAAAGATTACTTTCCTGAG

CCAGTGACTGTTAGCTGGAATAGTGGAGCCCTTACCTCCGGTGTCCAT

ACATTCCCCGCTGTGTTGCAATCATCTGGTCTCTATTCCCTTTCATCT

GTAGTTACCGTCCCTAGCTCCTCTCTGGGCACACAAACATATATTTGT

AACGTGAACCATAAACCCTCCAACACCAAAGTTGATAAGAAGGTCGAG

CCCAAATCTTGT
SEQ ID NO: 24
SynOA DVD1 Amino Acid Heavy Chain
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPQVQLQESGPGLVKP

-continued
SETLSLTCTVSGFSLIGYDLNWIRQPPGKGLEWIGIIWGDTTDYNSA

VKSRVTISKDTSKNQFSLKLSSVTAADTAVYYCARGGYWYATSYYFDY

WGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNV

NHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREP

QVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLS

LSPGK
SEQ ID NO: 25:
SynOA DVD1 DNA Heavy Chain
GAAGTACAATTGGTGGAAAGCGGCGGAGGCCTTGTCCAACCTGGCGGT

TCTTTGCGGCTGTCCTGTGCCGCTAGTGGTTTTACCTTTAGTGATGCC

TGGATGGACTGGGTGCGGCAGGCCCCTGGTAAGGGCCTGGAATGGGTC

GCTGAAATAAGAAATAAGGCAAATAACCATGCAAGACATTACGCTGAA

AGTGTGAAGGGCAGGTTCACTATATCCCGAGATAACGCAAAGAACAGT

TTGTACCTTCAGATGAACTCCTTGCGTGCCGAGGATACCGCCGTCTAC

TACTGCGCTCGCACATACTACTACGGTTCATCATACGGGTACTGCGAC

GTCTGGGGGCAAGGAACACTTGTCACCGTTTCTTCTGCCTCTACTAAG

GGACCCCAGGTTCAGTTGCAGGAGTCCGGGCCCGGTCTGGTAAAGCCT

TCTGAAACCCTGAGTTTGACCTGTACCGTGTCCGGTTTCTCACTGATT

GGCTATGATCTCAACTGGATACGACAGCCCCCCGGGAAGGGCCTGGAG

TGGATTGGCATCATCTGGGGAGATGGAACCACCGACTACAACTCCGCT

GTCAAAAGTAGAGTGACTATTTCCAAAGACACCAGCAAGAACCAATTC

TCACTGAAATTGAGTTCAGTTACAGCTGCCGACACTGCTGTTTACTAT

TGTGCAAGAGGGGATATTGGTATGCCACTTCCTATTATTTTGACTAT

TGGGGCCAGGGAACACTTGTAACAGTATCCTCAGCCTCAACAAAAGGA

CCATCTGTATTTCCCCTTGCACCCAGTTCAAAGTCTACTTCAGGTGGG

ACTGCCGCTCTCGGCTGTCTGGTAAAAGATTATTCCCCGAGCCAGTT

ACTGTAAGTTGGAATAGCGGTGCACTGACAAGTGGGGTCCATACTTTC

CCTGCCGTGCTTCAGAGTTCCGGCCTTTATTCACTCTCTAGTGTAGTT

ACCGTTCCCTCATCTAGCCTTGGAACCCAAACCTATATCTGTAATGTG

AATCATAAACCATCTAATACTAAGGTTGATAAAAAGGTTGAACCTAAG

AGCTGCGATAAAACACATACCTGTCCTCCTTGTCCTGCTCCTGAAGCT

GCTGGTGGACCTTCAGTGTTTCTGTTCCCCCCAAGCCAAAAGATACA

CTGATGATCTCTCGTACTCCTGAGGTTACTTGTGTCGTCGTCGATGTG

TCACACGAAGATCCCGAAGTGAAGTTCAACTGGTACGTCGATGGTGTT

GAAGTACACAATGCCAAAACAAAACCCAGAGAGGAGCAATACAATAGT

ACATACCGCGTAGTGTCTGTTCTCACCGTATTGCATCAGGACTGGCTG

AACGGTAAAGAGTACAAATGTAAAGTTTCTAATAAAGCACTCCCAGCC
```

```
CCTATAGAAAAGACCATCAGCAAAGCTAAAGGGCAGCCCCGTGAGCCA

CAAGTCTACACATTGCCTCCTAGTAGGGATGAGCTGACAAAAAATCAA

GTGTCCCTGACCTGCCTCGTGAAAGGATTTTATCCTTCTGATATAGCA

GTTGAATGGGAATCCAACGGTCAACCTGAGAATAATTATAAGACCACT

CCCCCAGTGCTGGATTCTGATGGCAGTTTCTTCTTGTATTCTAAATTG

ACTGTCGACAAATCCCGTTGGCAACAGGGAAATGTGTTTTCATGCTCT

GTTATGCACGAGGCTTTGCACAATCACTACACTCAGAAGTCCCTGAGC

TTGTCTCCAGGAAAA

SEQ ID NO: 26:
SynOA DVD1 Amino Acid Light Chain
DIQMTQSPSSLSASVGDRVTITCRTSENIYSYLAWYQQKPGKAPKLLI

YNAKTLAEGVPSRFSGSGSGTDFTLTISSLQPEDFATYYCQHHYGTPW

TFGQGTKLEIKRTVAAPDIQMTQSPSSLSASVGDRVTITCRASQSISN

NLNWYQQKPGKAPKLLIYYTSRFHSGVPSRFSGSGSGTDFTFTISSLQ

PEDIATYYCQQEHTLPYTFGQGTKLEIKRTVAAPSVFIFPPSDEQLKS

GTASVVCLLNNFYPREAKVQWKVDNALQSGNSQESVTEQDSKDSTYSL

SSTLTLSKADYEKHKVYACEVTHQGLSSPVTKSFNRGEC

SEQ ID NO: 27:
SynOA DVD1 DNA Light Chain
GACATACAGATGACACAGTCTCCTAGCTCCCTGTCCGCAAGCGTTGGA

GATAGAGTCACAATAACTTGTAGAACATCAGAAAACATATATAGCTAC

TTGGCTTGGTACCAACAGAAGCCTGGTAAGGCACCCAAGCTCCTCATA

TACAACGCCAAGACCCTTGCCGAGGGTGTGCCAAGCAGATTCAGCGGG

TCAGGGAGCGGGACCGATTTTACACTTACTATTTCCTCTTTGCAGCCC

GAAGACTTTGCTACTTACTACTGTCAGCACCACTACGGCACTCCTTGG

ACTTTCGGACAAGGTACTAAACTTGAAATAAAGAGGACCGTAGCCGCC

CCCGATATACAGATGACTCAAAGTCCTAGTTCCCTTTCCGCTAGCGTA

GGAGACCGCGTAACAATTACCTGTAGAGCATCACAAAGTATAAGCAAC

AATCTGAACTGGTACCAGCAGAAACCTGGGAAGGCCCCTAAGTTGCTG

ATCTATTACACCTCCAGGTTTCATAGTGGCGTACCATCTCGTTTCAGT

GGATCAGGTTCTGGCACCGATTTCACTTTTACCATATCCTCACTCCAG

CCCGAAGATATCGCTACCTACTATTGTCAACAGGAACACACCCTTCCT

TATACATTTGGCAGGGGACCAAGCTTGAGATCAAACGGACTGTGGCA

GCACCTAGTGTCTTCATATTCCCCCCTTCCGACGAGCAACTGAAAAGT

GGTACTGCTTCAGTAGTTTGCTTGTTAACAACTTCTATCCACGCGAA

GCAAAAGTGCAATGGAAGGTCGATAACGCACTTCAATCTGGTAACTCT

CAAGAAAGTGTCACAGAGCAGGACAGTAAGGATAGTACATATAGCCTT

AGTTCAACACTGACTCTTTCTAAGGCCGATTATGAGAAACACAAGGTA

TACGCTTGTGAAGTGACCCACCAGGGACTTTCTAGCCCAGTTACCAAA

TCCTTCAACAGAGGAGAGTGC

SEQ ID NO: 28:
SynOA DVD2 Amino Acid Heavy Chain
QVQLQESGPGLVKPSETLSLTCTVSGFSLIGYDLNWIRQPPGKGLEWI

GIIWGDGTTDYNSAVKSRVTISKDTSKNQFSLKLSSVTAADTAVYYCA

RGGYWYATSYYFDYWGQGTLVTVSSASTKGPEVQLVESGGGLVQPGGS

LRLSCAASGFTFSDAWMDWVRQAPGKGLEWVAEIRNKANNHARHYAES

VKGRFTISRDNAKNSLYLQMNSLRAEDTAVYYCARTYYYGSSYGYCDV

WGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNV

NHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREP

QVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLS

LSPGK

SEQ ID NO: 29
SynOA DVD2 DNA Heavy Chain
CAGGTACAGCTCCAGGAATCCGGGCCCGGTCTTGTGAAACCTTCAGAA

ACACTGTCTTTGACTTGTACAGTGAGTGGATTTTCTCTCATCGGGTAC

GATCTCAACTGGATCCGGCAACCTCCTGGGAAAGGTCTCGAATGGATA

GGGATCATCTGGGGCGATGGCACTACCGATTATAATTCAGCCGTGAAG

TCTCGAGTAACAATCTCCAAGGATACCAGTAAGAACCAGTTTAGTCTG

AAACTCAGCTCTGTTACAGCCGCCGACACAGCTGTCTACTATTGCGCC

AGGGGAGGGTATTGGTATGCTACCAGTTATTATTTCGACTATTGGGGA

CAGGGAACTTTGGTAACCGTCAGTAGTGCATCTACTAAAGGCCCCGAG

GTCCAGCTTGTTGAGTCTGGGGGTGGTCTCGTCCAACCTGGGGGTTCC

TTGCGGCTGTCATGTGCAGCTTCCGGCTTCACTTTTAGTGATGCTTGG

ATGGATTGGGTCCGGCAGGCCCCAGGTAAGGGTTTGGAATGGGTGGCC

GAAATAAGAAATAAGGCCAACAATCATGCTCGCCACTACGCAGAGTCC

GTAAAAGGACGATTTACAATCAGCCGTGACAACGCAAAAAATAGCTTG

TATCTTCAAATGAACAGTTTGAGGGCTGAGGATACAGCAGTGTATTAC

TGTGCTCGAACTTACTACTACGGGAGTAGTTATGGTTACTGTGATGTA

TGGGGTCAGGGAACTCTGGTAACCGTCTCAAGCGCTTCAACTAAAGGT

CCTTCAGTATTCCCCTTGGCTCCAAGCTCCAAGAGTACCAGTGGCGGT

ACCGCAGCTTTGGGCTGCCTGGTAAAAGATTATTTCCCAGAACCAGTA

ACTGTAAGCTGGAATAGCGGGCTTTGACATCAGGGGTACACACCTTT

CCAGCTGTGCTTCAGTCTTCAGGCTTGTACAGTTTGTCTTCCGTAGTC

ACAGTCCCATCTTCTAGTCTGGGGACCCAAACCTATATCTGTAATGTC

AATCATAAGCCCTCAAATACAAAAGTGGACAAAAAAGTAGAGCCTAAG

AGCTGTGATAAAACACATACATGCCCTCCTTGTCCTGCCCCCGAAGCC

GCCGGCGGTCCCTCAGTATTTCTTTTTCCACCAAAACCCAAAGATACC

CTCATGATCAGTCGCACCCCAGAAGTCACCTGTGTCGTGGTAGATGTA

AGCCACGAGGATCCCGAGGTCAAATTCAACTGGTATGTGGATGGCGTA

GAAGTTCACAACGCCAAGACAAAGCCCAGGGAAGAACAGTACAATTCA

ACCTACAGGGTTGTCTCTGTACTGACCGTCCTTCACCAAGACTGGTTG
```

-continued
AACGGTAAAGAGTATAAATGTAAGGTATCCAACAAAGCTTTGCCAGCA

CCTATAGAGAAAACCATCTCCAAAGCTAAGGGTCAACCCAGAGAGCCA

CAAGTGTATACCCTGCCTCCCAGTAGAGATGAACTGACAAAGAACCAA

GTTTCTCTGACTTGCTTGGTCAAAGGGTTCTATCCTAGCGACATCGCT

GTAGAATGGGAATCAAATGGACAACCTGAAAATAACTACAAGACTACC

CCACCCGTGCTTGACAGTGATGGCAGTTTTTTCCTTTACAGTAAGCTC

ACTGTCGACAAGAGCCGATGGCAGCAAGGCAACGTCTTCTCTTGTTCC

GTTATGCATGAGGCCCTCCACAACCATTATACCCAAAAGAGTTTGTCA

TTGTCCCCTGGTAAA

SEQ ID NO: 30:
SynOA DVD2 Amino Acid Light Chain
DIQMTQSPSSLSASVGDRVTITCRASQSISNNLNWYQQKPGKAPKLLI

YYTSRFHSGVPSRFSGSGSGTDFTFTISSLQPEDIATYYCQQEHTLPY

TFGQGTKLEIKRTVAAPDIQMTQSPSSLSASVGDRVTITCRTSENIYS

YLAWYQQKPGKAPKLLIYNAKTLAEGVPSRFSGSGSGTDFTLTISSLQ

PEDFATYYCQHHYGTPWTFGQGTKLEIKRTVAAPSVFIFPPSDEQLKS

GTASVVCLLNNFYPREAKVQWKVDNALQSGNSQESVTEQDSKDSTYSL

SSTLTLSKADYEKHKVYACEVTHQGLSSPVTKSFNRGEC

SEQ ID NO: 31:
SynOA DVD2 DNA Light Chain
GACATCCAGATGACACAGTCACCATCCTCTCTTAGTGCAAGTGTGGGC

GATCGGGTTACAATAACTTGTAGAGCCTCTCAATCAATTTCAAACAAT

CTGAATTGGTATCAACAGAAGCCTGGCAAGGCACCAAAACTTTTGATC

TACTACACTTCACGTTTCCATTCTGGTGTACCATCTCGCTTCTCCGGA

AGTGGAAGTGGCACAGATTTCACATTTACCATTAGTTCCTTGCAGCCC

GAAGATATAGCCACTTACTATTGTCAGCAGGAACATACCCTGCCATAC

ACTTTCGGCCAGGGCACAAAACTCGAGATCAAGCGTACTGTGGCAGCC

CCTGATATTCAGATGACCCAGTCCCCAAGTTCACTCTCAGCTTCTGTC

GGCGACCGTGTAACAATAACCTGCCGTACCTCTGAAAACATATACTCA

TACTTGGCCTGGTATCAACAAAAACCAGGTAAAGCTCCTAAGTTGCTC

ATCTATAATGCTAAGACTTTGGCTGAAGGAGTGCCCTCTCGATTCTCT

GGGTCAGGATCCGGAACAGATTTCACACTGACTATATCCAGCTTGCAA

CCAGAAGACTTCGCCACTTATTACTGCCAACATCACTATGGGACACCC

TGGACATTTGGGCAAGGAACCAAACTGGAGATAAAGCGGACTGTGGCC

GCACCTTCCGTTTTCATCTTTCCACCCTCTGACGAACAACTCAAATCA

GGGACTGCTTCAGTCGTGTGTCTCCTCAATAATTTTTATCCTCGGGAG

GCTAAAGTCCAATGGAAAGTAGACAATGCCCTCCAATCCGGGAATAGT

CAGGAAAGCGTCACAGAGCAAGATTCAAAAGACAGTACCTACTCATTG

TCTAGTACCCTTACCCTTAGTAAAGCAGACTACGAGAAACATAAGGTT

TATGCCTGCGAGGTGACTCACCAGGGGTTTGTCTAGCCCAGTGACTAAA

TCCTTCAATCGCGGGGAGTGT

SEQ ID NO: 32:
SynOA BF1-Amino Acid Heavy Chain
7B4 with C-Term Tanezumab scFv
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPSVFPLAPSSKSTSG

GTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPE

AAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALP

APIEKTISKAKGQPREPQVYTLPPSRDELTKNQVSLTCLVKGFYPSDI

AVEWESNGQPENNYKTTPPVLDSDGSFFLYSKLTVDKSRWQQGNVFSC

SVMHEALHNHYTQKSLSLSPGKGGGGSGGGGSGGGGSQVQLQESGPGL

VKPSETLSLTCTVSGFSLIGYDLNWIRQPPGKGLEWIGIIWGDTTDY

NSAVKSRVTISKDTSKNQFSLKLSSVTAADTAVYYCARGGYWYATSYY

FDYWGQGTLVTVSSGGGGSGGGGSGGGGSDIQMTQSPSSLSASVGDRV

TITCRASQSISNNLNWYQQKPGKAPKLLIYYTSRFHSGVPSRFSGSGS

GTDFTFTISSLQPEDIATYYCQQEHTLPYTFGQGTKLEIK

SEQ ID NO: 33:
SynOA BF1-DNA Heavy Chain
7B4 with C-Term Tanezumab scFv
GAGGTGCAGCTGGTGGAAAGCGGCGGGGGCTGGTGCAGCCCGGAGGC

TCACTGAGACTGTCTTGCGCTGCCAGCGGCTTCACCTTCAGCGACGCC

TGGATGGACTGGGTGAGGCAGGCCCCTGGGAAGGGGCTGGAGTGGGTG

GCTGAGATCCGGAATAAGGCCAATAACCACGCCAGGCACTATGCCGAG

AGTGTGAAAGGCAGATTTACCATCTCTAGGGACAATGCCAAGAACTCA

CTGTACCTGCAGATGAACTCCCTGAGAGCCGAGGACACCGCCGTGTAC

TACTGTGCCAGAACCTATTACTACGGAAGCAGCTACGGCTATTGCGAT

GTGTGGGGACAGGGAACCCTGGTGACTGTGTCTTCCTGAGCCTCCACC

AAGGGCCCCTCCGTGTTCCCACTGGCCCCGAGTAGCAAGTCTACCTCC

GGCGGGACAGCCGCACTGGGCTGCCTGGTGAAGGACTACTTTCCCGAG

CCTGTGACAGTGAGCTGGAATTCCGGGGCCCTGACATCAGGCGTGCAC

ACCTTCCCAGCCGTGCTCCAGAGCTCTGGCCTGTATAGTCTGAGCAGT

GTGGTGACCGTGCCCTCCAGCTCCCTGGGAACTCAGACCTATATCTGT

AACGTGAACCACAAGCCTTCTAATACCAAGGTGGATAAGAAAGTGGAA

CCAAAGTCATGCGACAAAACACACACCTGCCCCCCCTGCCCCGCCCCT

GAAGCCGCCGGCGGGCCTAGCGTGTTTCTGTTCCCTCCTAAGCCTAAG

GACACACTGATGATTTCCAGGACCCCCGAGGTGACCTGCGTCGTCGTG

GACGTGAGCCACGAGGACCCCGAGGTGAAATTCAACTGGTACGTGGAC

GGCGTGGAAGTGCACAACGCTAAAACCAAGCCTAGAGAGGAACAGTAC

AACTCTACATACAGGGTGGTGTCCGTCTTGACTGTGCTGCACCAGGAC

TGGCTGAACGGCAAGGAATATAAGTGCAAGGTGAGCAATAAAGCACTC

CCCGCCCCCATTGAAAAAACCATCAGCAAGGCTAAGGGCCAGCCTAGG

```
GAACCACAGGTGTATACCCTGCCACCTAGCAGAGACGAGCTGACCAAG
AATCAGGTGTCTCTGACATGTCTGGTGAAGGGGTTTTACCCTAGCGAC
ATTGCCGTCGAGTGGGAGTCTAATGGCCAGCCTGAGAACAATTATAAG
ACTACCCCTCCTGTGCTGGACAGTGATGGCTCATTTTTTCTGTACTCT
AAGCTGACAGTGGACAAGAGCAGGTGGCAGCAGGGCAATGTGTTCAGC
TGCAGCGTGATGCACGAGGCCCTGCATAATCATTATACCCAGAAGTCT
CTGTCTCTCAGCCCAGGCAAAGGCGGAGGGGGGTCTGGCGGCGGGGGT
TCCGGCGGCGGGGGCTCCCAGGTGCAGCTGCAGGAGAGCGGACCTGGC
CTGGTGAAACCCAGCGAGACCCTGTCCCTGACATGCACCGTGAGCGGC
TTCTCCCTGATCGGGTATGACCTGAATTGGATCCGGCAGCCTCCTGGC
AAGGGTCTGGAGTGGATCGGAATCATCTGGGGCGACGGCACCACCGAT
TATAACAGCGCCGTGAAGTCTCGGGTGACTATCTCTAAGGATACTTCC
AAGAACCAGTTTTCCCTGAAGCTGAGCTCTGTGACCGCTGCCGATACC
GCCGTGTACTACTGCGCCAGGGGCGGTTACTGGTACGCCACCAGCTAC
TACTTCGACTACTGGGGCCAGGGCACCCTGGTGACCGTGTCCAGCGGC
GGCGGCGGCTCTGGCGGTGGGGGCTCCGGCGGCGGAGGGTCTGACATT
CAGATGACCCAGAGCCCCTCCTCCCTGTCTGCCTCCGTGGGCGACAGA
GTGACCATCACATGTAGAGCCTCCCAGTCAATATCTAACAACCTGAAT
TGGTATCAGCAGAAGCCCGGCAAAGCCCCTAAGCTGCTGATTTACTAC
ACTTCTCGCTTTCACTCCGGAGTGCCCAGCAGATTTAGTGGGAGCGGC
TCTGGGACAGACTTCACTTTTACCATCAGTAGCCTGCAGCCCGAGGAC
ATCGCCACCTATTACTGCCAGCAGGAGCATACCCTGCCCTACACTTTC
GGACAGGGGACCAAGCTGGAGATCAAGTGA

Additional Constructs
SEQ ID NO: 34:
SynOA DVD3 Amino Acid Heavy Chain
EVQLVESGGGLVQPGGSLRLSCAASGFTFSDAWMDWVRQAPGKGLEWV
AEIRHKANDHAIFYDESVKGRFTISRDDSKNTVYLQMNSLRAEDTAVY
YCTSPFAYWGQGTLVTVSSASTKGPQVQLQESGPGLVKPSETLSLTCT
VSGFSLIGYDLNWIRQPPGKGLEWIGIIWGDGTTDYNSAVKSRVTISK
DTSKNQFSLKLSSVTAADTAVYYCARGGYWYATSYYFDYWGQGTLVTV
SSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKV
DKKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSR
DELTKNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 35:
SynOA DVD3 Amino Acid Light Chain
DIQMTQSPSSLSASVGDRVTITCKASQSVGTTIVWYQQKPGKAPKLLI
YSASNRHTGVPSRFSGSGSGTDFTLTISSLQPEDFATYYCQQYTSYPF
TFGQGTKLEIKRTVAAPDIQMTQSPSSLSASVGDRVTITCRASQSISN
NLNWYQQKPGKAPKLLIYYTSRFHSGVPSRFSGSGSGTDFTFTISSLQ
PEDIATYYCQQEHTLPYTFGQGTKLEIKRTVAAPSVFIFPPSDEQLKS
GTASVVCLLNNFYPREAKVQWKVDNALQSGNSQESVTEQDSKDSTYSL
SSTLTLSKADYEKHKVYACEVTHQGLSSPVTKSFNRGEC SEQ ID NO: 36:
SynOA DVD4 Amino Acid Heavy Chain
QVQLQESGPGLVKPSETLSLTCTVSGFSLIGYDLNWIRQPPGKGLEWI
GIIWGDGTTDYNSAVKSRVTISKDTSKNQFSLKLSSVTAADTAVYYCA
RGGYWYATSYYFDYWGQGTLVTVSSASTKGPEVQLVESGGGLVQPGGS
LRLSCAASGFTFSDAWMDWVRQAPGKGLEWVAEIRHKANDHAIFYDES
VKGRFTISRDDSKNTVYLQMNSLRAEDTAVYYCTSPFAYWGQGTLVTV
SSASTKGPASTKGPSVFPLAPSSKSTSGGTAALGCLVKDYFPEPVTVS
WNSGALTSGVHTFPAVLQSSGLYSLSSVVTVPSSSLGTQTYICNVNHK
PSNTKVDKKVEPKSCDKTHTCPPCPAPEAAGGPSVFLFPPKPKDTLMI
SRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVY
TLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSP
GK SEQ ID NO: 37:
SynOA DVD4 Amino Acid Light Chain
DIQMTQSPSSLSASVGDRVTITCRASQSISNNLNWYQQKPGKAPKLLI
YYTSRFHSGVPSRFSGSGSGTDFTFTISSLQPEDIATYYCQQEHTLPY
TFGQGTKLEIKRTVAAPDIQMTQSPSSLSASVGDRVTITCKASQSVGT
TIVWYQQKPGKAPKLLIYSASNRHTGVPSRFSGSGSGTDFTLTISSLQ
PEDFATYYCQQYTSYPFTFGQGTKLEIKRTVAAPSVFIFPPSDEQLKS
GTASVVCLLNNFYPREAKVQWKVDNALQSGNSQESVTEQDSKDSTYSL
SSTLTLSKADYEKHKVYACEVTHQGLSSPVTKSFNRGEC SEQ ID NO: 38:
SynOA CM2-Amino Acid 12F4 Heavy Chain
(with AA and KIH mutations):
EVQLLESGGGLVQPGGSLRLSCAASGFTFSDAWMDWVRQAPGKGLEWV
AEIRHKANDHAIFYDESVKGRFTISRDSKNTVYLQMNSLRAEDTAVYY
CTSPFAYWGQGTLVTVSSASTKGPSVFPLAPSSKSTSGGTAALGCLVK
DYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKA
KGQPREPQVCTLPPSRDELTKNQVSLSCAVKGFYPSDIAVEWESNGQP
ENNYKTTPPVLDSDGSFFLVSKLTVDKSRWQQGNVFSCSVMHEALHNH
YTQKSLSLSPGK SEQ ID NO: 39:
SynOA CM2-Amino Acid 12F4 Light Chain
DIQMTQSPSSLSASVGDRVTITCKASQSVGTTIVWTQQLPGKAPKLLI
YSASNRHTGVPSRFSGSGSGTDFTLTISSLQPEDFATYYCQQYTSYPF
```

SEQ ID NO: 40
SynOA BF4-Amino Acid 12F4 Heavy Chain
AA mutant + Tanezumab scFv
EVQLLESGGGLVQPGGSLRLSCAASGFTFSDAWMDWVRQAPGKGLEWV
AEIRHKANDHAIFYDESVKGRFTISRDSKNTVYLQMNSLRAEDTAVYY
CTSPFAYWGQGTLVTVSSASTKGPSVFPLAPSSKSTSGGTAALGCLVK
DYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKA
KGQPREPQVYTLPPSRDELTKNQVSLSCLVKGFYPSDIAVEWESNGQP
ENNYKTTPPVLDSDGSFFLYSKLTVDKSRWQQGNVFSCSVMHEALHNH
YTQKSLSLSPGKGGGGSGGGGSGGGGSQVQLQESGPGLVKPSETLSLT
CTVSGFSLIGYDLNWIRQPPGKGLEWIGIIWGDGTTDYNSAVKSRVTI
SKDTSKNQFSLKLSSVTAADTAVYYCARGGYWYATSYYFDWGQGTLV
TVSSGGGGSGGGGSGGGGSDIQMTQSPSSLSASVGDRVTITCRASQSI
SNNLNWYQQKPGKAPKLLIYYTSRFHSGVPSRFSGSGSGTDFTFTISS
LQPEDIATYYCQQEHTLPYTFGQGTKLEIK SEQ ID NO: 41
SynOA DVD9 Amino Acid 7B4 +
Tanezumab Heavy Chain
EVQLVESGGGLVQPGGSLRLSCAASGFTFSDAWMDWVRQAPGKGLEWV
AEIRNKANNHARHYAESVKGRFTISRDNAKNSLYLQMNSLRAEDTAVY
YCARTYYYGSSYGYCDVWGQGTLVTVSSASTKGPSVFPLAPQVQLQES
GPGLVKPSETLSLTCTVSGFSLIGYDLNWIRQPPGKGLEWIGIIWGDG
TTDYNSAVKSRVTISKDTSKNQFSLKLSSVTAADTAVYYCARGGYWYA
TSYYFDWGQGTLVTVSSASTKGPSVFPLAPSSKSTSGGTAALGCLVK
DYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKA
KGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNH
YTQKSLSLSPGK SEQ ID NO: 42
SynOA DVD9 Amino Acid 7B4 +
Tanezumab Light Chain
DIQMTQSPSSLSASVGDRVTITCRTSENIYSYLAWYQQKPGKAPKLLI
YNAKTLAEGVPSRFSGSGSGTDFTLTISSLQPEDFATYYCQHHYGTPW
TFGQGTKLEIKRTVAAPSVFIFPPDIQMTQSPSSLSASVGDRVTITCR
ASQSISNNLNWYQQKPGKAPKLLIYYTSRFHSGVPSRFSGSGSGTDFT
FTISSLQPEDIATYYCQQEHTLPYTFGQGTKLEIKRTVAAPSVFIFPP
SDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 43:
SynOA DVD10-Amino Acid Tanezumab +
7B4 Heavy Chain
QVQLQESGPGLVKPSETLSLTCTVSGFSLIGYDLNWIRQPPGKGLEWI
GIIWGDGTTDYNSAVKSRVTISKDTSKNQFSLKLSSVTAADTAVYYCA
RGGYWYATSYYFDYWGQGTLVTVSSASTKGPSVFPLAPEVQLVESGGG
LVQPGGSLRLSCAASGFTFSDAWMDWVRQAPGKGLEWVAEIRNKANNH
ARHYAESVKGRFTISRDNAKNSLYLQMNSLRAEDTAVYYCARTYYYGS
SYGYCDVWGQGTLVTVSSASTKGPSVFPLAPSSKSTSGGTAALGCLVK
DYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKA
KGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNH
YTQKSLSLSPGK SEQ ID NO: 44:
SynOA DVD10-Amino Acid Tanezumab +
7B4 Light Chain
DIQMTQSPSSLSASVGDRVTITCRASQSISNNLNWYQQKPGKAPKLLI
YYTSRFHSGVPSRFSGSGSGTDFTFTISSLQPEDIATYYCQQEHTLPY
TFGQGTKLEIKRTVAAPSVFIFPPDIQMTQSPSSLSASVGDRVTITCR
TSENIYSYLAWYQQKPGKAPKLLIYNAKTLAEGVPSRFSGSGSGTDFT
LTISSLQPEDFATYYCQHHYGTPWTFGQGTKLEIKRTVAAPSVFIFPP
SDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 45:
SynOA DVD11 Amino Acid 12F4 +
Tanezumab Heavy Chain
EVQLVESGGGLVQPGGSLRLSCAASGFTFSDAWMDWVRQAPGKGLEWV
AEIRHKANDHAIFYDESVKGRFTISRDDSKNTVYLQMNSLRAEDTAVY
YCTSPFAYWGQGTLVTVSSASTKGPSVFPLAPQVQLQESGPGLVKPSE
TLSLTCTVSGFSLIGYDLNWIRQPPGKGLEWIGIIWGDGTTDYNSAVK
SRVTISKDTSKNQFSLKLSSVTAADTAVYYCARGGYWYATSYYFDYWG
QGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNH
KPSNTKVDKKVEPKSCDKTHTCPPCPAPEAAGGPSVFLFPPKPKDTLM
ISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQV
YTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLS
PGK SEQ ID NO: 46:
SynOA DVD11 Amino Acid 12F4 +
Tanezumab Light Chain
DIQMTQSPSSLSASVGDRVTITCKASQSVGTTIVWYQQKPGKAPKLLIY

SASNRHTGVPSRFSGSGSGTDFTLTISSLQPEDFATYYCQQYTSYPFT

FGQGTKLEIKRTVAAPSVFIFPPDIQMTQSPSSLSASVGDRVTITCRA

SQSISNNLNWYQQKPGKAPKLLIYYTSRFHSGVPSRFSGSGSGTDFTF

TISSLQPEDIATYYCQQEHTLPYTFGQGTKLEIKRTVAAPSVFIFPPS

DEQLKSGTASVVCLLNNFYPREAKVQWKVDNALQSGNSQESVTEQDSK

DSTYSLSSTLTLSKADYEKHKVYACEVTHQGLSSPVTKSFNRGEC

SEQ ID NO: 47:
SynOA DVD12 Amino Acid Tanezumab +
12F4 Heavy Chain
QVQLQESGPGLVKPSETLSLTCTVSGFSLIGYDLNWIRQPPGKGLEWI

GIIWGDGTTDYNSAVKSRVTISKDTSKNQFSLKLSSVTAADTAVYYCA

RGGYWYATSYYFDYWGQGTLVTVSSASTKGPSVFPLAPEVQLVESGGG

LVQPGGSLRLSCAASGFTFSDAWMDWVRQAPGKGLEWVAEIRHKANDH

AIFYDESVKGRFTISRDDSKNTVYLQMNSLRAEDTAVYYCTSPFAYWG

QGTLVTVSSASTKGPASTKGPSVFPLAPSSKSTSGGTAALGCLVKDYF

PEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPK

PKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQ

KSLSLSPGK

SEQ ID NO: 48
SynOA DVD12 Amino Acid Tanezumab +
12F4 Light Chain
DIQMTQSPSSLSASVGDRVTITCRASQSISNNLNWYQQKPGKAPKLLI

YYTSRFHSGVPSRFSGSGSGTDFTFTISSLQPEDIATYYCQQEHTLPY

TFGQGTKLEIKRTVAAPSVFIFPPDIQMTQSPSSLSASVGDRVTITCK

ASQSVGTTIVWYQQKPGKAPKLLIYSASNRHTGVPSRFSGSGSGTDFT

LTISSLQPEDFATYYCQQYTSYPFTFGQGTKLEIKRTVAAPSVFIFPP

SDEQLKSGTASVVCLLNNFYPREAKVQWKVDNALQSGNSQESVTEQDS

KDSTYSLSSTLTLSKADYEKHKVYACEVTHQGLSSPVTKSFNRGEC

SEQ ID NO: 49:
ADAMTS 5 (CRB0017) HC with AA and
KIH mutations
EVQLLESGGGLVQPGGSLRLSCAASGFTFSSYWMHWVRQAPGKGLEWV

AYINPSTGYTEYNQKFKRFTISRDSKNTVYLQMNSLRAEDTAVYYCTS

GGYDDLGYWGQGTLVTVSSASTKGPSVFPLAPSSKSTSGGTAALGCLV

KDYFPEPVTVSWNSGALTSGVHTFPAVLQSSGLYSLSSVVTVPSSSLG

TQTYICNVNHKPSNTKVDKKVEPKSCDKTHTCPPCPAPEAAGGPSVFL

FPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISK

AKGQPREPQVCTLPPSRDELTKNQVSLSCAVKGFYPSDIAVEWESNGQ

PENNYKTTPPVLDSDGSFFLVSKLTVDKSRWQQGNVFSCSVMHEALHN

HYTQKSLSLSPGK

SEQ ID NO: 50:
SynOA CM8-Amino Acid p75NTR Fc Heavy Chain
w AA and KIH mutations
KEACPTGLYTHSGECCKACNLGEGVAQPCGANQTVCEPCLDSVTFSDV

VSATEPCKPCTECVGLQSMSAPCVEADDAVCRCAYGYYQDETTGRCEA

CRVCEAGSGLVFSCQDKQNTVCEECPDGTYSDEANHVDPCLPCTVCED

TERQLRECTRWADAECEEIPGRWITRSTPPEGSDSTAPSTQEPEAPPE

QDLIASTVAGVVTTVMGSSQPVVTRGTTDNDIEGRMDPKSCDKTHTCP

PCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKV

SNKALPAPIEKTISKAKGQPREPQVYTLPPCRDELTKNQVSLWCLVKG

FYPSDIAVEWESNGQPENNYKTTPPVLDSDGSFFLYSKLTVDKSRWQQ

GNVFSCSVMHEALHNHYTQKSLSLSPGK

SEQ ID NO: 51:
SynOA CM9-Amino Acid TrkA Fc Heavy Chain
w AA and KIH mutations
AAPCPDACCPHGSSGLRCTRDGALDSLHHLPGAENLTELYIENQQHLQ

HLELRDLRGLGELRNLTIVKSGLRFVAPDAFHFTPRLSRLNLSFNALE

SLSWKTVQGLSLQELVLSGNPLHCSCALRWLQRWEEEGLGGVPEQKLQ

CHGQGPLAHMPNASCGVPTLKVQVPNASVDVGDDVLLRCQVEGRGLEQ

AGWILTELEQSATVMKSGGLPSLGLTLANVTSDLNRKNVTCWAENDVG

RAEVSVQVNVSFPASVQLHTAVEMHHWCIPFSVDGQPAPSLRWLFNGS

VLNETSFIFTEFLEPAANETVRHGCLRLNQPTHVNNGNYTLLAANPFG

QASASIMAAFMDNPFEFNPEDPIPVSFSPVDTNSTSGDPVEIEGRIDP

KSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDW

LNGKEYKCKVSNKALPAPIEKTISKAKGQPREPQVYTLPPCRDELTKN

QVSLWCLVKGFYPSDIAVEWESNGQPENNYKTTPPVLDSDGSFFLYSK

LTVDKSRWQQGNVFSCSVMHEALHNHYTQKSLSLSPGK

SEQ ID NO: 52:
SynOA DM1-Amino Acid 7B4 Heavy Chain
with AA and Duobody (F405L) mutation
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPSVFPLAPSSKSTSG

GTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPE

AAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALP

APIEKTISKAKGQPREPQVYTLPPSRDELTKNQVSLCLVKGFYPSDI

AVEWESNGQPENNYKTTPPVLDSDGSFLLYSKLTVDKSRWQQGNVFSC

SVMHEALHNHYTQKSLSLSPGK

SEQ ID NO: 53:
SynOA DM1-Amino Acid Tanezumab Heavy Chain
w AA and Duobody (K409R) Mutant
QVQLQESGPGLVKPSE

TLSLTCTVSGFSLIGYDLNWIRQPPGKGLEWIGIIWGDGTTDYNSAVK

SRVTISKDTSKNQFSLKLSSVTAADTAVYYCARGGYWYATSYYFDYWG

QGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNH

KPSNTKVDKKVEPKSCDKTHTCPPCPAPEAAGGPSVFLFPPKPKDTLM

ISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQV

YTLPPSRDELTKNQVSLTCLVKGFYPSDIAVEWESNGQPENNYKTTPP

VLDSDGSFFLYSRLTVDKSRWQQGNVFSCSVMHEALHNHYTQKSLSLS

PGK

SEQ ID NO: 54:
SynOA DM1-Amino Acid Tanezumab Light Chain
w AA and Duobody (K409R) Mutant
DIQMTQSPSSLSASVGDRVTITCRASQSISNNLNWYQQKPGKAPKLLI

YYTSRFHSGVPSRFSGSGSGTDFTFTISSLQPEDIATYYCQQEHTLPY

TFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SEQ ID NO: 55:
SynOA DM3-Amino Acid 12F4 Heavy Chain
with AA and Duobody (F405L) Mutants
EVQLLESGGGLVQPGGSLRLSCAASGFTFSDAWMDWVRQAPGKGLEWV

AEIRHKANDHAIFYDESVKGRFTISRDSKNTVYLQMNSLRAEDTAVYY

CTSPFAYWGQGTLVTVSSASTKGPSVFPLAPSSKSTSGGTAALGCLVK

DYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLF

PPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKA

KGQPREPQVYTLPPSRDELTKNQVSLSCLVKGFYPSDIAVEWESNGQP

ENNYKTTPPVLDSDGSFLLYSKLTVDKSRWQQGNVFSCSVMHEALHNH

YTQKSLSLSPGK

SEQ ID NO: 56:
SynOA CM5-Amino Acid NGF (Fasinumab) Heavy Chain
w AA and KIH mutations
QVQLVQSGAEVKKPGASVKVSCKVSGFTLTELSIHWVRQAPGKGLEWM

GGFDPEDGETIYAQKFQGRVTMTEDTSTDTAYMELTSLRSEDTAVYYC

STIGVVTNFDNWGQGTLVTVSSASVAAPSVFIFPPSDEQLKSGTASVV

CLLNNFYPREAKVQWKVDNALQSGNSQESVTEQDSKDSTYSLSSTLTL

SKADYEKHKVYACEVTHQGLSSPVTKSFNRGECDKTHTCPPCPAPEAA

GGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAP

IEKTISKAKGQPREPQVYTLPPCRDELTKNQVSLWCLVKGFYPSDIAV

EWESNGQPENNYKTTPPVLDSDGSFFLYSKLTVDKSRWQQGNVFSCSV

MHEALHNHYTQKSLSLSPGK

SEQ ID NO: 57:
SynOA CM5-Amino Acid NGF (Fasinumab) Light Chain
DIQMTQSPSSLSASAGDRVTITCRASQAIRNDLGWYQQKPGKAPKRLI

YAAFNLQSGVPSRFSGSGSGTEFTLTISSLQPEDLASYYCQQYNRYPW

TFGQGTKVTVLSSASTKGPSVFPLAPSSKSTSGGTAALGCLVKDYFPE

PVTVSWNSGALTSGVHTFPAVLQSSGLYSLSSVVTVPSSSLGTQTYIC

NVNHKPSNTKVDKKVEPKSC

SEQ ID NO: 58:
SynOA DVD17-Amino Acid 7B4 +
Fasinumab DVD Heavy Chain w SS and AA mutant
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPQVQLVQSGAEVKKP

GASVKVSCKVSGFTLTELSIHWVRQAPGKGLEWMGGFDPEDGETIYAQ

KFQGRVTMTEDTSTDTAYMELTSLRSEDTAVYYCSTIGVVTNFDNWGQ

GTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHK

PSNTKVDKKVEPKSCDKTHTCPPCPAPEAAGGPSVFLFPPKPKDTLMI

SRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVY

TLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSP

GK

SEQ ID NO: 59:
SynOA DVD17-Amino Acid 7B4 +
Fasinumab DVD Light Chain w SS and AA mutant
DIQMTQSPSSLSASVGDRVTITCRTSENIYSYLAWYQQKPGKAPKLLI

YNAKTLAEGVPSRFSGSGSGTDFTLTISSLQPEDFATYYCHHYGTPW

TFGQGTKLEIKRTVAAPDIQMTQSPSSLSASAGDRVTITCRASQAIRN

DLGWYQQKPGKAPKRLIYAAFNLQSGVPSRFSGSGSGTEFTLTISSLQ

PEDLASYYCQQYNRYPWTFGQGTKLEIKRTVAAPSVFIFPPSDEQLKS

GTASVVCLLNNFYPREAKVQWKVDNALQSGNSQESVTEQDSKDSTYSL

SSTLTLSKADYEKHKVYACEVTHQGLSSPVTKSFNRGEC

SEQ ID NO: 60:
SynOA DVD18-Amino Acid 12F4 +
Fasinumab DVD Heavy Chain w SS and AA mutant
EVQLLESGGGLVQPGGSLRLSCAASGFTFSDAWMDWVRQAPGKGLEWV

AEIRHKANDHAIFYDESVKGRFTISRDSKNTVYLQMNSLRAEDTAVYY

CTSPFAYWGQGTLVTVSSASTKGPQVQLVQSGAEVKKPGASVKVSCKV

SGFTLTELSIHWVRQAPGKGLEWMGGFDPEDGETIYAQKFQGRVTMTE

DTSTDTAYMELTSLRSEDTAVYYCSTIGVVTNFDNWGQGTLVTVSSAS

TKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKV

EPKSCDKTHTCPPCPAPEAAGGPSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELT

KNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 61:
SynOA DVD18-Amino Acid 12F4 +
Fasinumab DVD Light Chain w SS and AA mutant
DIQMTQSPSSLSASVGDRVTITCKASQSVGTTIVWTQQLPGLAPKLLI

YSASNRHTGVPSRFSGSGSGTDFTLTISSLQPEDFATYYCQQYTSYPF

TFGQGTKEIKRTVAAPDIQMTQSPSSLSASAGDRVTITCRASQAIRND

LGWYQQKPGKAPKRLIYAAFNLQSGVPSRFSGSGSGTEFTLTISSLQP

EDLASYYCQQYNRYPWTFGQGTKLEIKRTVAAPSVFIFPPSDEQLKSG

TASVVCLLNNFYPREAKVQWKVDNALQSGNSQESVTEQDSKDSTYSLS

STLTLSKADYEKHKVYACEVTHQGLSSPVTKSFNRGEC

SEQ ID NO: 62:
SynOA DVD19-Amino Acid Fasinumab +
7B4 DVD Heavy Chain w SS and AA mutant
QVQLVQSGAEVKKPGASVKVSCKVSGFTLTELSIHWVRQAPGKGLEWM

GGFDPEDGETIYAQKFQGRVTMTEDTSTDTAYMELTSLRSEDTAVYYC

STIGVVTNFDNWGQGTLVTVSSASTKGPEVQLVESGGGLVQPGGSLRL

SCAASGFTFSDAWMDWVRQAPGKGLEWVAEIRNKANNHARHYAESVKG

RFTISRDNAKNSLYLQMNSLRAEDTAVYYCARTYYYGSSYGYCDVWGQ

GTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHK

PSNTKVDKKVEPKSCDKTHTCPPCPAPEAAGGPSVFLFPPKPKDTLMI

SRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVY

TLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSP

GK

SEQ ID NO: 63:
SynOA DVD19-Amino Acid Fasinumab +
7B4 DVD Light Chain w SS and AA mutant
DIQMTQSPSSLSASAGDRVTITCRASQAIRNDLGWYQQKPGKAPKRLI

YAAFNLQSGVPSRFSGSGSGTEFTLTISSLQPEDLASYYCQQYNRYPW

TFGQGTKLEIKRTVAAPDIQMTQSPSSLSASVGDRVTITCRTSENIYS

YLAWYQQKPGKAPKLLIYNAKTLAEGVPSRFSGSGSGTDFTLTISSLQ

PEDFATYYCQHHYGTPWTFGQGTKLEIKRTVAAPSVFIFPPSDEQLKS

GTASVVCLLNNFYPREAKVQWKVDNALQSGNSQESVTEQDSKDSTYSL

SSTLTLSKADYEKHKVYACEVTHQGLSSPVTKSFNRGEC

SEQ ID NO: 64:
SynOA DVD20-Amino Acid Fasinumab +
12F4 DVD Heavy Chain w SS and AA mutant
QVQLVQSGAEVKKPGASVKVSCKVSGFTLTELSIHWVRQAPGKGLEW

MGGFDPEDGETIYAQKFQGRVT

MTEDTSTDTAYMELTSLRSEDTAVYYCSTIGVVTNFDNWGQGTLVTVS

SASTKGPEVQLLESGGGLVQPGGSLRLSCAASGFTFSDAWMDWVRQAP

GKGLEWVAEIRHKANDHAIFYDESVKGRFTISRDSKNTVYLQMNSLRA

EDTAVYYCTSPFAYWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVM

HEALHNHYTQKSLSLSPGK

SEQ ID NO: 65:
SynOA DVD20-Amino Acid Fasinumab +
12F4 DVD Light Chain w SS and AA mutant
DIQMTQSPSSLSASAGDRVTITCRASQAIRNDLGWYQQKPGKAPKRLI

YAAFNLQSGVPSRFSGSGSGTEFTLTISSLQPEDLASYYCQQYNRYPW

TFGQGTKLEIKRTVAAPDIQMTQSPSSLSASVGDRVTITCKASQSVGT

TIVWTQQLPGLAPKLLIYSASNRHTGVPSRFSGSGSGTDFTLTISSLQ

PEDFATYYCQQYTSYPFTFGQGTKEIKRTVAAPSVFIFPPSDEQLKSG

TASVVCLLNNFYPREAKVQWKVDNALQSGNSQESVTEQDSKDSTYSLS

STLTLSKADYEKHKVYACEVTHQGLSSPVTKSFNRGEC

SEQ ID NO: 66:
SynOA DVD21-Amino Acid 7B4 +
Fasinumab DVD Heavy Chain
w LL and AA mutant
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPSVFPLAPQVQLVQS

GAEVKKPGASVKVSCKVSGFTLTELSIHWVRQAPGKGLEWMGGFDPED

GETIYAQKFQGRVTMTEDTSTDTAYMELTSLRSEDTAVYYCSTIGVVT

NFDNWGQGTLVTVSSASTKGPSVFPLAPSSKSTSGGTAALGCLVKDYF

PEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPK

PKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQ

KSLSLSPGK

SEQ ID NO: 67:
SynOA DVD21-Amino Acid 7B4 +
Fasinumab DVD Light Chain w LL and AA mutant
DIQMTQSPSSLSASVGDRVTITCRTSENIYSYLAWYQQKPGKAPKLLI

YNAKTLAEGVPSRFSGSGSGTDFTLTISSLQPEDFATYYCQHHYGTPW

TFGQGTKLEIKRTVAAPSVFIFPPDIQMTQSPSSLSASAGDRVTITCR

ASQAIRNDLGWYQQKPGKAPKRLIYAAFNLQSGVPSRFSGSGSGTEFT

-continued
LTISSLQPEDLASYYCQQYNRYPWTFGQGTKLEIKRTVAAPSVFIFPP
SDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 68:
SynOA DVD22-Amino Acid 12F4 +
Fasinumab DVD Heavy Chain w LL and AA mutant
EVQLLESGGGLVQPGGSLRLSCAASGFTFSDAWMDWVRQAPGKGLEWV
AEIRHKANDHAIFYDESVKGRFTISRDSKNTVYLQMNSLRAEDTAVYY
CTSPFAYWGQGTLVTVSSASTKGPSVFPLAPQVQLVQSGAEVKKPGAS
VKVSCKVSGFTLTELSIHWVRQAPGKGLEWMGGFDPEDGETIYAQKFQ
GRVTMTEDTSTDTAYMELTSLRSEDTAVYYCSTIGVVTNFDNWGQGTL
VTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSN
TKVDKKVEPKSCDKTHTCPPCPAPEAAGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 69:
SynOA DVD22-Amino Acid 12F4 +
Fasinumab DVD Light Chain w LL and AA mutant
DIQMTQSPSSLSASVGDRVTITCKASQSVGTTIVWTQQLPGLAPKLLI
YSASNRHTGVPSRFSGSGSGTDFTLTISSLQPEDFATYYCQQYTSYPF
TFGQGTKEIKRTVAAPSVFIFPPDIQMTQSPSSLSASAGDRVTITCRA
SQAIRNDLGWYQQKPGKAPKRLIYAAFNLQSGVPSRFSGSGSGTEFTL
TISSLQPEDLASYYCQQYNRYPWTFGQGTKLEIKRTVAAPSVFIFPPS
DEQLKSGTASVVCLLNNFYPREAKVQWKVDNALQSGNSQESVTEQDSK
DSTYSLSSTLTLSKADYEKHKVYACEVTHQGLSSPVTKSFNRGEC SEQ ID NO: 70:
SynOA DVD23-Amino Acid Fasinumab +
7B4 DVD Heavy Chain w LL and AA mutant
QVQLVQSGAEVKKPGASVKVSCKVSGFTLTELSIHWVRQAPGKGLEWM
GGFDPEDGETIYAQKFQGRVTMTEDTSTDTAYMELTSLRSEDTAVYYC
STIGVVTNFDNWGQGTLVTVSSASTKGPSVFPLAPEVQLVESGGGLVQ
PGGSLRLSCAASGFTFSDAWMDWVRQAPGKGLEWVAEIRNKANNHARH
YAESVKGRFTISRDNAKNSLYLQMNSLRAEDTAVYYCARTYYYGSSYG
YCDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTY
ICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQ
KSLSLSPGK SEQ ID NO: 71:
SynOA DVD23-Amino Acid Fasinumab +
7B4 DVD Light Chain w LL and AA mutant
DIQMTQSPSSLSASAGDRVTITCRASQAIRNDLGWYQQKPGKAPKRLI
YAAFNLQSGVPSRFSGSGSGTEFTLTISSLQPEDLASYYCQQYNRYPW
TFGQGTKLEIKRTVAAPSVFIFPPDIQMTQSPSSLSASVGDRVTITCR
TSENIYSYLAWYQQKPGKAPKLLIYNAKTLAEGVPSRFSGSGSGTDFT
LTISSLQPEDFATYYCQHHYGTPWTFGQGTKLEIKRTVAAPSVFIFPP
SDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 72:
SynOA DVD24-Amino Acid Fasinumab +
12F4 DVD Heavy Chain w LL and AA mutant
QVQLVQSGAEVKKPGASVKVSCKVSGFTLTELSIHWVRQAPGKGLEWM
GGFDPEDGETIYAQKFQGRVTMTEDTSTDTAYMELTSLRSEDTAVYYC
STIGVVTNFDNWGQGTLVTVSSASTKGPSVFPLAPEVQLLESGGGLVQ
PGGSLRLSCAASGFTFSDAWMDWVRQAPGKGLEWVAEIRHKANDHAIF
YDESVKGRFTISRDSKNTVYLQMNSLRAEDTAVYYCTSPFAYWGQGTL
VTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSN
TKVDKKVEPKSCDKTHTCPPCPAPEAAGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 73:
SynOA DVD24-Amino Acid Fasinumab +
12F4 DVD Light Chain w LL and AA mutant
DIQMTQSPSSLSASAGDRVTITCRASQAIRNDLGWYQQKPGKAPKRLI
YAAFNLQSGVPSRFSGSGSGTEFTLTISSLQPEDLASYYCQQYNRYPW
TFGQGTKLEIKRTVAAPSVFIFPPDIQMTQSPSSLSASVGDRVTITCK
ASQSVGTTIVWTQQLPGLAPKLLIYSASNRHTGVPSRFSGSGSGTDFT
LTISSLQPEDFATYYCQQYTSYPFTFGQGTKEIKRTVAAPSVFIFPPS
DEQLKSGTASVVCLLNNFYPREAKVQWKVDNALQSGNSQESVTEQDSK
DSTYSLSSTLTLSKADYEKHKVYACEVTHQGLSSPVTKSFNRGEC SEQ ID NO: 74:
SynOA DVD25-Amino Acid CRB0017 +
Tanezumab DVD Heavy Chain w LL and AA mutant
EVQLVESGGGLVQPGGSLRLSCAASGFTFSSYWMHWVRQAPGKGLEWV
AYINPSTGYTEYNQKFKRFTISRDDSKNTVYLQMNSLRAEDTAVYYCT
SGGYDDLGYWGQGTLVTVSSASTKGPQVQLQESGPGLVKPSETLSLTC
TVSGFSLIGYDLNWIRQPPGKGLEWIGIIWGDGTTDYNSAVKSRVTIS
KDTSKNQFSLKLSSVTAADTAVYYCARGGYWYATSYYFDYWGQGTLVT
VSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTK
VDKKVEPKSCDKTHTCPPCPAPEAAGGPSVFLEPPKPKDTLMISRTPE -continued
VTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPS

RDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

SEQ ID NO: 75:
SynOA DVD25-Amino Acid CRB0017 +
Tanezumab DVD Light Chain w LL and AA mutant
DIQMTQSPSSLSASVGDRVTITCRSSKSLLYKDGKTYLYWYQQKPGKA

PKLLIYLMSTRASGVPSRFSGSGSGTDFTLTISSLQPEDFATYYCQQL

VUYPYTFGQGTKLEIKRTVAAPDIQMTQSPSSLSASVGDRVTITCRAS

QSISNNLNWYQQKPGKAPKLLIYYTSRFHSGVPSRFSGSGSGTDFTFT

ISSLQPEDIATYYCQQEHTLPYTFGQGTKLEIKRTVAAPSVFIFPPSD

EQLKSGTASVVCLLNNFYPREAKVQWKVDNALQSGNSQESVTEQDSKD

STYSLSSTLTLSKADYEKHKVYACEVTHQGLSSPVTKSFNRGEC

SEQ ID NO: 76:
SynOA DVD26-Amino Acid CRB0017 +
Tanezumab DVD Heavy Chain w LL and AA mutant
EVQLVESGGGLVQPGGSLRLSCAASGFTFSSYWMHWVRQAPGKGLEWV

AYINPSTGYTEYNQKFKRFTISRDDSKNTVYLQMNSLRAEDTAVYYCT

SGGYDDLGYWGQGTLVTVSSASTKGPQVLVQSGAEVKKPGASVKVSC

KVSGFTLTELSIHWVRQAPGKGLEWMGGFDPEDGETIYAQKFQGRVTM

TEDTSTDTAYMELTSLRSEDTAVYYCSTIGVVTNFDNWGQGTLVTVSS

ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPEAAGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQ ID NO: 77:
SynOA DVD26-Amino Acid CRB0017 +
Tanezumab DVD Light Chain w LL and AA mutant
DIQMTQSPSSLSASVGDRVTITCRSSKSLLYKDGKTYLYWYQQKPGKA

PKLLIYLMSTRASGVPSRFSGSGSGTDFTLTISSLQPEDFATYYCQQL

VUYPYTFGQGTKLEIKRTVAAPDIQMTQSPSSLSASVGDRVTITCKAS

QSVGTTIVWTQQLPGLAPKLLIYSASNRHTGVPSRFSGSGSGTDFTLT

ISSLQPEDFATYYCQQYTSYPFTFGQGTKEIKRTVAAPSVFIFPPSDE

QLKSGTASVVCLLNNFYPREAKVQWKVDNALQSGNSQESVTEQDSKDS

TYSLSSTLTLSKADYEKHKVYACEVTHQGLSSPVTKSFNRGEC

SEQ ID NO: 78:
SynOA DVD27-Amino Acid CRB0017 +
Fulranumab DVD Heavy Chain w LL and AA mutant
EVQLVESGGGLVQPGGSLRLSCAASGFTFSSYWMHWVRQAPGKGLEWV

AYINPSTGYTEYNQKFKRFTISRDDSKNTVYLQMNSLRAEDTAVYYCT

SGGYDDLGYWGQGTLVTVSSASTKGPEVQLVESGGGLVQPGGSLRLSC

AASGFTLRSYSMNWVRQAPGKGLEWVSYISRSSHTIFYADSVKGRFTI

SRDNAKNSLYLQMDSLRDEDTAMYYCARVYSSGWHVSDYFDYWGQGIL

VTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSN

TKVDKKVEPKSCDKTHTCPPCPAPEAAGGPSVFLFPPKPKDTLMISRT

PEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLP

PSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

SEQ ID NO: 79:
SynOA DVD27-Amino Acid CRB0017 +
Fulranumab DVD Light Chain w LL and AA mutant
DIQMTQSPSSLSASVGDRVTITCRSSKSLLYKDGKTYLYWYQQKPGKA

PKLLIYLMSTRASGVPSRFSGSGSGTDFTLTISSLQPEDFATYYCQQL

VUYPYTFGQGTKLEIKRTVAAPAIQLTQSPSSLSASVGDRVTITCRAS

QGISSALAWYQQKPGKAPKLLIYDASSLESGVPSRFSGSGSGTDFTLT

ISSLQPEDFATYYCQQFNSYPLTFGGGTKLEIKRTVAAPSVFIFPPSD

EQLKSGTASVVCLLNNFYPREAKVQWKVDNALQSGNSQESVTEQDSKD

STYSLSSTLTLSKADYEKHKVYACEVTHQGLSSPVTKSFNRGEC

SEQ ID NO: 80:
SynOA DVD28-Amino Acid Tanezumab +
CRB0017 DVD Heavy Chain w LL and AA mutant
QVQLVQSGAEVKKPGASVKVSCKVSGFTLTELSIHWVRQAPGKGLEWM

GGFDPEDGETIYAQKFQGRVTMTEDTSTDTAYMELTSLRSEDTAVYYC

STIGVVTNFDNWGQGTLVTVSSASTKGPEVQLVESGGGLVQPGGSLRL

SCAASGFTFSSYWMHWVRQAPGKGLEWVAYINPSTGYTEYNQKFKRFT

ISRDDSKNTVYLQMNSLRAEDTAVYYCTSGGYDDLGYWGQGTLVTVSS

ASTKGPASTKGPSVFPLAPSSKSTSGGTAALGCLVKDYFPEPVTVSWN

SGALTSGVHTFPAVLQSSGLYSLSSVVTVPSSSLGTQTYICNVNHKPS

NTKVDKKVEPKSCDKTHTCPPCPAPEAAGGPSVFLFPPKPKDTLMISR

TPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTL

PPSRDELTKNQVSLTCLVKGFYPSDIAVEWESNGQPENNYKTTPPVLD

SDGSFFLYSKLTVDKSRWQQGNVFSCSVMHEALHNHYTQKSLSL

SEQ ID NO: 81:
SynOA DVD28-Amino Acid Tanezumab +
CRB0017 DVD Light Chain w LL and AA mutant
DIQMTQSPSSLSASVGDRVTITCKASQSVGTTIVWTQQLPGLAPKLLI

YSASNRHTGVPSRFSGSGSGTDFTLTISSLQPEDFATYYCQQYTSYPF

TFGQGTKEIKRTVAAPDIQMTQSPSSLSASVGDRVTITCRSSKSLLYK

DGKTYLYWYQQKPGKAPKLLIYLMSTRASGVPSRFSGSGSGTDFTLTI

SSLQPEDFATYYCQQLVUYPYTFGQGTKLEIKRTVAAPSVFIFPPSDE

QLKSGTASVVCLLNNFYPREAKVQWKVDNALQSGNSQESVTEQDSKDS

TYSLSSTLTLSKADYEKHKVYACEVTHQGLSSPVTKSFNRGEC

SEQ ID NO: 82:
SynOA DVD29-Amino Acid Fasinumab +
CRB0017 DVD Heavy Chain w LL and AA mutant
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASTKGPEVQLVESGGGLVQPG

GSLRLSCAASGFTFSSYWMHWVRQAPGKGLEWVAYINPSTGYTEYNQK

FKRFTISRDDSKNTVYLQMNSLRAEDTAVYYCTSGGYDDLGYWGQGTL

VTVSSASTKGPASTKGPSVFPLAPSSKSTSGGTAALGCLVKDYFPEPV

TVSWNSGALTSGVHTFPAVLQSSGLYSLSSVVTVPSSSLGTQTYICNV

NHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREP

QVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLS

L

SEQ ID NO: 83:
SynOA DVD29-Amino Acid Fasinumab +
CRB0017 DVD Light Chain w LL and AA mutant
AIQLTQSPSSLSASVGDRVTITCRASQGISSALAWYQQKPGKAPKLLI

YDASSLESGVPSRFSGSGSGTDFTLTISSLQPEDFATYYCQQFNSYPL

TFGGGTKLEIKRTVAAPDIQMTQSPSSLSASVGDRVTITCRSSKSLLY

KDGKTYLYWYQQKPGKAPKLLIYLMSTRASGVPSRFSGSGSGTDFTLT

ISSLQPEDFATYYCQQLVUYPYTFGQGTKLEIKRTVAAPSVFIFPPSD

EQLKSGTASVVCLLNNFYPREAKVQWKVDNALQSGNSQESVTEQDSKD

STYSLSSTLTLSKADYEKHKVYACEVTHQGLSSPVTKSFNRGEC

SEQ ID NO: 84:
SynOA DVD30-Amino Acid Fulranumab +
CRB0017 DVD Heavy Chain w LL and AA mutant
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASTKGPEVQLVESGGGLVQPG

GSLRLSCAASGFTFSSYWMHWVRQAPGKGLEWVAYINPSTGYTEYNQK

FKRFTISRDDSKNTVYLQMNSLRAEDTAVYYCTSGGYDDLGYWGQGTL

VTVSSASTKGPASTKGPSVFPLAPSSKSTSGGTAALGCLVKDYFPEPV

TVSWNSGALTSGVHTFPAVLQSSGLYSLSSVVTVPSSSLGTQTYICNV

NHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREP

QVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLS

L

SEQ ID NO: 85:
SynOA DVD30-Amino Acid Fulranumab +
CRB0017 DVD Light Chain w LL and AA mutant
AIQLTQSPSSLSASVGDRVTITCRASQGISSALAWYQQKPGKAPKLLI

YDASSLESGVPSRFSGSGSGTDFTLTISSLQPEDFATYYCQQFNSYPL

TFGGGTKLEIKRTVAAPDIQMTQSPSSLSASVGDRVTITCRSSKSLLY

KDGKTYLYWYQQKPGKAPKLLIYLMSTRASGVPSRFSGSGSGTDFTLT

ISSLQPEDFATYYCQQLVUYPYTFGQGTKLEIKRTVAAPSVFIFPPSD

EQLKSGTASVVCLLNNFYPREAKVQWKVDNALQSGNSQESVTEQDSKD

STYSLSSTLTLSKADYEKHKVYACEVTHQGLSSPVTKSFNRGEC

SEQ ID NO: 86:
SynOA DVD31-Amino Acid CRB0017 +
Tanezumab DVD Heavy Chain
w LL and AA mutant
EVQLVESGGGLVQPGGSLRLSCAASGFTFSSYWMHWVRQAPGKGLEWV

AYINPSTGYTEYNQKFKRFTISRDDSKNTVYLQMNSLRAEDTAVYYCT

SGGYDDLGYWGQGTLVTVSSASTKGPSVFPLAPQVQLQESGPGLVKPS

ETLSLTCTVSGFSLIGYDLNWIRQPPGKGLEWIGIIWGDTTDYNSAV

KSRVTISKDTSKNQFSLKLSSVTAADTAVYYCARGGYWYATSYYFDYW

GQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVN

HKPSNTKVDKKVEPKSCDKTHTCPPCPAPEAAGGPSVFLFPPKPKDTL

MISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSL

SPGK

SEQ ID NO: 87:
SynOA DVD31-Amino Acid CRB0017 +
Tanezumab DVD Light Chain w LL and AA mutant
DIQMTQSPSSLSASVGDRVTITCRSSKSLLYKDGKTYLYWYQQKPGKA

PKLLIYLMSTRASGVPSRFSGSGSGTDFTLTISSLQPEDFATYYCQQL

VUYPYTFGQGTKLEIKRTVAAPSVFIFPPDIQMTQSPSSLSASVGDRV

TITCRASQSISNNLNWYQQKPGKAPKLLIYYTSRFHSGVPSRFSGSGS

GTDFTFTISSLQPEDIATYYCQQEHTLPYTFGQGTKLEIKRTVAAPSV

FIFPPSDEQLKSGTASVVCLLNNFYPREAKVQWKVDNALQSGNSQESV

TEQDSKDSTYSLSSTLTLSKADYEKHKVYACEVTHQGLSSPVTKSFNR

GEC

SEQ ID NO: 88:
SynOA DVD32-Amino Acid CRB0017 +
Fasinumab DVD Heavy Chain w LL and AA mutant
EVQLVESGGGLVQPGGSLRLSCAASGFTFSSYWMHWVRQAPGKGLEWV

AYINPSTGYTEYNQKFKRFTISRDDSKNTVYLQMNSLRAEDTAVYYCT

SGGYDDLGYWGQGTLVTVSSASTKGPSVFPLAPQVQLVQSGAEVKKPG

ASVKVSCKVSGFTLTELSIHWVRQAPGKGLEWMGGFDPEDGETIYAQK

FQGRVTMTEDTSTDTAYMELTSLRSEDTAVYYCSTIGVVTNFDNWGQG

TLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMIS

RTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYT

LPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

K

SEQ ID NO: 89:
SynOA DVD32-Amino Acid CRB0017 +
Fasinumab DVD Light Chain w LL and AA mutant
DIQMTQSPSSLSASVGDRVTITCRSSKSLLYKDGKTYLYWYQQKPGKA

PKLLIYLMSTRASGVPSRFSGSGSGTDFTLTISSLQPEDFATYYCQQL

VUYPYTFGQGTKLEIKRTVAAPSVFIFPPPDIQMTQSPSSLSASVGDRV

TITCKASQSVGTTIVWTQQLPGLAPKLLIYSASNRHTGVPSRFSGSGS

GTDFTLTISSLQPEDFATYYCQQYTSYPFTFGQGTKEIKRTVAAPSVF

IFPPSDEQLKSGTASVVCLLNNFYPREAKVQWKVDNALQSGNSQESVT

EQDSKDSTYSLSSTLTLSKADYEKHKVYACEVTHQGLSSPVTKSFNRG

EC

SEQ ID NO: 90:
SynOA DVD33-Amino Acid CRB0017 +
Fulranumab DVD Heavy Chain w LL and AA mutant
EVQLVESGGGLVQPGGSLRLSCAASGFTFSSYWMHWVRQAPGKGLEWV

AYINPSTGYTEYNQKFKRFTISRDDSKNTVYLQMNSLRAEDTAVYYCT

SGGYDDLGYWGQGTLVTVSSASTKGPSVFPLAPEVQLVESGGGLVQPG

GSLRLSCAASGFTLRSYSMNWVRQAPGKGLEWVSYISRSSHTIFYADS

VKGRFTISRDNAKNSLYLQMDSLRDEDTAMYYCARVYSSGWHVSDYFD

YWGQGILVTVSSASTKGPSVFPLAPSSKSTSGGTAALGCLVKDYFPEP

VTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKD

TLMISRTPEVTCVVVDVSHEDPEVKFNWYVDGVEVHNAKTKPREEQYN

STYRVVSVLTVLHQDWLNGKEYKCKVSNKALPAPIEKTISKAKGQPRE

PQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSL

SLSPGK

SEQ ID NO: 91:
SynOA DVD33-Amino Acid CRB0017 +
Fulranumab DVD Light Chain w LL and AA mutant
DIQMTQSPSSLSASVGDRVTITCRSSKSLLYKDGKTYLYWYQQKPGKA

PKLLIYLMSTRASGVPSRFSGSGSGTDFTLTISSLQPEDFATYYCQQL

VUYPYTFGQGTKLEIKRTVAAPSVFIFPPAIQLTQSPSSLSASVGDRV

TITCRASQGISSALAWYQQKPGKAPKLLIYDASSLESGVPSRFSGSGS

GTDFTLTISSLQPEDFATYYCQQFNSYPLTFGGGTKLEIKRTVAAPSV

FIFPPSDEQLKSGTASVVCLLNNFYPREAKVQWKVDNALQSGNSQESV

TEQDSKDSTYSLSSTLTLSKADYEKHKVYACEVTHQGLSSPVTKSFNR

GEC

SEQ ID NO: 92:
SynOA DVD34-Amino Acid Tanezumab +
CRB0017 DVD Heavy Chain w LL and AA mutant
QVQLQESGPGLVKPSETLSLTCTVSGFSLIGYDLNWIRQPPGKGLEWI

GIIWGDGTTDYNSAVKSRVTISKDTSKNQFSLKLSSVTAADTAVYYCA

RGGYWYATSYYFDYWGQGTLVTVSSASTKGPSVFPLAPEVQLVESGGG

LVQPGGSLRLSCAASGFTFSSYWMHWVRQAPGKGLEWVAYINPSTGYT

EYNQKFKRFTISRDDSKNTVYLQMNSLRAEDTAVYYCTSGGYDDLGYW

GQGTLVTVSSASTKGPASTKGPSVFPLAPSSKSTSGGTAALGCLVKDY

FPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPP

KPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKG

QPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYT

QKSLSLSPGK

SEQ ID NO: 93:
SynOA DVD34-Amino Acid Tanezumab +
CRB0017 DVD Light Chain w LL and AA mutant
DIQMTQSPSSLSASVGDRVTITCRASQSISNNLNWYQQKPGKAPKLLI

YYTSRFHSGVPSRFSGSGSGTDFTFTISSLQPEDIATYYCQQEHTLPY

TFGQGTKLEIKRTVAAPSVFIFPPDIQMTQSPSSLSASVGDRVTITCR

SSKSLLYKDGKTYLYWYQQKPGKAPKLLIYLMSTRASGVPSRFSGSGS

GTDFTLTISSLQPEDFATYYCQQLVUYPYTFGQGTKLEIKRTVAAPSV

FIFPPSDEQLKSGTASVVCLLNNFYPREAKVQWKVDNALQSGNSQESV

TEQDSKDSTYSLSSTLTLSKADYEKHKVYACEVTHQGLSSPVTKSFNR

GEC

SEQ ID NO: 94:
SynOA DVD35-Amino Acid Fasinumab +
CRB0017 DVD Heavy Chain w LL and AA mutant
QVQLVQSGAEVKKPGASVKVSCKVSGFTLTELSIHWVRQAPGKGLEWM

GGFDPEDGETIYAQKFQGRVTMTEDTSTDTAYMELTSLRSEDTAVYYC

STIGVVTNFDNWGQGTLVTVSSASTKGPSVFPLAPEVQLVESGGGLVQ

PGGSLRLSCAASGFTFSSYWMHWVRQAPGKGLEWVAYINPSTGYTEYN

QKFKRFTISRDDSKNTVYLQMNSLRAEDTAVYYCTSGGYDDLGYWGQG

TLVTVSSASTKGPASTKGPSVFPLAPSSKSTSGGTAALGCLVKDYFPE

PVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKS

LSL

SEQ ID NO: 95:
SynOA DVD35-Amino Acid Fasinumab +
CRB0017 DVD Light Chain w LL and AA mutant
DIQMTQSPSSLSASVGDRVTITCKASQSVGTTIVWTQQLPGLAPKLLI

YSASNRHTGVPSRFSGSGSGTDFTLTISSLQPEDFATYYCQQYTSYPF

TFGQGTKEIKRTVAAPSVFIFPPDIQMTQSPSSLSASVGDRVTITCRS

SKSLLYKDGKTYLYWYQQKPGKAPKLLIYLMSTRASGVPSRFSGSGSG

TDFTLTISSLQPEDFATYYCQQLVUYPYTFGQGTKLEIKRTVAAPSVF

IFPPSDEQLKSGTASVVCLLNNFYPREAKVQWKVDNALQSGNSQESVT

EQDSKDSTYSLSSTLTLSKADYEKHKVYACEVTHQGLSSPVTKSFNRG

EC

SEQ ID NO: 96:
SynOA DVD36-Amino Acid Fulranumab +
CRB0017 DVD Heavy Chain w LL and AA mutant
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASTKGPSVFPLAPEVQLVESG

GGLVQPGGSLRLSCAASGFTFSSYWMHWVRQAPGKGLEWVAYINPSTG

YTEYNQKFKRFTISRDDSKNTVYLQMNSLRAEDTAVYYCTSGGYDDLG

YWGQGTLVTVSSASTKGPASTKGPSVFPLAPSSKSTSGGTAALGCLVK

DYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLF

PPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKA

KGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNH

YTQKSLSL

SEQ ID NO: 97:
SynOA DVD36-Amino Acid Fulranumab +
CRB0017 DVD Light Chain w LL and AA mutant
AIQLTQSPSSLSASVGDRVTITCRASQGISSALAWYQQKPGKAPKLLI

YDASSLESGVPSRFSGSGSGTDFTLTISSLQPEDFATYYCQQFNSYPL

TFGGGTKLEIKRTVAAPSVFIFPPDIQMTQSPSSLSASVGDRVTITCR

SSKSLLYKDGKTYLYWYQQKPGKAPKLLIYLMSTRASGVPSRFSGSGS

GTDFTLTISSLQPEDFATYYCQQLVUYPYTFGQGTKLEIKRTVAAPSV

FIFPPSDEQLKSGTASVVCLLNNFYPREAKVQWKVDNALQSGNSQESV

TEQDSKDSTYSLSSTLTLSKADYEKHKVYACEVTHQGLSSPVTKSFNR

GEC

SEQ ID NO: 98:
SynOA DM9-Amino Acid Fasinumab Heavy Chain
with AA and Duobody (K409R) Mutants
QVQLVQSGAEVKKPGASVKVSCKVSGFTLTELSIHWVRQAPGKGLEWM

GGFDPEDGETIYAQKFQGRVTMTEDTSTDTAYMELTSLRSEDTAVYYC

STIGVVTNFDNWGQGTLVTVSSASTKGPSVFPLAPSSKSTSGGTAALG

CLVKDYFPEPVTVSWNSGALTSGVHTFPAVLQSSGLYSLSSVVTVPSS

SLGTQTYICNVNHKPSNTKVDKKVEPKSCDKTHTCPPCPAPEAAGGPS

VFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWES

NGQPENNYKTTPPVLDSDGSFFLYSRLTVDKSRWQQGNVFSCSVMHEA

LHNHYTQKSLSLSPGK

SEQ ID NO: 99:
SynOA DM9-Amino Acid NGF (Fasinumab) Light Chain
DIQMTQSPSSLSASADGRVTITCRASQAIRNDLGWYQQKPGKAPKRLI

YAAFNLQSGVPSRFSGSGSGTEFTLTISSLQPEDLASYYCQQYNRYPW

TFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGE

C

SEQ ID NO: 100:
SynOA DM10-Amino Acid 7B4 Heavy Chain
with AA and Duobody (K409R) Mutants
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPSVFPLAPSSKSTSG

GTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPE

AAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALP

APIEKTISKAKGQPREPQVYTLPPSRDELTKNQVSLCLVKGFYPSDI

AVEWESNGQPENNYKTTPPVLDSDGSFFLYSRLTVDKSRWQQGNVFSC

SVMHEALHNHYTQKSLSLSPGK

SEQ ID NO: 101:
SynOA DM10-Amino Acid Fasinumab Heavy Chain
with AA and Duobody (F405L)
Mutants
QVQLVQSGAEVKKPGASVKVSCKVSGFTLTELSIHWVRQAPGKGLEWM

GGFDPEDGETIYAQKFQGRVTMTEDTSTDTAYMELTSLRSEDTAVYYC

STIGVVTNFDNWGQGTLVTVSSASTKGPSVFPLAPSSKSTSGGTAALG

CLVKDYFPEPVTVSWNSGALTSGVHTFPAVLQSSGLYSLSSVVTVPSS

SLGTQTYICNVNHKPSNTKVDKKVEPKSCDKTHTCPPCPAPEAAGGPS

VFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWES

NGQPENNYKTTPPVLDSDGSFKLYSKLTVDKSRWQQGNVFSCSVMHEA

LHNHYTQKSLSLSPGK

SEQ ID NO: 102 ADAMTS5 (12F4) HC with AA and
Duobody (K409R) Mutants
EVQLLESGGGLVQPGGSLRLSCAASGFTFSDAWMDWVRQAPGKGLEWV

AEIRHKANDHAIFYDESVKGRFTISRDSKNTVYLQMNSLRAEDTAVYY

CTSPFAYWGQGTLVTVSSASTKGPSVFPLAPSSKSTSGGTAALGCLVK

DYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLF

PPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKA

KGQPREPQVYTLPPSRDELTKNQVSLSCLVKGFYPSDIAVEWESNGQP

ENNYKTTPPVLDSDGSFFLYSRLTVDKSRWQQGNVFSCSVMHEALHNH

YTQKSLSLSPGK

SEQ ID NO: 103:
SynOA CM3-Amino Acid Fulranumab Heavy Chain
with AA and KIH mutations
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASVAAPSVFIFPPSDEQLKSG

TASVVCLLNNFYPREAKVQWKVDNALQSGNSQESVTEQDSKDSTYSLS

STLTLSKADYEKHKVYACEVTHQGLSSPVTKSFNRGECDKTHTCPPCP

APEAAGGPSVFLFPPKPKDTLMISRTPEVTCVVVDVSHEDPEVKFNWY

VDGVEVHNAKTKPREEQYNSTYRVVSVLTVLHQDWLNGKEYKCKVSNK

ALPAPIEKTISKAKGQPREPQVYTLPPCRDELTKNQVSLWCLVKGFYP

SDIAVEWESNGQPENNYKTTPPVLDSDGSFFLYSKLTVDKSRWQQGNV

FSCSVMHEALHNHYTQKSLSLSPGK

SEQ ID NO: 104:
SynOA CM3-Amino Acid NGF (Fulranumab) Light
Chain
AIQLTQSPSSLSASVGDRVTITCRASQGISSALAWYQQKPGKAPKLLI

YDASSLESGVPSRFSGSGSGTDFTLTISSLQPEDFATYYCQQFNSYPL

TFGGGTKVTVLSSASTKGPSVFPLAPSSKSTSGGTAALGCLVKDYFPE

PVTVSWNSGALTSGVHTFPAVLQSSGLYSLSSVVTVPSSSLGTQTYIC

NVNHKPSNTKVDKKVEPKSC

SEQ ID NO: 105:
SynOA DVD5-Amino Acid 7B4 +
Fulranumab DVD Heavy Chain w SS and AA
Mutaton
EVQLVESGGGLVQPGGSLRLSCAASGFTFSDAWMDWVRQAPGKGLEWV

AEIRNKANNHARHYAESVKGRFTISRDNAKNSLYLQMNSLRAEDTAVY

YCARTYYYGSSYGYCDVWGQGTLVTVSSASTKGPEVQLVESGGGLVQP

GGSLRLSCAASGFTLRSYSMNWVRQAPGKGLEWVSYISRSSHTIFYAD

SVKGRFTISRDNAKNSLYLQMDSLRDEDTAMYYCARVYSSGWHVSDYF

DYWGQGILVTVSSASTKGPSVFPLAPSSKSTSGGTAALGCLVKDYFPE

PVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKS

LSLSPGK

SEQ ID NO: 106:
SynOA DVD5-Amino Acid 7B4 +
Fulranumab DVD Light Chain w SS and AA Mutaton
DIQMTQSPSSLSASVGDRVTITCRTSENIYSYLAWYQQKPGKAPKLLI

YNAKTLAEGVPSRFSGSGSGTDFTLTISSLQPEDFATYYCQHHYGTPW

TFGQGTKLEIKRTVAAPAIQLTQSPSSLSASVGDRVTITCRASQGISS

ALAWYQQKPGKAPKLLIYDASSLESGVPSRFSGSGSGTDFTLTISSLQ

PEDFATYYCQQFNSYPLTFGGGTKLEIKRTVAAPSVFIFPPSDEQLKS

GTASVVCLLNNFYPREAKVQWKVDNALQSGNSQESVTEQDSKDSTYSL

SSTLTLSKADYEKHKVYACEVTHQGLSSPVTKSFNRGEC

SEQ ID NO: 107:
SynOA DVD7-Amino Acid 12F4 + Fulranumab
DVD Heavy Chain w SS and AA Mutation
EVQLLESGGGLVQPGGSLRLSCAASGFTFSDAWMDWVRQAPGKGLEWV

AEIRHKANDHAIFYDESVKGRFTISRDSKNTVYLQMNSLRAEDTAVYY

CTSPFAYWGQGTLVTVSSASTKGPEVQLVESGGGLVQPGGSLRLSCAA

SGFTLRSYSMNWVRQAPGKGLEWVSYISRSSHTIFYADSVKGRFTISR

DNAKNSLYLQMDSLRDEDTAMYYCARVYSSGWHVSDYFDYWGQGILVT

VSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTK

VDKKVEPKSCDKTHTCPPCPAPEAAGGPSVFLFPPKPKDTLMISRTPE

VTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPS

RDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

SEQ ID NO: 108:
SynOA DVD7-Amino Acid 12F4 +
Fulranumab DVD Light Chain w SS and AA
Mutation
DIQMTQSPSSLSASVGDRVTITCKASQSVGTTIVWTQQLPGLAPKLLI

YSASNRHTGVPSRFSGSGSGTDFTLTISSLQPEDFATYYCQQYTSYPF

TFGQGTKEIKRTVAAPAIQLTQSPSSLSASVGDRVTITCRASQGISSA

LAWYQQKPGKAPKLLIYDASSLESGVPSRFSGSGSGTDFTLTISSLQP

EDFATYYCQQFNSYPLTFGGGTKLEIKRTVAAPSVFIFPPSDEQLKSG

TASVVCLLNNFYPREAKVQWKVDNALQSGNSQESVTEQDSKDSTYSLS

STLTLSKADYEKHKVYACEVTHQGLSSPVTKSFNRGEC

SEQ ID NO: 109:
SynOA DVD6-Amino Acid Fulranumab +
7B4 DVD Heavy Chain w SS and AA Mutation
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASTKGPEVQLVESGGGLVQPG

GSLRLSCAASGFTFSDAWMDWVRQAPGKGLEWVAEIRNKANNHARHYA

ESVKGRFTISRDNAKNSLYLQMNSLRAEDTAVYYCARTYYYGSSYGYC

DVWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKS

LSLSPGK

SEQ ID NO: 110:
SynOA DVD6-Amino Acid Fulranumab +
7B4 DVD Light Chain w SS and AA Mutation
AIQLTQSPSSLSASVGDRVTITCRASQGISSALAWYQQKPGKAPKLLI

YDASSLESGVPSRFSGSGSGTDFTLTISSLQPEDFATYYCQQFNSYPL

TFGGGTKLEIKRTVAAPDIQMTQSPSSLSASVGDRVTITCRTSENIYS

YLAWYQQKPGKAPKLLIYNAKTLAEGVPSRFSGSGSGTDFTLTISSLQ

PEDFATYYCQHHYGTPWTFGQGTKLEIKRTVAAPSVFIFPPSDEQLKS

GTASVVCLLNNFYPREAKVQWKVDNALQSGNSQESVTEQDSKDSTYSL

SSTLTLSKADYEKHKVYACEVTHQGLSSPVTKSFNRGEC

SEQ ID NO: 111:
SynOA DVD8-Amino Acid Fulranumab +
7B4 DVD Heavy Chain w SS and AA
Mutation
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASTKGPEVQLLESGGGLVQPG

GSLRLSCAASGFTFSDAWMDWVRQAPGKGLEWVAEIRHKANDHAIFYD

ESVKGRFTISRDSKNTVYLQMNSLRAEDTAVYYCTSPFAYWGQGTLVT

VSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTK

VDKKVEPKSCDKTHTCPPCPAPEAAGGPSVFLFPPKPKDTLMISRTPE

VTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPS

RDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

SEQ ID NO: 112:
SynOA DVD8-Amino Acid Fulranumab +
7B4 DVD Light Chain w SS and AA Mutation
AIQLTQSPSSLSASVGDRVTITCRASQGISSALAWYQQKPGKAPKLLI

YDASSLESGVPSRFSGSGSGTDFTLTISSLQPEDFATYYCQQFNSYPL

TFGGGTKLEIKRTVAAPDIQMTQSPSSLSASVGDRVTITCKASQSVGT

TIVWTQQLPGLAPKLLIYSASNRHTGVPSRFSGSGSGTDFTLTISSLQ

PEDFATYYCQQYTSYPFTFGQGTKEIKRTVAAPSVFIFPPSDEQLKSG

TASVVCLLNNFYPREAKVQWKVDNALQSGNSQESVTEQDSKDSTYSLS

STLTLSKADYEKHKVYACEVTHQGLSSPVTKSFNRGEC

Seq #113:
SynOA DVD13-Amino Acid 7B4 +
Fulranumab DVD Heavy Chain w LL and AA Mutation
EVQLVESGGGLVQPGGSLRLSCAASGFTFSDAWMDWVRQAPGKGLEWV

AEIRNKANNHARHYAESVKGRFTISRDNKSLYLQMNSLRAEDTAVY

YCARTYYYGSSYGYCDVWGQGTLVTVSSASTKGPSVFPLAPEVQLVES

GGGLVQPGGSLRLSCAASGFTLRSYSMNWVRQAPGKGLEWVSYISRSS

HTIFYADSVKGRFTISRDNAKNSLYLQMDSLRDEDTAMYYCARVYSSG

WHVSDYFDYWGQGILVTVSSASTKGPSVFPLAPSSKSTSGGTAALGCL

VKDYFPEPVTVSWNSGALTSGVHTFPAVLQSSGLYSLSSVVTVPSSSL

GTQTYICNVNHKPSNTKVDKKVEPKSCDKTHTCPPCPAPEAAGGPSVF

LFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALH

NHYTQKSLSLSPGK

SEQ ID NO: 114:
SynOA DVD13-Amino Acid 7B4 +
Fulranumab DVD Light Chain w LL and AA
Mutation
DIQMTQSPSSLSASVGDRVTITCRTSENIYSYLAWYQQKPGKAPKLLI

YNAKTLAEGVPSRFSGSGSGTDFTLTISSLQPEDFATYYCQHHYGTPW

TFGQGTKLEIKRTVAAPSVFIFPPAIQLTQSPSSLSASVGDRVTITCR

ASQGISSALAWYQQKPGKAPKLLIYDASSLESGVPSRFSGSGSGTDFT

LTISSLQPEDFATYYCQQFNSYPLTFGGGTKLEIKRTVAAPSVFIFPP

SDEQLKSGTASVVCLLNNFYPREAKVQWKVDNALQSGNSQESVTEQDS

KDSTYSLSSTLTLSKADYEKHKVYACEVTHQGLSSPVTKSFNRGEC

SEQ ID NO: 115:
SynOA DVD15-Amino Acid 12F4 +
Fulranumab DVD Heavy Chain w LL and AA
Mutation
EVQLLESGGGLVQPGGSLRLSCAASGFTFSDAWMDWVRQAPGKGLEWV

AEIRHKANDHAIFYDESVKGRFTISRDSKNTVYLQMNSLRAEDTAVYY

CTSPFAYWGQGTLVTVSSASTKGPSVFPLAPEVQLVESGGGLVQPGGS

LRLSCAASGFTLRSYSMNWVRQAPGKGLEWVSYISRSSHTIFYADSVK

GRFTISRDNAKNSLYLQMDSLRDEDTAMYYCARVYSSGWHVSDYFDYW

GQGILVTVSSASTKGPSVFPLAPSSKSTSGGTAALGCLVKDYFPEPVT

VSWNSGALTSGVHTFPAVLQSSGLYSLSSVVTVPSSSLGTQTYICNVN

HKPSNTKVDKKVEPKSCDKTHTCPPCPAPEAAGGPSVFLFPPKPKDTL

MISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSL

SPGK

SEQ ID NO: 116:
SynOA DVD15-Amino Acid 12F4 +
Fulranumab DVD Light Chain w LL and AA
Mutation
DIQMTQSPSSLSASVGDRVTITCKASQSVGTTIVWTQQLPGLAPKLLI

YSASNRHTGVPSRFSGSGSGTDFTLTISSLQPEDFATYYCQQYTSYPF

TFGQGTKEIKRTVAAPSVFIFPPAIQLTQSPSSLSASVGDRVTITCRA

SQGISSALAWYQQKPGKAPKLLIYDASSLESGVPSRFSGSGSGTDFTL

-continued

TISSLQPEDFATYYCQQFNSYPLTFGGGTKLEIKRTVAAPSVFIFPPS

DEQLKSGTASVVCLLNNFYPREAKVQWKVDNALQSGNSQESVTEQDSK

DSTYSLSSTLTLSKADYEKHKVYACEVTHQGLSSPVTKSFNRGEC

SEQ ID NO: 117:
SynOA DVD14-Amino Acid Fulranumab +
7B4 DVD Heavy Chain
w LL and AA
Mutation
EVQLVESGGGLVQPGGSLRLSCAASGFTLRSYSMNWVRQAPGKGLEWV

SYISRSSHTIFYADSVKGRFTISRDNAKNSLYLQMDSLRDEDTAMYYC

ARVYSSGWHVSDYFDYWGQGILVTVSSASTKGPSVFPLAPEVQLVESG

GGLVQPGGSLRLSCAASGFTFSDAWMDWVRQAPGKGLEWVAEIRNKAN

NHARHYAESVKGRFTISRDNAKNSLYLQMNSLRAEDTAVYYCARTYYY
GSSYGYCDVWGQGTLVTVSSASTKGPSVFPLAPSSKSTSGGTAALGCL
VKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVF
LFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALH
NHYTQKSLSLSPGK SEQ ID NO: 118:
SynOA DVD14-Amino Acid Fulranumab +
7B4 DVD Light Chain w LL and AA
Mutation
AIQLTQSPSSLSASVGDRVTITCRASQGISSALAWYQQKPGKAPKLLI
YDASSLESGVPSRFSGSGSGTDFTLTISSLQPEDFATYYCQQFNSYPL
TFGGGTKLEIKRTVAAPSVFIFPPDIQMTQSPSSLSASVGDRVTITCR
TSENIYSYLAWYQQKPGKAPKLLIYNAKTLAEGVPSRFSGSGSGTDFT
LTISSLQPEDFATYYCQHHYGTPWTFGQGTKLEIKRTVAAPSVFIFPP
SDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 119:
SynOA DVD16-Amino Acid Fulranumab +
12F4 DVD Heavy Chain
w LL and AA
Mutation
EVQLVESGGGLVQPGGSLRLSCAASGFTLRSYSMNWVRQAPGKGLEWV
SYISRSSHTIFYADSVKGRFTISRDNAKNSLYLQMDSLRDEDTAMYYC
ARVYSSGWHVSDYFDYWGQGILVTVSSASTKGPSVFPLAPEVQLLESG
GGLVQPGGSLRLSCAASGFTFSDAWMDWVRQAPGKGLEWVAEIRHKAN
DHAIFYDESVKGRFTISRDSKNTVYLQMNSLRAEDTAVYYCTSPFAYW
GQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVN
HKPSNTKVDKKVEPKSCDKTHTCPPCPAPEAAGGPSVFLFPPKPKDTL
MISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTP -continued

PVLDSDGSFFLYSKLTVDKSRWQQGNVFSCSVMHEALHNHYTQKSLSL
SPGK

SEQ ID NO: 120:
SynOA DVD16-Amino Acid Fulranumab +
12F4 DVD Light Chain w LL and AA
Mutation
AIQLTQSPSSLSASVGDRVTITCRASQGISSALAWYQQKPGKAPKLLI
YDASSLESGVPSRFSGSGSGTDFTLTISSLQPEDFATYYCQQFNSYPL
TFGGGTKLEIKRTVAAPSVFIFPPDIQMTQSPSSLSASVGDRVTITCK
ASQSVGTTIVWTQQLPGLAPKLLIYSASNRHTGVPSRFSGSGSGTDFT
LTISSLQPEDFATYYCQQYTSYPFTFGQGTKEIKRTVAAPSVFIFPPS
DEQLKSGTASVVCLLNNFYPREAKVQWKVDNALQSGNSQESVTEQDSK
DSTYSLSSTLTLSKADYEKHKVYACEVTHQGLSSPVTKSFNRGEC SEQ ID NO: 121:
SynOA DM5-Amino Acid Fulranumab Heavy Chain
with AA and Duobody (K409R)
Mutants
EVQLVESGGGLVQPGGSLRLSCAASGFTLRSYSMNWVRQAPGKGLEWV
SYISRSSHTIFYADSVKGRFTISRDNAKNSLYLQMDSLRDEDTAMYYC
ARVYSSGWHVSDYFDYWGQGILVTVSSASTKGPSVFPLAPSSKSTSGG
TAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPEA
AGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIA
VEWESNGQPENNYKTTPPVLDSDGSFFLYSRLTVDKSRWQQGNVFSCS
VMHEALHNHYTQKSLSLSPGK SEQ ID NO: 122:
SynOA DM5-Amino Acid Fulranumab Light Chain
with AA and Duobody (K409R)
Mutants
AIQLTQSPSSLSASVGDRVTITCRASQGISSALAWYQQKPGKAPKLLI
YDASSLESGVPSRFSGSGSGTDFTLTISSLQPEDFATYYCQQFNSYPL
TFGGGTKLEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC SEQ ID NO: 123:
SynOA DM6-Amino Acid Fulranumab Heavy Chain
with AA and Duobody (F405L)
Mutants
EVQLVESGGGLVQPGGSLRLSCAASGFTLRSYSMNWVRQAPGKGLEWV
SYISRSSHTIFYADSVKGRFTISRDNAKNSLYLQMDSLRDEDTAMYYC
ARVYSSGWHVSDYFDYWGQGILVTVSSASTKGPSVFPLAPSSKSTSGG
TAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPEA
AGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIA

```
SEQ ID NO: 124:
SynOA DM2-Amino Acid Tanezumab Heavy Chain
w AA and Duobody (F405L)
Mutants
QVQLQESGPGLVKPSETLSLTCTVSGFSLIGYDLNWIRQPPGKGLEWI
GIIWGDGTTDYNSAVKSRVTISKDTSKNQFSLKLSSVTAADTAVYYCA
RGGYWYATSYYFDYWGQGTLVTVSSASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPEAAG
GPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVE
WESNGQPENNYKTTPPVLDSDGSFLLYSKLTVDKSRWQQGNVFSCSVM
HEALHNHYTQKSLSLSPGK SEQ ID NO: 125:
SynOA DM4-Amino Acid Tanezumab Heavy Chain
w AA and Duobody (F405L)
Mutants
QVQLQESGPGLVKPSETLSLTCTVSGFSLIGYDLNWIRQPPGKGLEWI
GIIWGDGTTDYNSAVKSRVTISKDTSKNQFSLKLSSVTAADTAVYYCA
RGGYWYATSYYFDYWGQGTLVTVSSASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPEAAG
GPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVE
WESNGQPENNYKTTPPVLDSDGSFLLYSKLTVDKSRWQQGNVFSCSVM
HEALHNHYTQKSLSLSPGK SEQ ID NO: 126:
SynOA CM11-Amino Acid M6495 Heavy Chain
with AA and KIH Mutants
EVQLLESGGGLVQPGGSLRLSCAASGFTFSGRTVSSYAMGWVRQAPGK
GLEWVAGISRSAERTYRFTISRDSKNTVYLQMNSLRAEDTAVYYCTSD
LDPNRIFSREEYAYWGQGTLVTVSSASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPEAAG
GPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPI
EKTISKAKGQPREPQVCTLPPSRDELTKNQVSLSCAVKGFYPSDIAVE
WESNGQPENNYKTTPPVLDSDGSFFLVSKLTVDKSRWQQGNVFSCSVM
HEALHNHYTQKSLSLSPGK SEQ ID NO: 127:
SynOA DM13-Amino Acid CRB0017 Heavy Chain
with AA and Duobody (F405L)
Mutants
EVQLLESGGGLVQPGGSLRLSCAASGFTFSSYWMHWVRQAPGKGLEWV
AYINPSTGYTEYNQKFKRFTISRDSKNTVYLQMNSLRAEDTAVYYCTS
GGYDDLGYWGQGTLVTVSSASTKGPSVFPLAPSSKSTSGGTAALGCLV
KDYFPEPVTVSWNSGALTSGVHTFPAVLQSSGLYSLSSVVTVPSSSLG
TQTYICNVNHKPSNTKVDKKVEPKSCDKTHTCPPCPAPEAAGGPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLSCLVKGFYPSDIAVEWESNGQ
PENNYKTTPPVLDSDGSFLLYSKLTVDKSRWQQGNVFSCSVMHEALHN
HYTQKSLSLSPGK SEQ ID NO: 128:
SynOA DM13-Amino Acid CRB0017 Light Chain
DIQMTQSPSSLSASVGDRVTITCRSSKSLLYKDGKTYLYWTQQLPGLA
PKLLIYLMSTRASGVPSRFSGSGSGTDFTLTISSLQPEDFATYYCQQL
VUYPYTFGQGTKLEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC SEQ ID NO: 129:
SynOA DM14-Amino Acid CRB0017 Heavy Chain
with AA and Duobody (K409R)
Mutants
EVQLLESGGGLVQPGGSLRLSCAASGFTFSSYWMHWVRQAPGKGLEWV
AYINPSTGYTEYNQKFKRFTISRDSKNTVYLQMNSLRAEDTAVYYCTS
GGYDDLGYWGQGTLVTVSSASTKGPSVFPLAPSSKSTSGGTAALGCLV
KDYFPEPVTVSWNSGALTSGVHTFPAVLQSSGLYSLSSVVTVPSSSLG
TQTYICNVNHKPSNTKVDKKVEPKSCDKTHTCPPCPAPEAAGGPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLSCLVKGFYPSDIAVEWESNGQ
PENNYKTTPPVLDSDGSFFLYSRLTVDKSRWQQGNVFSCSVMHEALHN
HYTQKSLSLSPGK SEQ ID NO: 130:
SynOA BF2-Amino Acid 7B4 Heavy Chain
AA mutant + Fulranumab scFv
EVQLVESGGGLVQPGGSLRLSCAASGFTFSDAWMDWVRQAPGKGLEWV
AEIRNKANNHARHYAESVKGRFTISRDNAKNSLYLQMNSLRAEDTAVY
YCARTYYYGSSYGYCDVWGQGTLVTVSSASTKGPSVFPLAPSSKSTSG
GTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPE
AAGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALP
APIEKTISKAKGQPREPQVYTLPPSRDELTKNQVSLTCLVKGFYPSDI
AVEWESNGQPENNYKTTPPVLDSDGSFFLYSKLTVDKSRWQQGNVFSC
```

-continued

SVMHEALHNHYTQKSLSLSPGKGGGGSGGGGSGGGGSEVQLVESGGGL
VQPGGSLRLSCAASGFTLRSYSMNWVRQAPGKGLEWVSYISRSSHTIF
YADSVKGRFTISRDNAKNSLYLQMDSLRDEDTAMYYCARVYSSGWHVS
DYFDYWGQGILVTVSSGGGGSGGGGSGGGGSAIQLTQSPSSLSASVGD
RVTITCRASQGISSALAWYQQKPGKAPKLLIYDASSLESGVPSRFSGS
GSGTDFTLTISSLQPEDFATYYCQQFNSYPLTFGGGTKLEIK

SEQ ID NO: 131:
SynOA BF3-Amino Acid 7B4 HC with AA mutant + NGF (Fasinumab) scFv
EVQLVESGGGLVQPGGSLRLSCAASGFTFSDAWMDWVRQAPGKGLEWV
AEIRNKANNHARHYAESVKGRFTISRDNAKNSLYLQMNSLRAEDTAVY
YCARTYYYGSSYGYCDVWGQGTLVTVSSASTKGPSVFPLAPSSKSTSG
GTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPE
AAGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALP
APIEKTISKAKGQPREPQVYTLPPSRDELTKNQVSLTCLVKGFYPSDI
AVEWESNGQPENNYKTTPPVLDSDGSFFLYSKLTVDKSRWQQGNVFSC
SVMHEALHNHYTQKSLSLSPGKGGGGSGGGGSGGGGSQVQLVQSGAEV
KKPGASVKVSCKVSGFTLTELSIHWVRQAPGKGLEWMGGFDPEDGETI
YAQKFQGRVTMTEDTSTDTAYMELTSLRSEDTAVYYCSTIGVVTNFDN
WGQGTLVTVSSGGGGSGGGGSGGGGSDIQMTQSPSSLSASAGDRVTIT
CRASQAIRNDLGWYQQKPGKAPKRLIYAAFNLQSGVPSRFSGSGSGTE
FTLTISSLQPEDLASYYCQQYNRYPWTFGQGTKLEIK SEQ ID NO: 132:
SynOA BF5-Amino Acid 12F4 HC with AA mutant + NGF (Fulranumab) scFv
EVQLLESGGGLVQPGGSLRLSCAASGFTFSDAWMDWVRQAPGKGLEWV
AEIRHKANDHAIFYDESVKGRFTISRDSKNTVYLQMNSLRAEDTAVYY
CTSPFAYWGQGTLVTVSSASTKGPSVFPLAPSSKSTSGGTAALGCLVK
DYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKA
KGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNH
YTQKSLSLSPGKGGGGSGGGGSGGGGSEVQLVESGGGLVQPGGSLRLS
CAASGFTLRSYSMNWVRQAPGKGLEWVSYISRSSHTIFYADSVKGRFT
ISRDNAKNSLYLQMDSLRDEDTAMYYCARVYSSGWHVSDYFDYWGQGI
LVTVSSGGGGSGGGGSGGGGSAIQLTQSPSSLSASVGDRVTITCRASQ
GISSALAWYQQKPGKAPKLLIYDASSLESGVPSRFSGSGSGTDFTLTI
SSLQPEDFATYYCQQFNSYPLTFGGGTKLEIK -continued SEQ ID NO: 133:
SynOA BF6-Amino Acid 12F4 HC with AA mutant + Fasinumab scFv
EVQLLESGGGLVQPGGSLRLSCAASGFTFSDAWMDWVRQAPGKGLEWV
AEIRHKANDHAIFYDESVKGRFTISRDSKNTVYLQMNSLRAEDTAVYY
CTSPFAYWGQGTLVTVSSASTKGPSVFPLAPSSKSTSGGTAALGCLVK
DYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKA
KGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNH
YTQKSLSLSPGKGGGGSGGGGSGGGGSQVQLVQSGAEVKKPGASVKVS
CKVSGFTLTELSIHWVRQAPGKGLEWMGGFDPEDGETIYAQKFQGRVT
MTEDTSTDTAYMELTSLRSEDTAVYYCSTIGVVTNFDNWGQGTLVTVS
SGGGGSGGGGSGGGGSDIQMTQSPSSLSASAGDRVTITCRASQAIRND
LGWYQQKPGKAPKRLIYAAFNLQSGVPSRFSGSGSGTEFTLTISSLQP
EDLASYYCQQYNRYPWTFGQGTKLEIK SEQ ID NO: 134:
SynOA BF7-Amino Acid M6495 HC with AA mutant + Tanezumab scFv
EVQLLESGGGLVQPGGSLRLSCAASGFTFSGRTVSSYAMGWVRQAPGK
GLEWVAGISRSAERTYRFTISRDSKNTVYLQMNSLRAEDTAVYYCTSD
LDPNRIFSREEYAYWGQGTLVTVSSASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPEAAG
GPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVM
HEALHNHYTQKSLSLSPGKGGGGSGGGGSGGGGSQVQLQESGPGLVKP
SETLSLTCTVSGFSLIGYDLNWIRQPPGKGLEWIGIIWGDGTTDYNSA
VKSRVTISKDTSKNQFSLKLSSVTAADTAVYYCARGGYWYATSYYFDY
WGQGTLVTVSSGGGGSGGGGSGGGGSDIQMTQSPSSLSASVGDRVTIT
CRASQSISNNLNWYQQKPGKAPKLLIYYTSRFHSGVPSRFSGSGSGTD
FTFTISSLQPEDIATYYCQQEHTLPYTFGQGTKLEIK SEQ ID NO: 135:
SynOA BF8-Amino Acid M6495 HC with AA mutant + Fulranumab scFv
EVQLLESGGGLVQPGGSLRLSCAASGFTFSGRTVSSYAMGWVRQAPGK
GLEWVAGISRSAERTYRFTISRDSKNTVYLQMNSLRAEDTAVYYCTSD
LDPNRIFSREEYAYWGQGTLVTVSSASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPEAAG
GPSVFLFPPKPKDTLMISRTPEVTCVVVDVSHEDPEVKFNWYVDGVEV -continued

HNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVM

HEALHNHYTQKSLSLSPGKGGGGSGGGGSGGGGSEVQLVESGGGLVQP

GGSLRLSCAASGFTLRSYSMNWVRQAPGKGLEWVSYISRSSHTIFYAD

SVKGRFTISRDNAKNSLYLQMDSLRDEDTAMYYCARVYSSGWHVSDYF

DYWGQGILVTVSSGGGGSGGGGSGGGGSAIQLTQSPSSLSASVGDRVT

ITCRASQGISSALAWYQQKPGKAPKLLIYDASSLESGVPSRFSGSGSG

TDFTLTISSLQPEDFATYYCQQFNSYPLTFGGGTKLEIK

SEQ ID NO: 136:
SynOA BF9-Amino Acid M6495 HC with AA mutant +
Fasinumab scFv
EVQLLESGGGLVQPGGSLRLSCAASGFTFSGRTVSSYAMGWVRQAPGK

GLEWVAGISRSAERTYRFTISRDSKNTVYLQMNSLRAEDTAVYYCTSD

LDPNRIFSREEYAYWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVM

HEALHNHYTQKSLSLSPGKGGGGSGGGGSGGGGSQVQLVQSGAEVKKP

GASVKVSCKVSGFTLTELSIHWVRQAPGKGLEWMGGFDPEDGETIYAQ

KFQGRVTMTEDTSTDTAYMELTSLRSEDTAVYYCSTIGVVTNFDNWGQ

GTLVTVSSGGGGSGGGGSGGGGSDIQMTQSPSSLSASAGDRVTITCRA

SQAIRNDLGWYQQKPGKAPKRLIYAAFNLQSGVPSRFSGSGSGTEFTL

TISSLQPEDLASYYCQQYNRYPWTFGQGTKLEIK

SEQ ID NO: 137:
SynOA BF10-Amino Acid CRB0017 HC with
AA mutant + Tanezumab scFv
EVQLLESGGGLVQPGGSLRLSCAASGFTFSSYWMHWVRQAPGKGLEWV

AYINPSTGYTEYNQKFKRFTISRDSKNTVYLQMNSLRAEDTAVYYCTS

GGYDDLGYWGQGTLVTVSSASTKGPSVFPLAPSSKSTSGGTAALGCLV

KDYFPEPVTVSWNSGALTSGVHTFPAVLQSSGLYSLSSVVTVPSSSLG

TQTYICNVNHKPSNTKVDKKVEPKSCDKTHTCPPCPAPEAAGGPSVFL

FPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHN

HYTQKSLSLSPGKGGGGSGGGGSGGGGSQVQLQESGPGLVKPSETLSL

TCTVSGFSLIGYDLNWIRQPPGKGLEWIGIIWGDGTTDYNSAVKSRVT

ISKDTSKNQFSLKLSSVTAADTAVYYCARGGYWYATSYYFDYWGQGTL

VTVSSGGGGSGGGGSGGGGSDIQMTQSPSSLSASVGDRVTITCRASQS

ISNNLNWYQQKPGKAPKLLIYYTSRFHSGVPSRFSGSGSGTDFTFTIS

SLQPEDIATYYCQQEHTLPYTFGQGTKLEIK

SEQ ID NO: 138:
SynOA BF11-Amino Acid CRB0017 HC with AA mutant +
Fulranumab scFv
EVQLLESGGGLVQPGGSLRLSCAASGFTFSSYWMHWVRQAPGKGLEWV

AYINPSTGYTEYNQKFKRFTISRDSKNTVYLQMNSLRAEDTAVYYCTS

GGYDDLGYWGQGTLVTVSSASTKGPSVFPLAPSSKSTSGGTAALGCLV

KDYFPEPVTVSWNSGALTSGVHTFPAVLQSSGLYSLSSVVTVPSSSLG

TQTYICNVNHKPSNTKVDKKVEPKSCDKTHTCPPCPAPEAAGGPSVFL

FPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHN

HYTQKSLSLSPGKGGGGSGGGGSGGGGSEVQLVESGGGLVQPGGSLRL

SCAASGFTLRSYSMNWVRQAPGKGLEWVSYISRSSHTIFYADSVKGRF

TISRDNAKNSLYLQMDSLRDEDTAMYYCARVYSSGWHVSDYFDYWGQG

ILVTVSSGGGGSGGGGSGGGGSAIQLTQSPSSLSASVGDRVTITCRAS

QGISSALAWYQQKPGKAPKLLIYDASSLESGVPSRFSGSGSGTDFTLT

ISSLQPEDFATYYCQQFNSYPLTFGGGTKLEIK

SEQ ID NO: 139:
SynOA BF12-Amino Acid CRB0017 HC with AA mutant +
Fasinumab scFv
EVQLLESGGGLVQPGGSLRLSCAASGFTFSSYWMHWVRQAPGKGLEWV

AYINPSTGYTEYNQKFKRFTISRDSKNTVYLQMNSLRAEDTAVYYCTS

GGYDDLGYWGQGTLVTVSSASTKGPSVFPLAPSSKSTSGGTAALGCLV

KDYFPEPVTVSWNSGALTSGVHTFPAVLQSSGLYSLSSVVTVPSSSLG

TQTYICNVNHKPSNTKVDKKVEPKSCDKTHTCPPCPAPEAAGGPSVFL

FPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHN

HYTQKSLSLSPGKGGGGSGGGGSGGGGSQVQLVQSGAEVKKPGASVKV

SCKVSGFTLTELSIHWVRQAPGKGLEWMGGFDPEDGETIYAQKFQGRV

TMTEDTSTDTAYMELTSLRSEDTAVYYCSTIGVVTNFDNWGQGTLVTV

SSGGGGSGGGGSGGGGSDIQMTQSPSSLSASAGDRVTITCRASQAIRN

DLGWYQQKPGKAPKRLIYAAFNLQSGVPSRFSGSGSGTEFTLTISSLQ

PEDLASYYCQQYNRYPWTFGQGTKLEIK

Target Sequences and Species Homology
(Mature Amino Acid Sequence)
SEQ ID NO: 140:
Human ADAMTS5
MLLGWASLLLCAFRLPLAAVGPAATPAQDKAGQPPTAAAAAQPRRRQG

EEVQERAEPPGHPHPLAQRRRSKGLVQNIDQLYSGGGKVGYLVYAGGR

RFLLDLERDGSVGIAGFVPAGGGTSAPWRHRSHCFYRGTVDGSPRSLA

VFDLCGGLDGFFAVKHARYTLKPLLRGPWAEEEKGRVYGDGSARILHV

-continued

YTREGFSFEALPPRASCETPASTPEAHEHAPAHSNPSGRAALASQLLD
QSALSPAGGSGPQTWWRRRRRSISRARQVELLLVADASMARLYGRGLQ
HYLLTLASIANRLYSHASIENHIRLAVVKVVVLGDKDKSLEVSKNAAT
TLKNFCKWQHQHNQLGDDHEEHYDAAILFTREDLCGHHSCDTLGMADV
GTICSPERSCAVIEDDGLHAAFTVAHEIGHLLGLSHDDSKFCEETFGS
TEDKRLMSSILTSIDASKPWSKCTSATITEFLDDGHGNCLLDLPRKQI
LGPEELPGQTYDATQQCNLTFGPEYSVCPGMDVCARLWCAVVRQGQMV
CLTKKLPAVEGTPCGKGRICLQGKCVDKTKKKYYSTSSHGNWGSWGSW
GQCSRSCGGGVQFAYRHCNNPAPRNNGRYCTGKRAIYRSCSLMPCPPN
GKSFRHEQCEAKNGYQSDAKGVKTFVEWVPKYAGVLPADVCKLTCRAK
GTGYYVVFSPKVTDGTECRLYSNSVCVRGKCVRTGCDGIIGSKLQYDK
CGVCGGDNSSCTKIVGTFNKKSKGYTDVVRIPEGATHIKVRQFKAKDQ
TRFTAYLALKKKNGEYLINGKYMISTSETIIDINGTVMNYSGWSHRDD
FLHGMGYSATKEILIVQILATDPTKPLDVRYSFEVPKKSTPKVNSVTS
HGSNKVGSHTSQPQWVTGPWLACSRTCDTGWHTRTVQCQDGNRKLAKG
CPLSQRPSAFKQCLLKKC

SEQ ID NO: 141:
Cynomolgus ADAMTS5
MLLGWASLLLCAFRLPLAAAGPAAAPAQDKAGQPATAAAAAQPSRRQG
EEVQERTEPPGHPHPLAQRRSSKGLVQNIDQLYSGGGKVGYLVYAGGR
RFLLDLERDGSVGTAGFVPTGGGTSAPWRHRSHCFYRGTVDGSPRSLA
VFDLCGGLDGFFAVKHARYTLKPLLRGPWAEEETGRVYGDGSARILHV
YTREGFSFEALQPRASCETPASTPEPHERPPAHSNPGGRAALASQLLD
QSAVSPAGGPGPQTWWRRRRRSISRARQVELLLVADASMARLYGRGLQ
HYLLTLASIANRLYSHASIENHIRLAVVKVVVLGDKDKSLEVSKNAAT
TLKNFCKWQHQHNQLGDDHEEHYDAAILFTREDLCGHHSCDTLGMADV
GTICSPERSCAVIEDDGLHAAFTVAHEIGHLLGLSHDDSKFCEETFGS
TEDKRLMSSILTSIDASKPWSKCTSATITEFLDDGHGNCLLDQPRKQI
LGPEELPGQTYDATQQCNLTFGPEYSVCPGMDVCARLWCAVVRQGQMV
CLTKKLPAVEGTPCGKGRICLQGKCVDKTKKKYYSTSSHGNWGSWGSW
GQCSRSCGGGVQFAYRHCNNPAPRNNGRYCTGKRAIYRSCGLMPCPPN
GKSFRHEQCEAKNGYQSDAKGVKTFVEWVPKYAGVLPADVCKLTCRAK
GTGYYVVFSPKVTDGTECRPYSNSVCVRGKCVRTGCDSIIGSKLQYDK
CGVCGGDNSSCTKIVGTFNKKSKGYTDVVRIPEGATHIKVRQFKAKDQ
TRFTAYLALKKKNGEYLINGKYMISTSETIIDINGTVMNYSGWSHRDD
FLHGMGYSATKEILIVQILATDPTKPLDVRYSFFVPKKSTPKVNSVTS
HGSNKVGSHTSQLQWVTGPWLACSRTCDTGWHTRTVQCQDGNRKLAKG
CPLSQRPSAFKQCLLKKC SEQ ID NO: 142:
Feline ADAMTS5
MLLGWASLLLCALRLPPVAAGPAAAPAQDTAGQPRAAAAAQPRGRQG
EEAQERAEPPGHPHPLAPQRRSGGLVHNIDQIYAGGGKVGYLVYAGGR
RFLLDLERDGSLGAAGFAPAGSGPGASRRHRDHCFHRGTVDGSPRSLA
VFDLCGGLDGFFAVKHARYTLKPLLRGPRAEAEAGRVYGDGSSRVLHV
YTREGFSFEAVPPRASCETPASPPGPRERPPAHGGPGPRWELAPPFPD
QTVPSSEGTQGPQTWWRRRRRSISRARQVELLLVADASMARMYGRGLQ
HYLLTLASIANRLYSHASIENHIRLAVVKVVVLGDKDKSLEVSKNAAT
TLKNFCKWQHQHNQLEDDHEEHHDAAILFTREDLCGHHSCDTLGMADV
GTICSPERSCAVIEDDGLHAAFTVAHEIGHLLGLSHDDSKFCEENFGS
TEDKRLMSSILTSIDASKPWSKCTSATITEFLDDGHGNCLLDVPRQQI
SGPEELPGQTYDATQQCNLTFGPEYSVCPGMDVCTRLWCAVVRQGQMV
CLTKKLPAVEGTPCGKGRICLQGKCVDKTKKKYYSTSSHGNWGSWGPW
GQCSRSCGGGVQFAYRHCNNPAPRNSGRYCTGKRAIYRSCSVTPCPPN
GKSFRHEQCEAKNGYQSDAKGVKTFVEWVPKYAGVLLGDVCKLTCRAK
GTGYYVVFSPKVTDGTECRPYSNSVCVRGKCVRTGCDGIIGSRLQYDK
CAVCGGDNSSCTKVVGTFNKKSKGYTDVVRIPEGATHIKVRQFKAKDQ
TRFTAYLALKKKNGEYLINGKYMISTSETIIDINGTVMNYSGWSHRDD
FLHGMGYSATKEILIVQILATDPTKALDVRYSFFVPKKSTQKVNSVSS
HGSNKVGSHTPQLQWVTGPWLACSRTCDTGWHTRTVQCQDANRKLAKG
CLLSQRPSAFKQCLLKKC SEQ ID NO: 143:
Canine ADAMTS5
MLLGWASLLLGALRLPPVAAGPAAAPAQDKAGQPWAAAAAAQPRRRQG
EEAREPAEPPGHPHPLAPQRRSSGLVQNVDQIYAGGGKVGYLVYAGGR
RFLLDLERDGSVGAAGSAPAGRGPGAPRRHRDHCFYRGTVDGSPRSLA
VLDLCGGLDGFFAVRHARYTLKPLLRGPWAGAGAGAEAERVYGDGSPR
ILHVYTREGFSFEALPPRTSCETPASPPGPRERPPAHSSPDPRWSPAP
PFPAPPAASPDGGPGPQTWWRRRRRSISRARQVELLLVADASMARMYG
RGLQHYLLTLASIANRLYSHASIENHIRLAVVKVVVLGDKDKSLEVSK
NAATTLKNFCKWQHQHNQLGDDHEEHYDAAILFTREDLCGHHSCDTLG
MADVGTICSPERSCAVIEDDGLHAAFTVAHEIGHLLGLSHDDSKFCEE
NFGSTEDKRLMSSILTSIDASKPWSKCTSATITEFLDDGHGNCLLDLP
RKQILGPEELPGQTYDATQQCNLTFGPEYSVCPGMDVCARLWCAVVRQ
GQMVCLTKKLPAVEGTPCGKGRICLQGKCVDKTKKKYYSTSSHGNWGS
WGSWGQCSRSCGGGVQFAYRHCNNPAPRNNGRYCTGKRAIYRSCNVTP
CPPNGKSFRHEQCEAKNGYQSDAKGVKTFVEWVPKYAGVLLGDVCKLT
CRAKGTGYYVVFSPKVTDGTECRPYSNSVCVRGKCVRTGCDGIIGSKL
QYDKCAVCGGDNSSCTKVVGTFNKKSKGYTDVVRIPEGATHIKVRQFK
AKDQTRFTAYLALKKKNGEYLINGKYMISTSETIIDINGTVMNYSGWS
HRDDFLHGMGYSATKEILIVQILATDPTKALDVRYSFFVPKKSTQKVN
SVTSHASNKVGSHTPQLQWVTGPWLACSRTCDTGWHTRTVQCQDANRK
LAKGCLLSQRPSAFKQCLLKKC SEQ ID NO: 144:
Horse ADAMTS5
MLLGWASLLLCALRLPLVAAGPAAAPAQDKTGQPRAAAAAAQPRRRQG
EEAQERAEPPGHPHPLAPQRRSSGLVQNIDQIYSGGGKVGYLVYAGGR
RFLLDLERDGSVGAAGFVPVGGGPSATRRHRGHCFYRGTVDGSPRSLA
VFDLCGGLDGFFAVKHARYTLKPLLRGPWAETETGRVYGDGSARILHV
YTREGFSFEALPPRTSCETPASPPGSRERPPAHSSPEPRWALAPQFPD
QSATSSDGGQGSQTWRRRRRSISRARQVELLLVADASMARMYGRGLQH
YLLTLASIANRLYSHASIENHIRLAVVKMVVLGDKDKSLEVSKNAATT
LKNFCKWQHQHNQLGDDHEEHYDAAILFTREDLCGHHSCDTLGMADVG
TICSPERSCAVIEDDGLHAAFTVAHEIGHLLGLSHDDSKFCEENFGST
EEKRLMSSILTSIDASKPWSKCTSATITEFLDDGHGNCLLDLPRKQIL
GPEELPGQTYDATQQCNLTFGPEYSVCPGMDVCARLWCAVVRQGQMVC
LTKKLPAVEGTPCGKGRICLQGKCVDKTKKKYYSTSSHGNWGSWGSWG
QCSRSCGGGVQFAYRHCNNPAPRNNGRYCTGKRAIYRSCSVTPCPANG
KSFRHEQCEAKNGYQSDAKGVKTFVEWVPKYAGVLPGDVCKLTCRAKG
TGYYVVFSPKVTDGTECRPYSNSVCVRGKCVRTGCDGIIGSKLQYDKC
GVCGGDNSSCTKVVGTFNKKSKGYTDVVRIPEGATHIKVRQFKTKDQT
RFTAYLALKKKNGEYLINGKYMISTSETIIDINGTVMNYSGWSHRDDF
LHGMGYSATKEILIVQILATDPTKALDVRYSFFVPKKPTQKGNSVTSH
GSNKVGSTTPQLQWVTGPWLACSRTCDTGWHTRTVQCQDGNRKLAKGC
LLSQRPSAFKQCLLKKC SEQ ID NO: 145:
Mouse ADAMTS5
MRLEWAPLLLLLLLLSASCLSLAADSPAAAPAQDKTRQPQAAAAAAEP
DQPQGEETRERGHLQPLAGQRRSGGLVQNIDQLYSGGGKVGYLVYAGG
RRFLLDLERDDTVGAAGSIVTAGGGLSASSGHRGHCFYRGTVDGSPRS
LAVFDLCGGLDGFFAVKHARYTLKPLLRGSWAEYERIYGDGSSRILHV
YNREGFSFEALPPRASCETPASPSGPQESPSVHSRSRRRSALAPQLLD
HSAFSPSGNAGPQTWWRRRRRSISRARQVELLLVADSSMARMYGRGLQ
HYLLTLASIANRLYSHASIENHIRLAVVKVVVLTDKDTSLEVSKNAAT
TLKNFCKWQHQHNQLGDDHEEHYDAAILFTREDLCGHHSCDTLGMADV
GTICSPERSCAVIEDDGLHAAFTVAHEIGHLLGLSHDDSKFCEENFGT
TEDKRLMSSILTSIDASKPWSKCTSATITEFLDDGHGNCLLDLPRKQI
LGPEELPGQTYDATQQCNLTFGPEYSVCPGMDVCARLWCAVVRQGQMV
CLTKKLPAVEGTPCGKGRVCLQGKCVDKTKKKYYSTSSHGNWGSWGPW
GQCSRSCGGGVQFAYRHCNNPAPRNSGRYCTGKRAIYRSCSVTPCPPN
GKSFRHEQCEAKNGYQSDAKGVKTFVEWVPKYAGVLPADVCKLTCRAK
GTGYYVVFSPKVTDGTECRPYSNSVCVRGRCVRTGCDGIIGSKLQYDK
CGVCGGDNSSCTKIIGTFNKKSKGYTDVVRIPEGATHIKVRQFKAKDQ
TRFTAYLALKKKTGEYLINGKYMISTSETIIDINGTVMNYSGWSHRDD
FLHGMGYSATKEILIVQILATDPTKALDVRYSFFVPKKTTQKVNSVIS
HGSNKVGPHSTQLQWVTGPWLACSRTCDTGWHTRTVQCQDGNRKLAKG
CLLSQRPSAFKQCLLKKC SEQ ID NO: 146:
Rat ADAMTS5
MRLEWASLLLLLLLLCASCLALAADNPAAAPAQDKTRQPRAAAAAAQP
DQRQWEETQERGHPQPLARQRRSSGLVQNIDQLYSGGGKVGYLVYAGG
RRFLLDLERDDTVGAAGGIVTAGGLSASSGHRGHCFYRGTVDGSPRSL
AVFDLCGGLDGFFAVKHARYTLKPLLRGSWAESERVYGDGSSRILHVY
TREGFSFEALPPRTSCETPASPSGAQESPSVHSSSRRRTELAPQLLDH
SAFSPAGNAGPQTWWRRRRRSISRARQVELLLVADSSMAKMYGRGLQH
YLLTLASIANRLYSHASIENHIRLAVVKVVVLTDKSLEVSKNAATTLK
NFCKWQHQHNQLGDDHEEHYDAAILFTREDLCGHHSCDTLGMADVGTI
CSPERSCAVIEDDGLHAAFTVAHEIGHLLGLSHDDSKFCEENFGSTED
KRLMSSILTSIDASKPWSKCTSATITEFLDDGHGNCLLDVPRKQILGP
EELPGQTYDATQQCNLTFGPEYSVCPGMDVCARLWCAVVRQGQMVCLT
KKLPAVEGTPCGKGRICLQGKCVDKTKKKYYSTSSHGNWGSWGPWGQC
SRSCGGGVQFAYRHCNNPAPRNSGRYCTGKRAIYRSCSVIPCPPNGKS
FRHEQCEAKNGYQSDAKGVKTFVEWVPKYAGVLPADVCKLTCRAKGTG
YYVVFSPKVTDGTECRPYSNSVCVRGRCVRTGCDGIIGSKLQYDKCGV
CGGDNSSCTKIIGTFNKKSKGYTDVVRIPEGATHIKVRQFKAKDQTRF
TAYLALKKKTGEYLINGKYMISTSETIIDINGTVMNYSGWSHRDDFLH
GMGYSATKEILIVQILATDPTKALDVRYSFFVPKKTTQKVNSVISHSS
NKVGLHSPQLQWVTGPWLACSRTCDTGWHTRTVQCQDGNRKLAKGCIL
SQRPSAFKQCLLKKC

| ADAMTS5 Protein Sequence Homology (% Identity) | | | | | | |
| --- | --- | --- | --- | --- | --- | --- |
|  | Human | Cynomolgus | Dog | Cat | Horse | Mouse | Rat |
| Human |  | 97.74 | 93.1 | 91.40 | 93.66 | 90.8 | 91.6 |
| Cynomolgus | 97.74 |  | 93.5 | 91.51 | 94.09 | 90.5 | 91.5 |
| Dog | 93.1 | 93.5 |  | 94.33 | 94.54 | 92.0 | 92.3 |
| Cat | 91.40 | 91.51 | 94.33 |  | 94.09 | 89.93 | 90.59 |
| Horse | 93.66 | 94.09 | 94.54 | 94.09 |  | 91.26 | 91.69 |
| Mouse | 90.8 | 90.5 | 92.0 | 89.93 | 91.26 |  | 96.7 |
| Rat | 91.6 | 91.5 | 92.3 | 90.59 | 91.69 | 96.7 |  |

SEQ ID NO: 147: Human Beta-NGF
MSMLFYTLITAFLIGIQAEPHSESNVPAGHTIPQAHWTKLQHSLD
TALRRARSAPAAAIAARVAGQTRNITVDPRLFKKRRLRSPRVLFS
TQPPREAADTQDLDFEVGGAAPFNRTHRSKRSSSHPIFHRGEFSV
CDSVSVWVGDKTTATDIKGKEVMVLGEVNINNSVFKQYFFETKCR
DPNPVDSGCRGIDSKHWNSYCTTTHTFVKALTMDGKQAAWRFIRI
DTACVCVLSRKAVRRA

```
SEQ ID NO: 148: Cynomolgus Beta-NGF
MSMLFYTLITAFLIGIQAEPHSESNVPAGHTIPQAHWTKLQHSLD

TALRRVRSAPAVAIAARVAGQTRNITVDPRLFKKRRLRSPRVLFS

TQPPPEAADTQDLDFEVGGAAPFNRTHRSKRSSSHPIFHRGEFSV

CDSVSVWVGDKTTATDIKGKEVMVLGEVNINNSVFKQYFFETKCR

DPNPVDSGCRGIDSKHWNSYCTTTHTFVKALTMDGKQAAWRFIRI

DTACVCVLSRKAVRRA

SEQ ID NO: 149: Canine Beta-NGF
MSMLFYTLITALLIGIRAEPHPESHVPAGHAIPAHWTKLQHSLD

TALRRARSAPAGAIAARVTGQTRNITVDPKLFKKRRLRSPRVLFS

THPPPVAADAQDLDLEAGSTASVNRTHRSKRSSSHPVFHRGEFSV

CDSVSVWVGDKTTATDIKGKEVMVLGEVNINNSVFKQYFFETKCR

DPTPVDSGCRGIDSKHWNSYCTTTHTFVKALTMDGKQAAWRFIRI

DTACVCVLSRKAGRRA

SEQ ID NO: 150: Feline Beta-NGF
MSMLSYTLITALLIGIQAEPHPESNVPAGHTIPQAHWTKLQHSLD

TALRRARSTPAGAIAARVAGQTRNITVDPKLFKKRRLRSPRVLFS

THPPPVAADTQGLDLEAGGAASFNRTHRSKRSSSHPVFHRGEFSV

CDSVSVWVGDKTTATDIKGKEVMVLGEVNINNSVFKQYFFETKCR

DPTPVDSGCRGIDSKHWNSYCTTTHTFVKALTMDGKQAAWRFIRI

DTACVCVLSRKAGRRA

SEQ ID NO: 151: Horse Beta-NGF
MSMLFYTLITALLIGTQAEPHTESNVPAGHAIPQAHWTKLQHSLD

TALRRARSAPARAIAARVAGQTRNITVDPKLFKKRRLRSPRVLFS

TQPPPVAADTQDLDFEAGGAASFNRTHRSKRSSSHPVFHRGEFSV

CDSVSVWVGDKTTATDIKGKEVMVLGEVNINNSVFKQYFFETKCR

DPNPVDSGCRGIDSKHWNSYCTTTHTFVKALTMDGKQAAWRFIRI

DTACVCVLSRKTGRKA

SEQ ID NO: 152: Mouse Beta-NGF
MSMLFYTLITAFLIGVQAEPYTDSNVPEGDSVPEAHWTKLQHSLD

TALRRARSAPTAPIAARVTGQTRNITVDPRLFKKRRLHSPRVLFS

TQPPPTSSDTLDLDFQAHGTIPFNRTHRSKRSSTHPVFHMGEFSV

CDSVSVWVGDKTTATDIKGKEVTVLAEVNINNSVFRQYFFETKCR

ASNPVESGCRGIDSKHWNSYCTTTHTFVKALTTDEKQAAWRFIRI

DTACVCVLSRKATRRG

SEQ ID NO: 153: Rat Beta-NGF
MSMLFYTLITAFLIGVQAEPYTDSNVPEGDSVPEAHWTKLQHSLD

TALRRARSAPAEPIAARVTGQTRNITVDPKLFKKRRLRSPRVLFS

TQPPPTSSDTLDLDFQAHGTISFNRTHRSKRSSTHPVFHMGEFSV

CDSVSVWVGDKTTATDIKGKEVTVLGEVNINNSVFKQYFFETKCR

APNPVESGCRGIDSKHWNSYCTTTHTFVKALTTDDKQAAWRFIRI

DTACVCVLSRKAARRG
```

| BETA-NGF Protein Sequence Homology (% Identity) | | | | | | |
|---|---|---|---|---|---|---|
|  | Human | Cynomolgus | Dog | Cat | Horse | Mouse | Rat |
| Human |  | 98.8 | 90.9 | 93.36 | 94.19 | 85.1 | 85.9 |
| Cynomolgus | 98.8 |  | 90.9 | 93.36 | 94.19 | 83.5 | 86.2 |
| Dog | 90.9 | 90.9 |  | 95.02 | 93.36 | 82.2 | 85.1 |
| Cat | 93.36 | 93.36 | 95.02 |  | 95.02 | 82.16 | 85.06 |
| Horse | 94.19 | 94.19 | 93.36 | 95.02 |  | 84.23 | 87.14 |
| Mouse | 85.1 | 83.5 | 82.2 | 82.16 | 84.23 |  | 95.9 |
| Rat | 85.9 | 86.2 | 85.1 | 85.06 | 87.14 | 95.9 |  |

SEQUENCE LISTING

```
Sequence total quantity: 159
SEQ ID NO: 1            moltype = AA  length = 454
FEATURE                 Location/Qualifiers
source                  1..454
                        mol_type = protein
                        organism = synthetic construct
SEQUENCE: 1
EVQLVESGGG LVQPGGSLRL SCAASGFTFS DAWMDWVRQA PGKGLEWVAE IRNKANNHAR   60
HYAESVKGRF TISRDNAKNS LYLQMNSLRA EDTAVYYCAR TYYYGSSYGY CDVWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                              454

SEQ ID NO: 2            moltype = AA  length = 214
FEATURE                 Location/Qualifiers
source                  1..214
                        mol_type = protein
                        organism = synthetic construct
SEQUENCE: 2
DIQMTQSPSS LSASVGDRVT ITCRTSENIY SYLAWYQQKP GKAPKLLIYN AKTLAEGVPS   60
RFSGSGSGTD FTLTISSLQP EDFATYYCQH HYGTPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 3                moltype = AA  length = 444
FEATURE                     Location/Qualifiers
source                      1..444
                            mol_type = protein
                            organism = synthetic construct
SEQUENCE: 3
EVQLLESGGG LVQPGGSLRL SCAASGFTFS DAWMDWVRQA PGKGLEWVAE IRHKANDHAI   60
FYDESVKGRF TISRDSKNTV YLQMNSLRAE DTAVYYCTSP FAYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 4                moltype = AA  length = 214
FEATURE                     Location/Qualifiers
source                      1..214
                            mol_type = protein
                            organism = synthetic construct
SEQUENCE: 4
DIQMTQSPSS LSASVGDRVT ITCKASQSVG TTIVWTQQLP GKAPKLLIYS ASNRHTGVPS   60
RFSGSGSGTD FTFTISSLQP EDFATYYCQQ YTSYPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 5                moltype = AA  length = 446
FEATURE                     Location/Qualifiers
source                      1..446
                            mol_type = protein
                            organism = synthetic construct
SEQUENCE: 5
QVQLQESGPG LVKPSETLSL TCTVSGFSLI GYDLNWIRQP PGKGLEWIGI IWGDGTTDYN   60
SAVKSRVTIS KDTSKNQFSL KLSSVTAADT AVYYCARGGY WYATSYYFDY WGQGTLVTVS  120
SASTKGPSVF PLAPCSRSTS ESTAALGCLV KDYFPEPVTV SWNSGALTSG VHTFPAVLQS  180
SGLYSLSSVV TVPSSNFGTQ TYTCNVDHKP SNTKVDKTVE RKCCVECPPC PAPPVAGPSV  240
FLFPPKPKDT LMISRTPEVT CVVVDVSHED PEVQFNWYVD GVEVHNAKTK PREEQFNSTF  300
RVVSVLTVVH QDWLNGKEYK CKVSNKGLPS SIEKTISKTK GQPEPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                       446

SEQ ID NO: 6                moltype = AA  length = 214
FEATURE                     Location/Qualifiers
source                      1..214
                            mol_type = protein
                            organism = synthetic construct
VARIANT                     190
                            note = X can be any amino acid
SEQUENCE: 6
DIQMTQSPSS LSASVGDRVT ITCRASQSIS NNLNWYQQKP GKAPKLLIYY TSRFHSGVPS   60
RFSGSGSGTD FTFTISSLQP EDIATYYCQQ EHTLPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHX VYACEVTHQG LSSPVTKSFN RGEC                              214

SEQ ID NO: 7                moltype = AA  length = 449
FEATURE                     Location/Qualifiers
source                      1..449
                            mol_type = protein
                            organism = synthetic construct
SEQUENCE: 7
EVQLVESGGG LVQPGGSLRL SCAASGFTLR SYSMNWVRQA PGKGLEWVSY ISRSSHTIFY   60
ADSVKGRFTI SRDNAKNSLY LQMDSLRDED TAMYYCARVY SSGWHVSDYF DYWGQGILVT  120
VSSASTKGPS VFPLAPCSRS TSESTAALGC LVKDYFPEPV TVSWNSGALT SGVHTFPAVL  180
QSSGLYSLSS VVTVPSSNFG TQTYTCNVDH KPSNTKVDKT VERKCCVECP PCPAPPVAGP  240
SVFLFPPKPK DTLMISRTPE VTCVVVDVSH EDPEVQFNWY VDGVEVHNAK TKPREEQFNS  300
TFRVVSVLTV VHQDWLNGKE YKCKVSNKGL PAPIEKTISK TKGQPREPQV YTLPPSREEM  360
TKNQVSLTCL VKGFYPSDIA VEWESNGQPE NNYKTTPPML DSDGSFFLYS KLTVDKSRWQ  420
QGNVFSCSVM HEALHNHYTQ KSLSLSPGK                                    449

SEQ ID NO: 8                moltype = AA  length = 214
FEATURE                     Location/Qualifiers
source                      1..214
                            mol_type = protein
                            organism = synthetic construct
SEQUENCE: 8
AIQLTQSPSS LSASVGDRVT ITCRASQGIS SALAWYQQKP GKAPKLLIYD ASSLESGVPS   60
RFSGSGSGTD FTLTISSLQP EDFATYYCQQ FNSYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 9              moltype = AA  length = 445
FEATURE                   Location/Qualifiers
source                    1..445
                          mol_type = protein
                          organism = synthetic construct
SEQUENCE: 9
QVQLVQSGAE VKKPGASVKV SCKVSGFTLT ELSIHWVRQA PGKGLEWMGG FDPEDGETIY     60
AQKFQGRVTM TEDTSTDTAY MELTSLRSED TAVYYCSTIG VVTNFDNWGQ GTLVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGK                                         445

SEQ ID NO: 10             moltype = AA  length = 214
FEATURE                   Location/Qualifiers
source                    1..214
                          mol_type = protein
                          organism = synthetic construct
SEQUENCE: 10
DIQMTQSPSS LSASAGDRVT ITCRASQAIR NDLGWYQQKP GKAPKRLIYA AFNLQSGVPS     60
RFSGSGSGTE FTLTISSLQP EDLASYYCQQ YNRYPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 11             moltype = AA  length = 10
FEATURE                   Location/Qualifiers
source                    1..10
                          mol_type = protein
                          organism = synthetic construct
SEQUENCE: 11
GRTVSSYAMG                                                            10

SEQ ID NO: 12             moltype = AA  length = 5
FEATURE                   Location/Qualifiers
source                    1..5
                          mol_type = protein
                          organism = synthetic construct
SEQUENCE: 12
SYWMH                                                                  5

SEQ ID NO: 13             moltype = AA  length = 16
FEATURE                   Location/Qualifiers
source                    1..16
                          mol_type = protein
                          organism = synthetic construct
SEQUENCE: 13
RSSKSLLYKD GKTYLY                                                     16

SEQ ID NO: 14             moltype = AA  length = 460
FEATURE                   Location/Qualifiers
source                    1..460
                          mol_type = protein
                          organism = synthetic construct
SEQUENCE: 14
KEACPTGLYT HSGECCKACN LGEGVAQPCG ANQTVCEPCL DSVTFSDVVS ATEPCKPCTE     60
CVGLQSMSAP CVEADDAVCR CAYGYYQDET TGRCEACRVC EAGSGLVFSC QDKQNTVCEE    120
CPDGTYSDEA NHVDPCLPCT VCEDTERQLR ECTRWADAEC EEIPGRWITR STPPEGSDST    180
APSTQEPEAP PEQDLIASTV AGVVTTVMGS SQPVVTRGTT DNDIEGRMDP KSCDKTHTCP    240
PCPAPEAAGG PSVFLFPPKP KDTLMISRTP EVTCVVVDVS HEDPEVKFNW YVDGVEVHNA    300
KTKPREEQYN STYRVVSVLT VLHQDWLNGK EYKCKVSNKA LPAPIEKTIS KAKGQPREPQ    360
VYTLPPSRDE LTKNQVSLTC LVKGFYPSDI AVEWESNGQP ENNYKTTPPV LDSDGSFFLY    420
SKLTVDKSRW QQGNVFSCSV MHEALHNHYT QKSLSLSPGK                          460

SEQ ID NO: 15             moltype = AA  length = 614
FEATURE                   Location/Qualifiers
source                    1..614
                          mol_type = protein
                          organism = synthetic construct
SEQUENCE: 15
AAPCPDACCP HGSSGLRCTR DGALDSLHHL PGAENLTELY IENQQHLQHL ELRDLRGLGE     60
LRNLTIVKSG LRFVAPDAFH FTPRLSRLNL SFNALESLSW KTVQGLSLQE LVLSGNPLHC    120
SCALRWLQRW EEEGLGGVPE QKLQCHGQGP LAHMPNASCG VPTLKVQVPN ASVDVGDDVL    180
LRCQVEGRGL EQAGWILTEL EQSATVMKSG GLPSLGLTLA NVTSDLNRKN VTCWAENDVG    240
RAEVSVQVNV SFPASVQLHT AVEMHHWCIP FSVDGQPAPS LRWLFNGSVL NETSFIFTEF    300
LEPAANETVR HGCLRLNQPT HVNNGNYTLL AANPFGQASA SIMAAFMDNP FEFNPEDPIP    360
VSFSPVDTNS TSGDPVEIEG RIDPKSCDKT HTCPPCPAPE AAGGPSVFLF PPKPKDTLMI    420
```

```
SRTPEVTCVV VDVSHEDPEV KFNWYVDGVE VHNAKTKPRE EQYNSTYRVV SVLTVLHQDW   480
LNGKEYKCKV SNKALPAPIE KTISKAKGQP REPQVYTLPP SRDELTKNQV SLTCLVKGFY   540
PSDIAVEWES NGQPENNYKT TPPVLDSDGS FFLYSKLTVD KSRWQQGNVF SCSVMHEALH   600
NHYTQKSLSL SPGK                                                    614

SEQ ID NO: 16           moltype = AA  length = 454
FEATURE                 Location/Qualifiers
source                  1..454
                        mol_type = protein
                        organism = synthetic construct
SEQUENCE: 16
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
AAGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVCTLPP   360
SRDELTKNQV SLSCAVKGFY PSDIAVEWES NGQPENNYKT TPPVLDSDGS FFLVSKLTVD   420
KSRWQQGNVF SCSVMHEALH NHYTQKSLSL SPGK                              454

SEQ ID NO: 17           moltype = DNA  length = 1362
FEATURE                 Location/Qualifiers
source                  1..1362
                        mol_type = other DNA
                        organism = synthetic construct
SEQUENCE: 17
gaagtccaac ttgtggaaag tggtggggga cttgtgcaac ctggcggatc actccgtctc    60
agttgtgccg ctagtggttt tacctttttcc gatgcttgga tggattgggt tagacaagct   120
cctgggaaag gattggagtg ggttgcagaa atccgcaaca aggcaaataa ccacgccaga   180
cactacgctg agagtgtcaa aggtcgcttt actataagta gataacgac caaaaatagt   240
ctttacttgc aaatgaactc cctccgggcc gaggacactg ctgtttacta ctgcgcaagg   300
acatactatt acgtagctc atacggatat tgtgatgttt ggggacaagg tacactcgtt   360
accgtcagta cgctagcac taaggggcca tcagtattcc ccctggctcc cagctccaaa   420
tctacctcag gaggaacagc agctctgggt tgccttgtaa aagactactt tcctgaacct   480
gttactgtta gctggaatag tggagctctt acaagcggcg tacatacttt ccctgccgtg   540
ttgcagtcta gtggtctta ctctctttct tctgtagtaa ctgtacctag tagctccttg   600
ggtacacaaa cctacatatg taacgtcaat cataagccta gcaataccaa agtagataaa   660
aaagttgagc ctaaaagttg tgacaaaacc cacacttgcc ctcctgccc tgcacccgag   720
gccgcagggg gaccctcagt cttcctgttt cctccaaaac ctaaagacac tttgatgata   780
tccaggaccc ccgaggtaac ctgtgtggtt gtagatgtta gccatgaaga tcccgaggta   840
aagttcaact ggtatgttga tggggtagag gtgcataacg ctaaaactaa acctcggag   900
gaacagtaca attcaactta cagggttgta agcgtactca cagtcctgca ccaagactgg   960
ctgaatggca aggagtataa atgtaaagta tcctaacagg cactgcccgc tcctattgaa  1020
aagacaatat caaaagctaa ggggcagcca cgagaaccc aggtgtgcac cctcccccca  1080
tccagagatg aacttaccaa aaatcaagtg agcttgtcct gcgctgtcaa aggattctat  1140
ccttcagata tagccgtgga gtgggaaagt aacggccagc ctgaaaacaa ttataagaca  1200
acaccacccg tgctggacag cgatggtagt ttttttctgg tcagcaagtt gactgtagat  1260
aagtctcgat ggcagcaggg caatgttttc agttgttctg taatgcacga agctcttcat  1320
aatcactata ctcagaagtc tctttcactt agccccggca aa                    1362

SEQ ID NO: 18           moltype = AA  length = 214
FEATURE                 Location/Qualifiers
source                  1..214
                        mol_type = protein
                        organism = synthetic construct
SEQUENCE: 18
DIQMTQSPSS LSASVGDRVT ITCRTSENIY SYLAWYQQKP GKAPKLLIYN AKTLAEGVPS    60
RFSGSGSGTD FTLTISSLQP EDFATYYCQH HYGTPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 19           moltype = DNA  length = 642
FEATURE                 Location/Qualifiers
source                  1..642
                        mol_type = other DNA
                        organism = synthetic construct
SEQUENCE: 19
gacatacaaa tgactcaatc tccatcttcc ttgtctgctt cagtaggaga ccgagttaca    60
attacttgcc gcacttccga gaacatttac tcatatctgg cttggtatca gcaaaagcca   120
ggtaaggccc caaaactcct tatctataat gctaagactc ttgctgaggg agtacccagt   180
aggttttccg gttccggttc aggcacagat ttcacactca ctatttcttc actccagcct   240
gaggacttcg ctacttatta ttgccaacat cactacggga caccctggac tttcgggcaa   300
gggactaaac tggaaataaa acgtaccgtg gctgccccaa gtgtcttcat atttccccca   360
tctgatgagc aactcaaatc aggtactgct tctgttgttt gccttctcaa cattttttat   420
ccacgtgagc aaaagtcca gtggaaggtg acaacgccc tgcaatcagg taacagtcag   480
gagtcagtga cagaacaaga tagcaaagac agtacttatt cccttccag caccctgacc   540
ctctctaaag ctgactatga aaacataag gtctacgcct gtgaagtaac acatcaaggt   600
cttttcatctc cagtcaccaa gtctttcaac agggggggagt gt                   642
```

```
SEQ ID NO: 20               moltype = AA    length = 455
FEATURE                     Location/Qualifiers
source                      1..455
                            mol_type = protein
                            organism = synthetic construct
SEQUENCE: 20
QVQLQESGPG LVKPSETLSL TCTVSGFSLI GYDLNWIRQP PGKGLEWIGI IWGDGTTDYN    60
SAVKSRVTIS KDTSKNQFSL KLSSVTAADT AVYYCARGGY WYATSYYFDY WGQGTLVTVS   120
SASVAAPSVF IFPPSDEQLK SGTASVVCLL NNFYPREAKV QWKVDNALQS GNSQESVTEQ   180
DSKDSTYSLS STLTLSKADY EKHKVYACEV THQGLSSPVT KSFNRGECDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PCRDELTKNQ VSLWCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 21               moltype = DNA   length = 1365
FEATURE                     Location/Qualifiers
source                      1..1365
                            mol_type = other DNA
                            organism = synthetic construct
SEQUENCE: 21
caggtgcagc tccaagaatc aggcccaggc ttggtgaaac cctcagaaac tctcagcctc    60
acatgcactg tgtctggctt tagcctgatt ggttatgacc tcaactggat tcgtcaaccc   120
cccggcaagg gtctgaatg gatcggaatc atctggggag atggaactac agactacaat   180
agtgccgtaa agtcccgagt gacaataagt aaagacacat ccaagaacca gttttcactc   240
aaacttttcct cagtcaccgc tgctgacaca gcagtctatt attgcgcaag aggtggatac   300
tggtatgcta caagctacta cttcgattac tggggacagg gtaccttgt gaccgtatcc   360
tccgcatccg tggcagcccc tagtgtattc atcttccctc cttcagatga gcaactcaag   420
tcaggaactg cctcagtcgt gtgtttgttg aataacttct acccacgtga agccaaagtc   480
caatggaagt tcgataatgc cttgcaatcc gggaacagtc aagagtcagt gaccgagcag   540
gacagtaaag acagtactta ctctttgtca tctaccctta cccttccaa ggctgactac   600
gagaaacata aggtgtacgc ttgcgaagta actcaccagg gactcagtag cccagttacc   660
aaatcattca cagaggaga atgtgataag actcatacct gcccccctg tcctgctccc   720
gaggctgctg ggggcccatc tgtctttctg tttcccccaa agcctaagga tactctgatg   780
atttctcgaa ctcccgaggt cacttgcgta gtagtagacg tcagtcacga agacccagaa   840
gtcaagttca attggtatgt agatggggta gaagtgcata atgctaagac taaacctcga   900
gaggagcagt acaactcaac ttacagggtc gttagcgtat tgaccgtcct ccatcaagat   960
tggctcaacg gaaaagaata caaatgtaaa gtgtctaata aggcccctgcc cgcacctatc  1020
gaaaaaacaa tctctaaggc taaagggcag ccacgtgaac cacaagtata tactctgcca  1080
ccttgccgcg atgagttgac taaaaaccag gtgagtttgt ggtgtttggt aaaaggctt   1140
tacccttctg acatagccgt ggaatgggag tccaacgggc aaccagagaa caattacaa   1200
acaactcctc ctgtcctgga cagtgacggt tcttttttc tctattcaaa gctgaccgtg  1260
gacaagtcaa gatggcaaca gggcaacgtc ttctcttgta gtgtgatgca cgaagccttg  1320
cataatcatt atacccagaa atccctttca ctctctcctg gtaag                  1365

SEQ ID NO: 22               moltype = AA    length = 212
FEATURE                     Location/Qualifiers
source                      1..212
                            mol_type = protein
                            organism = synthetic construct
SEQUENCE: 22
DIQMTQSPSS LSASVGDRVT ITCRASQSIS NNLNWYQQKP GKAPKLLIYY TSRFHSGVPS    60
RFSGSGSGTD FTFTISSLQP EDIATYYCQQ EHTLPYTFGQ GTKVTVLSSA STKGPSVFPL   120
APSSKSTSGG TAALGCLVKD YFPEPVTVSW NSGALTSGVH TFPAVLQSSG LYSLSSVVTV   180
PSSSLGTQTY ICNVNHKPSN TKVDKKVEPK SC                                 212

SEQ ID NO: 23               moltype = DNA   length = 636
FEATURE                     Location/Qualifiers
source                      1..636
                            mol_type = other DNA
                            organism = synthetic construct
SEQUENCE: 23
gacatacaga tgacacagag cccctcttcc ttgtctgctt ctgtgggtga tcgcgtcaca    60
attacctgcc gcgctagtca atccatatca aacaacctga actggtatca acagaagccc   120
ggaaaggccc ccaagctcct catttactac acatccagat tccactccgg tgttccatct   180
aggttcagcg gctcagggtc tggcacagac ttcacattca aatcagctc acttcagccc   240
gaggacatag ctacatacta ttgtcagcag gaacacacac tcccttacac atttggccaa   300
ggaaccaaag taactgtact tcatccgca agcactaagg gtccatcagt ctttccactt   360
gcaccttcat ctaaatccac ctcaggtggt actgcagcac tcggttgtt ggtaaaagat   420
tactttcctg agccagtgac tgttagctgg aatagtggag ccttacctc cggtgtccat   480
acattccccg ctgtgttgca atcatctggt ctctattccc tttcatcgt agttaccgtc   540
cctagctcct ctctgggcac acaaacatat atttgtaacg tgaaccataa accctccaac   600
accaaagttg ataagaaggt cgagcccaaa tcttgt                             636

SEQ ID NO: 24               moltype = AA    length = 581
FEATURE                     Location/Qualifiers
source                      1..581
                            mol_type = protein
                            organism = synthetic construct
```

```
SEQUENCE: 24
EVQLVESGGG LVQPGGSLRL SCAASGFTFS DAWMDWVRQA PGKGLEWVAE IRNKANNHAR   60
HYAESVKGRF TISRDNAKNS LYLQMNSLRA EDTAVYYCAR TYYYGSSYGY CDVWGQGTLV  120
TVSSASTKGP QVQLQESGPG LVKPSETLSL TCTVSGFSLI GYDLNWIRQP PGKGLEWIGI  180
IWGDGTTDYN SAVKSRVTIS KDTSKNQFSL KLSSVTAADT AVYYCARGGY WYATSYYFDY  240
WGQGTLVTVS SASTKGPSVF PLAPSSKSTS GGTAALGCLV KDYFPEPVTV SWNSGALTSG  300
VHTFPAVLQS SGLYSLSSVV TVPSSSLGTQ TYICNVNHKP SNTKVDKKVE PKSCDKTHTC  360
PPCPAPEAAG GPSVFLFPPK PKDTLMISRT PEVTCVVVDV SHEDPEVKFN WYVDGVEVHN  420
AKTKPREEQY NSTYRVVSVL TVLHQDWLNG KEYKCKVSNK ALPAPIEKTI SKAKGQPREP  480
QVYTLPPSRD ELTKNQVSLT CLVKGFYPSD IAVEWESNGQ PENNYKTTPP VLDSDGSFFL  540
YSKLTVDKSR WQQGNVFSCS VMHEALHNHY TQKSLSLSPG K                     581

SEQ ID NO: 25           moltype = DNA  length = 1743
FEATURE                 Location/Qualifiers
source                  1..1743
                        mol_type = other DNA
                        organism = synthetic construct
SEQUENCE: 25
gaagtacaat tggtggaaag cggcggaggc cttgtccaac tggcggttc tttgcggctg    60
tcctgtgccg ctagtggttt tacctttagt gatgcctgga tggactgggt gcggcaggcc  120
cctggtaagg gcctggaatg ggtcgctgaa ataagaaata aggcaaataa ccatgcaaga  180
cattacgctg aaagtgtgaa gggcaggttc actatatccc gagataacgc aaagaacagt  240
ttgtaccttc agatgaactc cttgcgtgcc gaggataccg ccgtctacta ctgcgctcgc  300
acatactact acggttcatc atacgggtac tgcgacgtct gggggcaagg aacacttgtc  360
accgtttctt ctgcctctac taaggacacc caggttcagt tgcaggagtc cgggcccggt  420
ctggtaaagc cttctgaaac cctgagtttg acctgtaccg tgtccggttc ctcactgatt  480
ggctatgatc tcaactggat acgacagccc cccgggaagg gcctggagtg gattggcatc  540
atctggggag atggaaccac cgactacaac tccgctgtca aaagtagagt gactatttcc  600
aaagacacca gcaagaacca attctcactg aaattgagtt cagttacagc tgccgacact  660
gctgttttat attgtgcaag aggggggatat tggtatgcaa cttcctatta ttttgactat  720
tggggccagg gaacacttgt aacagtatcc tcagcctcaa caaaaggacc atctgtattt  780
ccccttgcac ccagttcaaa gtctacttca ggtgggactg ccgctctcgg ctgtctggta  840
aaagattatt tccccgagcc agttactgta agttggaata gcggtgcact gacaagtggg  900
gtccatactt tccctgccgt gcttcagagt tccggccttt attcactcte tagtgtagtt  960
accgttccct catcctagcct tggaacccaa acctatatct gtaatgtgaa tcataaacca  1020
tctaatacta aggttgataa aaaggttgaa cctaagagct gcgataaaac acatacctgt  1080
cctccttgtc ctgctcctga agctgctggt ggaccttcag tgtttctgtt ccccccccaag 1140
ccaaaagata cactgatgat ctccgtgact cctgaggtta cttgtgtcgt cgtcgatgtg  1200
tcacacgaag atcccgaagt gaagttcaac tggtacgtcg atggtgttga agtacacaat  1260
gccaaaacaa aacccagaga ggagcaatac aatagtacat accgcgtagt gtctgttctc  1320
accgtattgc atcaggactg gctgaacggt aaagagtaca aatgtaaagt ttctaataaa  1380
gcactcccag cccctataga aaagaccatc agcaaagcta aagggcagcc ccgtgagcca  1440
caagtctaca cattgcctcc tagtagggat gagctgacaa aaaatcaagt gtccctgacc  1500
tgcctcgtga aaggatttta tccttctgat atagcagttg aatgggaatc caacggtcaa  1560
cctgagaata attataagac cactccccca gtgctggatt ctgatggcag tttcttcttg  1620
tattctaaat tgactgtcga caaatcccgt tggcaacagg gaaatgtgtt ttcatgctct  1680
gttatgcacg aggctttgca caatcactac actcagaagt ccctgagctt gtctccagga  1740
aaa                                                                1743

SEQ ID NO: 26           moltype = AA  length = 327
FEATURE                 Location/Qualifiers
source                  1..327
                        mol_type = protein
                        organism = synthetic construct
SEQUENCE: 26
DIQMTQSPSS LSASVGDRVT ITCRTSENIY SYLAWYQQKP GKAPKLLIYN AKTLAEGVPS   60
RFSGSGSGTD FTLTISSLQP EDFATYYCQH HYGTPWTFGQ GTKLEIKRTV AAPDIQMTQS  120
PSSLSASVGD RVTITCRASQ SISNNLNWYQ QKPGKAPKLL IYYTSRFHSG VPSRFSGSGS  180
GTDFTFTISS LQPEDIATYY CQQEHTLPYT FGQGTKLEIK RTVAAPSVFI FPPSDEQLKS  240
GTASVVCLLN NFYPREAKVQ WKVDNALQSG NSQESVTEQD SKDSTYSLSS TLTLSKADYE  300
KHKVYACEVT HQGLSSPVTK SFNRGEC                                      327

SEQ ID NO: 27           moltype = DNA  length = 981
FEATURE                 Location/Qualifiers
source                  1..981
                        mol_type = other DNA
                        organism = synthetic construct
SEQUENCE: 27
gacatacaga tgacacagtc tcctagctcc ctgtccgcaa gcgttggaga tagagtcaca   60
ataacttgta gaacatcaga aacatatat agctacttgg cttggtacca acagaagcct  120
ggtaaggcac ccaagctcct catatacaac gccaagaccc ttgccgaggg tgtgccaagc  180
agattcagcg gtcagggag cgggaccgat tttacactta ctatttcctc tttgcagccc  240
gaagactttg ctacttacta ctgtcagcac cactacggca ctccttggac tttcggacaa  300
ggtactaaac ttgaaataaa gaggaccgta gccgccccta tatacagat gactcaaagt  360
cctagttccc tttccgctag cgtaggagac gcgtaacaa ttacctgtag agcatcacaa  420
agtataagca acaatctgaa ctggtaccag cagaaacctg gaaggccccc taagttgctg  480
atctattaca cctccaggtt tcatagtggc gtaccatctc gtttcagtgg atcaggttcc  540
ggcaccgatt tcactttttac catatcctca ctccagcccg aagatatcgc tacctactat  600
tgtcaacagg aacacaccct tccttataca tttgggcagg ggaccaagct tgagatcaaa  660
```

```
cggactgtgg cagcacctag tgtcttcata ttccccccctt ccgacgagca actgaaaagt    720
ggtactgctt cagtagtttg cttgttgaac aacttctatc cacgcgaagc aaaagtgcaa    780
tggaaggtcg ataacgcact tcaatctggt aactctcaag aaagtgtcac agagcaggac    840
agtaaggata gtacatatag ccttagttca cactgactc tttctaaggc cgattatgag    900
aaacacaagg tatacgcttg tgaagtgacc caccaggac tttctagccc agttaccaaa    960
tccttcaaca gaggagagtg c                                              981

SEQ ID NO: 28             moltype = AA  length = 581
FEATURE                   Location/Qualifiers
source                    1..581
                          mol_type = protein
                          organism = synthetic construct
SEQUENCE: 28
QVQLQESGPG LVKPSETLSL TCTVSGFSLI GYDLNWIRQP PGKGLEWIGI IWGDGTTDYN    60
SAVKSRVTIS KDTSKNQFSL KLSSVTAADT AVYYCARGGY WYATSYYFDY WGQGTLVTVS   120
SASTKGPEVQ LVESGGGLVQ PGGSLRLSCA ASGFTFSDAW MDWVRQAPGK GLEWVAEIRN   180
KANNHARHYA ESVKGRFTIS RDNAKNSLYL QMNSLRAEDT AVYYCARTYY YGSSYGYCDV   240
WGQGTLVTVS SASTKGPSVF PLAPSSKSTS GGTAALGCLV KDYFPEPVTV SWNSGALTSG   300
VHTFPAVLQS SGLYSLSSVV TVPSSSLGTQ TYICNVNHKP SNTKVDKKVE PKSCDKTHTC   360
PPCPAPEAAG GPSVFLFPPK PKDTLMISRT PEVTCVVVDV SHEDPEVKFN WYVDGVEVHN   420
AKTKPREEQY NSTYRVVSVL TVLHQDWLNG KEYKCKVSNK ALPAPIEKTI SKAKGQPREP   480
QVYTLPPSRD ELTKNQVSLT CLVKGFYPSD IAVEWESNGQ PENNYKTTPP VLDSDGSFFL   540
YSKLTVDKSR WQQGNVFSCS VMHEALHNHY TQKSLSLSPG K                        581

SEQ ID NO: 29             moltype = DNA  length = 1743
FEATURE                   Location/Qualifiers
source                    1..1743
                          mol_type = other DNA
                          organism = synthetic construct
SEQUENCE: 29
caggtacagc tccaggaatc cgggcccggt cttgtgaaac cttcagaaac actgtctttg    60
acttgtacag tgagtggatt ttctctcatc gggtacgatc tcaactggat ccggcaacct   120
cctgggaaag gtctcgaatg gataggggatc atctggggcg atggcactac cgattataat   180
tcagccgtga agtctcgagt aacaatctcc aaggatacca gtaagaacca gtttagtctg   240
aaactcagct ctgttacagc cgccgacaca gctgtctact attgcgcag ggggagggtat   300
tggtatgcta ccagttatta tttcgactat tggggacagg gaactttggt aaccgtcagt   360
agtgcatcta ctaaaggccc cgaggtccag cttgttgagt ctgggggtgg tctcgtccaa   420
cctgggggtt ccttgcggct gtcatgtgca gcttccggct tcacttttag tgatgcttgg   480
atggattggg tccggcaggc cccaggtaag ggtttggcga aataagaaat                540
aaggccaaca atcatgctcg ccactacgca gagtccgtaa aaggacgatt acaatcagc    600
cgtgacaacg caaaaatag cttgtatctt caaatgaaca gtttgagggc tgaggataca    660
gcagtgtatt actgtgctcg aacttactac tacgggagta gttatggtta ctgtgatgta   720
tggggtcagg gaactcttgg taaccgtctca agccgcttcaa ctaaaggtcc ttcagtattc   780
cccttggctc caagctccaa gagtaccagt ggcggtaccg cagctttggg ctgcctggta   840
aaagattatt tcccagaacc agtaactgta agctggaata cgggggcttt gacatcaggg   900
gtacacacct ttccagctgt gcttcagtct tcaggcttgt acagtttgtc ttccgtagtc    960
acagtcccat cttctagtct ggggacccaa acctatatct gtaatgtcaa tcataagcgt   1020
tcaaatacaa aagtggacaa aaaagtagag cctaagagct gtgataaaac acatacatgc   1080
cctccttgtc ctgcccccga agccgccggc ggtccctcag tatttctttt tccaccaaaa   1140
cccaaagata ccctcatgat cagtcgcacc ccagaagtca cctgtgtcgt ggtagatgta   1200
agccacgagg atcccgaggt caaattcaac tggtatgtgg atggcgtaga agttcacaac   1260
gccaagacaa agcccaggga agaacagtac aattcaacct acagggttgt ctctgtactg   1320
accgtccttc accaagactg gttgaacggt aaagagtata atgtaaggt atccaacaaa   1380
gctttgccag caccctataga gaaaaccatc tccaaagcta agggtcaacc cagagagcca   1440
caagtgtata ccctgcctcc cagtagagat gaactgacaa agaaccaagt ttctctgact   1500
tgcttggtca aagggttcta tcctagcgac atcgctgtag aatgggaatc aaatggacaa   1560
cctgaaaata actacaagac taccccaccc gtgcttgaca gtgatggcag ttttttcctt   1620
tacagtaagc tcactgtcga caagagccga tggcagcaag caacgtctt ctcttgttcc    1680
gttatgcatg aggccctcca caaccattat acccaaaaga gtttgtcatt gtcccctggt   1740
aaa                                                                 1743

SEQ ID NO: 30             moltype = AA  length = 327
FEATURE                   Location/Qualifiers
source                    1..327
                          mol_type = protein
                          organism = synthetic construct
SEQUENCE: 30
DIQMTQSPSS LSASVGDRVT ITCRASQSIS NNLNWYQQKP GKAPKLLIYY TSRFHSGVPS    60
RFSGSGSGTD FTFTISSLQP EDIATYYCQQ EHTLPYTFGQ GTKLEIKRTV AAPDIQMTQS   120
PSSLSASVGD RVTITCRTSE NIYSYLAWYQ QKPGKAPKLL IYNAKTLAEG VPSRFSGSGS   180
GTDFTLTISS LQPEDFATYY CQHHYGTPWT FGQGTKLEIK RTVAAPSVFI FPPSDEQLKS   240
GTASVVCLLN NFYPREAKVQ WKVDNALQSG NSQESVTEQD SKDSTYSLSS TLTLSKADYE   300
KHKVYACEVT HQGLSSPVTK SFNRGEC                                        327

SEQ ID NO: 31             moltype = DNA  length = 981
FEATURE                   Location/Qualifiers
source                    1..981
                          mol_type = other DNA
                          organism = synthetic construct
```

```
SEQUENCE: 31
gacatccaga tgacacagtc accatcctct cttagtgcaa gtgtgggcga tcgggttaca    60
ataacttgta gagcctctca atcaatttca aacaatctga attggtatca acagaagcct   120
ggcaaggcac caaaacttt gatctactac acttcacgtt tccattctgg tgtaccatct   180
cgcttctccg gaagtggaag tggcacagat ttcacattta ccattagttc cttgcagcct   240
gaagatatag ccacttacta ttgtcagcag gaacataccc tgccatacac tttcggccaa   300
ggcacaaaac tcgagatcaa gcgtactgtg gcagccctg atattcagat gacccagtcc   360
ccaagttcac tctcagcttc tgtcggcgac cgtgtaacaa taacctgccg tacctctgaa   420
aacatatact catacttggc ctggtatcaa caaaaaccag gtaaagctcc taagttgctc   480
atctataatg ctaagacttt ggctgaagga gtgcctctc gattctctgg gtcaggatcc   540
ggaacagatt tcacactgac tatatccagc ttgcaaccag aagcttcgc cacttattac   600
tgccaacatc actatgggac accctggaca tttgggcaag aaccaaact ggagataaag   660
cggactgtgg ccgcaccttc cgttttcatc tttccaccct ctgacgaaca actcaaatca   720
ggcactgctt cagtcgtgtg tctcctcaat aattttatc ctcgggaggc taaagtccaa   780
tggaaagtag acaatgccct ccaatccggg aatagtcagg aaagcgtcac agagcaagat   840
tcaaaagaca gtacctactc attgtctagt acccttaccc ttagtaaagc agactacgag   900
aaacataagg tttatgcctg cgaggtgact caccagggt tgtctagccc agtgactaaa   960
tccttcaatc gcgggagtg t                                              981

SEQ ID NO: 32           moltype = AA  length = 712
FEATURE                 Location/Qualifiers
source                  1..712
                        mol_type = protein
                        organism = synthetic construct
SEQUENCE: 32
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
AAGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPGKGGGGSG GGGSGGGGSQ VQLQESGPGL   480
VKPSETLSLT CTVSGFSLIG YDLNWIRQPP GKGLEWIGII WGDGTTDYNS AVKSRVTISK   540
DTSKNQFSLK LSSVTAADTA VYYCARGGYW YATSYYFDYW GQGTLVTVSS GGGGSGGGGS   600
GGGGSDIQMT QSPSSLSASV GDRVTITCRA SQSISNNLNW YQQKPGKAPK LLIYYTSRFH   660
SGVPSRFSGS GSGTDFTFTI SSLQPEDIAT YYCQQEHTLP YTFGQGTKLE IK           712

SEQ ID NO: 33           moltype = DNA  length = 2142
FEATURE                 Location/Qualifiers
source                  1..2142
                        mol_type = other DNA
                        organism = synthetic construct
SEQUENCE: 33
gaggtgcagc tggtggaaag cggcgggggg ctggtgcagc ccggaggctc actgagactg    60
tcttgcgctg ccagcggctt caccttcagc gacgcctgga tggactgggt gaggcaggc   120
cctgggaagg ggctggagtg ggtggctgag atccggaata aggccaataa ccacgccagg   180
cactatgccg agagtgtgaa aggcagattt accatctcta gggacaatgc caagaactca   240
ctgtacctgc agatgaactc cctgagagcc gaggacaccg ccgtgtacta ctgtgccaga   300
acctattact acggaagcag ctacggctat tgcgatgtgt ggggacaggg aaccctggtg   360
actgtgtctt cctgagcctc caccaagggc ccctccgtg tcccactggc cccgagtagc   420
aagtctacct ccggcgggac agccgcactg gctgcctgg tgaaggacta cttccccgag   480
cctgtgacag tgagctggaa ttccggggc ctgacatcag gcgtgcacac cttcccagcc   540
gtgctccaga gctctggcct gtatagtctg agcagtgtgg tgaccgtgcc ctccagctcc   600
ctgggaactc agacctatat ctgtaacgtg aaccacacgc cttctaatac caaggtggat   660
aagaaagtgg aaccaaagtc atgcgacaaa acacacacct gcccccctg ccccgcccct   720
gaagccgccg gcgggcctag cgtgtttctg ttccctccta gcctaagga cactgatg    780
atttccagga ccccgaggt gacctgcgtc gtcgtggacg tgagccacga ggaccccgag   840
gtgaaattca actggtacgt ggacggcgtg gaagtgcaca acgctaaaac caagcctaga   900
gaggaacagt acaactctac acagggtgt gtccgtct tgactgtgct gcaccaggac   960
tggctgaacg gcaaggaata aagtgcaag tgagcaata aagcactccc cgcccccatt   1020
gaaaaaacca tcagcaaggc taagggccaa cctaggaac cacaggtgta ccctgcca   1080
cctagcagag acgagctgac caagaatcag gtgtctctga catgtctggt gaaggggttt   1140
tacccctagcg acattgccgt cgagtgggag tctaatggcc agcctgagaa caattataag   1200
actacccctc ctgtgctgga cagtgatggc tcattttttc tgtactctaa gctgacagtg   1260
gacaagagca ggtggcagca gggcaatgtg ttcagctgca gcgtgatgca cgaggccctg   1320
cataatcatt acccagaa gtctctgtct ctcagcccag gcaaggcgg aggggggtct   1380
ggcggcgggg gttccggcgg cggggctc caggtgcagc tgcagagag cggacctggc   1440
ctgtgaaac ccagcgagac cctgtccctg acatgcacg tgagcggctt ctccctgatc   1500
gggtatgacc tgaattggat ccggcagcct cctggcaagg gtctgagtg atcggaatc   1560
atctgggggcg acggcaccac cgattataac agcgccgtga agtctcgggt gactatctct   1620
aaggatactt ccaagaacca gttttccctg aagctgagct ctgtgaccgc tgccgatacc   1680
gccgtgtact actgcgccag gggcggttac tggtacgcca ccagctacta cttcgactac   1740
tggggccagg gcaccctggt gaccgtgtcc agcggcgtgg gcggttggg cggagcggc   1800
tccggcggcg agggtctga cattcagatg acccagagcc cctcctcct gtctgcctca   1860
gtgggcgaca gagtgaccat cacatgtaga gcctccagt caatatctaa caacctgaat   1920
tggtatcagc agaagcccgg caagccccct aagctgctga tttactacac ttctcgcttt   1980
cactccggag tgcccagcag atttagtggg agcggctctg gacagacttt cacttttacc   2040
atcagtagcc tgcagcccga ggacatcgcc acctattact gccagcagga gcataccctg   2100
```

```
cctacactt tcggacaggg gaccaagctg gagatcaagt ga                    2142

SEQ ID NO: 34           moltype = AA   length = 572
FEATURE                 Location/Qualifiers
source                  1..572
                        mol_type = protein
                        organism = synthetic construct
SEQUENCE: 34
EVQLVESGGG LVQPGGSLRL SCAASGFTFS DAWMDWVRQA PGKGLEWVAE IRHKANDHAI  60
FYDESVKGRF TISRDDSKNT VYLQMNSLRA EDTAVYYCTS PFAYWGQGTL VTVSSASTKG 120
PQVQLQESGP GLVKPSETLS LTCTVSGFSL IGYDLNWIRQ PPGKGLEWIG IIWGDGTTDY 180
NSAVKSRVTI SKDTSKNQFS LKLSSVTAAD TAVYYCARGG YWYATSYYFD YWGQGTLVTV 240
SSASTKGPSV FPLAPSSKST SGGTAALGCL VKDYFPEPVT VSWNSGALTS GVHTFPAVLQ 300
SSGLYSLSSV VTVPSSSLGT QTYICNVNHK PSNTKVDKKV EPKSCDKTHT CPPCPAPEAA 360
GGPSVFLFPP KPKDTLMISR TPEVTCVVVD VSHEDPEVKF NWYVDGVEVH NAKTKPREEQ 420
YNSTYRVVSV LTVLHQDWLN GKEYKCKVSN KALPAPIEKT ISKAKGQPRE PQVYTLPPSR 480
DELTKNQVSL TCLVKGFYPS DIAVEWESNG QPENNYKTTP PVLDSDGSFF LYSKLTVDKS 540
RWQQGNVFSC SVMHEALHNH YTQKSLSLSP GK                              572

SEQ ID NO: 35           moltype = AA   length = 327
FEATURE                 Location/Qualifiers
source                  1..327
                        mol_type = protein
                        organism = synthetic construct
SEQUENCE: 35
DIQMTQSPSS LSASVGDRVT ITCKASQSVG TTIVWYQQKP GKAPKLLIYS ASNRHTGVPS  60
RFSGSGSGTD FTLTISSLQP EDFATYYCQQ YTSYPFTFGQ GTKLEIKRTV AAPDIQMTQS 120
PSSLSASVGD RVTITCRASQ SISNNLNWYQ QKPGKAPKLL IYYTSRFHSG VPSRFSGSGS 180
GTDFTFTISS LQPEDIATYY CQQEHTLPYT FGQGTKLEIK RTVAAPSVFI FPPSDEQLKS 240
GTASVVCLLN NFYPREAKVQ WKVDNALQSG NSQESVTEQD SKDSTYSLSS TLTLSKADYE 300
KHKVYACEVT HQGLSSPVTK SFNRGEC                                    327

SEQ ID NO: 36           moltype = AA   length = 578
FEATURE                 Location/Qualifiers
source                  1..578
                        mol_type = protein
                        organism = synthetic construct
SEQUENCE: 36
QVQLQESGPG LVKPSETLSL TCTVSGFSLI GYDLNWIRQP PGKGLEWIGI IWGDGTTDYN  60
SAVKSRVTIS KDTSKNQFSL KLSSVTAADT AVYYCARGGY WYATSYYFDY WGQGTLVTVS 120
SASTKGPEVQ LVESGGGLVQ PGGSLRLSCA ASGFTFSDAW MDWVRQAPGK GLEWVAEIRH 180
KANDHAIFYD ESVKGRFTIS RDDSKNTVYL QMNSLRAEDT AVYYCTSPFA YWGQGTLVTV 240
SSASTKGPAS TKGPSVFPLA PSSKSTSGGT AALGCLVKDY FPEPVTVSWN SGALTSGVHT 300
FPAVLQSSGL YSLSSVVTVP SSSLGTQTYI CNVNHKPSNT KVDKKVEPKS CDKTHTCPPC 360
PAPEAAGGPS VFLFPPKPKD TLMISRTPEV TCVVVDVSHE DPEVKFNWYV DGVEVHNAKT 420
KPREEQYNST YRVVSVLTVL HQDWLNGKEY KCKVSNKALP APIEKTISKA KGQPREPQVY 480
TLPPSRDELT KNQVSLTCLV KGFYPSDIAV EWESNGQPEN NYKTTPPVLD SDGSFFLYSK 540
LTVDKSRWQQ GNVFSCSVMH EALHNHYTQK SLSLSPGK                        578

SEQ ID NO: 37           moltype = AA   length = 327
FEATURE                 Location/Qualifiers
source                  1..327
                        mol_type = protein
                        organism = synthetic construct
SEQUENCE: 37
DIQMTQSPSS LSASVGDRVT ITCRASQSIS NNLNWYQQKP GKAPKLLIYY TSRFHSGVPS  60
RFSGSGSGTD FTFTISSLQP EDIATYYCQQ EHTLPYTFGQ GTKLEIKRTV AAPDIQMTQS 120
PSSLSASVGD RVTITCKASQ SVGTTIVWYQ QKPGKAPKLL IYSASNRHTG VPSRFSGSGS 180
GTDFTLTISS LQPEDFATYY CQQYTSYPFT FGQGTKLEIK RTVAAPSVFI FPPSDEQLKS 240
GTASVVCLLN NFYPREAKVQ WKVDNALQSG NSQESVTEQD SKDSTYSLSS TLTLSKADYE 300
KHKVYACEVT HQGLSSPVTK SFNRGEC                                    327

SEQ ID NO: 38           moltype = AA   length = 444
FEATURE                 Location/Qualifiers
source                  1..444
                        mol_type = protein
                        organism = synthetic construct
SEQUENCE: 38
EVQLLESGGG LVQPGGSLRL SCAASGFTFS DAWMDWVRQA PGKGLEWVAE IRHKANDHAI  60
FYDESVKGRF TISRDKNTV YLQMNSLRAE DTAVYYCTSP FAYWGQGTLV TVSSASTKGP 120
SVFPLAPSSK STSGGTAALG CLVKDYFPEP VTVSWNSGAL TSGVHTFPAV LQSSGLYSLS 180
SVVTVPSSSL GTQTYICNVN HKPSNTKVDK KVEPKSCDKT HTCPPCPAPE AAGGPSVFLF 240
PPKPKDTLMI SRTPEVTCVV VDVSHEDPEV KFNWYVDGVE VHNAKTKPRE EQYNSTYRVV 300
SVLTVLHQDW LNGKEYKCKV SNKALPAPIE KTISKAKGQP REPQVCTLPP SRDELTKNQV 360
SLSCAVKGFY PSDIAVEWES NGQPENNYKT TPPVLDSDGS FFLVSKLTVD KSRWQQGNVF 420
SCSVMHEALH NHYTQKSLSL SPGK                                       444

SEQ ID NO: 39           moltype = AA   length = 214
FEATURE                 Location/Qualifiers
```

```
source                          1..214
                                mol_type = protein
                                organism = synthetic construct
SEQUENCE: 39
DIQMTQSPSS LSASVGDRVT ITCKASQSVG TTIVWTQQLP GKAPKLLIYS ASNRHTGVPS    60
RFSGSGSGTD FTLTISSLQP EDFATYYCQQ YTSYPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 40                   moltype = AA  length = 702
FEATURE                         Location/Qualifiers
source                          1..702
                                mol_type = protein
                                organism = synthetic construct
SEQUENCE: 40
EVQLLESGGG LVQPGGSLRL SCAASGFTFS DAWMDWVRQA PGKGLEWVAE IRHKANDHAI    60
FYDESVKGRF TISRDSKNTV YLQMNSLRAE DTAVYYCTSP FAYWGQGTLV TVSSASTKGP   120
SVFPLAPSSK STSGGTAALG CLVKDYFPEP VTVSWNSGAL TSGVHTFPAV LQSSGLYSLS   180
SVVTVPSSSL GTQTYICNVN HKPSNTKVDK KVEPKSCDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVYTLPP SRDELTKNQV   360
SLSCLVKGFY PSDIAVEWES NGQPENNYKT TPPVLDSDGS FFLYSKLTVD KSRWQQGNVF   420
SCSVMHEALH NHYTQKSLSL SPGKGGGGSG GGGSGGGGSQ VQLQESGPGL VKPSETLSLT   480
CTVSGFSLIG YDLNWIRQPP GKGLEWIGII WGDGTTDYNS AVKSRVTISK DTSKNQFSLK   540
LSSVTAADTA VYYCARGGYW YATSYYFDYW GQGTLVTVSS GGGGSGGGGS GGGGSDIQMT   600
QSPSSLSASV GDRVTITCRA SQSISNNLNW YQQKPGKAPK LLIYYTSRFH SGVPSRFSGS   660
GSGTDFTFTI SSLQPEDIAT YYCQQEHTLP YTFGQGTKLE IK                     702

SEQ ID NO: 41                   moltype = AA  length = 588
FEATURE                         Location/Qualifiers
source                          1..588
                                mol_type = protein
                                organism = synthetic construct
SEQUENCE: 41
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP SVFPLAPQVQ LQESGPGLVK PSETLSLTCT VSGFSLIGYD LNWIRQPPGK   180
GLEWIGIIWG DGTTDYNSAV KSRVTISKDT SKNQFSLKLS SVTAADTAVY YCARGGYWYA   240
TSYYFDYWGQ GTLVTVSSAS TKGPSVFPLA PSSKSTSGGT AALGCLVKDY FPEPVTVSWN   300
SGALTSGVHT FPAVLQSSGL YSLSSVVTVP SSSLGTQTYI CNVNHKPSNT KVDKKVEPKS   360
CDKTHTCPPC PAPEAAGGPS VFLFPPKPKD TLMISRTPEV TCVVVDVSHE DPEVKFNWYV   420
DGVEVHNAKT KPREEQYNST YRVVSVLTVL HQDWLNGKEY KCKVSNKALP APIEKTISKA   480
KGQPREPQVY TLPPSRDELT KNQVSLTCLV KGFYPSDIAV EWESNGQPEN NYKTTPPVLD   540
SDGSFFLYSK LTVDKSRWQQ GNVFSCSVMH EALHNHYTQK SLSLSPGK               588

SEQ ID NO: 42                   moltype = AA  length = 334
FEATURE                         Location/Qualifiers
source                          1..334
                                mol_type = protein
                                organism = synthetic construct
SEQUENCE: 42
DIQMTQSPSS LSASVGDRVT ITCRTSENIY SYLAWYQQKP GKAPKLLIYN AKTLAEGVPS    60
RFSGSGSGTD FTLTISSLQP EDFATYYCQH HYGTPWTFGQ GTKLEIKRTV AAPSVFIFPP   120
DIQMTQSPSS LSASVGDRVT ITCRASQSIS NNLNWYQQKP GKAPKLLIYY TSRFHSGVPS   180
RFSGSGSGTD FTFTISSLQP EDIATYYCQQ EHTLPYTFGQ GTKLEIKRTV AAPSVFIFPP   240
SDEQLKSGTA SVVCLLNNFY PREAKVQWKV DNALQSGNSQ ESVTEQDSKD STYSLSSTLT   300
LSKADYEKHK VYACEVTHQG LSSPVTKSFN RGEC                               334

SEQ ID NO: 43                   moltype = AA  length = 588
FEATURE                         Location/Qualifiers
source                          1..588
                                mol_type = protein
                                organism = synthetic construct
SEQUENCE: 43
QVQLQESGPG LVKPSETLSL TCTVSGFSLI GYDLNWIRQP PGKGLEWIGI IWGDGTTDYN    60
SAVKSRVTIS KDTSKNQFSL KLSSVTAADT AVYYCARGGY WYATSYYFDY WGQGTLVTVS   120
SASTKGPSVF PLAPEVQLVE SGGGLVQPGG SLRLSCAASG FTFSDAWMDW VRQAPGKGLE   180
WVAEIRNKAN NHARHYAESV KGRFTISRDN AKNSLYLQMN SLRAEDTAVY YCARTYYYGS   240
SYGYCDVWGQ GTLVTVSSAS TKGPSVFPLA PSSKSTSGGT AALGCLVKDY FPEPVTVSWN   300
SGALTSGVHT FPAVLQSSGL YSLSSVVTVP SSSLGTQTYI CNVNHKPSNT KVDKKVEPKS   360
CDKTHTCPPC PAPEAAGGPS VFLFPPKPKD TLMISRTPEV TCVVVDVSHE DPEVKFNWYV   420
DGVEVHNAKT KPREEQYNST YRVVSVLTVL HQDWLNGKEY KCKVSNKALP APIEKTISKA   480
KGQPREPQVY TLPPSRDELT KNQVSLTCLV KGFYPSDIAV EWESNGQPEN NYKTTPPVLD   540
SDGSFFLYSK LTVDKSRWQQ GNVFSCSVMH EALHNHYTQK SLSLSPGK               588

SEQ ID NO: 44                   moltype = AA  length = 334
FEATURE                         Location/Qualifiers
source                          1..334
                                mol_type = protein
```

```
SEQUENCE: 44
DIQMTQSPSS LSASVGDRVT ITCRASQSIS NNLNWYQQKP GKAPKLLIYY TSRFHSGVPS    60
RFSGSGSGTD FTFTISSLQP EDIATYYCQQ EHTLPYTFGQ GTKLEIKRTV AAPSVFIFPP   120
DIQMTQSPSS LSASVGDRVT ITCRTSENIY SYLAWYQQKP GKAPKLLIYY AKTLAEGVPS   180
RFSGSGSGTD FTLTISSLQP EDFATYYCQH HYGTPWTFGQ GTKLEIKRTV AAPSVFIFPP   240
SDEQLKSGTA SVVCLLNNFY PREAKVQWKV DNALQSGNSQ ESVTEQDSKD STYSLSSTLT   300
LSKADYEKHK VYACEVTHQG LSSPVTKSFN RGEC                               334

SEQ ID NO: 45            moltype = AA   length = 579
FEATURE                  Location/Qualifiers
source                   1..579
                         mol_type = protein
                         organism = synthetic construct
SEQUENCE: 45
EVQLVESGGG LVQPGGSLRL SCAASGFTFS DAWMDWVRQA PGKGLEWVAE IRHKANDHAI    60
FYDESVKGRF TISRDDSKNT VYLQMNSLRA EDTAVYYCTS PFAYWGQGTL VTVSSASTKG   120
PSVFPLAPQV QLQESGPGLV KPSETLSLTC TVSGFSLIGY DLNWIRQPPG KGLEWIGIIW   180
GDGTTDYNSA VKSRVTISKD TSKNQFSLKL SSVTAADTAV YYCARGGYWY ATSYYFDYWG   240
QGTLVTVSSA STKGPSVFPL APSSKSTSGG TAALGCLVKD YFPEPVTVSW NSGALTSGVH   300
TFPAVLQSSG LYSLSSVVTV PSSSLGTQTY ICNVNHKPSN TKVDKKVEPK SCDKTHTCPP   360
CPAPEAAGGP SVFLFPPKPK DTLMISRTPE VTCVVVDVSH EDPEVKFNWY VDGVEVHNAK   420
TKPREEQYNS TYRVVSVLTV LHQDWLNGKE YKCKVSNKAL PAPIEKTISK AKGQPREPQV   480
YTLPPSRDEL TKNQVSLTCL VKGFYPSDIA VEWESNGQPE NNYKTTPPVL DSDGSFFLYS   540
KLTVDKSRWQ QGNVFSCSVM HEALHNHYTQ KSLSLSPGK                          579

SEQ ID NO: 46            moltype = AA   length = 334
FEATURE                  Location/Qualifiers
source                   1..334
                         mol_type = protein
                         organism = synthetic construct
SEQUENCE: 46
DIQMTQSPSS LSASVGDRVT ITCKASQSVG TTIVWYQQKP GKAPKLLIYS ASNRHTGVPS    60
RFSGSGSGTD FTLTISSLQP EDFATYYCQQ YTSYPFTFGQ GTKLEIKRTV AAPSVFIFPP   120
DIQMTQSPSS LSASVGDRVT ITCRASQSIS NNLNWYQQKP GKAPKLLIYY TSRFHSGVPS   180
RFSGSGSGTD FTFTISSLQP EDIATYYCQQ EHTLPYTFGQ GTKLEIKRTV AAPSVFIFPP   240
SDEQLKSGTA SVVCLLNNFY PREAKVQWKV DNALQSGNSQ ESVTEQDSKD STYSLSSTLT   300
LSKADYEKHK VYACEVTHQG LSSPVTKSFN RGEC                               334

SEQ ID NO: 47            moltype = AA   length = 585
FEATURE                  Location/Qualifiers
source                   1..585
                         mol_type = protein
                         organism = synthetic construct
SEQUENCE: 47
QVQLQESGPG LVKPSETLSL TCTVSGFSLI GYDLNWIRQP PGKGLEWIGI IWGDGTTDYN    60
SAVKSRVTIS KDTSKNQFSL KLSSVTAADT AVYYCARGGY WYATSYYFDY WGQGTLVTVS   120
SASTKGPSVF PLAPEVQLVE SGGGLVQPGG SLRLSCAASG FTFSDAWMDW VRQAPGKGLE   180
WVAEIRHKAN DHAIFYDESV KGRFTISRDD SKNTVYLQMN SLRAEDTAVY YCTSPFAYWG   240
QGTLVTVSSA STKGPASTKG PSVFPLAPSS KSTSGGTAAL GCLVKDYFPE PVTVSWNSGA   300
LTSGVHTFPA VLQSSGLYSL SSVVTVPSSS LGTQTYICNV NHKPSNTKVD KKVEPKSCDK   360
THTCPPCPAP EAAGGPSVFL FPPKPKDTLM ISRTPEVTCV VVDVSHEDPE VKFNWYVDGV   420
EVHNAKTKPR EEQYNSTYRV VSVLTVLHQD WLNGKEYKCK VSNKALPAPI EKTISKAKGQ   480
PREPQVYTLP PSRDELTKNQ VSLTCLVKGF YPSDIAVEWE SNGQPENNYK TTPPVLDSDG   540
SFFLYSKLTV DKSRWQQGNV FSCSVMHEAL HNHYTQKSLS LSPGK                   585

SEQ ID NO: 48            moltype = AA   length = 334
FEATURE                  Location/Qualifiers
source                   1..334
                         mol_type = protein
                         organism = synthetic construct
SEQUENCE: 48
DIQMTQSPSS LSASVGDRVT ITCRASQSIS NNLNWYQQKP GKAPKLLIYY TSRFHSGVPS    60
RFSGSGSGTD FTFTISSLQP EDIATYYCQQ EHTLPYTFGQ GTKLEIKRTV AAPSVFIFPP   120
DIQMTQSPSS LSASVGDRVT ITCKASQSVG TTIVWYQQKP GKAPKLLIYS ASNRHTGVPS   180
RFSGSGSGTD FTLTISSLQP EDFATYYCQQ YTSYPFTFGQ GTKLEIKRTV AAPSVFIFPP   240
SDEQLKSGTA SVVCLLNNFY PREAKVQWKV DNALQSGNSQ ESVTEQDSKD STYSLSSTLT   300
LSKADYEKHK VYACEVTHQG LSSPVTKSFN RGEC                               334

SEQ ID NO: 49            moltype = AA   length = 445
FEATURE                  Location/Qualifiers
source                   1..445
                         mol_type = protein
                         organism = synthetic construct
SEQUENCE: 49
EVQLLESGGG LVQPGGSLRL SCAASGFTFS SYWMHWVRQA PGKGLEWVAY INPSTGYTEY    60
NQKFKRFTIS RDSKNTVYLQ MNSLRAEDTA VYYCTSGGYD DLGYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
```

```
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVCTLP PSRDELTKNQ    360
VSLSCAVKGF YPSDIAVEWE SNGQPENNYK TTPPVLDSDG SFFLVSKLTV DKSRWQQGNV    420
FSCSVMHEAL HNHYTQKSLS LSPGK                                         445

SEQ ID NO: 50            moltype = AA   length = 460
FEATURE                  Location/Qualifiers
source                   1..460
                         mol_type = protein
                         organism = synthetic construct
SEQUENCE: 50
KEACPTGLYT HSGECCKACN LGEGVAQPCG ANQTVCEPCL DSVTFSDVVS ATEPCKPCTE    60
CVGLQSMSAP CVEADDAVCR CAYGYYQDET TGRCEACRVC EAGSGLVFSC QDKQNTVCEE    120
CPDGTYSDEA NHVDPCLPCT VCEDTERQLR ECTRWADAEC EEIPGRWITR STPPEGSDST    180
APSTQEPEAP PEQDLIASTV AGVVTTVMGS SQPVVTRGTT DNDIEGRMDP KSCDKTHTCP    240
PCPAPEAAGG PSVFLFPPKP KDTLMISRTP EVTCVVVDVS HEDPEVKFNW YVDGVEVHNA    300
KTKPREEQYN STYRVVSVLT VLHQDWLNGK EYKCKVSNKA LPAPIEKTIS KAKGQPREPQ    360
VYTLPPCRDE LTKNQVSLWC LVKGFYPSDI AVEWESNGQP ENNYKTTPPV LDSDGSFFLY    420
SKLTVDKSRW QQGNVFSCSV MHEALHNHYT QKSLSLSPGK                         460

SEQ ID NO: 51            moltype = AA   length = 614
FEATURE                  Location/Qualifiers
source                   1..614
                         mol_type = protein
                         organism = synthetic construct
SEQUENCE: 51
AAPCPDACCP HGSSGLRCTR DGALDSLHHL PGAENLTELY IENQQHLQHL ELRDLRGLGE    60
LRNLTIVKSG LRFVAPDAFH FTPRLSRLNL SFNALESLSW KTVQGLSQE LVLSGNPLHC     120
SCALRWLQRW EEEGLGGVPE QKLQCHGQGP LAHMPNASCG VPTLKVQVPN ASVDVGDDVL    180
LRCQVEGRGL EQAGWILTEL EQSATVMKSG GLPSLGLTLA NVTSDLNRKN VTCWAENDVG    240
RAEVSVQVNV SFPASVQLHT AVEMHHWCIP FSVDGQPAPS LRWLFNGSVL NETSFIFTEF    300
LEPAANETVR HGCLRLNQPT HVNNGNYTLL AANPFGQASA SIMAAFMDNP FEFNPEDPIP    360
VSFSPVDTNS TSGDPVEIEG RIDPKSCDKT HTCPPCPAPE AAGGPSVFLF PPKPKDTLMI    420
SRTPEVTCVV VDVSHEDPEV KFNWYVDGVE VHNAKTKPRE EQYNSTYRVV SVLTVLHQDW    480
LNGKEYKCKV SNKALPAPIE KTISKAKGQP REPQVYTLPP CRDELTKNQV SLWCLVKGFY    540
PSDIAVEWES NGQPENNYKT TPPVLDSDGS FFLYSKLTVD KSRWQQGNVF SCSVMHEALH    600
NHYTQKSLSL SPGK                                                      614

SEQ ID NO: 52            moltype = AA   length = 454
FEATURE                  Location/Qualifiers
source                   1..454
                         mol_type = protein
                         organism = synthetic construct
SEQUENCE: 52
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSNTKVDK KVEPKSCDKT HTCPPCPAPE    240
AAGGPSVFLF PPKPKDTLMI SRTPEVTCVV VDVSHEDPEV KFNWYVDGVE VHNAKTKPRE    300
EQYNSTYRVV SVLTVLHQDW LNGKEYKCKV SNKALPAPIE KTISKAKGQP REPQVYTLPP    360
SRDELTKNQV SLSCLVKGFY PSDIAVEWES NGQPENNYKT TPPVLDSDGS FLLYSKLTVD    420
KSRWQQGNVF SCSVMHEALH NHYTQKSLSL SPGK                               454

SEQ ID NO: 53            moltype = AA   length = 451
FEATURE                  Location/Qualifiers
source                   1..451
                         mol_type = protein
                         organism = synthetic construct
SEQUENCE: 53
QVQLQESGPG LVKPSETLSL TCTVSGFSLI GYDLNWIRQP PGKGLEWIGI IWGDGTTDYN    60
SAVKSRVTIS KDTSKNQFSL KLSSVTAADT AVYYCARGGY WYATSYYPDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSRLTVDKSR    420
WQQGNVFSCS VMHEALHNHY TQKSLSLSPG K                                   451

SEQ ID NO: 54            moltype = AA   length = 214
FEATURE                  Location/Qualifiers
source                   1..214
                         mol_type = protein
                         organism = synthetic construct
SEQUENCE: 54
DIQMTQSPSS LSASVGDRVT ITCRASQSIS NNLNWYQQKP GKAPKLLIYY TSRFHSGVPS    60
RFSGSGSGTD FTFTISSLQP EDIATYYCQQ EHTLPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214
```

```
SEQ ID NO: 55            moltype = AA  length = 444
FEATURE                  Location/Qualifiers
source                   1..444
                         mol_type = protein
                         organism = synthetic construct
SEQUENCE: 55
EVQLLESGGG LVQPGGSLRL SCAASGFTFS DAWMDWVRQA PGKGLEWVAE IRHKANDHAI    60
FYDESVKGRF TISRDKNTV  YLQMNSLRAE DTAVYYCTSP FAYWGQGTLV TVSSASTKGP   120
SVFPLAPSSK STSGGTAALG CLVKDYFPEP VTVSWNSGAL TSGVHTFPAV LQSSGLYSLS   180
SVVTVPSSSL GTQTYICNVN HKPSNTKVDK KVEPKSCDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVYTLPP SRDELTKNQV   360
SLSCLVKGFY PSDIAVEWES NGQPENNYKT TPPVLDSDGS FLLYSKLTVD KSRWQQGNVF   420
SCSVMHEALH NHYTQKSLSL SPGK                                         444

SEQ ID NO: 56            moltype = AA  length = 452
FEATURE                  Location/Qualifiers
source                   1..452
                         mol_type = protein
                         organism = synthetic construct
SEQUENCE: 56
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIG VVTNFDNWGQ GTLVTVSSAS   120
VAAPSVFIFP PSDEQLKSGT ASVVCLLNNF YPREAKVQWK VDNALQSGNS QESVTEQDSK   180
DSTYSLSSTL TLSKADYEKH KVYACEVTHQ GLSSPVTKSF NRGECDKTHT CPPCPAPEAA   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPCR   360
DELTKNQVSL WCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 57            moltype = AA  length = 212
FEATURE                  Location/Qualifiers
source                   1..212
                         mol_type = protein
                         organism = synthetic construct
SEQUENCE: 57
DIQMTQSPSS LSASAGDRVT ITCRASQAIR NDLGWYQQKP GKAPKRLIYA AFNLQSGVPS    60
RFSGSGSGTE FTLTISSLQP EDLASYYCQQ YNRYPWTFGQ GTKVTVLSSA STKGPSVFPL   120
APSSKSTSGG TAALGCLVKD YFPEPVTVSW NSGALTSGVH TFPAVLQSSG LYSLSSVVTV   180
PSSSLGTQTY ICNVNHKPSN TKVDKKVEPK SC                                212

SEQ ID NO: 58            moltype = AA  length = 578
FEATURE                  Location/Qualifiers
source                   1..578
                         mol_type = protein
                         organism = synthetic construct
SEQUENCE: 58
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP QVQLVQSGAE VKKPGASVKV SCKVSGFTLT ELSIHWVRQA PGKGLEWMGG   180
FDPEDGETIY AQKFQGRVTM TEDTSTDTAY MELTSLRSED TAVYYCSTIG VVTNFDNWGQ   240
GTLVTVSSAS TKGPSVFPLA PSSKSTSGGT AALGCLVKDY FPEPVTVSWN SGALTSGVHT   300
FPAVLQSSGL YSLSSVVTVP SSSLGTQTYI CNVNHKPSNT KVDKKVEPKS CDKTHTCPPC   360
PAPEAAGGPS VFLFPPKPKD TLMISRTPEV TCVVVDVSHE DPEVKFNWYV DGVEVHNAKT   420
KPREEQYNST YRVVSVLTVL HQDWLNGKEY KCKVSNKALP APIEKTISKA KGQPREPQVY   480
TLPPSRDELT KNQVSLTCLV KGFYPSDIAV EWESNGQPEN NYKTTPPVLD SDGSFFLYSK   540
LTVDKSRWQQ GNVFSCSVMH EALHNHYTQK SLSLSPGK                          578

SEQ ID NO: 59            moltype = AA  length = 327
FEATURE                  Location/Qualifiers
source                   1..327
                         mol_type = protein
                         organism = synthetic construct
SEQUENCE: 59
DIQMTQSPSS LSASVGDRVT ITCRTSENIY SYLAWYQQKP GKAPKLLIYN AKTLAEGVPS    60
RFSGSGSGTD FTLTISSLQP EDFATYYCQH HYGTPWTFGQ GTKLEIKRTV AAPDIQMTQS   120
PSSLSASAGD RVTITCRASQ AIRNDLGWYQ QKPGKAPKRL IYAAFNLQSG VPSRFSGSGS   180
GTEFTLTISS LQPEDLASYY CQQYNRYPWT FGQGTKLEIK RTVAAPSVFI FPPSDEQLKS   240
GTASVVCLLN NFYPREAKVQ WKVDNALQSG NSQESVTEQD SKDSTYSLSS TLTLSKADYE   300
KHKVYACEVT HQGLSSPVTK SFNRGEC                                      327

SEQ ID NO: 60            moltype = AA  length = 568
FEATURE                  Location/Qualifiers
source                   1..568
                         mol_type = protein
                         organism = synthetic construct
SEQUENCE: 60
EVQLLESGGG LVQPGGSLRL SCAASGFTFS DAWMDWVRQA PGKGLEWVAE IRHKANDHAI    60
FYDESVKGRF TISRDKNTV  YLQMNSLRAE DTAVYYCTSP FAYWGQGTLV TVSSASTKGP   120
```

```
QVQLVQSGAE VKKPGASVKV SCKVSGFTLT ELSIHWVRQA PGKGLEWMGG FDPEDGETIY    180
AQKFQGRVTM TEDTSTDTAY MELTSLRSED TAVYYCSTIG VVTNFDNWGQ GTLVTVSSAS    240
TKGPSVFPLA PSSKSTSGGT AALGCLVKDY FPEPVTVSWN SGALTSGVHT FPAVLQSSGL    300
YSLSSVVTVP SSSLGTQTYI CNVNHKPSNT KVDKKVEPKS CDKTHTCPPC PAPEAAGGPS    360
VFLFPPKPKD TLMISRTPEV TCVVVDVSHE DPEVKFNWYV DGVEVHNAKT KPREEQYNST    420
YRVVSVLTVL HQDWLNGKEY KCKVSNKALP APIEKTISKA KGQPREPQVY TLPPSRDELT    480
KNQVSLTCLV KGFYPSDIAV EWESNGQPEN NYKTTPPVLD SDGSFFLYSK LTVDKSRWQQ    540
GNVFSCSVMH EALHNHYTQK SLSLSPGK                                      568

SEQ ID NO: 61             moltype = AA  length = 326
FEATURE                   Location/Qualifiers
source                    1..326
                          mol_type = protein
                          organism = synthetic construct
SEQUENCE: 61
DIQMTQSPSS LSASVGDRVT ITCKASQSVG TTIVWTQQLP GLAPKLLIYS ASNRHTGVPS     60
RFSGSGSGTD FTLTISSLQP EDFATYYCQQ YTSYPFTFGQ GTKEIKRTVA APDIQMTQSP    120
SSLSASAGDR VTITCRASQA IRNDLGWYQQ KPGKAPKRLI YAAFNLQSGV PSRFSGSGSG    180
TEFTLTISSL QPEDLASYYC QQYNRYPWTF GQGTKLEIKR TVAAPSVFIF PPSDEQLKSG    240
TASVVCLLNN FYPREAKVQW KVDNALQSGN SQESVTEQDS KDSTYSLSST LTLSKADYEK    300
HKVYACEVTH QGLSSPVTKS FNRGEC                                        326

SEQ ID NO: 62             moltype = AA  length = 578
FEATURE                   Location/Qualifiers
source                    1..578
                          mol_type = protein
                          organism = synthetic construct
SEQUENCE: 62
QVQLVQSGAE VKKPGASVKV SCKVSGFTLT ELSIHWVRQA PGKGLEWMGG FDPEDGETIY     60
AQKFQGRVTM TEDTSTDTAY MELTSLRSED TAVYYCSTIG VVTNFDNWGQ GTLVTVSSAS    120
TKGPEVQLVE SGGGLVQPGG SLRLSCAASG FTFSDAWMDW VRQAPGKGLE WVAEIRNKAN    180
NHARHYAESV KGRFTISRDN AKNSLYLQMN SLRAEDTAVY YCARTYYYGS SYGYCDVWGQ    240
GTLVTVSSAS TKGPSVFPLA PSSKSTSGGT AALGCLVKDY FPEPVTVSWN SGALTSGVHT    300
FPAVLQSSGL YSLSSVVTVP SSSLGTQTYI CNVNHKPSNT KVDKKVEPKS CDKTHTCPPC    360
PAPEAAGGPS VFLFPPKPKD TLMISRTPEV TCVVVDVSHE DPEVKFNWYV DGVEVHNAKT    420
KPREEQYNST YRVVSVLTVL HQDWLNGKEY KCKVSNKALP APIEKTISKA KGQPREPQVY    480
TLPPSRDELT KNQVSLTCLV KGFYPSDIAV EWESNGQPEN NYKTTPPVLD SDGSFFLYSK    540
LTVDKSRWQQ GNVFSCSVMH EALHNHYTQK SLSLSPGK                           578

SEQ ID NO: 63             moltype = AA  length = 327
FEATURE                   Location/Qualifiers
source                    1..327
                          mol_type = protein
                          organism = synthetic construct
SEQUENCE: 63
DIQMTQSPSS LSASAGDRVT ITCRASQAIR NDLGWYQQKP GKAPKRLIYA AFNLQSGVPS     60
RFSGSGSGTE FTLTISSLQP EDLASYYCQQ YNRYPWTFGQ GTKLEIKRTV AAPDIQMTQS    120
PSSLSASVGD RVTITCRTSE NIYSYLAWYQ QKPGKAPKLL IYNAKTLAEG VPSRFSGSGS    180
GTDFTLTISS LQPEDFATYY CQHHYGTPWT FGQGTKLEIK RTVAAPSVFI FPPSDEQLKS    240
GTASVVCLLN NFYPREAKVQ WKVDNALQSG NSQESVTEQD SKDSTYSLSS TLTLSKADYE    300
KHKVYACEVT HQGLSSPVTK SFNRGEC                                       327

SEQ ID NO: 64             moltype = AA  length = 568
FEATURE                   Location/Qualifiers
source                    1..568
                          mol_type = protein
                          organism = synthetic construct
SEQUENCE: 64
QVQLVQSGAE VKKPGASVKV SCKVSGFTLT ELSIHWVRQA PGKGLEWMGG FDPEDGETIY     60
AQKFQGRVTM TEDTSTDTAY MELTSLRSED TAVYYCSTIG VVTNFDNWGQ GTLVTVSSAS    120
TKGPEVQLLE SGGGLVQPGG SLRLSCAASG FTFSDAWMDW VRQAPGKGLE WVAEIRHKAN    180
DHAIFYDESV KGRFTISRDS KNTVYLQMNS LRAEDTAVYY CTSPFAYWGQ GTLVTVSSAS    240
TKGPSVFPLA PSSKSTSGGT AALGCLVKDY FPEPVTVSWN SGALTSGVHT FPAVLQSSGL    300
YSLSSVVTVP SSSLGTQTYI CNVNHKPSNT KVDKKVEPKS CDKTHTCPPC PAPEAAGGPS    360
VFLFPPKPKD TLMISRTPEV TCVVVDVSHE DPEVKFNWYV DGVEVHNAKT KPREEQYNST    420
YRVVSVLTVL HQDWLNGKEY KCKVSNKALP APIEKTISKA KGQPREPQVY TLPPSRDELT    480
KNQVSLTCLV KGFYPSDIAV EWESNGQPEN NYKTTPPVLD SDGSFFLYSK LTVDKSRWQQ    540
GNVFSCSVMH EALHNHYTQK SLSLSPGK                                      568

SEQ ID NO: 65             moltype = AA  length = 326
FEATURE                   Location/Qualifiers
source                    1..326
                          mol_type = protein
                          organism = synthetic construct
SEQUENCE: 65
DIQMTQSPSS LSASAGDRVT ITCRASQAIR NDLGWYQQKP GKAPKRLIYA AFNLQSGVPS     60
RFSGSGSGTE FTLTISSLQP EDLASYYCQQ YNRYPWTFGQ GTKLEIKRTV AAPDIQMTQS    120
PSSLSASVGD RVTITCKASQ SVGTTIVWTQ QLPGLAPKLL IYSASNRHTG VPSRFSGSGS    180
GTDFTLTISS LQPEDFATYY CQQYTSYPFT FGQGTKEIKR TVAAPSVFIF PPSDEQLKSG    240
```

```
TASVVCLLNN FYPREAKVQW KVDNALQSGN SQESVTEQDS KDSTYSLSST LTLSKADYEK   300
HKVYACEVTH QGLSSPVTKS FNRGEC                                       326

SEQ ID NO: 66           moltype = AA  length = 585
FEATURE                 Location/Qualifiers
source                  1..585
                        mol_type = protein
                        organism = synthetic construct
SEQUENCE: 66
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP SVFPLAPQVQ LVQSGAEVKK PGASVKVSCK VSGFTLTELS IHWVRQAPGK   180
GLEWMGGFDP EDGETIYAQK FQGRVTMTED TSTDTAYMEL TSLRSEDTAV YYCSTIGVVT   240
NFDNWGQGTL VTVSSASTKG PSVFPLAPSS KSTSGGTAAL GCLVKDYFPE PVTVSWNSGA   300
LTSGVHTFPA VLQSSGLYSL SSVVTVPSSS LGTQTYICNV NHKPSNTKVD KKVEPKSCDK   360
THTCPPCPAP EAAGGPSVFL FPPKPKDTLM ISRTPEVTCV VVDVSHEDPE VKFNWYVDGV   420
EVHNAKTKPR EEQYNSTYRV VSVLTVLHQD WLNGKEYKCK VSNKALPAPI EKTISKAKGQ   480
PREPQVYTLP PSRDELTKNQ VSLTCLVKGF YPSDIAVEWE SNGQPENNYK TTPPVLDSDG   540
SFFLYSKLTV DKSRWQQGNV FSCSVMHEAL HNHYTQKSLS LSPGK                  585

SEQ ID NO: 67           moltype = AA  length = 334
FEATURE                 Location/Qualifiers
source                  1..334
                        mol_type = protein
                        organism = synthetic construct
SEQUENCE: 67
DIQMTQSPSS LSASVGDRVT ITCRTSENIY SYLAWYQQKP GKAPKLLIYN AKTLAEGVPS    60
RFSGSGSGTD FTLTISSLQP EDFATYYCQH HYGTPWTFGQ GTKLEIKRTV AAPSVFIFPP   120
DIQMTQSPSS LSASAGDRVT ITCRASQAIR NDLGWYQQKP GKAPKRLIYA AFNLQSGVPS   180
RFSGSGSGTE FTLTISSLQP EDLASYYCQQ YNRYPWTFGQ GTKLEIKRTV AAPSVFIFPP   240
SDEQLKSGTA SVVCLLNNFY PREAKVQWKV DNALQSGNSQ ESVTEQDSKD STYSLSSTLT   300
LSKADYEKHK VYACEVTHQG LSSPVTKSFN RGEC                              334

SEQ ID NO: 68           moltype = AA  length = 575
FEATURE                 Location/Qualifiers
source                  1..575
                        mol_type = protein
                        organism = synthetic construct
SEQUENCE: 68
EVQLLESGGG LVQPGGSLRL SCAASGFTFS DAWMDWVRQA PGKGLEWVAE IRHKANDHAI    60
FYDESVKGRF TISRDSKNTV YLQMNSLRAE DTAVYYCTSP FAYWGQGTLV TVSSASTKGP   120
SVFPLAPQVQ LVQSGAEVKK PGASVKVSCK VSGFTLTELS IHWVRQAPGK GLEWMGGFDP   180
EDGETIYAQK FQGRVTMTED TSTDTAYMEL TSLRSEDTAV YYCSTIGVVT NFDNWGQGTL   240
VTVSSASTKG PSVFPLAPSS KSTSGGTAAL GCLVKDYFPE PVTVSWNSGA LTSGVHTFPA   300
VLQSSGLYSL SSVVTVPSSS LGTQTYICNV NHKPSNTKVD KKVEPKSCDK THTCPPCPAP   360
EAAGGPSVFL FPPKPKDTLM ISRTPEVTCV VVDVSHEDPE VKFNWYVDGV EVHNAKTKPR   420
EEQYNSTYRV VSVLTVLHQD WLNGKEYKCK VSNKALPAPI EKTISKAKGQ PREPQVYTLP   480
PSRDELTKNQ VSLTCLVKGF YPSDIAVEWE SNGQPENNYK TTPPVLDSDG SFFLYSKLTV   540
DKSRWQQGNV FSCSVMHEAL HNHYTQKSLS LSPGK                             575

SEQ ID NO: 69           moltype = AA  length = 333
FEATURE                 Location/Qualifiers
source                  1..333
                        mol_type = protein
                        organism = synthetic construct
SEQUENCE: 69
DIQMTQSPSS LSASVGDRVT ITCKASQSVG TTIVWTQQLP GLAPKLLIYS ASNRHTGVPS    60
RFSGSGSGTD FTLTISSLQP EDFATYYCQQ YTSYPFTFGQ GTKEIKRTVA APSVFIFPPD   120
IQMTQSPSSL SASAGDRVTI TCRASQAIRN DLGWYQQKPG KAPKRLIYAA FNLQSGVPSR   180
FSGSGSGTEF TLTISSLQPE DLASYYCQQY NRYPWTFGQG TKLEIKRTVA APSVFIFPPS   240
DEQLKSGTAS VVCLLNNFYP REAKVQWKVD NALQSGNSQE SVTEQDSKDS TYSLSSTLTL   300
SKADYEKHKV YACEVTHQGL SSPVTKSFNR GEC                               333

SEQ ID NO: 70           moltype = AA  length = 585
FEATURE                 Location/Qualifiers
source                  1..585
                        mol_type = protein
                        organism = synthetic construct
SEQUENCE: 70
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIG VVTNFDNWGQ GTLVTVSSAS   120
TKGPSVFPLA PEVQLVESGG GLVQPGGSLR LSCAASGFTF SDAWMDWVRQ APGKGLEWVA   180
EIRNKANNHA RHYAESVKGR FTISRDNAKN SLYLQMNSLR AEDTAVYYCA RTYYYGSSYG   240
YCDVWGQGTL VTVSSASTKG PSVFPLAPSS KSTSGGTAAL GCLVKDYFPE PVTVSWNSGA   300
LTSGVHTFPA VLQSSGLYSL SSVVTVPSSS LGTQTYICNV NHKPSNTKVD KKVEPKSCDK   360
THTCPPCPAP EAAGGPSVFL FPPKPKDTLM ISRTPEVTCV VVDVSHEDPE VKFNWYVDGV   420
EVHNAKTKPR EEQYNSTYRV VSVLTVLHQD WLNGKEYKCK VSNKALPAPI EKTISKAKGQ   480
PREPQVYTLP PSRDELTKNQ VSLTCLVKGF YPSDIAVEWE SNGQPENNYK TTPPVLDSDG   540
SFFLYSKLTV DKSRWQQGNV FSCSVMHEAL HNHYTQKSLS LSPGK                  585
```

```
SEQ ID NO: 71            moltype = AA   length = 334
FEATURE                  Location/Qualifiers
source                   1..334
                         mol_type = protein
                         organism = synthetic construct
SEQUENCE: 71
DIQMTQSPSS LSASAGDRVT ITCRASQAIR NDLGWYQQKP GKAPKRLIYA AFNLQSGVPS    60
RFSGSGSGTE FTLTISSLQP EDLASYYCQQ YNRYPWTFGQ GTKLEIKRTV AAPSVFIFPP   120
DIQMTQSPSS LSASVGDRVT ITCRTSENIY SYLAWYQQKP GKAPKLLIYN AKTLAEGVPS   180
RFSGSGSGTD FTLTISSLQP EDFATYYCQH HYGTPWTFGQ GTKLEIKRTV AAPSVFIFPP   240
SDEQLKSGTA SVVCLLNNFY PREAKVQWKV DNALQSGNSQ ESVTEQDSKD STYSLSSTLT   300
LSKADYEKHK VYACEVTHQG LSSPVTKSFN RGEC                              334

SEQ ID NO: 72            moltype = AA   length = 575
FEATURE                  Location/Qualifiers
source                   1..575
                         mol_type = protein
                         organism = synthetic construct
SEQUENCE: 72
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIG VVTNFDNWGQ GTLVTVSSAS   120
TKGPSVFPLA PEVQLLESGG GLVQPGGSLR LSCAASGFTF SDAWMDWVRQ APGKGLEWVA   180
EIRHKANDHA IFYDESVKGR FTISRDSKNT VYLQMNSLRA EDTAVYYCTS PFAYWGQGTL   240
VTVSSASTKG PSVFPLAPSS KSTSGGTAAL GCLVKDYFPE PVTVSWNSGA LTSGVHTFPA   300
VLQSSGLYSL SSVVTVPSSS LGTQTYICNV NHKPSNTKVD KKVEPKSCDK THTCPPCPAP   360
EAAGGPSVFL FPPKPKDTLM ISRTPEVTCV VVDVSHEDPE VKFNWYVDGV EVHNAKTKPR   420
EEQYNSTYRV VSVLTVLHQD WLNGKEYKCK VSNKALPAPI EKTISKAKGQ PREPQVYTLP   480
PSRDELTKNQ VSLTCLVKGF YPSDIAVEWE SNGQPENNYK TTPPVLDSDG SFFLYSKLTV   540
DKSRWQQGNV FSCSVMHEAL HNHYTQKSLS LSPGK                             575

SEQ ID NO: 73            moltype = AA   length = 333
FEATURE                  Location/Qualifiers
source                   1..333
                         mol_type = protein
                         organism = synthetic construct
SEQUENCE: 73
DIQMTQSPSS LSASAGDRVT ITCRASQAIR NDLGWYQQKP GKAPKRLIYA AFNLQSGVPS    60
RFSGSGSGTE FTLTISSLQP EDLASYYCQQ YNRYPWTFGQ GTKLEIKRTV AAPSVFIFPP   120
DIQMTQSPSS LSASVGDRVT ITCKASQSVG TTIVWTQQLP GLAPKLLIYS ASNRHTGVPS   180
RFSGSGSGTD FTLTISSLQP EDFATYYCQQ YTSYPFTFGQ GTKEIKRTVA APSVFIFPPS   240
DEQLKSGTAS VVCLLNNFYP REAKVQWKVD NALQSGNSQE SVTEQDSKDS TYSLSSTLTL   300
SKADYEKHKV YACEVTHQGL SSPVTKSFNR GEC                               333

SEQ ID NO: 74            moltype = AA   length = 573
FEATURE                  Location/Qualifiers
source                   1..573
                         mol_type = protein
                         organism = synthetic construct
SEQUENCE: 74
EVQLVESGGG LVQPGGSLRL SCAASGFTFS SYWMHWVRQA PGKGLEWVAY INPSTGYTEY    60
NQKFKRFTIS RDDSKNTVYL QMNSLRAEDT AVYYCTSGGY DDLGYWGQGT LVTVSSASTK   120
GPQVQLQESG PGLVKPSETL SLTCTVSGFS LIGYDLNWIR QPPGKGLEWI GIIWGDTTD    180
YNSAVKSRVT ISKDTKNQF SLKLSSVTAA DTAVYYCARG GYWYATSYYF DYWGQGTLVT   240
VSSASTKGPS VFPLAPSSKS TSGGTAALGC LVKDYFPEPV TVSWNSGALT SGVHTFPAVL   300
QSSGLYSLSS VVTVPSSSLG TQTYICNVNH KPSNTKVDKK VEPKSCDKTH TCPPCPAPEA   360
AGGPSVFLFP PKPKDTLMIS RTPEVTCVVV DVSHEDPEVK FNWYVDGVEV HNAKTKPREE   420
QYNSTYRVVS VLTVLHQDWL NGKEYKCKVS NKALPAPIEK TISKAKGQPR EPQVYTLPPS   480
RDELTKNQVS LTCLVKGFYP SDIAVEWESN GQPENNYKTT PPVLDSDGSF FLYSKLTVDK   540
SRWQQGNVFS CSVMHEALHN HYTQKSLSLS PGK                               573

SEQ ID NO: 75            moltype = AA   length = 332
FEATURE                  Location/Qualifiers
source                   1..332
                         mol_type = protein
                         organism = synthetic construct
SEQUENCE: 75
DIQMTQSPSS LSASVGDRVT ITCRSSKSLL YKDGKTYLYW YQQKPGKAPK LLIYLMSTRA    60
SGVPSRFSGS GSGTDFTLTI SSLQPEDFAT YYCQQLVUYP YTFGQGTKLE IKRTVAAPDI   120
QMTQSPSSLS ASVGDRVTIT CRASQSISNN LNWYQQKPGK APKLLIYYTS RFHSGVPSRF   180
SGSGSGTDFT FTISSLQPED IATYYCQQEH TLPYTFGQGT KLEIKRTVAA PSVFIFPPSD   240
EQLKSGTASV VCLLNNFYPR EAKVQWKVDN ALQSGNSQES VTEQDSKDST YSLSSTLTLS   300
KADYEKHKVY ACEVTHQGLS SPVTKSFNRG EC                                332

SEQ ID NO: 76            moltype = AA   length = 570
FEATURE                  Location/Qualifiers
source                   1..570
                         mol_type = protein
                         organism = synthetic construct
```

```
SEQUENCE: 76
EVQLVESGGG LVQPGGSLRL SCAASGFTFS SYWMHWVRQA PGKGLEWVAY INPSTGYTEY    60
NQKFKRFTIS RDDSKNTVYL QMNSLRAEDT AVYYCTSGGY DDLGYWGQGT LVTVSSASTK   120
GPQVQLVQSG AEVKKPGASV KVSCKVSGFT LTELSIHWVR QAPGKGLEWM GGFDPEDGET   180
IYAQKFQGRV TMTEDTSTDT AYMELTSLRS EDTAVYYCST IGVVTNFDNW GQGTLVTVSS   240
ASTKGPSVFP LAPSSKSTSG GTAALGCLVK DYFPEPVTVS WNSGALTSGV HTFPAVLQSS   300
GLYSLSSVVT VPSSSLGTQT YICNVNHKPS NTKVDKKVEP KSCDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LPAPIEKTIS KAKGQPREPQ VYTLPPSRDE   480
LTKNQVSLTC LVKGFYPSDI AVEWESNGQP ENNYKTTPPV LDSDGSFFLY SKLTVDKSRW   540
QQGNVFSCSV MHEALHNHYT QKSLSLSPGK                                    570

SEQ ID NO: 77              moltype = AA  length = 331
FEATURE                    Location/Qualifiers
source                     1..331
                           mol_type = protein
                           organism = synthetic construct
SEQUENCE: 77
DIQMTQSPSS LSASVGDRVT ITCRSSKSLL YKDGKTYLYW YQQKPGKAPK LLIYLMSTRA    60
SGVPSRFSGS GSGTDFTLTI SSLQPEDFAT YYCQQLVUYP YTFGQGTKLE IKRTVAAPDI   120
QMTQSPSSLS ASVGDRVTIT CKASQSVGTT IVWTQQLPGL APKLLIYSAS NRHTGVPSRF   180
SGSGSGTDFT LTISSLQPED FATYYCQQYT SYPPTFGGQT KEIKRTVAAP SVFIFPPSDE   240
QLKSGTASVV CLLNNFYPRE AKVQWKVDNA LQSGNSQESV TEQDSKDSTY SLSSTLTLSK   300
ADYEKHKVYA CEVTHQGLSS PVTKSFNRGE C                                  331

SEQ ID NO: 78              moltype = AA  length = 575
FEATURE                    Location/Qualifiers
source                     1..575
                           mol_type = protein
                           organism = synthetic construct
SEQUENCE: 78
EVQLVESGGG LVQPGGSLRL SCAASGFTFS SYWMHWVRQA PGKGLEWVAY INPSTGYTEY    60
NQKFKRFTIS RDDSKNTVYL QMNSLRAEDT AVYYCTSGGY DDLGYWGQGT LVTVSSASTK   120
GPEVQLVESG GGLVQPGGSL RLSCAASGFT LRSYSMNWVR QAPGKGLEWV SYISRSSHTI   180
FYADSVKGRF TISRDNAKNS LYLQMDSLRD EDTAMYYCAR VYSSGWHVSD YFDYWGQGIL   240
VTVSSASTKG PSVFPLAPSS KSTSGGTAAL GCLVKDYFPE PVTVSWNSGA LTSGVHTFPA   300
VLQSSGLYSL SSVVTPVSSS LGTQTYICNV NHKPSNTKVD KKVEPKSCDK THTCPPCPAP   360
EAAGGPSVFL FPPKPKDTLM ISRTPEVTCV VVDVSHEDPE VKFNWYVDGV EVHNAKTKPR   420
EEQYNSTYRV VSVLTVLHQD WLNGKEYKCK VSNKALPAPI EKTISKAKGQ PREPQVYTLP   480
PSRDELTKNQ VSLTCLVKGF YPSDIAVEWE SNGQPENNYK TTPPVLDSDG SFFLYSKLTV   540
DKSRWQQGNV FSCSVMHEAL HNHYTQKSLS LSPGK                              575

SEQ ID NO: 79              moltype = AA  length = 332
FEATURE                    Location/Qualifiers
source                     1..332
                           mol_type = protein
                           organism = synthetic construct
SEQUENCE: 79
DIQMTQSPSS LSASVGDRVT ITCRSSKSLL YKDGKTYLYW YQQKPGKAPK LLIYLMSTRA    60
SGVPSRFSGS GSGTDFTLTI SSLQPEDFAT YYCQQLVUYP YTFGQGTKLE IKRTVAAPAI   120
QLTQSPSSLS ASVGDRVTIT CRASQGISSA LAWYQQKPGK APKLLIYDAS SLESGVPSRF   180
SGSGSGTDFT LTISSLQPED FATYYCQQFN SYPLTFGGGT KLEIKRTVAA PSVFIFPPSD   240
EQLKSGTASV VCLLNNFYPR EAKVQWKVDN ALQSGNSQES VTEQDSKDST YSLSSTLTLS   300
KADYEKHKVY ACEVTHQGLS SPVTKSFNRG EC                                 332

SEQ ID NO: 80              moltype = AA  length = 572
FEATURE                    Location/Qualifiers
source                     1..572
                           mol_type = protein
                           organism = synthetic construct
SEQUENCE: 80
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIG VVTNFDNWGQ GTLVTVSSAS   120
TKGPEVQLVE SGGGLVQPGG SLRLSCAASG FTFSSYWMHW VRQAPGKGLE WVAYINPSTG   180
YTEYNQKFKR FTISRDDSKN TVYLQMNSLR AEDTAVYYCT SGGYDDLGYW GQGTLVTVSS   240
ASTKGPASTK GPSVFPLAPS SKSTSGGTAA LGCLVKDYFP EPVTVSWNSG ALTSGVHTFP   300
AVLQSSGLYS LSSVVTVPSS SLGTQTYICN VNHKPSNTKV DKKVEPKSCD KTHTCPPCPA   360
PEAAGGPSVF LFPPKPKDTL MISRTPEVTC VVVDVSHEDP EVKFNWYVDG VEVHNAKTKP   420
REEQYNSTYR VVSVLTVLHQ DWLNGKEYKC KVSNKALPAP IEKTISKAKG QPREPQVYTL   480
PPSRDELTKN QVSLTCLVKG FYPSDIAVEW ESNGQPENNY KTTPPVLDSD GSFFLYSKLT   540
VDKSRWQQGN VFSCSVMHEA LHNHYTQKSL SL                                 572

SEQ ID NO: 81              moltype = AA  length = 331
FEATURE                    Location/Qualifiers
source                     1..331
                           mol_type = protein
                           organism = synthetic construct
SEQUENCE: 81
DIQMTQSPSS LSASVGDRVT ITCKASQSVG TTIVWTQQLP GLAPKLLIYS ASNRHTGVPS    60
```

```
RFSGSGSGTD FTLTISSLQP EDFATYYCQQ YTSYPFTFGQ GTKEIKRTVA APDIQMTQSP  120
SSLSASVGDR VTITCRSSKS LLYKDGKTYL YWYQQKPGKA PKLLIYLMST RASGVPSRFS  180
GSGSGTDFTL TISSLQPEDF ATYYCQQLVU YPYTFGQGTK LEIKRTVAAP SVFIFPPSDE  240
QLKSGTASVV CLLNNFYPRE AKVQWKVDNA LQSGNSQESV TEQDSKDSTY SLSSTLTLSK  300
ADYEKHKVYA CEVTHQGLSS PVTKSFNRGE C                                331

SEQ ID NO: 82          moltype = AA   length = 577
FEATURE                Location/Qualifiers
source                 1..577
                       mol_type = protein
                       organism = synthetic construct
SEQUENCE: 82
EVQLVESGGG LVQPGGSLRL SCAASGFTLR SYSMNWVRQA PGKGLEWVSY ISRSSHTIFY   60
ADSVKGRFTI SRDNAKNSLY LQMDSLRDED TAMYYCARVY SSGWHVSDYF DYWGQGILVT  120
VSSSASTKGPE VQLVESGGGL VQPGGSLRLS CAASGFTFSS YWMHWVRQAP GKGLEWVAYI  180
NPSTGYTEYN QKFKRFTISR DDSKNTVYLQ MNSLRAEDTA VYYCTSGGYD DLGYWGQGTL  240
VTVSSASTKG PASTKGPSVF PLAPSSKSTS GGTAALGCLV KDYFPEPVTV SWNSGALTSG  300
VHTFPAVLQS SGLYSLSSVV TVPSSSLGTQ TYICNVNHKP SNTKVDKKVE PKSCDKTHTC  360
PPCPAPEAAG GPSVFLFPPK PKDTLMISRT PEVTCVVVDV SHEDPEVKFN WYVDGVEVHN  420
AKTKPREEQY NSTYRVVSVL TVLHQDWLNG KEYKCKVSNK ALPAPIEKTI SKAKGQPREP  480
QVYTLPPSRD ELTKNQVSLT CLVKGFYPSD IAVEWESNGQ PENNYKTTPP VLDSDGSFFL  540
YSKLTVDKSR WQQGNVFSCS VMHEALHNHY TQKSLSL                          577

SEQ ID NO: 83          moltype = AA   length = 332
FEATURE                Location/Qualifiers
source                 1..332
                       mol_type = protein
                       organism = synthetic construct
SEQUENCE: 83
AIQLTQSPSS LSASVGDRVT ITCRASQGIS SALAWYQQKP GKAPKLLIYD ASSLESGVPS   60
RFSGSGSGTD FTLTISSLQP EDFATYYCQQ FNSYPLTFGG GTKLEIKRTV AAPDIQMTQS  120
PSSLSASVGD RVTITCRSSK SLLYKDGKTY LYWYQQKPGK APKLLIYLMS TRASGVPSRF  180
SGSGSGTDFT LTISSLQPED FATYYCQQLV UYPYTFGQGT KLEIKRTVAA PSVFIFPPSD  240
EQLKSGTASV VCLLNNFYPR EAKVQWKVDN ALQSGNSQES VTEQDSKDST YSLSSTLTLS  300
KADYEKHKVY ACEVTHQGLS SPVTKSFNRG EC                               332

SEQ ID NO: 84          moltype = AA   length = 577
FEATURE                Location/Qualifiers
source                 1..577
                       mol_type = protein
                       organism = synthetic construct
SEQUENCE: 84
EVQLVESGGG LVQPGGSLRL SCAASGFTLR SYSMNWVRQA PGKGLEWVSY ISRSSHTIFY   60
ADSVKGRFTI SRDNAKNSLY LQMDSLRDED TAMYYCARVY SSGWHVSDYF DYWGQGILVT  120
VSSSASTKGPE VQLVESGGGL VQPGGSLRLS CAASGFTFSS YWMHWVRQAP GKGLEWVAYI  180
NPSTGYTEYN QKFKRFTISR DDSKNTVYLQ MNSLRAEDTA VYYCTSGGYD DLGYWGQGTL  240
VTVSSASTKG PASTKGPSVF PLAPSSKSTS GGTAALGCLV KDYFPEPVTV SWNSGALTSG  300
VHTFPAVLQS SGLYSLSSVV TVPSSSLGTQ TYICNVNHKP SNTKVDKKVE PKSCDKTHTC  360
PPCPAPEAAG GPSVFLFPPK PKDTLMISRT PEVTCVVVDV SHEDPEVKFN WYVDGVEVHN  420
AKTKPREEQY NSTYRVVSVL TVLHQDWLNG KEYKCKVSNK ALPAPIEKTI SKAKGQPREP  480
QVYTLPPSRD ELTKNQVSLT CLVKGFYPSD IAVEWESNGQ PENNYKTTPP VLDSDGSFFL  540
YSKLTVDKSR WQQGNVFSCS VMHEALHNHY TQKSLSL                          577

SEQ ID NO: 85          moltype = AA   length = 332
FEATURE                Location/Qualifiers
source                 1..332
                       mol_type = protein
                       organism = synthetic construct
SEQUENCE: 85
AIQLTQSPSS LSASVGDRVT ITCRASQGIS SALAWYQQKP GKAPKLLIYD ASSLESGVPS   60
RFSGSGSGTD FTLTISSLQP EDFATYYCQQ FNSYPLTFGG GTKLEIKRTV AAPDIQMTQS  120
PSSLSASVGD RVTITCRSSK SLLYKDGKTY LYWYQQKPGK APKLLIYLMS TRASGVPSRF  180
SGSGSGTDFT LTISSLQPED FATYYCQQLV UYPYTFGQGT KLEIKRTVAA PSVFIFPPSD  240
EQLKSGTASV VCLLNNFYPR EAKVQWKVDN ALQSGNSQES VTEQDSKDST YSLSSTLTLS  300
KADYEKHKVY ACEVTHQGLS SPVTKSFNRG EC                               332

SEQ ID NO: 86          moltype = AA   length = 580
FEATURE                Location/Qualifiers
source                 1..580
                       mol_type = protein
                       organism = synthetic construct
SEQUENCE: 86
EVQLVESGGG LVQPGGSLRL SCAASGFTFS SYWMHWVRQA PGKGLEWVAY INPSTGYTEY   60
NQKFKRFTIS RDDSKNTVYL QMNSLRAEDT AVYYCTSGGY DDLGYWGQGT LVTVSSASTK  120
GPSVFPLAPQ VQLQESGPGL VKPSETLSLT CTVSGFSLIG YDLNWIRQPP GKGLEWIGII  180
WGDGTTDYNS AVKSRVTISK DTSKNQFSLK LSSVTAADTA VYYCARGGYW YATSYYPDYW  240
GQGTLVTVSS ASTKGPSVFP LAPSSKSTSG GTAALGCLVK DYFPEPVTVS WNSGALTSGV  300
HTFPAVLQSS GLYSLSSVVT VPSSSLGTQT YICNVNHKPS NTKVDKKVEP KSCDKTHTCP  360
PCPAPEAAGG PSVFLFPPKP KDTLMISRTP EVTCVVVDVS HEDPEVKFNW YVDGVEVHNA  420
```

```
KTKPREEQYN STYRVVSVLT VLHQDWLNGK EYKCKVSNKA LPAPIEKTIS KAKGQPREPQ  480
VYTLPPSRDE LTKNQVSLTC LVKGFYPSDI AVEWESNGQP ENNYKTTPPV LDSDGSFFLY  540
SKLTVDKSRW QQGNVFSCSV MHEALHNHYT QKSLSLSPGK                       580

SEQ ID NO: 87           moltype = AA  length = 339
FEATURE                 Location/Qualifiers
source                  1..339
                        mol_type = protein
                        organism = synthetic construct
SEQUENCE: 87
DIQMTQSPSS LSASVGDRVT ITCRSSKSLL YKDGKTYLYW YQQKPGKAPK LLIYLMSTRA   60
SGVPSRFSGS GSGTDFTLTI SSLQPEDFAT YYCQQLVUYP YTFGQGTKLE IKRTVAAPSV  120
FIFPPDIQMT QSPSSLSASV GDRVTITCRA SQSISNNLNW YQQKPGKAPK LLIYYTSRFH  180
SGVPSRFSGS GSGTDFTFTI SSLQPEDIAT YYCQQEHTLP YTFGQGTKLE IKRTVAAPSV  240
FIFPPPSDEQL KSGTASVVCL LNNFYPREAK VQWKVDNALQ SGNSQESVTE QDSKDSTYSL  300
SSTLTLSKAD YEKHKVYACE VTHQGLSSPV TKSFNRGEC                         339

SEQ ID NO: 88           moltype = AA  length = 577
FEATURE                 Location/Qualifiers
source                  1..577
                        mol_type = protein
                        organism = synthetic construct
SEQUENCE: 88
EVQLVESGGG LVQPGGSLRL SCAASGFTFS SYWMHWVRQA PGKGLEWVAY INPSTGYTEY   60
NQKFKRFTIS RDDSKNTVYL QMNSLRAEDT AVYYCTSGGY DDLGYWGQGT LVTVSSASTK  120
GPSVFPLAPQ VQLVQSGAEV KKPGASVKVS CKVSGFTLTE LSIHWVRQAP GKGLEWMGGF  180
DPEDGETIYA QKFQGRVTMT EDTSTDTAYM ELTSLRSEDT AVYYCSTIGV VTNFDNWGQG  240
TLVTVSSAST KGPSVFPLAP SSKSTSGGTA ALGCLVKDYF PEPVTVSWNS GALTSGVHTF  300
PAVLQSSGLY SLSSVVTVPS SSLGTQTYIC NVNHKPSNTK VDKKVEPKSC DKTHTCPPCP  360
APEAAGGPSV FLFPPKPKDT LMISRTPEVT CVVVDVSHED PEVKFNWYVD GVEVHNAKTK  420
PREEQYNSTY RVVSVLTVLH QDWLNGKEYK CKVSNKALPA PIEKTISKAK GQPREPQVYT  480
LPPSRDELTK NQVSLTCLVK GFYPSDIAVE WESNGQPENN YKTTPPVLDS DGSFFLYSKL  540
TVDKSRWQQG NVFSCSVMHE ALHNHYTQKS LSLSPGK                           577

SEQ ID NO: 89           moltype = AA  length = 338
FEATURE                 Location/Qualifiers
source                  1..338
                        mol_type = protein
                        organism = synthetic construct
SEQUENCE: 89
DIQMTQSPSS LSASVGDRVT ITCRSSKSLL YKDGKTYLYW YQQKPGKAPK LLIYLMSTRA   60
SGVPSRFSGS GSGTDFTLTI SSLQPEDFAT YYCQQLVUYP YTFGQGTKLE IKRTVAAPSV  120
FIFPPDIQMT QSPSSLSASV GDRVTITCKA SQSVGTTIVW TQQLPGLAPK LLIYSASNRH  180
TGVPSRFSGS GSGTDFTLTI SSLQPEDFAT YYCQQYTSYP FTFGQGTKEI KRTVAAPSVF  240
IFPPSDEQLK SGTASVVCLL NNFYPREAKV QWKVDNALQS GNSQESVTEQ DSKDSTYSLS  300
STLTLSKADY EKHKVYACEV THQGLSSPVT KSFNRGEC                          338

SEQ ID NO: 90           moltype = AA  length = 582
FEATURE                 Location/Qualifiers
source                  1..582
                        mol_type = protein
                        organism = synthetic construct
SEQUENCE: 90
EVQLVESGGG LVQPGGSLRL SCAASGFTFS SYWMHWVRQA PGKGLEWVAY INPSTGYTEY   60
NQKFKRFTIS RDDSKNTVYL QMNSLRAEDT AVYYCTSGGY DDLGYWGQGT LVTVSSASTK  120
GPSVFPLAPE VQLVESGGGL VQPGGSLRLS CAASGFTLRS YSMNWVRQAP GKGLEWVSYI  180
SRSSHTIFYA DSVKGRFTIS RDNAKNSLYL QMDSLRDEDT AMYYCARVYS SGWHVSDYFD  240
YWGQGILVTV SSASTKGPSV FPLAPSSKST SGGTAALGCL VKDYFPEPVT VSWNSGALTS  300
GVHTFPAVLQ SSGLYSLSSV VTVPSSSLGT QTYICNVNHK PSNTKVDKKV EPKSCDKTHT  360
CPPCPAPEAA GGPSVFLFPP KPKDTLMISR TPEVTCVVVD VSHEDPEVKF NWYVDGVEVH  420
NAKTKPREEQ YNSTYRVVSV LTVLHQDWLN GKEYKCKVSN KALPAPIEKT ISKAKGQPRE  480
PQVYTLPPSR DELTKNQVSL TCLVKGFYPS DIAVEWESNG QPENNYKTTP PVLDSDGSFF  540
LYSKLTVDKS RWQQGNVFSC SVMHEALHNH YTQKSLSLSP GK                     582

SEQ ID NO: 91           moltype = AA  length = 339
FEATURE                 Location/Qualifiers
source                  1..339
                        mol_type = protein
                        organism = synthetic construct
SEQUENCE: 91
DIQMTQSPSS LSASVGDRVT ITCRSSKSLL YKDGKTYLYW YQQKPGKAPK LLIYLMSTRA   60
SGVPSRFSGS GSGTDFTLTI SSLQPEDFAT YYCQQLVUYP YTFGQGTKLE IKRTVAAPSV  120
FIFPPAIQLT QSPSSLSASV GDRVTITCRA SQGISSALAW YQQKPGKAPK LLIYDASSLE  180
SGVPSRFSGS GSGTDFTLTI SSLQPEDFAT YYCQQFNSYP LTFGGGTKLE IKRTVAAPSV  240
FIFPPSDEQL KSGTASVVCL LNNFYPREAK VQWKVDNALQ SGNSQESVTE QDSKDSTYSL  300
SSTLTLSKAD YEKHKVYACE VTHQGLSSPV TKSFNRGEC                         339

SEQ ID NO: 92           moltype = AA  length = 586
FEATURE                 Location/Qualifiers
```

```
                        source              1..586
                                            mol_type = protein
                                            organism = synthetic construct
SEQUENCE: 92
QVQLQESGPG LVKPSETLSL TCTVSGFSLI GYDLNWIRQP PGKGLEWIGI IWGDGTTDYN    60
SAVKSRVTIS KDTSKNQFSL KLSSVTAADT AVYYCARGGY WYATSYYFDY WGQGTLVTVS   120
SASTKGPSVF PLAPEVQLVE SGGGLVQPGG SLRLSCAASG FTFSSYWMHW VRQAPGKGLE   180
WVAYINPSTG YTEYNQKFKR FTISRDDSKN TVYLQMNSLR AEDTAVYYCT SGGYDDLGYW   240
GQGTLVTVSS ASTKGPASTK GPSVPPLAPS SKSTSGGTAA LGCLVKDYFP EPVTVSWNSG   300
ALTSGVHTFP AVLQSSGLYS LSSVVTVPSS SLGTQTYICN VNHKPSNTKV DKKVEPKSCD   360
KTHTCPPCPA PEAAGGPSVF LFPPKPKDTL MISRTPEVTC VVVDVSHEDP EVKFNWYVDG   420
VEVHNAKTKP REEQYNSTYR VVSVLTVLHQ DWLNGKEYKC KVSNKALPAP IEKTISKAKG   480
QPREPQVYTL PPSRDELTKN QVSLTCLVKG FYPSDIAVEW ESNGQPENNY KTTPPVLDSD   540
GSFFLYSKLT VDKSRWQQGN VFSCSVMHEA LHNHYTQKSL SLSPGK                 586

SEQ ID NO: 93               moltype = AA  length = 339
FEATURE                     Location/Qualifiers
source                      1..339
                            mol_type = protein
                            organism = synthetic construct
SEQUENCE: 93
DIQMTQSPSS LSASVGDRVT ITCRASQSIS NNLNWYQQKP GKAPKLLIYY TSRFHSGVPS    60
RFSGSGSGTD FTFTISSLQP EDIATYYCQQ EHTLPYTFGQ GTKLEIKRTV AAPSVFIFPP   120
DIQMTQSPSS LSASVGDRVT ITCRSSKSLL YKDGKTYLYW YQQKPGKAPK LLIYLMSTRA   180
SGVPSRFSGS GSGTDFTLTI SSLQPEDFAT YYCQQLVUYP YTFGQGTKLE IKRTVAAPSV   240
FIFPPSDEQL KSGTASVVCL LNNFYPREAK VQWKVDNALQ SGNSQESVTE QDSKDSTYSL   300
SSTLTLSKAD YEKHKVYACE VTHQGLSSPV TKSFNRGEC                         339

SEQ ID NO: 94               moltype = AA  length = 579
FEATURE                     Location/Qualifiers
source                      1..579
                            mol_type = protein
                            organism = synthetic construct
SEQUENCE: 94
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIG VVTNFDNWGQ GTLVTVSSAS   120
TKGPSVFPLA PEVQLVESGG GLVQPGGSLR LSCAASGFTF SSYWMHWVRQ APGKGLEWVA   180
YINPSTGYTE YNQKFKRFTI SRDDSKNTVY LQMNSLRAED TAVYYCTSGG YDDLGYWGQG   240
TLVTVSSAST KGPASTKGPS VFPLAPSSKS TSGGTAALGC LVKDYFPEPV TVSWNSGALT   300
SGVHTFPAVL QSSGLYSLSS VVTVPSSSLG TQTYICNVNH KPSNTKVDKK VEPKSCDKTH   360
TCPPCPAPEA AGGPSVFLFP PKPKDTLMIS RTPEVTCVVV DVSHEDPEVK FNWYVDGVEV   420
HNAKTKPREE QYNSTYRVVS VLTVLHQDWL NGKEYKCKVS NKALPAPIEK TISKAKGQPR   480
EPQVYTLPPS RDELTKNQVS LTCLVKGFYP SDIAVEWESN GQPENNYKTT PPVLDSDGSF   540
FLYSKLTVDK SRWQQGNVFS CSVMHEALHN HYTQKSLSL                         579

SEQ ID NO: 95               moltype = AA  length = 338
FEATURE                     Location/Qualifiers
source                      1..338
                            mol_type = protein
                            organism = synthetic construct
SEQUENCE: 95
DIQMTQSPSS LSASVGDRVT ITCKASQSVG TTIVWTQQLP GLAPKLLIYS ASNRHTGVPS    60
RFSGSGSGTD FTLTISSLQP EDFATYYCQQ YTSYPFTFGQ GTKEIKRTVA APSVFIFPPD   120
IQMTQSPSSL SASVGDRVTI TCRSSKSLLY KDGKTYLYWY QQKPGKAPKL LIYLMSTRAS   180
GVPSRFSGSG SGTDFTLTIS SLQPEDFATY YCQQLVUYPY TFGQGTKLEI KRTVAAPSVF   240
IFPPSDEQLK SGTASVVCLL NNFYPREAKV QWKVDNALQS GNSQESVTEQ DSKDSTYSLS   300
STLTLSKADY EKHKVYACEV THQGLSSPVT KSFNRGEC                          338

SEQ ID NO: 96               moltype = AA  length = 584
FEATURE                     Location/Qualifiers
source                      1..584
                            mol_type = protein
                            organism = synthetic construct
SEQUENCE: 96
EVQLVESGGG LVQPGGSLRL SCAASGFTLR SYSMNWVRQA PGKGLEWVSY ISRSSHTIFY    60
ADSVKGRFTI SRDNAKNSLY LQMDSLRDED TAMYYCARVY SSGWHVSDYF DYWGQGILVT   120
VSSASTKGPS VFPLAPEVQL VESGGGLVQP GGSLRLSCAA SGFTFSSYWM HWVRQAPGKG   180
LEWVAYINPS TGYTEYNQKF KRFTISRDDS KNTVYLQMNS LRAEDTAVYY CTSGGYDDLG   240
YWGQGTLVTV SSASTKGPAS TKGPSVFPLA PSSKSTSGGT AALGCLVKDY FPEPVTVSWN   300
SGALTSGVHT FPAVLQSSGL YSLSSVVTVP SSSLGTQTYI CNVNHKPSNT KVDKKVEPKS   360
CDKTHTCPPC PAPEAAGGPS VFLFPPKPKD TLMISRTPEV TCVVVDVSHE DPEVKFNWYV   420
DGVEVHNAKT KPREEQYNST YRVVSVLTVL HQDWLNGKEY KCKVSNKALP APIEKTISKA   480
KGQPREPQVY TLPPSRDELT KNQVSLTCLV KGFYPSDIAV EWESNGQPEN NYKTTPPVLD   540
SDGSFFLYSK LTVDKSRWQQ GNVFSCSVMH EALHNHYTQK SLSL                   584

SEQ ID NO: 97               moltype = AA  length = 339
FEATURE                     Location/Qualifiers
source                      1..339
                            mol_type = protein
```

```
                        organism = synthetic construct
SEQUENCE: 97
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPLTFGG GTKLEIKRTV AAPSVFIFPP   120
DIQMTQSPSS LSASVGDRVT ITCRSSKSLL YKDGKTYLYW YQQKPGKAPK LLIYLMSTRA   180
SGVPSRFSGS GSGTDFTLTI SSLQPEDFAT YYCQQLVUYP YTFGQGTKLE IKRTVAAPSV   240
FIFPPSDEQL KSGTASVVCL LNNFYPREAK VQWKVDNALQ SGNSQESVTE QDSKDSTYSL   300
SSTLTLSKAD YEKHKVYACE VTHQGLSSPV TKSFNRGEC                          339

SEQ ID NO: 98           moltype = AA  length = 448
FEATURE                 Location/Qualifiers
source                  1..448
                        mol_type = protein
                        organism = synthetic construct
SEQUENCE: 98
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIG VVTNFDNWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPEAAGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSR LTVDKSRWQQ   420
GNVFSCSVMH EALHNHYTQK SLSLSPGK                                      448

SEQ ID NO: 99           moltype = AA  length = 214
FEATURE                 Location/Qualifiers
source                  1..214
                        mol_type = protein
                        organism = synthetic construct
SEQUENCE: 99
DIQMTQSPSS LSASAGDRVT ITCRASQAIR NDLGWYQQKP GKAPKRLIYA AFNLQSGVPS    60
RFSGSGSGTE FTLTISSLQP EDLASYYCQQ YNRYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 100          moltype = AA  length = 454
FEATURE                 Location/Qualifiers
source                  1..454
                        mol_type = protein
                        organism = synthetic construct
SEQUENCE: 100
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
AAGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLSCLVKGFY PSDIAVEWES NGQPENNYKT TPPVLDSDGS FFLYSRLTVD   420
KSRWQQGNVF SCSVMHEALH NHYTQKSLSL SPGK                               454

SEQ ID NO: 101          moltype = AA  length = 448
FEATURE                 Location/Qualifiers
source                  1..448
                        mol_type = protein
                        organism = synthetic construct
SEQUENCE: 101
QVQLVQSGAE VKKPGASVKV SCKVSGFTLT ELSIHWVRQA PGKGLEWMGG FDPEDGETIY    60
AQKFQGRVTM TEDTSTDTAY MELTSLRSED TAVYYCSTIG VVTNFDNWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPEAAGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFKLYSK LTVDKSRWQQ   420
GNVFSCSVMH EALHNHYTQK SLSLSPGK                                      448

SEQ ID NO: 102          moltype = AA  length = 444
FEATURE                 Location/Qualifiers
source                  1..444
                        mol_type = protein
                        organism = synthetic construct
SEQUENCE: 102
EVQLLESGGG LVQPGGSLRL SCAASGFTFS DAWMDWVRQA PGKGLEWVAE IRHKANDHAI    60
FYDESVKGRF TISRDSKNTV YLQMNSLRAE DTAVYYCTSP FAYWGQGTLV TVSSASTKGP   120
SVFPLAPSSK STSGGTAALG CLVKDYFPEP VTVSWNSGAL TSGVHTFPAV LQSSGLYSLS   180
SVVTVPSSSL GTQTYICNVN HKPSNTKVDK KVEPKSCDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVYTLPP SRDELTKNQV   360
SLSCLVKGFY PSDIAVEWES NGQPENNYKT TPPVLDSDGS FFLYSRLTVD KSRWQQGNVF   420
SCSVMHEALH NHYTQKSLSL SPGK                                          444
```

```
SEQ ID NO: 103          moltype = AA  length = 457
FEATURE                 Location/Qualifiers
source                  1..457
                        mol_type = protein
                        organism = synthetic construct
SEQUENCE: 103
EVQLVESGGG LVQPGGSLRL SCAASGFTLR SYSMNWVRQA PGKGLEWVSY ISRSSHTIFY    60
ADSVKGRFTI SRDNAKNSLY LQMDSLRDED TAMYYCARVY SSGWHVSDYF DYWGQGILVT   120
VSSASVAAPS VFIFPPSDEQ LKSGTASVVC LLNNFYPREA KVQWKVDNAL QSGNSQESVT   180
EQDSKDSTYS LSSTLTLSKA DYEKHKVYAC EVTHQGLSSP VTKSFNRGEC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPCRDELTK NQVSLWCLVK GFYPSDIAVE WESNGQPENN YKTTPPVLDS DGSFFLYSKL   420
TVDKSRWQQG NVFSCSVMHE ALHNHYTQKS LSLSPGK                            457

SEQ ID NO: 104          moltype = AA  length = 212
FEATURE                 Location/Qualifiers
source                  1..212
                        mol_type = protein
                        organism = synthetic construct
SEQUENCE: 104
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPLTFGG GTKVTVLSSA STKGPSVFPL   120
APSSKSTSGG TAALGCLVKD YFPEPVTVSW NSGALTSGVH TFPAVLQSSG LYSLSSVVTV   180
PSSSLGTQTY ICNVNHKPSN TKVDKKVEPK SC                                 212

SEQ ID NO: 105          moltype = AA  length = 583
FEATURE                 Location/Qualifiers
source                  1..583
                        mol_type = protein
                        organism = synthetic construct
SEQUENCE: 105
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP EVQLVESGGG LVQPGGSLRL SCAASGFTLR SYSMNWVRQA PGKGLEWVSY   180
ISRSSHTIFY ADSVKGRFTI SRDNAKNSLY LQMDSLRDED TAMYYCARVY SSGWHVSDYF   240
DYWGQGILVT VSSASTKGPS VFPLAPSSKS TSGGTAALGC LVKDYFPEPV TVSWNSGALT   300
SGVHTFPAVL QSSGLYSLSS VVTVPSSSLG TQTYICNVNH KPSNTKVDKK VEPKSCDKTH   360
TCPPCPAPEA AGGPSVFLFP PKPKDTLMIS RTPEVTCVVV DVSHEDPEVK FNWYVDGVEV   420
HNAKTKPREE QYNSTYRVVS VLTVLHQDWL NGKEYKCKVS NKALPAPIEK TISKAKGQPR   480
EPQVYTLPPS RDELTKNQVS LTCLVKGFYP SDIAVEWESN GQPENNYKTT PPVLDSDGSF   540
FLYSKLTVDK SRWQQGNVFS CSVMHEALHN HYTQKSLSLS PGK                     583

SEQ ID NO: 106          moltype = AA  length = 327
FEATURE                 Location/Qualifiers
source                  1..327
                        mol_type = protein
                        organism = synthetic construct
SEQUENCE: 106
DIQMTQSPSS LSASVGDRVT ITCRTSENIY SYLAWYQQKP GKAPKLLIYN AKTLAEGVPS    60
RFSGSGSGTD FTLTISSLQP EDFATYYCQH HYGTPWTFGQ GTKLEIKRTV AAPAIQLTQS   120
PSSLSASVGD RVTITCRASQ GISSALAWYQ QKPGKAPKLL IYDASSLESG VPSRFSGSGS   180
GTDFTLTISS LQPEDFATYY CQQFNSYPLT FGGGTKLEIK RTVAAPSVFI FPPSDEQLKS   240
GTASVVCLLN NFYPREAKVQ WKVDNALQSG NSQESVTEQD SKDSTYSLSS TLTLSKADYE   300
KHKVYACEVT HQGLSSPVTK SFNRGEC                                       327

SEQ ID NO: 107          moltype = AA  length = 573
FEATURE                 Location/Qualifiers
source                  1..573
                        mol_type = protein
                        organism = synthetic construct
SEQUENCE: 107
EVQLLESGGG LVQPGGSLRL SCAASGFTFS DAWMDWVRQA PGKGLEWVAE IRHKANDHAI    60
FYDESVKGRF TISRDSKNTV YLQMNSLRAE DTAVYYCTSP FAYWGQGTLV TVSSASTKGP   120
EVQLVESGGG LVQPGGSLRL SCAASGFTLR SYSMNWVRQA PGKGLEWVSY ISRSSHTIFY   180
ADSVKGRFTI SRDNAKNSLY LQMDSLRDED TAMYYCARVY SSGWHVSDYF DYWGQGILVT   240
VSSASTKGPS VFPLAPSSKS TSGGTAALGC LVKDYFPEPV TVSWNSGALT SGVHTFPAVL   300
QSSGLYSLSS VVTVPSSSLG TQTYICNVNH KPSNTKVDKK VEPKSCDKTH TCPPCPAPEA   360
AGGPSVFLFP PKPKDTLMIS RTPEVTCVVV DVSHEDPEVK FNWYVDGVEV HNAKTKPREE   420
QYNSTYRVVS VLTVLHQDWL NGKEYKCKVS NKALPAPIEK TISKAKGQPR EPQVYTLPPS   480
RDELTKNQVS LTCLVKGFYP SDIAVEWESN GQPENNYKTT PPVLDSDGSF FLYSKLTVDK   540
SRWQQGNVFS CSVMHEALHN HYTQKSLSLS PGK                                573

SEQ ID NO: 108          moltype = AA  length = 326
FEATURE                 Location/Qualifiers
source                  1..326
                        mol_type = protein
                        organism = synthetic construct
```

```
SEQUENCE: 108
DIQMTQSPSS LSASVGDRVT ITCKASQSVG TTIVWTQQLP GLAPKLLIYS ASNRHTGVPS      60
RFSGSGSGTD FTLTISSLQP EDFATYYCQQ YTSYPFTFGQ GTKEIKRTVA APAIQLTQSP     120
SSLSASVGDR VTITCRASQG ISSALAWYQQ KPGKAPKLLI YDASSLESGV PSRFSGSGSG     180
TDFTLTISSL QPEDFATYYC QQFNSYPLTF GGGTKLEIKR TVAAPSVFIF PPSDEQLKSG     240
TASVVCLLNN FYPREAKVQW KVDNALQSGN SQESVTEQDS KDSTYSLSST LTLSKADYEK     300
HKVYACEVTH QGLSSPVTKS FNRGEC                                         326

SEQ ID NO: 109          moltype = AA   length = 583
FEATURE                 Location/Qualifiers
source                  1..583
                        mol_type = protein
                        organism = synthetic construct
SEQUENCE: 109
EVQLVESGGG LVQPGGSLRL SCAASGFTLR SYSMNWVRQA PGKGLEWVSY ISRSSHTIFY      60
ADSVKGRFTI SRDNAKNSLY LQMDSLRDED TAMYYCARVY SSGWHVSDYF DYWGQGILVT     120
VSSASTKGPE VQLVESGGGL VQPGGSLRLS CAASGFTLRS AWMDWVRQAP GKGLEWVAEI     180
RNKANNHARH YAESVKGRFT ISRDNAKNSL YLQMNSLRAE DTAVYYCART YYYGSSYGYC     240
DVWGQGTLVT VSSASTKGPS VFPLAPSSKS TSGGTAALGC LVKDYFPEPV TVSWNSGALT     300
SGVHTFPAVL QSSGLYSLSS VVTVPSSSLG TQTYICNVNH KPSNTKVDKK VEPKSCDKTH     360
TCPPCPAPEA AGGPSVFLFP PKPKDTLMIS RTPEVTCVVV DVSHEDPEVK FNWYVDGVEV     420
HNAKTKPREE QYNSTYRVVS VLTVLHQDWL NGKEYKCKVS NKALPAPIEK TISKAKGQPR     480
EPQVYTLPPS RDELTKNQVS LTCLVKGFYP SDIAVEWESN GQPENNYKTT PPVLDSDGSF     540
FLYSKLTVDK SRWQQGNVFS CSVMHEALHN HYTQKSLSLS PGK                      583

SEQ ID NO: 110          moltype = AA   length = 327
FEATURE                 Location/Qualifiers
source                  1..327
                        mol_type = protein
                        organism = synthetic construct
SEQUENCE: 110
AIQLTQSPSS LSASVGDRVT ITCRASQGIS SALAWYQQKP GKAPKLLIYD ASSLESGVPS      60
RFSGSGSGTD FTLTISSLQP EDFATYYCQQ FNSYPLTFGG GTKLEIKRTV AAPDIQMTQS     120
PSSLSASVGD RVTITCRTSE NIYSYLAWYQ QKPGKAPKLI YNAKTLAEG VPSRFSGSGS     180
GTDFTLTISS LQPEDFATYY CQHHYGTPWT FGQGTKLEIK RTVAAPSVFI FPPSDEQLKS     240
GTASVVCLLN NFYPREAKVQ WKVDNALQSG NSQESVTEQD SKDSTYSLSS TLTLSKADYE     300
KHKVYACEVT HQGLSSPVTK SFNRGEC                                        327

SEQ ID NO: 111          moltype = AA   length = 573
FEATURE                 Location/Qualifiers
source                  1..573
                        mol_type = protein
                        organism = synthetic construct
SEQUENCE: 111
EVQLVESGGG LVQPGGSLRL SCAASGFTLR SYSMNWVRQA PGKGLEWVSY ISRSSHTIFY      60
ADSVKGRFTI SRDNAKNSLY LQMDSLRDED TAMYYCARVY SSGWHVSDYF DYWGQGILVT     120
VSSASTKGPE VQLLESGGGL VQPGGSLRLS CAASGFTLRS AWMDWVRQAP GKGLEWVAEI     180
RHKANDHAIF YDESVKGRFT ISRDSKNTVY LQMNSLRAED TAVYYCTSPF AYWGQGTLVT     240
VSSASTKGPS VFPLAPSSKS TSGGTAALGC LVKDYFPEPV TVSWNSGALT SGVHTFPAVL     300
QSSGLYSLSS VVTVPSSSLG TQTYICNVNH KPSNTKVDKK VEPKSCDKTH TCPPCPAPEA     360
AGGPSVFLFP PKPKDTLMIS RTPEVTCVVV DVSHEDPEVK FNWYVDGVEV HNAKTKPREE     420
QYNSTYRVVS VLTVLHQDWL NGKEYKCKVS NKALPAPIEK TISKAKGQPR EPQVYTLPPS     480
RDELTKNQVS LTCLVKGFYP SDIAVEWESN GQPENNYKTT PPVLDSDGSF FLYSKLTVDK     540
SRWQQGNVFS CSVMHEALHN HYTQKSLSLS PGK                                 573

SEQ ID NO: 112          moltype = AA   length = 326
FEATURE                 Location/Qualifiers
source                  1..326
                        mol_type = protein
                        organism = synthetic construct
SEQUENCE: 112
AIQLTQSPSS LSASVGDRVT ITCRASQGIS SALAWYQQKP GKAPKLLIYD ASSLESGVPS      60
RFSGSGSGTD FTLTISSLQP EDFATYYCQQ FNSYPLTFGG GTKLEIKRTV AAPDIQMTQS     120
PSSLSASVGD RVTITCKASQ SVGTTIVWTQ QLPGLAPKLL IYSASNRHTG VPSRFSGSGS     180
GTDFTLTISS LQPEDFATYY CQQYTSYPFT FGQGTKEIKR TVAAPSVFIF PPSDEQLKSG     240
TASVVCLLNN FYPREAKVQW KVDNALQSGN SQESVTEQDS KDSTYSLSST LTLSKADYEK     300
HKVYACEVTH QGLSSPVTKS FNRGEC                                         326

SEQ ID NO: 113          moltype = AA   length = 590
FEATURE                 Location/Qualifiers
source                  1..590
                        mol_type = protein
                        organism = synthetic construct
SEQUENCE: 113
EVQLVESGGG LVQPGGSLRL SCAASGFTFS DAWMDWVRQA PGKGLEWVAE IRNKANNHAR      60
HYAESVKGRF TISRDNAKNS LYLQMNSLRA EDTAVYYCAR TYYYGSSYGY CDVWGQGTLV     120
TVSSASTKGP SVFPLAPEVQ LVESGGGLVQ PGGSLRLSCA ASGFTLRSYS MNWVRQAPGK     180
GLEWVSYISR SSHTIFYADS VKGRFTISRD NAKNSLYLQM DSLRDEDTAM YYCARVYSSG     240
WHVSDYFDYW GQGILVTVSS ASTKGPSVFP LAPSSKSTSG GTAALGCLVK DYFPEPVTVS     300
```

```
WNSGALTSGV HTFPAVLQSS GLYSLSSVVT VPSSSLGTQT YICNVNHKPS NTKVDKKVEP    360
KSCDKTHTCP PCPAPEAAGG PSVFLFPPKP KDTLMISRTP EVTCVVVDVS HEDPEVKFNW    420
YVDGVEVHNA KTKPREEQYN STYRVVSVLT VLHQDWLNGK EYKCKVSNKA LPAPIEKTIS    480
KAKGQPREPQ VYTLPPSRDE LTKNQVSLTC LVKGFYPSDI AVEWESNGQP ENNYKTTPPV    540
LDSDGSFFLY SKLTVDKSRW QQGNVFSCSV MHEALHNHYT QKSLSLSPGK              590

SEQ ID NO: 114          moltype = AA   length = 334
FEATURE                 Location/Qualifiers
source                  1..334
                        mol_type = protein
                        organism = synthetic construct
SEQUENCE: 114
DIQMTQSPSS LSASVGDRVT ITCRTSENIY SYLAWYQQKP GKAPKLLIYN AKTLAEGVPS     60
RFSGSGSGTD FTLTISSLQP EDFATYYCQH HYGTPWTFGQ GTKLEIKRTV AAPSVFIFPP    120
AIQLTQSPSS LSASVGDRVT ITCRASQGIS SALAWYQQKP GKAPKLLIYD ASSLESGVPS    180
RFSGSGSGTD FTLTISSLQP EDFATYYCQQ FNSYPLTFGG GTKLEIKRTV AAPSVFIFPP    240
SDEQLKSGTA SVVCLLNNFY PREAKVQWKV DNALQSGNSQ ESVTEQDSKD STYSLSSTLT    300
LSKADYEKHK VYACEVTHQG LSSPVTKSFN RGEC                                334

SEQ ID NO: 115          moltype = AA   length = 580
FEATURE                 Location/Qualifiers
source                  1..580
                        mol_type = protein
                        organism = synthetic construct
SEQUENCE: 115
EVQLLESGGG LVQPGGSLRL SCAASGFTFS DAWMDWVRQA PGKGLEWVAE IRHKANDHAI     60
FYDESVKGRF TISRDSKNTV YLQMNSLRAE DTAVYYCTSP FAYWGQGTLV TVSSASTKGP    120
SVFPLAPEVQ LVESGGGLVQ PGGSLRLSCA ASGFTLRSYS MNWVRQAPGK GLEWVSYISR    180
SSHTIFYADS VKGRFTISRD NAKNSLYLQM DSLRDEDTAM YYCARVYSSG WHVSDYFDYW    240
GQGILVTVSS ASTKGPSVFP LAPSSKSTSG GTAALGCLVK DYFPEPVTVS WNSGALTSGV    300
HTFPAVLQSS GLYSLSSVVT VPSSSLGTQT YICNVNHKPS NTKVDKKVEP KSCDKTHTCP    360
PCPAPEAAGG PSVFLFPPKP KDTLMISRTP EVTCVVVDVS HEDPEVKFNW YVDGVEVHNA    420
KTKPREEQYN STYRVVSVLT VLHQDWLNGK EYKCKVSNKA LPAPIEKTIS KAKGQPREPQ    480
VYTLPPSRDE LTKNQVSLTC LVKGFYPSDI AVEWESNGQP ENNYKTTPPV LDSDGSFFLY    540
SKLTVDKSRW QQGNVFSCSV MHEALHNHYT QKSLSLSPGK                          580

SEQ ID NO: 116          moltype = AA   length = 333
FEATURE                 Location/Qualifiers
source                  1..333
                        mol_type = protein
                        organism = synthetic construct
SEQUENCE: 116
DIQMTQSPSS LSASVGDRVT ITCKASQSVG TTIVWTQQLP GLAPKLLIYS ASNRHTGVPS     60
RFSGSGSGTD FTLTISSLQP EDFATYYCQQ YTSYPFTFGQ GTKEIKRTVA APSVFIFPPA    120
IQLTQSPSSL SASVGDRVTI TCRASQGISS ALAWYQQKPG KAPKLLIYDA SSLESGVPSR    180
FSGSGSGTDF TLTISSLQPE DFATYYCQQF NSYPLTFGGG TKLEIKRTVA APSVFIFPPS    240
DEQLKSGTAS VVCLLNNFYP REAKVQWKVD NALQSGNSQE SVTEQDSKDS TYSLSSTLTL    300
SKADYEKHKV YACEVTHQGL SSPVTKSFNR GEC                                 333

SEQ ID NO: 117          moltype = AA   length = 590
FEATURE                 Location/Qualifiers
source                  1..590
                        mol_type = protein
                        organism = synthetic construct
SEQUENCE: 117
EVQLVESGGG LVQPGGSLRL SCAASGFTLR SYSMNWVRQA PGKGLEWVSY ISRSSHTIFY     60
ADSVKGRFTI SRDNAKNSLY LQMDSLRDED TAMYYCARVY SSGWHVSDYF DYWGQGILVT    120
VSSASTKGPS VFPLAPEVQL VESGGGLVQP GGSLRLSCAA SGFTFSDAWM DWVRQAPGKG    180
LEWVAEIRNK ANNHARHYAE SVKGRFTISR DNAKNSLYLQ MNSLRAEDTA VYYCARTYYY    240
GSSYGYCDVW GQGTLVTVSS ASTKGPSVFP LAPSSKSTSG GTAALGCLVK DYFPEPVTVS    300
WNSGALTSGV HTFPAVLQSS GLYSLSSVVT VPSSSLGTQT YICNVNHKPS NTKVDKKVEP    360
KSCDKTHTCP PCPAPEAAGG PSVFLFPPKP KDTLMISRTP EVTCVVVDVS HEDPEVKFNW    420
YVDGVEVHNA KTKPREEQYN STYRVVSVLT VLHQDWLNGK EYKCKVSNKA LPAPIEKTIS    480
KAKGQPREPQ VYTLPPSRDE LTKNQVSLTC LVKGFYPSDI AVEWESNGQP ENNYKTTPPV    540
LDSDGSFFLY SKLTVDKSRW QQGNVFSCSV MHEALHNHYT QKSLSLSPGK               590

SEQ ID NO: 118          moltype = AA   length = 334
FEATURE                 Location/Qualifiers
source                  1..334
                        mol_type = protein
                        organism = synthetic construct
SEQUENCE: 118
AIQLTQSPSS LSASVGDRVT ITCRASQGIS SALAWYQQKP GKAPKLLIYD ASSLESGVPS     60
RFSGSGSGTD FTLTISSLQP EDFATYYCQQ FNSYPLTFGG GTKLEIKRTV AAPSVFIFPP    120
DIQMTQSPSS LSASVGDRVT ITCRTSENIY SYLAWYQQKP GKAPKLLIYN AKTLAEGVPS    180
RFSGSGSGTD FTLTISSLQP EDFATYYCQH HYGTPWTFGQ GTKLEIKRTV AAPSVFIFPP    240
SDEQLKSGTA SVVCLLNNFY PREAKVQWKV DNALQSGNSQ ESVTEQDSKD STYSLSSTLT    300
LSKADYEKHK VYACEVTHQG LSSPVTKSFN RGEC                                334
```

```
SEQ ID NO: 119          moltype = AA   length = 580
FEATURE                 Location/Qualifiers
source                  1..580
                        mol_type = protein
                        organism = synthetic construct
SEQUENCE: 119
EVQLVESGGG LVQPGGSLRL SCAASGFTLR SYSMNWVRQA PGKGLEWVSY ISRSSHTIFY    60
ADSVKGRFTI SRDNAKNSLY LQMDSLRDED TAMYYCARVY SSGWHVSDYF DYWGQGILVT   120
VSSSASTKGPS VFPLAPEVQL LESGGGLVQP GGSLRLSCAA SGFTFSDAWM DWVRQAPGKG  180
LEWVAEIRHK ANDHAIFYDE SVKGRFTISR DSKNTVYLQM NSLRAEDTAV YYCTSPFAYW   240
GQGTLVTVSS ASTKGPSVFP LAPSSKSTSG GTAALGCLVK DYFPEPVTVS WNSGALTSGV   300
HTFPAVLQSS GLYSLSSVVT VPSSSLGTQT YICNVNHKPS NTKVDKKVEP KSCDKTHTCP   360
PCPAPEAAGG PSVFLFPPKP KDTLMISRTP EVTCVVVDVS HEDPEVKFNW YVDGVEVHNA   420
KTKPREEQYN STYRVVSVLT VLHQDWLNGK EYKCKVSNKA LPAPIEKTIS KAKGQPREPQ   480
VYTLPPSRDE LTKNQVSLTC LVKGFYPSDI AVEWESNGQP ENNYKTTPPV LDSDGSFFLY   540
SKLTVDKSRW QQGNVFSCSV MHEALHNHYT QKSLSLSPGK                         580

SEQ ID NO: 120          moltype = AA   length = 333
FEATURE                 Location/Qualifiers
source                  1..333
                        mol_type = protein
                        organism = synthetic construct
SEQUENCE: 120
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPLTFGG GTKLEIKRTV AAPSVFIFPP   120
DIQMTQSPSS LSASVGDRVT ITCKASQSVG TTIVWTQQLP GLAPKLLIYS ASNRHTGVPS   180
RFSGSGSGTD FTLTISSLQP EDFATYYCQQ YTSYPFTFGQ GTKEIKRTVA APSVFIFPPS   240
DEQLKSGTAS VVCLLNNFYP REAKVQWKVD NALQSGNSQE SVTEQDSKDS TYSLSSTLTL   300
SKADYEKHKV YACEVTHQGL SSPVTKSFNR GEC                                333

SEQ ID NO: 121          moltype = AA   length = 453
FEATURE                 Location/Qualifiers
source                  1..453
                        mol_type = protein
                        organism = synthetic construct
SEQUENCE: 121
EVQLVESGGG LVQPGGSLRL SCAASGFTLR SYSMNWVRQA PGKGLEWVSY ISRSSHTIFY    60
ADSVKGRFTI SRDNAKNSLY LQMDSLRDED TAMYYCARVY SSGWHVSDYF DYWGQGILVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSRLTVDK   420
SRWQQGNVFS CSVMHEALHN HYTQKSLSLS PGK                                453

SEQ ID NO: 122          moltype = AA   length = 214
FEATURE                 Location/Qualifiers
source                  1..214
                        mol_type = protein
                        organism = synthetic construct
SEQUENCE: 122
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPLTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 123          moltype = AA   length = 453
FEATURE                 Location/Qualifiers
source                  1..453
                        mol_type = protein
                        organism = synthetic construct
SEQUENCE: 123
EVQLVESGGG LVQPGGSLRL SCAASGFTLR SYSMNWVRQA PGKGLEWVSY ISRSSHTIFY    60
ADSVKGRFTI SRDNAKNSLY LQMDSLRDED TAMYYCARVY SSGWHVSDYF DYWGQGILVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF LLYSKLTVDK   420
SRWQQGNVFS CSVMHEALHN HYTQKSLSLS PGK                                453

SEQ ID NO: 124          moltype = AA   length = 451
FEATURE                 Location/Qualifiers
source                  1..451
                        mol_type = protein
                        organism = synthetic construct
SEQUENCE: 124
QVQLQESGPG LVKPSETLSL TCTVSGFSLI GYDLNWIRQP PGKGLEWIGI IWGDGTTDYN    60
SAVKSRVTIS KDTSKNQFSL KLSSVTAADT AVYYCARGGY WYATSYYFDY WGQGTLVTVS   120
```

```
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFLL YSKLTVDKSR    420
WQQGNVFSCS VMHEALHNHY TQKSLSLSPG K                                   451

SEQ ID NO: 125          moltype = AA  length = 451
FEATURE                 Location/Qualifiers
source                  1..451
                        mol_type = protein
                        organism = synthetic construct
SEQUENCE: 125
QVQLQESGPG LVKPSETLSL TCTVSGFSLI GYDLNWIRQP PGKGLEWIGI IWGDGTTDYN     60
SAVKSRVTIS KDTSKNQFSL KLSSVTAADT AVYYCARGGY WYATSYYFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFLL YSKLTVDKSR    420
WQQGNVFSCS VMHEALHNHY TQKSLSLSPG K                                   451

SEQ ID NO: 126          moltype = AA  length = 451
FEATURE                 Location/Qualifiers
source                  1..451
                        mol_type = protein
                        organism = synthetic construct
SEQUENCE: 126
EVQLLESGGG LVQPGGSLRL SCAASGFTFS GRTVSSYAMG WVRQAPGKGL EWVAGISRSA     60
ERTYRFTISR DSKNTVYLQM NSLRAEDTAV YYCTSDLDPN RIFSREEYAY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVCTLPPSRD    360
ELTKNQVSLS CAVKGFYPSD IAVEWESNGQ PENNYKTTPP VLDSDGSFFL VSKLTVDKSR    420
WQQGNVFSCS VMHEALHNHY TQKSLSLSPG K                                   451

SEQ ID NO: 127          moltype = AA  length = 445
FEATURE                 Location/Qualifiers
source                  1..445
                        mol_type = protein
                        organism = synthetic construct
SEQUENCE: 127
EVQLLESGGG LVQPGGSLRL SCAASGFTFS SYWMHWVRQA PGKGLEWVAY INPSTGYTEY     60
NQKFKRFTIS RDSKNTVYLQ MNSLRAEDTA VYYCTSGGYD DLGYWGQGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP EAAGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSRDELTKNQ    360
VSLSCLVKGF YPSDIAVEWE SNGQPENNYK TTPPVLDSDG SFLLYSKLTV DKSRWQQGNV    420
FSCSVMHEAL HNHYTQKSLS LSPGK                                          445

SEQ ID NO: 128          moltype = AA  length = 219
FEATURE                 Location/Qualifiers
source                  1..219
                        mol_type = protein
                        organism = synthetic construct
SEQUENCE: 128
DIQMTQSPSS LSASVGDRVT ITCRSSKSLL YKDGKTYLYW TQQLPGLAPK LLIYLMSTRA     60
SGVPSRFSGS GSGTDFTLTI SSLQPEDFAT YYCQQLVUYP YTFGQGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 129          moltype = AA  length = 445
FEATURE                 Location/Qualifiers
source                  1..445
                        mol_type = protein
                        organism = synthetic construct
SEQUENCE: 129
EVQLLESGGG LVQPGGSLRL SCAASGFTFS SYWMHWVRQA PGKGLEWVAY INPSTGYTEY     60
NQKFKRFTIS RDSKNTVYLQ MNSLRAEDTA VYYCTSGGYD DLGYWGQGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP EAAGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSRDELTKNQ    360
VSLSCLVKGF YPSDIAVEWE SNGQPENNYK TTPPVLDSDG SFFLYSRLTV DKSRWQQGNV    420
FSCSVMHEAL HNHYTQKSLS LSPGK                                          445

SEQ ID NO: 130          moltype = AA  length = 714
```

```
FEATURE                  Location/Qualifiers
source                   1..714
                         mol_type = protein
                         organism = synthetic construct
SEQUENCE: 130
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
AAGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPGKGGGGSG GGGSGGGGSE VQLVESGGGL   480
VQPGGSLRLS CAASGFTLRS YSMNWVRQAP GKGLEWVSYI SRSSHTIFYA DSVKGRFTIS   540
RDNAKNSLYL QMDSLRDEDT AMYYCARVYS SGWHVSDYFD YWGQGILVTV SSGGGGSGGG   600
GSGGGGSAIQ LTQSPSSLSA SVGDRVTITC RASQGISSAL AWYQQKPGKA PKLLIYDASS   660
LESGVPSRFS GSGSGTDFTL TISSLQPEDF ATYYCQQFNS YPLTFGGGTK LEIK         714

SEQ ID NO: 131           moltype = AA  length = 709
FEATURE                  Location/Qualifiers
source                   1..709
                         mol_type = protein
                         organism = synthetic construct
SEQUENCE: 131
EVQLVESGGG LVQPGGSLRL SCAASGFTFS DAWMDWVRQA PGKGLEWVAE IRNKANNHAR    60
HYAESVKGRF TISRDNAKNS LYLQMNSLRA EDTAVYYCAR TYYYGSSYGY CDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
AAGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPGKGGGGSG GGGSGGGGSQ VQLVQSGAEV   480
KKPGASVKVS CKVSGFTLTE LSIHWVRQAP GKGLEWMGGF DPEDGETIYA QKFQGRVTMT   540
EDTSTDTAYM ELTSLRSEDT AVYYCSTIGV VTNFDNWGQG TLVTVSSGGG GSGGGGSGGG   600
GSDIQMTQSP SSLSASAGDR VTITCRASQA IRNDLGWYQQ KPGKAPKRLI YAAFNLQSGV   660
PSRFSGSGSG TEFTLTISSL QPEDLASYYC QQYNRYPWTF GQGTKLEIK               709

SEQ ID NO: 132           moltype = AA  length = 704
FEATURE                  Location/Qualifiers
source                   1..704
                         mol_type = protein
                         organism = synthetic construct
SEQUENCE: 132
EVQLLESGGG LVQPGGSLRL SCAASGFTFS DAWMDWVRQA PGKGLEWVAE IRHKANDHAI    60
FYDESVKGRF TISRDSKNTV YLQMNSLRAE DTAVYYCTSP FAYWGQGTLV TVSSASTKGP   120
SVFPLAPSSK STSGGTAALG CLVKDYFPEP VTVSWNSGAL TSGVHTFPAV LQSSGLYSLS   180
SVVTVPSSSL GTQTYICNVN HKPSNTKVDK KVEPKSCDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVYTLPP SRDELTKNQV   360
SLTCLVKGFY PSDIAVEWES NGQPENNYKT TPPVLDSDGS FFLYSKLTVD KSRWQQGNVF   420
SCSVMHEALH NHYTQKSLSL SPGKGGGGSG GGGSGGGGSE VQLVESGGGL VQPGGSLRLS   480
CAASGFTLRS YSMNWVRQAP GKGLEWVSYI SRSSHTIFYA DSVKGRFTIS RDNAKNSLYL   540
QMDSLRDEDT AMYYCARVYS SGWHVSDYFD YWGQGILVTV SSGGGGSGGG GSGGGGSAIQ   600
LTQSPSSLSA SVGDRVTITC RASQGISSAL AWYQQKPGKA PKLLIYDASS LESGVPSRFS   660
GSGSGTDFTL TISSLQPEDF ATYYCQQFNS YPLTFGGGTK LEIK                    704

SEQ ID NO: 133           moltype = AA  length = 699
FEATURE                  Location/Qualifiers
source                   1..699
                         mol_type = protein
                         organism = synthetic construct
SEQUENCE: 133
EVQLLESGGG LVQPGGSLRL SCAASGFTFS DAWMDWVRQA PGKGLEWVAE IRHKANDHAI    60
FYDESVKGRF TISRDSKNTV YLQMNSLRAE DTAVYYCTSP FAYWGQGTLV TVSSASTKGP   120
SVFPLAPSSK STSGGTAALG CLVKDYFPEP VTVSWNSGAL TSGVHTFPAV LQSSGLYSLS   180
SVVTVPSSSL GTQTYICNVN HKPSNTKVDK KVEPKSCDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVYTLPP SRDELTKNQV   360
SLTCLVKGFY PSDIAVEWES NGQPENNYKT TPPVLDSDGS FFLYSKLTVD KSRWQQGNVF   420
SCSVMHEALH NHYTQKSLSL SPGKGGGGSG GGGSGGGGSQ VQLVQSGAEV KKPGASVKVS   480
CKVSGFTLTE LSIHWVRQAP GKGLEWMGGF DPEDGETIYA QKFQGRVTMT EDTSTDTAYM   540
ELTSLRSEDT AVYYCSTIGV VTNFDNWGQG TLVTVSSGGG GSGGGGSGGG GSDIQMTQSP   600
SSLSASAGDR VTITCRASQA IRNDLGWYQQ KPGKAPKRLI YAAFNLQSGV PSRFSGSGSG   660
TEFTLTISSL QPEDLASYYC QQYNRYPWTF GQGTKLEIK                          699

SEQ ID NO: 134           moltype = AA  length = 709
FEATURE                  Location/Qualifiers
source                   1..709
                         mol_type = protein
```

```
                          organism = synthetic construct
SEQUENCE: 134
EVQLLESGGG LVQPGGSLRL SCAASGFTFS GRTVSSYAMG WVRQAPGKGL EWVAGISRSA    60
ERTYRFTISR DSKNTVYLQM NSLRAEDTAV YYCTSDLDPN RIFSREEYAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSQVQL QESGPGLVKP   480
SETLSLTCTV SGFSLIGYDL NWIRQPPGKG LEWIGIIWGD GTTDYNSAVK SRVTISKDTS   540
KNQFSLKLSS VTAADTAVYY CARGGYWYAT SYYFDYWGQG TLVTVSSGGG GSGGGGSGGG   600
GSDIQMTQSP SSLSASVGDR VTITCRASQS ISNNLNWYQQ KPGKAPKLLI YYTSRFHSGV   660
PSRFSGSGSG TDFTFTISSL QPEDIATYYC QQEHTLPYTF GQGTKLEIK               709

SEQ ID NO: 135            moltype = AA   length = 711
FEATURE                   Location/Qualifiers
source                    1..711
                          mol_type = protein
                          organism = synthetic construct
SEQUENCE: 135
EVQLLESGGG LVQPGGSLRL SCAASGFTFS GRTVSSYAMG WVRQAPGKGL EWVAGISRSA    60
ERTYRFTISR DSKNTVYLQM NSLRAEDTAV YYCTSDLDPN RIFSREEYAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSEVQL VESGGGLVQP   480
GGSLRLSCAA SGFTLRSYSM NWVRQAPGKG LEWVSYISRS SHTIFYADSV KGRFTISRDN   540
AKNSLYLQMD SLRDEDTAMY YCARVYSSGW HVSDYFDYWG QGILVTVSSG GGGSGGGGSG   600
GGGSAIQLTQ SPSSLSASVG DRVTITCRAS QGISSALAWY QQKPGKAPKL LIYDASSLES   660
GVPSRFSGSG SGTDFTLTIS SLQPEDFATY YCQQFNSYPL TFGGGTKLEI K            711

SEQ ID NO: 136            moltype = AA   length = 706
FEATURE                   Location/Qualifiers
source                    1..706
                          mol_type = protein
                          organism = synthetic construct
SEQUENCE: 136
EVQLLESGGG LVQPGGSLRL SCAASGFTFS GRTVSSYAMG WVRQAPGKGL EWVAGISRSA    60
ERTYRFTISR DSKNTVYLQM NSLRAEDTAV YYCTSDLDPN RIFSREEYAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSQVQL VQSGAEVKKP   480
GASVKVSCKV SGFTLTELSI HWVRQAPGKG LEWMGGFDPE DGETIYAQKF QGRVTMTEDT   540
STDTAYMELT SLRSEDTAVY YCSTIGVVTN FDNWGQGTLV TVSSGGGGSG GGGSGGGGSD   600
IQMTQSPSSL SASAGDRVTI TCRASQAIRN DLGWYQQKPG KAPKRLIYAA FNLQSGVPSR   660
FSGSGSGTEF TLTISSLQPE DLASYYCQQY NRYPWTFGQG TKLEIK                  706

SEQ ID NO: 137            moltype = AA   length = 703
FEATURE                   Location/Qualifiers
source                    1..703
                          mol_type = protein
                          organism = synthetic construct
SEQUENCE: 137
EVQLLESGGG LVQPGGSLRL SCAASGFTFS SYWMHWVRQA PGKGLEWVAY INPSTGYTEY    60
NQKFKRFTIS RDSKNTVYLQ MNSLRAEDTA VYYCTSGGYD DLGYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGKGGGGS GGGGSGGGGS QVQLQESGPG LVKPSETLSL   480
TCTVSGFSLI GYDLNWIRQP PGKGLEWIGI IWGDGTTDYN SAVKSRVTIS KDTSKNQFSL   540
KLSSVTAADT AVYYCARGGY WYATSYYFDY WGQGTLVTVS SGGGGSGGGG SGGGGSDIQM   600
TQSPSSLSAS VGDRVTITCR ASQSISNNLN WYQQKPGKAP KLLIYYTSRF HSGVPSRFSG   660
SGSGTDFTFT ISSLQPEDIA TYYCQQEHTL PYTFGQGTKL EIK                     703

SEQ ID NO: 138            moltype = AA   length = 705
FEATURE                   Location/Qualifiers
source                    1..705
                          mol_type = protein
                          organism = synthetic construct
SEQUENCE: 138
EVQLLESGGG LVQPGGSLRL SCAASGFTFS SYWMHWVRQA PGKGLEWVAY INPSTGYTEY    60
```

```
NQKFKRFTIS RDSKNTVYLQ MNSLRAEDTA VYYCTSGGYD DLGYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKGGGGS GGGGSGGGGS EVQLVESGGG LVQPGGSLRL  480
SCAASGFTLR SYSMNWVRQA PGKGLEWVSY ISRSSHTIFY ADSVKGRFTI SRDNAKNSLY  540
LQMDSLRDED TAMYYCARVY SSGWHVSDYF DYWGQGILVT VSSGGGGSGG GGSGGGGSAI  600
QLTQSPSSLS ASVGDRVTIT CRASQGISSA LAWYQQKPGK APKLLIYDAS SLESGVPSRF  660
SGSGSGTDFT LTISSLQPED FATYYCQQFN SYPLTFGGGT KLEIK              705

SEQ ID NO: 139          moltype = AA   length = 700
FEATURE                 Location/Qualifiers
source                  1..700
                        mol_type = protein
                        organism = synthetic construct
SEQUENCE: 139
EVQLLESGGG LVQPGGSLRL SCAASGFTFS SYWMHWVRQA PGKGLEWVAY INPSTGYTEY   60
NQKFKRFTIS RDSKNTVYLQ MNSLRAEDTA VYYCTSGGYD DLGYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKGGGGS GGGGSGGGGS QVQLVQSGAE VKKPGASVKV  480
SCKVSGFTLT ELSIHWVRQA PGKGLEWMGG FDPEDGETIY AQKFQGRVTM TEDTSTDTAY  540
MELTSLRSED TAVYYCSTIG VVTNFDNWGQ GTLVTVSSGG GGSGGGGSGG GGSDIQMTQS  600
PSSLSASAGD RVTITCRASQ AIRNDLGWYQ QKPGKAPKRL IYAAFNLQSG VPSRFSGSGS  660
GTEFTLTISS LQPEDLASYY CQQYNRYPWT FGQGTKLEIK                    700

SEQ ID NO: 140          moltype = AA   length = 930
FEATURE                 Location/Qualifiers
source                  1..930
                        mol_type = protein
                        organism = Homo sapiens
SEQUENCE: 140
MLLGWASLLL CAFRLPLAAV GPAATPAQDK AGQPPTAAAA AQPRRRQGEE VQERAEPPGH   60
PHPLAQRRRS KGLVQNIDQL YSGGGKVGYL VYAGGRRFLL DLERDGSVGI AGFVPAGGGT  120
SAPWRHRSHC FYRGTVDGSP RSLAVFDLCG GLDGFFAVKH ARYTLKPLLR GPWAEEEKGR  180
VYGDGSARIL HVYTREGFSF EALPPRASCE TPASTPEAHE HAPAHSNPSG RAALASQLLD  240
QSALSPAGGS GPQTWWRRRR RSISRARQVE LLLLVADASM A RLYGRGLQHY LLTLASIANR  300
LYSHASIENH IRLAVVKVVV LGDKDKSLEV SKNAATTLKN FCKWQHQHNQ LGDDHEEHYD  360
AAILFTREDL CGHHSCDTLG MADVGTICSP ERSCAVIEDD GLHAAFTVAH EIGHLLGLSH  420
DDSKFCEETF GSTEDKRLMS SILTSIDASK PWSKCTSATI TEFLDDGHGN CLLDLPRKQI  480
LGPEELPGQT YDATQQCNLT FGPEYSVCPG MDVCARLWCA VVRQGQMVCL TKKLPAVEGT  540
PCGKGRICLQ GKCVDKTKKK YYSTSSHGNW GSWGSWGQCS RSCGGGVQFA YRHCNNPAPR  600
NNGRYCTGKR AIYRSCSLMP CPPNGKSFRH EQCEAKNGYQ SDAKGVKTFV EWVPKYAGVL  660
PADVCKLTCR AKGTGYYVVF SPKVTDGTEC RLYSNSVCVR GKCVRTGCDG IIGSKLQYDK  720
CGVCGGDNSS CTKIVGTFNK KSKGYTDVVR IPEGATHIKV RQFKAKDQTR FTAYLALKKK  780
NGEYLINGKY MISTSETIID INGTVMNYSG WSHRDDFLHG MGYSATKEIL IVQILATDPT  840
KPLDVRYSFF VPKKSTPKVN SVTSHGSNKV GSHTSQPQWV TGPWLACSRT CDTGWHTRTV  900
QCQDGNRKLA KGCPLSQRPS AFKQCLLKKC                               930

SEQ ID NO: 141          moltype = AA   length = 930
FEATURE                 Location/Qualifiers
source                  1..930
                        mol_type = protein
                        organism = Macaca fascicularis
SEQUENCE: 141
MLLGWASLLL CAFRLPLAAA GPAAAPAQDK AGQPATAAAA AQPSRRQGEE VQERTEPPGH   60
PHPLAQRRSS KGLVQNIDQL YSGGGKVGYL VYAGGRRFLL DLERDGSVGT AGFVPTGGGT  120
SAPWRHRSHC FYRGTVDGSP RSLAVFDLCG GLDGFFAVKH ARYTLKPLLR GPWAEEETGR  180
VYGDGSARIL HVYTREGFSF EALQPRASCE TPASTPEPHE RPPAHSNPGG RAALASQLLD  240
QSAVSPAGGP GPQTWWRRRR RSISRARQVE LLLLVADASM A RLYGRGLQHY LLTLASIANR  300
LYSHASIENH IRLAVVKVVV LGDKDKSLEV SKNAATTLKN FCKWQHQHNQ LGDDHEEHYD  360
AAILFTREDL CGHHSCDTLG MADVGTICSP ERSCAVIEDD GLHAAFTVAH EIGHLLGLSH  420
DDSKFCEETF GSTEDKRLMS SILTSIDASK PWSKCTSATI TEFLDDGHGN CLLDQPRKQI  480
LGPEELPGQT YDATQQCNLT FGPEYSVCPG MDVCARLWCA VVRQGQMVCL TKKLPAVEGT  540
PCGKGRICLQ GKCVDKTKKK YYSTSSHGNW GSWGSWGQCS RSCGGGVQFA YRHCNNPAPR  600
NNGRYCTGKR AIYRSCGLMP CPPNGKSFRH EQCEAKNGYQ SDAKGVKTFV EWVPKYAGVL  660
PADVCKLTCR AKGTGYYVVF SPKVTDGTEC RPYSNSVCVR GKCVRTGCDS IIGSKLQYDK  720
CGVCGGDNSS CTKIVGTFNK KSKGYTDVVR IPEGATHIKV RQFKAKDQTR FTAYLALKKK  780
NGEYLINGKY MISTSETIID INGTVMNYSG WSHRDDFLHG MGYSATKEIL IVQILATDPT  840
KPLDVRYSFF VPKKSTPKVN SVTSHGSNKV GSHTSQLQWV TGPWLACSRT CDTGWHTRTV  900
QCQDGNRKLA KGCPLSQRPS AFKQCLLKKC                               930

SEQ ID NO: 142          moltype = AA   length = 930
FEATURE                 Location/Qualifiers
```

```
                          source          1..930
                                          mol_type = protein
                                          organism = Felis sp.
SEQUENCE: 142
MLLGWASLLL  CALRLPPVAA  GPAAAPAQDT  AGQPRAAAAA  AQPRGRQGEE  AQERAEPPGH    60
PHPLAPQRRS  GGLVHNIDQI  YAGGGKVGYL  VYAGGRRFLL  DLERDGSLGA  AGFAPAGSGP   120
GASRRHRDHC  FHRGTVDGSP  RSLAVFDLCG  GLDGFFAVKH  ARYTLKPLLR  GPRAEAEAGR   180
VYGDGSSRVL  HVYTREGFSF  EAVPPRASCE  TPASPPGPRE  RPPAHGGPGP  RWELAPPFPD   240
QTVPSSEGTQ  GPQTWWRRRR  RSISRARQVE  LLLVADASMA  RMYGRGLQHY  LLTLASIANR   300
LYSHASIENH  IRLAVVKVVV  LGDKDKSLEV  SKNAATTLKN  FCKWQHQHNQ  LEDDHEEHHD   360
AAILFTREDL  CGHHSCDTLG  MADVGTICSP  ERSCAVIEDD  GLHAAFTVAH  EIGHLLGLSH   420
DDSKFCEENF  GSTEDKRLMS  SILTSIDASK  PWSKCTSATI  TEFLDDGHGN  CLLDVPRQQI   480
SGPEELPGQT  YDATQQCNLT  FGPEYSVCPG  MDVCTRLWCA  VVRQGQMVCL  TKKLPAVEGT   540
PCGKGRICLQ  GKCVDKTKKK  YYSTSSHGNW  GSWGPWGQCS  RSCGGGVQFA  YRHCNNPAPR   600
NSGRYCTGKR  AIYRSCSVTP  CPPNGKSFRH  EQCEAKNGYQ  SDAKGVKTFV  EWVPKYAGVL   660
LGDVCKLTCR  AKGTGYYVVF  SPKVTDGTEC  RPYSNSVCVR  GKCVRTGCDG  IIGSRLQYDK   720
CAVCGGDNSS  CTKVVGTFNK  KSKGYTDVVR  IPEGATHIKV  RQFKAKDQTR  FTAYLALKKK   780
NGEYLINGKY  MISTSETIID  INGTVMNYSG  WSHRDDFLHG  MGYSATKEIL  IVQILATDPT   840
KALDVRYSFF  VPKKSTQKVN  SVSSHGSNKV  GSHTPQLQWV  TGPWLACSRT  CDTGWHTRTV   900
QCQDANRKLA  KGCLLSQRPS  AFKQCLLKKC                                       930

SEQ ID NO: 143           moltype = AA   length = 934
FEATURE                  Location/Qualifiers
source                   1..934
                         mol_type = protein
                         organism = Canis sp.
SEQUENCE: 143
MLLGWASLLL  GALRLPPVAA  GPAAAPAQDK  AGQPWAAAAA  AQPRRRQGEE  AREPAEPPGH    60
PHPLAPQRRS  SGLVQNVDQI  YAGGGKVGYL  VYAGGRRFLL  DLERDGSVGA  AGSAPAGRGP   120
GAPRRHRDHC  FYRGTVDGSP  RSLAVLDLCG  GLDGFFAVRH  ARYTLKPLLR  GPWAGAGAGA   180
EAERVYGDGS  PRILHVYTRE  GFSFEALPPR  TSCETPASPP  GPRERPPAHS  SPDPRWSPAP   240
PFPAPPAASP  DGGPGPQTWW  RRRRRSISRA  RQVELLLVAD  ASMARMYGRG  LQHYLLTLAS   300
IANRLYSHAS  IENHIRLAVV  KVVVLGDKDK  SLEVSKNAAT  TLKNFCKWQH  QHNQLGDDHE   360
EHYDAAILFT  REDLCGHHSC  DTLGMADVGT  ICSPERSCAV  IEDDGLHAAF  TVAHEIGHLL   420
GLSHDDSKFC  EENFGSTEDK  RLMSSILTSI  DASKPWSKCT  SATITEFLDD  GHGNCLLDLP   480
RKQILGPEEL  PGQTYDATQQ  CNLTFGPEYS  VCPGMDVCAR  LWCAVVRQGQ  MVCLTKKLPA   540
VEGTPCGKGR  ICLQGKCVDK  TKKKYYSTSS  HGNWGSWGSW  GQCSRSCGGG  VQFAYRHCNN   600
PAPRNNGRYC  TGKRAIYRSC  NVTPCPPNGK  SFRHEQCEAK  NGYQSDAKGV  KTFVEWVPKY   660
AGVLLGDVCK  LTCRAKGTGY  YVVFSPKVTD  GTECRPYSNS  VCVRGKCVRT  GCDGIIGSKL   720
QYDKCAVCGG  DNSSCTKVVG  TFNKKSKGYT  DVVRIPEGAT  HIKVRQFKAK  DQTRFTAYLA   780
LKKKNGEYLI  NGKYMISTSE  TIIDINGTVM  NYSGWSHRDD  FLHGMGYSAT  KEILIVQILA   840
TDPTKALDVR  YSFFVPKKST  QKVNSVTSHA  SNKVGSHTPQ  LQWVTGPWLA  CSRTCDTGWH   900
TRTVQCQDAN  RKLAKGCLLS  QRPSAFKQCL  LKKC                                 934

SEQ ID NO: 144           moltype = AA   length = 929
FEATURE                  Location/Qualifiers
source                   1..929
                         mol_type = protein
                         organism = Equus caballus
SEQUENCE: 144
MLLGWASLLL  CALRLPLVAA  GPAAAPAQDK  TGQPRAAAAA  AQPRRRQGEE  AQERAEPPGH    60
PHPLAPQRRS  SGLVQNIDQI  YSGGGKVGYL  VYAGGRRFLL  DLERDGSVGA  AGFVPVGGGP   120
SATRRHRGHC  FYRGTVDGSP  RSLAVFDLCG  GLDGFFAVKH  ARYTLKPLLR  GPWAETETGR   180
VYGDGSARIL  HVYTREGFSF  EALPPRTSCE  TPASPPGSRE  RPPAHSSPEP  RWALAPQFPD   240
QSATSSDGGQ  GSQTWRRRRR  SISRARQVEL  LLVADASMAR  MYGRGLQHYL  LTLASIANRL   300
YSHASIENHI  RLAVVKMVVL  GDKDKSLEVS  KNAATTLKNF  CKWQHQHNQL  GDDHEEHYDA   360
AILFTREDLC  GHHSCDTLGM  ADVGTICSPE  RSCAVIEDDG  LHAAFTVAHE  IGHLLGLSHD   420
DSKFCEENFG  STEEKRLMSS  ILTSIDASKP  WSKCTSATIT  EFLDDGHGNC  LLDLPRKQIL   480
GPEELPGQTY  DATQQCNLTF  GPEYSVCPGM  DVCARLWCAV  VRQGQMVCLT  KKLPAVEGTP   540
CGKGRICLQG  KCVDKTKKKY  YSTSSHGNWG  SWGSWGQCSR  SCGGGVQFAY  RHCNNPAPRN   600
NGRYCTGKRA  IYRSCSVTPC  PANGKSFRHE  QCEAKNGYQS  DAKGVKTFVE  WVPKYAGVLP   660
GDVCKLTCRA  KGTGYYVVFS  PKVTDGTECR  PYSNSVCVRG  KCVRTGCDGI  IGSKLQYDKC   720
GVCGGDNSSC  TKVVGTFNKK  SKGYTDVVRI  PEGATHIKVR  QFKTKDQTRF  TAYLALKKKN   780
GEYLINGKYM  ISTSETIIDI  NGTVMNYSGW  SHRDDFLHGM  GYSATKEILI  VQILATDPTK   840
ALDVRYSFFV  PKKPTQKGNS  VTSHGSNKVG  STTPQLQWVT  GPWLACSRTC  DTGWHTRTVQ   900
CQDGNRKLAK  GCLLSQRPSA  FKQCLLKKC                                        929

SEQ ID NO: 145           moltype = AA   length = 930
FEATURE                  Location/Qualifiers
source                   1..930
                         mol_type = protein
                         organism = Mus musculus
SEQUENCE: 145
MRLEWAPLLL  LLLLLSASCL  SLAADSPAAA  PAQDKTRQPQ  AAAAAAEPDQ  PQGEETRERG    60
HLQPLAGQRR  SGGLVQNIDQ  LYSGGGKVGY  LVYAGGRRFL  LDLERDDTVG  AAGSIVTAGG   120
GLSASSSGHRG  HCFYRGTVDG  SPRSLAVFDL  CGGLDGFFAV  KHARYTLKPL  LRGSWAEYER   180
IYGDGSSRIL  HVYNREGFSF  EALPPRASCE  TPASPSGPQE  SPSVHSRSRR  RSALAPQLLD   240
HSAFSPSGNA  GPQTWWRRRR  RSISRARQVE  LLLVADSSMA  RMYGRGLQHY  LLTLASIANR   300
LYSHASIENH  IRLAVVKVVV  LTDKDTSLEV  SKNAATTLKN  FCKWQHQHNQ  LGDDHEEHYD   360
```

```
AAILFTREDL CGHHSCDTLG MADVGTICSP ERSCAVIEDD GLHAAFTVAH EIGHLLGLSH    420
DDSKFCEENF GTTEDKRLMS SILTSIDASK PWSKCTSATI TEFLDDGHGN CLLDLPRKQI    480
LGPEELPGQT YDATQQCNLT FGPEYSVCPG MDVCARLWCA VVRQGQMVCL TKKLPAVEGT    540
PCGKGRVCLQ GKCVDKTKKK YYSTSSHGNW GSWGPWGQCS RSCGGGVQFA YRHCNNPAPR    600
NSGRYCTGKR AIYRSCSVTP CPPNGKSFRH EQCEAKNGYQ SDAKGVKTFV EWVPKYAGVL    660
PADVCKLTCR AKGTGYYVVF SPKVTDGTEC RPYSNSVCVR GRCVRTGCDG IIGSKLQYDK    720
CGVCGGDNSS CTKIIGTFNK KSKGYTDVVR IPEGATHIKV RQFKAKDQTR FTAYLALKKK    780
TGEYLINGKY MISTSETIID INGTVMNYSG WSHRDDFLHG MGYSATKEIL IVQILATDPT    840
KALDVRYSFF VPKKTTQKVN SVISHGSNKV GPHSTQLQWV TGPWLACSRT CDTGWHTRTV    900
QCQDGNRKLA KGCLLSQRPS AFKQCLLKKC                                    930

SEQ ID NO: 146          moltype = AA  length = 927
FEATURE                 Location/Qualifiers
source                  1..927
                        mol_type = protein
                        organism = Rattus sp.
SEQUENCE: 146
MRLEWASLLL LLLLLCASCL ALAADNPAAA PAQDKTRQPR AAAAAAQPDQ RQWEETQERG     60
HPQPLARQRR SSGLVQNIDQ LYSGGGKVGY LVYAGGRRFL LDLERDDTVG AAGGIVTAGG    120
LSASSGHRGH CFYRGTVDGS PRSLAVFDLC GGLDGFFAVK HARYTLKPLL RGSWAESERV    180
YGDGSSRILH VYTREGFSFE ALPPRTSCET PASPSGAQES PSVHSSSRRR TELAPQLLDH    240
SAFSPAGNAG PQTWWRRRRR SISRARQVEL LLVADSSMAK MYGRGLQHYL LTLASIANRL    300
YSHASIENHI RLAVVKVVVL TDKSLEVSKN AATTLKNFCK WQHQHNQLGD DHEEHYDAAI    360
LFTREDLCGH HSCDTLGMAD VGTICSPERS CAVIEDDGLH AAFTVAHEIG HLLGLSHDDS    420
KFCEENFGST EDKRLMSSIL TSIDASKPWS KCTSATITEF LDDGHGNCLL DVPRKQILGP    480
EELPGQTYDA TQQCNLTFGP EYSVCPGMDV CARLWCAVVR QGQMVCLTKK LPAVEGTPCG    540
KGRICLQGKC VDKTKKKYYS TSSHGNWGSW GPWGQCSRSC GGGVQFAYRH CNNPAPRNSG    600
RYCTGKRAIY RSCSVIPCPP NGKSFRHEQC EAKNGYQSDA KGVKTFVEWV PKYAGVLPAD    660
VCKLTCRAKG TGYYVVFSPK VTDGTECRPY SNSVCVRGRC VRTGCDGIIG SKLQYDKCGV    720
CGGDNSSCTK IIGTFNKKSK GYTDVVRIPE GATHIKVRQF KAKDQTRFTA YLALKKKTGE    780
YLINGKYMIS TSETIIDING TVMNYSGWSH RDDFLHGMGY SATKEILIVQ ILATDPTKAL    840
DVRYSFFVPK KTTQKVNSVI SHSSNKVGLH SPQLQWVTGP WLACSRTCDT GWHTRTVQCQ    900
DGNRKLAKGC ILSQRPSAFK QCLLKKC                                       927

SEQ ID NO: 147          moltype = AA  length = 241
FEATURE                 Location/Qualifiers
source                  1..241
                        mol_type = protein
                        organism = Homo sapiens
SEQUENCE: 147
MSMLFYTLIT AFLIGIQAEP HSESNVPAGH TIPQAHWTKL QHSLDTALRR ARSAPAAAIA     60
ARVAGQTRNI TVDPRLFKKR RLRSPRVLFS TQPPREAADT QDLDFEVGGA APFNRTHRSK    120
RSSSHPIFHR GEFSVCDSVS VWWGDKTTAT DIKGKEVMVL GEVNINNSVF KQYFFETKCR    180
DPNPVDSGCR GIDSKHWNSY CTTTHTFVKA LTMDGKQAAW RFIRIDTACV CVLSRKAVRR    240
A                                                                   241

SEQ ID NO: 148          moltype = AA  length = 241
FEATURE                 Location/Qualifiers
source                  1..241
                        mol_type = protein
                        organism = Macaca fascicularis
SEQUENCE: 148
MSMLFYTLIT AFLIGIQAEP HSESNVPAGH TIPQAHWTKL QHSLDTALRR VRSAPAVAIA     60
ARVAGQTRNI TVDPRLFKKR RLRSPRVLFS TQPPPEAADT QDLDFEVGGA APFNRTHRSK    120
RSSSHPIFHR GEFSVCDSVS VWWGDKTTAT DIKGKEVMVL GEVNINNSVF KQYFFETKCR    180
DPNPVDSGCR GIDSKHWNSY CTTTHTFVKA LTMDGKQAAW RFIRIDTACV CVLSRKAVRR    240
A                                                                   241

SEQ ID NO: 149          moltype = AA  length = 241
FEATURE                 Location/Qualifiers
source                  1..241
                        mol_type = protein
                        organism = Canis sp.
SEQUENCE: 149
MSMLFYTLIT ALLIGIRAEP HPESHVPAGH AIPHAHWTKL QHSLDTALRR ARSAPAGAIA     60
ARVTGQTRNI TVDPKLFKKR RLRSPRVLFS THPPPVAADA QDLDLEAGST ASVNRTHRSK    120
RSSSHPVFHR GEFSVCDSVS VWWGDKTTAT DIKGKEVMVL GEVNINNSVF KQYFFETKCR    180
DPTPVDSGCR GIDSKHWNSY CTTTHTFVKA LTMDGKQAAW RFIRIDTACV CVLSRKAGRR    240
A                                                                   241

SEQ ID NO: 150          moltype = AA  length = 241
FEATURE                 Location/Qualifiers
source                  1..241
                        mol_type = protein
                        organism = Felis sp.
SEQUENCE: 150
MSMLSYTLIT ALLIGIQAEP HPESNVPAGH TIPQAHWTKL QHSLDTALRR ARSTPAGAIA     60
ARVAGQTRNI TVDPKLFKKR RLRSPRVLFS THPPPVAADT QGLDLEAGGA ASFNRTHRSK    120
RSSSHPVFHR GEFSVCDSVS VWWGDKTTAT DIKGKEVMVL GEVNINNSVF KQYFFETKCR    180
```

```
DPTPVDSGCR GIDSKHWNSY CTTTHTFVKA LTMDGKQAAW RFIRIDTACV CVLSRKAGRR    240
A                                                                   241

SEQ ID NO: 151          moltype = AA   length = 241
FEATURE                 Location/Qualifiers
source                  1..241
                        mol_type = protein
                        organism = Equus caballus
SEQUENCE: 151
MSMLFYTLIT ALLIGTQAEP HTESNVPAGH AIPQAHWTKL QHSLDTALRR ARSAPARAIA    60
ARVAGQTRNI TVDPKLFKKR RLRSPRVLFS TQPPPVAADT QDLDFEAGGA ASFNRTHRSK    120
RSSSHPVFHR GEFSVCDSVS VWVGDKTTAT DIKGKEVMVL GEVNINNSVF KQYFFETKCR    180
DPNPVDSGCR GIDSKHWNSY CTTTHTFVKA LTMDGKQAAW RFIRIDTACV CVLSRKTGRK    240
A                                                                   241

SEQ ID NO: 152          moltype = AA   length = 241
FEATURE                 Location/Qualifiers
source                  1..241
                        mol_type = protein
                        organism = Mus musculus
SEQUENCE: 152
MSMLFYTLIT AFLIGVQAEP YTDSNVPEGD SVPEAHWTKL QHSLDTALRR ARSAPTAPIA    60
ARVTGQTRNI TVDPRLFKKR RLHSPRVLFS TQPPPTSSDT LDLDFQAHGT IPFNRTHRSK    120
RSSTHPVFHM GEFSVCDSVS VWVGDKTTAT DIKGKEVTVL AEVNINNSVF RQYFFETKCR    180
ASNPVESGCR GIDSKHWNSY CTTTHTFVKA LTTDEKQAAW RFIRIDTACV CVLSRKATRR    240
G                                                                   241

SEQ ID NO: 153          moltype = AA   length = 241
FEATURE                 Location/Qualifiers
source                  1..241
                        mol_type = protein
                        organism = Rattus sp.
SEQUENCE: 153
MSMLFYTLIT AFLIGVQAEP YTDSNVPEGD SVPEAHWTKL QHSLDTALRR ARSAPAEPIA    60
ARVTGQTRNI TVDPKLFKKR RLRSPRVLFS TQPPPTSSDT LDLDFQAHGT ISFNRTHRSK    120
RSSTHPVFHM GEFSVCDSVS VWVGDKTTAT DIKGKEVTVL GEVNINNSVF KQYFFETKCR    180
APNPVESGCR GIDSKHWNSY CTTTHTFVKA LTTDDKQAAW RFIRIDTACV CVLSRKAARR    240
G                                                                   241

SEQ ID NO: 154          moltype = AA   length = 10
FEATURE                 Location/Qualifiers
source                  1..10
                        mol_type = protein
                        organism = synthetic construct
SEQUENCE: 154
GISRSAERTY                                                          10

SEQ ID NO: 155          moltype = AA   length = 15
FEATURE                 Location/Qualifiers
source                  1..15
                        mol_type = protein
                        organism = synthetic construct
SEQUENCE: 155
DLDPNRIFSR EEYAY                                                    15

SEQ ID NO: 156          moltype = AA   length = 16
FEATURE                 Location/Qualifiers
source                  1..16
                        mol_type = protein
                        organism = synthetic construct
SEQUENCE: 156
YINPSTGYTE YNQKFK                                                   16

SEQ ID NO: 157          moltype = AA   length = 8
FEATURE                 Location/Qualifiers
source                  1..8
                        mol_type = protein
                        organism = synthetic construct
SEQUENCE: 157
GGYDDLGY                                                            8

SEQ ID NO: 158          moltype = AA   length = 7
FEATURE                 Location/Qualifiers
source                  1..7
                        mol_type = protein
                        organism = synthetic construct
SEQUENCE: 158
LMSTRAS                                                             7
```

```
SEQ ID NO: 159         moltype = AA  length = 9
FEATURE                Location/Qualifiers
source                 1..9
                       mol_type = protein
                       organism = synthetic construct
SEQUENCE: 159
QQLVUYPYT                                                               9
```

The invention claimed is:

1. A composition comprising:
an antibody with two or more antigen binding components,
wherein at least one antigen binding component is capable of binding to human ADAMTS5,
and wherein at least one antigen binding component is capable of binding to nerve growth factor (NGF).

2. The composition of claim 1, wherein said antibody is a monoclonal antibody or fragment thereof.

3. The composition of claim 2, wherein said monoclonal antibody or fragment thereof is mouse, feline, canine, equine, chimeric, humanized, or fully human.

4. The composition of claim 1, wherein the antigen binding component capable of binding to NGF is selected from the group consisting of: tanezumab, fasinumab, fulranumab, TrkA Fc and/or p75NTR Fc.

5. The composition of claim 1, wherein the antigen binding component capable of binding to NGF consists of tanezumab.

6. The composition of claim 1, wherein one antigen binding component selectively binds with high affinity to one or more ADAMTS5 molecules and wherein one antigen binding protein selectively binds with high affinity to one or more NGF molecules.

7. The composition of claim 1, further comprising pharmaceutically acceptable excipients.

8. The composition of claim 1, wherein the binding protein with two or more antigen binding components comprises a bispecific antibody, and wherein the bispecific antibody is selected from the group consisting of: SynOA CM1 (SEQ ID NO: 16, SEQ ID NO: 18, SEQ ID NO: 20 and SEQ ID NO: 22), SynOA CM2 (SEQ ID NO: 38, SEQ ID NO: 39, SEQ ID NO: 20 and SEQ ID NO: 22), SynOA CM3 (SEQ ID NO: 16, SEQ ID NO: 18, SEQ ID NO: 103 and SEQ ID NO: 104), SynOA CM4 (SEQ ID NO: 38, SEQ ID NO: 39, SEQ ID NO: 103 and SEQ ID NO: 104), SynOA CM5 (SEQ ID NO: 16, SEQ ID NO: 18, SEQ ID NO: 56 and SEQ ID NO: 57, SynOA CM6 (SEQ ID NO: 38, SEQ ID NO: 39, SEQ ID NO: 56 and SEQ ID NO: 57), SynOA CM7 (SEQ ID NO: 16, SEQ ID NO: 18 and SEQ ID NO: 50), SynOA CM8 (SEQ ID NO: 38, SEQ ID NO: 39 and SEQ ID NO: 50), SynOA CM9 (SEQ ID NO: 16, SEQ ID NO: 18 and SEQ ID NO: 51), SynOA CM10 (SEQ ID NO: 38, SEQ ID NO: 39 and SEQ ID NO: 51), SynOA DM1 (SEQ ID NO: 52, SEQ ID NO: 18, SEQ ID NO: 53 and SEQ ID NO: 54), SynOA DM2 (SEQ ID NO: 100, SEQ ID NO: 18, SEQ ID NO: 124 and SEQ ID NO: 54), SynOA DM3 (SEQ ID NO: 55, SEQ ID NO: 39, SEQ ID NO: 53 and SEQ ID NO: 54), SynOA DM4 (SEQ ID NO: 102, SEQ ID NO: 39, SEQ ID NO: 125 and SEQ ID NO: 54), SynOA DM5 (SEQ ID NO: 52, SEQ ID NO: 18, SEQ ID NO: 121 and SEQ ID NO: 122), SynOA DM6 (SEQ ID NO: 100, SEQ ID NO: 18, SEQ ID NO: 123 and SEQ ID NO: 122), SynOA DM7 (SEQ ID NO: 55, SEQ ID NO: 39, SEQ ID NO: 121 and SEQ ID NO: 122), SynOA DM8 (SEQ ID NO: 102, SEQ ID NO: 39, SEQ ID NO: 123 and SEQ ID NO: 122), SynOA DM9 (SEQ ID NO: 52, SEQ ID NO: 18, SEQ ID NO: 98 and SEQ ID NO: 99), SynOA DM10 (SEQ ID NO:100, SEQ ID NO: 18, SEQ ID NO: 101 and SEQ ID NO: 99), SynOA DM11 (SEQ ID NO: 55, SEQ ID NO: 39, SEQ ID NO: 98 and SEQ ID NO: 99), or SynOA DM12 (SEQ ID NO: 102, SEQ ID NO: 39, SEQ ID NO: 101 and SEQ ID NO: 99).

9. The composition of claim 1, wherein the antibody comprises SynOA CM1 (SEQ ID NO: 16, SEQ ID NO: 18, SEQ ID NO: 20 and SEQ ID NO: 22), SynOA CM2 (SEQ ID NO: 38, SEQ ID NO: 39, SEQ ID NO: 20 and SEQ ID NO: 22), SynOA CM3 (SEQ ID NO: 16, SEQ ID NO: 18, SEQ ID NO: 103 and SEQ ID NO: 104), SynOA CM4 (SEQ ID NO: 38, SEQ ID NO: 39, SEQ ID NO: 103 and SEQ ID NO: 104), SynOA CM5 (SEQ ID NO: 16, SEQ ID NO: 18, SEQ ID NO: 56 and SEQ ID NO: 57), or SynOA CM6 (SEQ ID NO: 38, SEQ ID NO: 39, SEQ ID NO: 56 and SEQ ID NO: 57).

10. The composition of claim 1, wherein the antibody comprises SynOA CM1 (SEQ ID NO: 16, SEQ ID NO: 18, SEQ ID NO: 20 and SEQ ID NO: 22), or SynOA CM2 (SEQ ID NO: 38, SEQ ID NO: 39, SEQ ID NO: 20 and SEQ ID NO: 22).

11. The composition of claim 1, wherein the antibody consists of SynOA CM1 (SEQ ID NO: 16, SEQ ID NO: 18, SEQ ID NO: 20 and SEQ ID NO: 22).

12. The composition of claim 1, wherein the antibody consists of SynOA DM1 (SEQ ID NO: 52, SEQ ID NO: 18, SEQ ID NO: 53 and SEQ ID NO: 54), SynOA DM2 (SEQ ID NO: 100, SEQ ID NO: 18, SEQ ID NO: 124 and SEQ ID NO: 54), SynOA DM3 (SEQ ID NO: 55, SEQ ID NO: 39, SEQ ID NO: 53 and SEQ ID NO: 54), SynOA DM4 (SEQ ID NO: 102, SEQ ID NO: 39, SEQ ID NO: 125 and SEQ ID NO: 54), SynOA DM5 (SEQ ID NO: 52, SEQ ID NO: 18, SEQ ID NO: 121 and SEQ ID NO: 122), SynOA DM6 (SEQ ID NO: 100, SEQ ID NO: 18, SEQ ID NO: 123 and SEQ ID NO: 122), SynOA DM7 (SEQ ID NO: 55, SEQ ID NO: 39, SEQ ID NO: 121 and SEQ ID NO: 122), SynOA DM8 (SEQ ID NO: 102, SEQ ID NO: 39, SEQ ID NO: 123 and SEQ ID NO: 122), SynOA DM9 (SEQ ID NO: 52, SEQ ID NO: 18, SEQ ID NO: 98 and SEQ ID NO: 99), SynOA DM10 (SEQ ID NO:100, SEQ ID NO: 18, SEQ ID NO: 101 and SEQ ID NO: 99), SynOA DM11 (SEQ ID NO: 55, SEQ ID NO: 39, SEQ ID NO: 98 and SEQ ID NO: 99), or SynOA DM12 (SEQ ID NO: 102, SEQ ID NO: 39, SEQ ID NO: 101 and SEQ ID NO: 99).

13. The composition of claim 1, wherein the antibody consists of SynOA DM1 (SEQ ID NO: 52, SEQ ID NO: 18, SEQ ID NO: 53 and SEQ ID NO: 54), SynOA DM2 (SEQ ID NO: 100, SEQ ID NO: 18, SEQ ID NO: 124 and SEQ ID NO: 54), SynOA DM3 (SEQ ID NO: 55, SEQ ID NO: 39, SEQ ID NO: 53 and SEQ ID NO: 54), or SynOA DM4 (SEQ ID NO: 102, SEQ ID NO: 39, SEQ ID NO: 125 and SEQ ID NO: 54).

14. The composition of claim 1, wherein the antigen binding component capable of binding to ADAMTS5 consists of 7B4 (SEQ ID NO: 1 and SEQ ID NO: 2), or 12F4 (SEQ ID NO: 3 and SEQ ID NO: 4).

15. The composition of claim 12, wherein the antigen binding component capable of binding to ADAMTS5 consists of 7B4 (SEQ ID NO: 1 and SEQ ID NO: 2).

16. The composition of claim 12, wherein the antigen binding component capable of binding to ADAMTS5 consists of 12F4 (SEQ ID NO: 3 and SEQ ID NO: 4).

* * * * *